(12) United States Patent
Wesche et al.

(10) Patent No.: US 11,976,125 B2
(45) Date of Patent: *May 7, 2024

(54) B CELL MATURATION ANTIGEN BINDING PROTEINS

(71) Applicant: Harpoon Therapeutics, Inc., South San Francisco, CA (US)

(72) Inventors: Holger Wesche, San Francisco, CA (US); Bryan D. Lemon, Mountain View, CA (US); Richard J. Austin, South San Francisco, CA (US)

(73) Assignee: HARPOON THERAPEUTICS, INC., South San Francisco, CA (US)

(*) Notice: Subject to any disclaimer, the term of this patent is extended or adjusted under 35 U.S.C. 154(b) by 466 days.

This patent is subject to a terminal disclaimer.

(21) Appl. No.: 17/150,272

(22) Filed: Jan. 15, 2021

(65) Prior Publication Data

US 2021/0171649 A1 Jun. 10, 2021

Related U.S. Application Data

(62) Division of application No. 16/159,545, filed on Oct. 12, 2018, now Pat. No. 10,927,180.

(60) Provisional application No. 62/572,375, filed on Oct. 13, 2017.

(51) Int. Cl.
| | |
|---|---|
| *C07K 16/28* | (2006.01) |
| *A61K 47/68* | (2017.01) |
| *A61P 35/00* | (2006.01) |
| *A61P 35/02* | (2006.01) |
| *A61P 35/04* | (2006.01) |
| *C07K 16/18* | (2006.01) |
| *A61K 39/00* | (2006.01) |

(52) U.S. Cl.
CPC ...... *C07K 16/2878* (2013.01); *A61K 47/6849* (2017.08); *A61P 35/00* (2018.01); *A61P 35/02* (2018.01); *A61P 35/04* (2018.01); *C07K 16/18* (2013.01); *C07K 16/2809* (2013.01); *A61K 2039/505* (2013.01); *C07K 2317/21* (2013.01); *C07K 2317/22* (2013.01); *C07K 2317/24* (2013.01); *C07K 2317/31* (2013.01); *C07K 2317/33* (2013.01); *C07K 2317/52* (2013.01); *C07K 2317/565* (2013.01); *C07K 2317/569* (2013.01); *C07K 2317/73* (2013.01); *C07K 2317/732* (2013.01); *C07K 2317/734* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 4,943,533 A | 7/1990 | Mendelsohn et al. |
| 5,061,620 A | 10/1991 | Tsukamoto et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,759,808 A | 6/1998 | Casterman et al. |
| 5,766,886 A | 6/1998 | Studnicka et al. |
| 5,773,292 A | 6/1998 | Bander |
| 5,800,988 A | 9/1998 | Casterman et al. |
| 5,811,097 A | 9/1998 | Allison et al. |
| 5,840,526 A | 11/1998 | Casterman et al. |
| 5,843,439 A | 12/1998 | Anderson et al. |
| 5,844,093 A | 12/1998 | Kettleborough et al. |
| 5,858,358 A | 1/1999 | June et al. |
| 5,859,205 A | 1/1999 | Adair et al. |
| 5,874,541 A | 2/1999 | Casterman et al. |
| 5,883,223 A | 3/1999 | Gray |
| 5,977,318 A | 11/1999 | Linsley et al. |
| 6,005,079 A | 12/1999 | Casterman et al. |
| 6,015,695 A | 1/2000 | Casterman et al. |
| 6,051,227 A | 4/2000 | Allison et al. |
| 6,107,090 A | 8/2000 | Bander |
| 6,120,766 A | 9/2000 | Hale et al. |
| 6,136,311 A | 10/2000 | Bander |

(Continued)

FOREIGN PATENT DOCUMENTS

| | | |
|---|---|---|
| CA | 2992797 A1 | 2/2017 |
| CA | 2994579 A1 | 2/2017 |

(Continued)

OTHER PUBLICATIONS

Ryan et al (MCT, 6(11):3009-3018, 2007).*

(Continued)

*Primary Examiner* — Brad Duffy
(74) *Attorney, Agent, or Firm* — WILSON SONSINI GOODRICH & ROSATI

(57) ABSTRACT

Disclosed herein are B cell maturation antigen binding proteins with improved binding affinities and improved ability to mediate killing of cancer cells expressing B cell maturation antigen (BCMA). Pharmaceutical compositions comprising the binding proteins disclosed herein and methods of treatment of a cancer or a metastasis thereof using such formulations are further provided.

20 Claims, 36 Drawing Sheets

Specification includes a Sequence Listing.

(56) References Cited

U.S. PATENT DOCUMENTS

| | | |
|---|---|---|
| 6,210,669 B1 | 4/2001 | Aruffo et al. |
| 6,303,121 B1 | 10/2001 | Kwon |
| 6,326,193 B1 | 12/2001 | Liu et al. |
| 6,331,415 B1 | 12/2001 | Cabilly et al. |
| 6,352,694 B1 | 3/2002 | June et al. |
| 6,355,476 B1 | 3/2002 | Kwon et al. |
| 6,362,325 B1 | 3/2002 | Kwon |
| 6,407,213 B1 | 6/2002 | Carter et al. |
| 6,534,055 B1 | 3/2003 | June et al. |
| 6,548,640 B1 | 4/2003 | Winter |
| 6,569,997 B1 | 5/2003 | Kwon |
| 6,670,453 B2 | 12/2003 | Frenken et al. |
| 6,682,736 B1 | 1/2004 | Hanson et al. |
| 6,692,964 B1 | 2/2004 | June et al. |
| 6,759,518 B1 | 7/2004 | Kontermann et al. |
| 6,767,711 B2 | 7/2004 | Bander |
| 6,797,514 B2 | 9/2004 | Berenson et al. |
| 6,808,710 B1 | 10/2004 | Wood et al. |
| 6,867,041 B2 | 3/2005 | Berenson et al. |
| 6,887,466 B2 | 5/2005 | June et al. |
| 6,887,673 B2 | 5/2005 | Kunkel et al. |
| 6,905,680 B2 | 6/2005 | June et al. |
| 6,905,681 B1 | 6/2005 | June et al. |
| 6,905,685 B2 | 6/2005 | Kwon |
| 6,905,874 B2 | 6/2005 | Berenson et al. |
| 6,974,863 B2 | 12/2005 | Kwon |
| 6,984,720 B1 | 1/2006 | Korman et al. |
| 7,034,121 B2 | 4/2006 | Carreno et al. |
| 7,060,808 B1 | 6/2006 | Goldstein et al. |
| 7,067,318 B2 | 6/2006 | June et al. |
| 7,144,575 B2 | 12/2006 | June et al. |
| 7,163,680 B2 | 1/2007 | Bander |
| 7,172,869 B2 | 2/2007 | June et al. |
| 7,175,843 B2 | 2/2007 | June et al. |
| 7,214,493 B2 | 5/2007 | Kunkel et al. |
| 7,232,566 B2 | 6/2007 | June et al. |
| 7,247,301 B2 | 7/2007 | Van De Winkel et al. |
| 7,262,276 B2 | 8/2007 | Huang et al. |
| 7,288,638 B2 | 10/2007 | Jure-Kunkel et al. |
| 7,488,802 B2 | 2/2009 | Collins et al. |
| 7,595,378 B2 | 9/2009 | Van De Winkel et al. |
| 7,605,238 B2 | 10/2009 | Korman et al. |
| 7,666,414 B2 | 2/2010 | Bander |
| 7,723,484 B2 | 5/2010 | Beidler et al. |
| 7,807,162 B2 | 10/2010 | Silence |
| 7,812,135 B2 | 10/2010 | Smith et al. |
| 7,850,971 B2 | 12/2010 | Maddon et al. |
| 7,939,072 B2 | 5/2011 | Yarden et al. |
| 7,943,743 B2 | 5/2011 | Korman et al. |
| 8,008,449 B2 | 8/2011 | Korman et al. |
| 8,114,965 B2 | 2/2012 | Maddon et al. |
| 8,153,768 B2 | 4/2012 | Kunz et al. |
| 8,168,757 B2 | 5/2012 | Finnefrock et al. |
| 8,188,223 B2 | 5/2012 | Beirnaert et al. |
| 8,236,308 B2 | 8/2012 | Kischel et al. |
| 8,354,509 B2 | 1/2013 | Carven et al. |
| 8,388,967 B2 | 3/2013 | Smith et al. |
| 8,470,330 B2 | 6/2013 | Schuelke et al. |
| 8,552,156 B2 | 10/2013 | Takayanagi et al. |
| 8,609,089 B2 | 12/2013 | Langermann et al. |
| 8,623,356 B2 | 1/2014 | Christopherson et al. |
| 8,629,244 B2 | 1/2014 | Kolkman et al. |
| 8,703,135 B2 | 4/2014 | Beste et al. |
| 8,709,424 B2 | 4/2014 | Schebye et al. |
| 8,779,105 B2 | 7/2014 | Korman et al. |
| 8,784,821 B1 | 7/2014 | Kufer et al. |
| 8,846,042 B2 | 9/2014 | Zhou |
| 8,900,587 B2 | 12/2014 | Carven et al. |
| 8,907,071 B2 | 12/2014 | Sullivan et al. |
| 8,937,164 B2 | 1/2015 | Descamps et al. |
| 8,986,972 B2 | 3/2015 | Stull et al. |
| 9,089,615 B2 | 7/2015 | Stull et al. |
| 9,089,616 B2 | 7/2015 | Stull et al. |
| 9,089,617 B2 | 7/2015 | Stull et al. |
| 9,090,683 B2 | 7/2015 | Stull et al. |
| 9,107,961 B2 | 8/2015 | Stull et al. |
| 9,126,984 B2 | 9/2015 | Crosignani et al. |
| 9,127,071 B2 | 9/2015 | Yoshida et al. |
| 9,133,271 B1 | 9/2015 | Stull et al. |
| 9,155,803 B1 | 10/2015 | Stull et al. |
| 9,169,316 B2 | 10/2015 | Baty et al. |
| 9,309,327 B2 | 4/2016 | Humphreys et al. |
| 9,327,022 B2 | 5/2016 | Zhang et al. |
| 9,334,318 B1 | 5/2016 | Stull et al. |
| 9,340,621 B2 | 5/2016 | Kufer et al. |
| 9,345,787 B2 | 5/2016 | Hemminki et al. |
| 9,352,051 B1 | 5/2016 | Stull et al. |
| 9,353,182 B2 | 5/2016 | Stull et al. |
| 9,358,304 B1 | 6/2016 | Stull et al. |
| 9,359,442 B2 | 6/2016 | Hoffee et al. |
| 9,422,368 B2 | 8/2016 | Spee et al. |
| 9,480,757 B2 | 11/2016 | Stull et al. |
| 9,481,724 B2 | 11/2016 | Ravetch et al. |
| 9,486,537 B2 | 11/2016 | Stull et al. |
| 9,624,185 B1 | 4/2017 | Xu |
| 9,642,918 B2 | 5/2017 | Bruederle et al. |
| 9,708,412 B2 | 7/2017 | Baeuerle et al. |
| 9,764,042 B1 | 9/2017 | Stull et al. |
| 9,770,518 B1 | 9/2017 | Stull et al. |
| 9,775,916 B1 | 10/2017 | Stull et al. |
| 9,855,343 B2 | 1/2018 | Stull et al. |
| 9,861,708 B2 | 1/2018 | Stull et al. |
| 9,867,887 B1 | 1/2018 | Stull et al. |
| 9,878,053 B2 | 1/2018 | Stull et al. |
| 9,920,115 B2 | 3/2018 | Dubridge et al. |
| 9,931,420 B2 | 4/2018 | Stull et al. |
| 9,931,421 B2 | 4/2018 | Stull et al. |
| 9,937,268 B2 | 4/2018 | Stull et al. |
| 10,066,016 B2 | 9/2018 | Dubridge et al. |
| 10,100,106 B2 | 10/2018 | Dubridge et al. |
| 10,137,204 B2 | 11/2018 | Stull et al. |
| 10,428,120 B2 | 10/2019 | Kontermann et al. |
| 10,543,271 B2 | 1/2020 | Wesche et al. |
| 10,544,221 B2 | 1/2020 | Dubridge et al. |
| 10,730,954 B2 | 8/2020 | Wesche et al. |
| 10,815,311 B2 | 10/2020 | Wesche et al. |
| 10,844,134 B2 | 11/2020 | Baeuerle et al. |
| 10,849,973 B2 | 12/2020 | Dubridge et al. |
| 10,927,180 B2 | 2/2021 | Wesche et al. |
| 10,954,311 B2 | 3/2021 | Baeuerle et al. |
| 11,111,311 B2 | 9/2021 | Yoshida et al. |
| 11,136,403 B2 * | 10/2021 | Wesche ................. A61P 35/00 |
| 11,180,563 B2 | 11/2021 | Wesche et al. |
| 2002/0015704 A1 | 2/2002 | Bander |
| 2002/0051780 A1 | 5/2002 | Lindhofer et al. |
| 2002/0081296 A1 | 6/2002 | Theill et al. |
| 2003/0031673 A1 | 2/2003 | Bander |
| 2003/0092892 A1 | 5/2003 | Frenken et al. |
| 2004/0101519 A1 | 5/2004 | June et al. |
| 2005/0042664 A1 | 2/2005 | Wu et al. |
| 2005/0048617 A1 | 3/2005 | Wu et al. |
| 2005/0095244 A1 | 5/2005 | Jure-Kunkel et al. |
| 2005/0100543 A1 | 5/2005 | Hansen et al. |
| 2005/0175606 A1 | 8/2005 | Huang et al. |
| 2006/0034810 A1 | 2/2006 | Riley et al. |
| 2006/0046971 A1 | 3/2006 | Stuhler et al. |
| 2006/0121005 A1 | 6/2006 | Berenson et al. |
| 2006/0228364 A1 | 10/2006 | Dennis et al. |
| 2006/0252096 A1 | 11/2006 | Zha et al. |
| 2007/0014794 A1 | 1/2007 | Carter et al. |
| 2007/0178082 A1 | 8/2007 | Silence et al. |
| 2007/0269422 A1 | 11/2007 | Beirnaert et al. |
| 2008/0069772 A1 | 3/2008 | Stuhler et al. |
| 2008/0260757 A1 | 10/2008 | Holt et al. |
| 2009/0028880 A1 | 1/2009 | Beirnaert et al. |
| 2009/0041789 A1 | 2/2009 | Elsaesser-Beile et al. |
| 2009/0117108 A1 | 5/2009 | Wang et al. |
| 2009/0136494 A1 | 5/2009 | Ponath et al. |
| 2009/0252683 A1 | 10/2009 | Kischel et al. |
| 2009/0259026 A1 | 10/2009 | Tomlinson et al. |
| 2010/0022452 A1 | 1/2010 | Silence |
| 2010/0028330 A1 | 2/2010 | Collins et al. |
| 2010/0122358 A1 | 5/2010 | Bruggemann et al. |
| 2010/0150918 A1 | 6/2010 | Kufer et al. |

(56) References Cited

U.S. PATENT DOCUMENTS

| | | |
|---|---|---|
| 2010/0166734 A1 | 7/2010 | Dolk |
| 2010/0189651 A1 | 7/2010 | Stagliano et al. |
| 2010/0189727 A1 | 7/2010 | Rodeck et al. |
| 2010/0266531 A1 | 10/2010 | Hsieh et al. |
| 2010/0291112 A1 | 11/2010 | Kellner et al. |
| 2010/0311119 A1 | 12/2010 | Hermans et al. |
| 2011/0129458 A1 | 6/2011 | Dolk et al. |
| 2011/0150892 A1 | 6/2011 | Thudium et al. |
| 2011/0165621 A1 | 7/2011 | Dreier et al. |
| 2011/0262439 A1 | 10/2011 | Kufer et al. |
| 2011/0275787 A1 | 11/2011 | Kufer et al. |
| 2011/0313135 A1 | 12/2011 | Vanhove et al. |
| 2012/0039899 A1 | 2/2012 | Olsen et al. |
| 2012/0039906 A1 | 2/2012 | Olive |
| 2012/0114649 A1 | 5/2012 | Langermann et al. |
| 2012/0231024 A1 | 9/2012 | Elsaesser-Beile et al. |
| 2012/0237977 A1 | 9/2012 | Daugherty et al. |
| 2012/0263677 A1 | 10/2012 | Eagle et al. |
| 2012/0328619 A1 | 12/2012 | Fey et al. |
| 2013/0017199 A1 | 1/2013 | Langermann |
| 2013/0017200 A1 | 1/2013 | Scheer et al. |
| 2013/0136744 A1 | 5/2013 | Bouche et al. |
| 2013/0183321 A1 | 7/2013 | Smith et al. |
| 2013/0197201 A1 | 8/2013 | Vasquez et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0330335 A1 | 12/2013 | Bremel et al. |
| 2014/0004121 A1 | 1/2014 | Fanslow, III et al. |
| 2014/0004575 A1 | 1/2014 | Ito et al. |
| 2014/0023664 A1 | 1/2014 | Lowman et al. |
| 2014/0044728 A1 | 2/2014 | Takayanagi et al. |
| 2014/0045195 A1 | 2/2014 | Daugherty et al. |
| 2014/0065152 A1 | 3/2014 | Kwon |
| 2014/0072565 A1 | 3/2014 | Kwon |
| 2014/0072566 A1 | 3/2014 | Kwon |
| 2014/0073767 A1 | 3/2014 | Lee et al. |
| 2014/0088295 A1 | 3/2014 | Smith et al. |
| 2014/0093511 A1 | 4/2014 | Lonberg et al. |
| 2014/0161828 A1 | 6/2014 | Armitage et al. |
| 2014/0205601 A1 | 7/2014 | Beirnaert et al. |
| 2014/0220002 A1 | 8/2014 | Ponte et al. |
| 2014/0242075 A1 | 8/2014 | Parren et al. |
| 2014/0302037 A1 | 10/2014 | Borges et al. |
| 2014/0322218 A1 | 10/2014 | Xiao et al. |
| 2014/0348841 A1 | 11/2014 | Schebye et al. |
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |
| 2015/0079109 A1 | 3/2015 | Li et al. |
| 2015/0093336 A1 | 4/2015 | Van Ginderachter et al. |
| 2015/0174268 A1 | 6/2015 | Li et al. |
| 2015/0183875 A1 | 7/2015 | Cobbold et al. |
| 2015/0225367 A1 | 8/2015 | Crosignani et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2015/0328332 A1 | 11/2015 | Stull et al. |
| 2016/0017058 A1 | 1/2016 | Kim et al. |
| 2016/0024174 A1 | 1/2016 | Odunsi et al. |
| 2016/0032011 A1 | 2/2016 | Zhang et al. |
| 2016/0032019 A1 | 2/2016 | Xiao et al. |
| 2016/0039942 A1 | 2/2016 | Cobbold et al. |
| 2016/0046724 A1 | 2/2016 | Brogdon et al. |
| 2016/0068605 A1 | 3/2016 | Nemeth et al. |
| 2016/0115241 A1 | 4/2016 | Yan et al. |
| 2016/0130331 A1 | 5/2016 | Stull et al. |
| 2016/0185875 A1 | 6/2016 | Cheng et al. |
| 2016/0194399 A1 | 7/2016 | Irving et al. |
| 2016/0215063 A1 | 7/2016 | Bernett et al. |
| 2016/0229913 A1 | 8/2016 | Bosques et al. |
| 2016/0251438 A1 | 9/2016 | Lucas et al. |
| 2016/0251440 A1 | 9/2016 | Roobrouck et al. |
| 2016/0257721 A1 | 9/2016 | Lieber et al. |
| 2016/0263087 A1 | 9/2016 | Crosignani et al. |
| 2016/0319040 A1 | 11/2016 | Dreier et al. |
| 2016/0340444 A1 | 11/2016 | Baeuerle et al. |
| 2016/0355842 A1 | 12/2016 | Parks et al. |
| 2017/0029502 A1 | 2/2017 | Raum et al. |
| 2017/0037130 A1 | 2/2017 | Raum et al. |
| 2017/0037149 A1 | 2/2017 | Raum et al. |
| 2017/0051068 A1 | 2/2017 | Pillarisetti et al. |
| 2017/0152316 A1 | 6/2017 | Cobbold et al. |
| 2017/0158771 A1 | 6/2017 | Glennie et al. |
| 2017/0204164 A1 | 7/2017 | Himmler et al. |
| 2017/0274094 A1 | 9/2017 | Stull et al. |
| 2017/0275373 A1 | 9/2017 | Kufer et al. |
| 2017/0306014 A1 | 10/2017 | Cornen et al. |
| 2017/0334979 A1 | 11/2017 | Dubridge et al. |
| 2017/0334997 A1 | 11/2017 | Dubridge et al. |
| 2017/0349660 A1 | 12/2017 | Saville et al. |
| 2017/0362310 A1 | 12/2017 | Shoemaker |
| 2017/0369563 A1 | 12/2017 | Dubridge et al. |
| 2018/0016323 A1 | 1/2018 | Brandenburg et al. |
| 2018/0036306 A1 | 2/2018 | Jones et al. |
| 2018/0134789 A1 | 5/2018 | Baeuerle et al. |
| 2018/0148508 A1 | 5/2018 | Wang et al. |
| 2018/0327511 A1 | 11/2018 | Satoh et al. |
| 2018/0346601 A1 | 12/2018 | Dettling et al. |
| 2019/0016811 A1 | 1/2019 | Lucas et al. |
| 2019/0023786 A1 | 1/2019 | Broderick et al. |
| 2019/0031749 A1 | 1/2019 | Dubridge et al. |
| 2019/0046656 A1 | 2/2019 | Stull et al. |
| 2019/0062427 A1 | 2/2019 | Rosenthal et al. |
| 2019/0092862 A1 | 3/2019 | Cui et al. |
| 2019/0112381 A1 | 4/2019 | Wesche et al. |
| 2019/0127483 A1 | 5/2019 | Li |
| 2019/0225702 A1 | 7/2019 | Baeuerle et al. |
| 2019/0247510 A1 | 8/2019 | Stull et al. |
| 2020/0115461 A1 | 4/2020 | Evnin et al. |
| 2020/0148771 A1 | 5/2020 | Paeuerle et al. |
| 2020/0155520 A1 | 5/2020 | Colburn et al. |
| 2020/0231672 A1 | 7/2020 | Dubridge et al. |
| 2020/0270362 A1 | 8/2020 | Wesche et al. |
| 2020/0289646 A1 | 9/2020 | Wesche et al. |
| 2020/0352998 A1 | 11/2020 | Albertson et al. |
| 2021/0047439 A1 | 2/2021 | Wesche et al. |
| 2021/0095047 A1 | 4/2021 | Baeuerle et al. |
| 2021/0100902 A1 | 4/2021 | Dubridge et al. |
| 2021/0179735 A1 | 6/2021 | Baeuerle et al. |
| 2021/0269530 A1 | 9/2021 | Lin et al. |
| 2021/0284728 A1 | 9/2021 | Lin et al. |
| 2021/0292421 A1 | 9/2021 | Lin et al. |
| 2021/0355219 A1 | 11/2021 | Lin et al. |
| 2021/0380715 A1 | 12/2021 | Yoshida et al. |
| 2022/0017626 A1 | 1/2022 | Wesche et al. |
| 2022/0054544 A1 | 2/2022 | Lin et al. |
| 2022/0098311 A1 | 3/2022 | Wesche et al. |
| 2022/0112297 A1 | 4/2022 | Wesche et al. |
| 2022/0267462 A1 | 8/2022 | Wesche et al. |

FOREIGN PATENT DOCUMENTS

| | | |
|---|---|---|
| CN | 1563092 A | 1/2005 |
| CN | 101646689 A | 2/2010 |
| CN | 101809035 A | 8/2010 |
| CN | 104520324 A | 4/2015 |
| CN | 105968201 A | 9/2016 |
| CN | 105968204 A | 9/2016 |
| CN | 108026174 A | 5/2018 |
| CN | 109593786 A | 4/2019 |
| EP | 0239400 A2 | 9/1987 |
| EP | 0519596 A1 | 12/1992 |
| EP | 0592106 A1 | 4/1994 |
| EP | 1378520 A1 | 1/2004 |
| EP | 1736484 A1 | 12/2006 |
| EP | 2336179 A1 | 6/2011 |
| EP | 2581113 A1 | 4/2013 |
| EP | 2817338 A2 | 12/2014 |
| EP | 3038659 A1 | 7/2016 |
| EP | 3093293 A1 | 11/2016 |
| EP | 3093294 A1 | 11/2016 |

(56) References Cited

FOREIGN PATENT DOCUMENTS

| | | |
|---|---|---|
| EP | 3095797 A1 | 11/2016 |
| EP | 3107576 A1 | 12/2016 |
| EP | 3146979 A1 | 3/2017 |
| EP | 3261650 A1 | 1/2018 |
| EP | 3337517 A2 | 6/2018 |
| EP | 3458050 A1 | 3/2019 |
| EP | 3193929 B1 | 6/2019 |
| EP | 3556400 A1 | 10/2019 |
| FR | 901228 A | 7/1945 |
| JP | 2005501517 A | 1/2005 |
| JP | 2005518789 A | 6/2005 |
| JP | 2007535915 A | 12/2007 |
| JP | 2008278814 A | 11/2008 |
| JP | 2015501135 A | 1/2015 |
| JP | 2016500655 A | 1/2016 |
| JP | 2019052750 A | 4/2019 |
| WO | WO-9109967 A1 | 7/1991 |
| WO | WO-9307105 A1 | 4/1993 |
| WO | WO-9404678 A1 | 3/1994 |
| WO | WO-9937681 A2 | 7/1999 |
| WO | WO-0043507 A1 | 7/2000 |
| WO | WO-0130381 A2 | 5/2001 |
| WO | WO-0190190 A2 | 11/2001 |
| WO | WO-0196584 A2 | 12/2001 |
| WO | WO-0222685 A2 | 3/2002 |
| WO | WO-02055082 A1 | 7/2002 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004035607 A2 | 4/2004 |
| WO | WO-2004041867 A2 | 5/2004 |
| WO | WO-2004042404 A1 | 5/2004 |
| WO | WO-2004049794 A2 | 6/2004 |
| WO | WO-2004056312 A2 | 7/2004 |
| WO | WO-2004099249 A2 | 11/2004 |
| WO | WO-2005003168 A2 | 1/2005 |
| WO | WO-2005009465 A1 | 2/2005 |
| WO | WO-2005040220 A1 | 5/2005 |
| WO | WO-2005095456 A1 | 10/2005 |
| WO | WO-2006020258 A2 | 2/2006 |
| WO | WO-2006072625 A2 | 7/2006 |
| WO | WO-2006072626 A1 | 7/2006 |
| WO | WO-2006105021 A2 | 10/2006 |
| WO | WO-2006121168 A1 | 11/2006 |
| WO | WO-2006122786 A2 | 11/2006 |
| WO | WO-2006122787 A1 | 11/2006 |
| WO | WO-2007005874 A2 | 1/2007 |
| WO | WO-2007024715 A2 | 3/2007 |
| WO | WO-2007042261 A2 | 4/2007 |
| WO | WO-2007042573 A2 | 4/2007 |
| WO | WO-2007062466 A1 | 6/2007 |
| WO | WO-2007113648 A2 | 10/2007 |
| WO | WO-2007115230 A2 | 10/2007 |
| WO | WO-2008028977 A2 | 3/2008 |
| WO | WO-2008084106 A1 | 7/2008 |
| WO | WO-2009009116 A2 | 1/2009 |
| WO | WO-2009025846 A2 | 2/2009 |
| WO | WO-2009030285 A1 | 3/2009 |
| WO | WO-2009035577 A1 | 3/2009 |
| WO | WO-2009101611 A1 | 8/2009 |
| WO | WO-2009114335 A2 | 9/2009 |
| WO | WO-2009147248 A2 | 12/2009 |
| WO | WO-2010003118 A1 | 1/2010 |
| WO | WO-2010012557 A1 | 2/2010 |
| WO | WO-2010019570 A2 | 2/2010 |
| WO | WO-2010027827 A2 | 3/2010 |
| WO | WO-2010037836 A2 | 4/2010 |
| WO | WO-2010037837 A2 | 4/2010 |
| WO | WO-2010065939 A1 | 6/2010 |
| WO | WO-2010077634 A1 | 7/2010 |
| WO | WO-2010081173 A2 | 7/2010 |
| WO | WO-2011028683 A1 | 3/2011 |
| WO | WO-2011039368 A2 | 4/2011 |
| WO | WO-2011051327 A2 | 5/2011 |
| WO | WO-2011066342 A2 | 6/2011 |
| WO | WO-2011070024 A1 | 6/2011 |
| WO | WO-2011107553 A1 | 9/2011 |
| WO | WO-2011131407 A1 | 10/2011 |
| WO | WO-2011140249 A2 | 11/2011 |
| WO | WO-2011155607 A1 | 12/2011 |
| WO | WO-2012071411 A2 | 5/2012 |
| WO | WO-2012122444 A1 | 9/2012 |
| WO | WO-2012131053 A1 | 10/2012 |
| WO | WO-2012138475 A1 | 10/2012 |
| WO | WO-2012145493 A1 | 10/2012 |
| WO | WO-2012158818 A2 | 11/2012 |
| WO | WO-2012160448 A2 | 11/2012 |
| WO | WO-2012163805 A1 | 12/2012 |
| WO | WO-2012175400 A1 | 12/2012 |
| WO | WO-2013006490 A2 | 1/2013 |
| WO | WO-2013036130 A1 | 3/2013 |
| WO | WO-2013039954 A1 | 3/2013 |
| WO | WO-2013072406 A1 | 5/2013 |
| WO | WO-2013072415 A1 | 5/2013 |
| WO | WO-2013079174 A1 | 6/2013 |
| WO | WO-2013087699 A1 | 6/2013 |
| WO | WO-2013104804 A2 | 7/2013 |
| WO | WO-2013110531 A1 | 8/2013 |
| WO | WO-2013119716 A1 | 8/2013 |
| WO | WO-2013126712 A1 | 8/2013 |
| WO | WO-2013128027 A1 | 9/2013 |
| WO | WO-2013128194 A1 | 9/2013 |
| WO | WO-2013132044 A1 | 9/2013 |
| WO | WO-2013158856 A2 | 10/2013 |
| WO | WO-2013169264 A1 | 11/2013 |
| WO | WO-2013173223 A1 | 11/2013 |
| WO | WO-2014008218 A1 | 1/2014 |
| WO | WO-2014012085 A2 | 1/2014 |
| WO | WO-2014033304 A2 | 3/2014 |
| WO | WO-2014036357 A1 | 3/2014 |
| WO | WO-2014047231 A1 | 3/2014 |
| WO | WO-2014055648 A1 | 4/2014 |
| WO | WO-2014094122 A1 | 6/2014 |
| WO | WO-2014125273 A1 | 8/2014 |
| WO | WO-2014132072 A1 | 9/2014 |
| WO | WO-2014138306 A1 | 9/2014 |
| WO | WO-2014140358 A1 | 9/2014 |
| WO | WO-2014144689 A1 | 9/2014 |
| WO | WO-2014151910 A1 | 9/2014 |
| WO | WO-2014153270 A1 | 9/2014 |
| WO | WO-2015026684 A1 | 2/2015 |
| WO | WO-2015031667 A2 | 3/2015 |
| WO | WO-2015042246 A1 | 3/2015 |
| WO | WO-2015082499 A2 | 6/2015 |
| WO | WO-2015103072 A1 | 7/2015 |
| WO | WO-2015121812 A1 | 8/2015 |
| WO | WO-2015140717 A1 | 9/2015 |
| WO | WO-2015142675 A2 | 9/2015 |
| WO | WO-2015146437 A1 | 10/2015 |
| WO | WO-2015150097 A1 | 10/2015 |
| WO | WO-2015150447 A1 | 10/2015 |
| WO | WO-2015173764 A1 | 11/2015 |
| WO | WO-2015184099 A1 | 12/2015 |
| WO | WO-2015184207 A1 | 12/2015 |
| WO | WO-2015187835 A2 | 12/2015 |
| WO | WO-2016009029 A1 | 1/2016 |
| WO | WO-2016026772 A1 | 2/2016 |
| WO | WO-2016032334 A1 | 3/2016 |
| WO | WO-2016046778 A2 | 3/2016 |
| WO | WO-2016055551 A1 | 4/2016 |
| WO | WO-2016071283 A1 | 5/2016 |
| WO | WO-2016071293 A2 | 5/2016 |
| WO | WO-2016075099 A1 | 5/2016 |
| WO | WO-2016087531 A1 | 6/2016 |
| WO | WO-2016105450 A1 | 6/2016 |
| WO | WO-2016125017 A1 | 8/2016 |
| WO | WO-2016130819 A2 | 8/2016 |
| WO | WO-2016134333 A1 | 8/2016 |
| WO | WO-2016134335 A2 | 8/2016 |
| WO | WO-2016147144 A1 | 9/2016 |
| WO | WO-2016171999 A2 | 10/2016 |
| WO | WO-2016179003 A1 | 11/2016 |

(56) References Cited

FOREIGN PATENT DOCUMENTS

| | | |
|---|---|---|
| WO | WO-2016179518 A2 | 11/2016 |
| WO | WO-2016180982 A1 | 11/2016 |
| WO | WO-2016181348 A1 | 11/2016 |
| WO | WO-2016182064 A1 | 11/2016 |
| WO | WO-2016187101 A2 | 11/2016 |
| WO | WO-2016187594 A1 | 11/2016 |
| WO | WO-2016210447 A1 | 12/2016 |
| WO | WO-2017007700 A1 | 1/2017 |
| WO | WO-2017021349 A1 | 2/2017 |
| WO | WO-2017025038 A1 | 2/2017 |
| WO | WO-2017025698 A1 | 2/2017 |
| WO | WO-2017025868 A1 | 2/2017 |
| WO | WO-2017027392 A1 | 2/2017 |
| WO | WO-2017031104 A1 | 2/2017 |
| WO | WO-2017041749 A1 | 3/2017 |
| WO | WO-2017079528 A1 | 5/2017 |
| WO | WO-2017093969 A1 | 6/2017 |
| WO | WO-2017134134 A1 | 8/2017 |
| WO | WO-2017136549 A1 | 8/2017 |
| WO | WO-2017156178 A1 | 9/2017 |
| WO | WO-2017157305 A1 | 9/2017 |
| WO | WO-2017161206 A1 | 9/2017 |
| WO | WO-2017162587 A1 | 9/2017 |
| WO | WO-2017201488 A1 | 11/2017 |
| WO | WO-2017201493 A1 | 11/2017 |
| WO | WO-2017220988 A1 | 12/2017 |
| WO | WO-2018017863 A1 | 1/2018 |
| WO | WO-2018017864 A2 | 1/2018 |
| WO | WO-2018026953 A1 | 2/2018 |
| WO | WO-2018027203 A1 | 2/2018 |
| WO | WO-2018033798 A1 | 2/2018 |
| WO | WO-2018048975 A1 | 3/2018 |
| WO | WO-2018067993 A1 | 4/2018 |
| WO | WO-2018071777 A1 | 4/2018 |
| WO | WO-2018075359 A1 | 4/2018 |
| WO | WO-2018083204 A1 | 5/2018 |
| WO | WO-2018085469 A2 | 5/2018 |
| WO | WO-2018098354 A1 | 5/2018 |
| WO | WO-2018098356 A1 | 5/2018 |
| WO | WO-2018106529 A1 | 6/2018 |
| WO | WO-2018106588 A1 | 6/2018 |
| WO | WO-2018110555 A1 | 6/2018 |
| WO | WO-2018115859 A1 | 6/2018 |
| WO | WO-2018133877 A1 | 7/2018 |
| WO | WO-2018136725 A1 | 7/2018 |
| WO | WO-2018160671 A1 | 9/2018 |
| WO | WO-2018160754 A2 | 9/2018 |
| WO | WO-2018165619 A1 | 9/2018 |
| WO | WO-2018183366 A1 | 10/2018 |
| WO | WO-2018204717 A1 | 11/2018 |
| WO | WO-2018209298 A1 | 11/2018 |
| WO | WO-2018209304 A1 | 11/2018 |
| WO | WO-2018232020 A1 | 12/2018 |
| WO | WO-2019011852 A1 | 1/2019 |
| WO | WO-2019011855 A1 | 1/2019 |
| WO | WO-2019025983 A1 | 2/2019 |
| WO | WO-2019075359 A1 | 4/2019 |
| WO | WO-2019075378 A1 | 4/2019 |
| WO | WO-2019136305 A1 | 7/2019 |
| WO | WO-2019222278 A1 | 11/2019 |
| WO | WO-2019222282 A1 | 11/2019 |
| WO | WO-2019222283 A1 | 11/2019 |
| WO | WO-2019229701 A2 | 12/2019 |
| WO | WO-2019246004 A1 | 12/2019 |
| WO | WO-2020053263 A1 | 3/2020 |
| WO | WO-2020060593 A1 | 3/2020 |
| WO | WO-2020061482 A1 | 3/2020 |
| WO | WO-2020061526 A1 | 3/2020 |
| WO | WO-2020069028 A1 | 4/2020 |
| WO | WO-2020092792 A2 | 5/2020 |
| WO | WO-2020097403 A1 | 5/2020 |
| WO | WO-2019166650 A9 | 8/2020 |
| WO | WO-2020181145 A1 | 9/2020 |
| WO | WO-2020232303 A1 | 11/2020 |
| WO | WO-2020252349 A1 | 12/2020 |
| WO | WO-2020261093 A1 | 12/2020 |
| WO | WO-2020263830 A1 | 12/2020 |
| WO | WO-2021097060 A1 | 5/2021 |
| WO | WO-2021168303 A1 | 8/2021 |
| WO | WO-2021231434 A1 | 11/2021 |
| WO | WO-2022031884 A2 | 2/2022 |
| WO | WO-2022032006 A2 | 2/2022 |
| WO | WO-2022098909 A1 | 5/2022 |
| WO | WO-2022212732 A1 | 10/2022 |
| WO | WO-2022256498 A1 | 12/2022 |
| WO | WO-2022256499 A2 | 12/2022 |
| WO | WO-2022256500 A2 | 12/2022 |
| WO | WO-2022272033 A2 | 12/2022 |
| WO | WO-2023064945 A2 | 4/2023 |

OTHER PUBLICATIONS

Fang et al. Characterization of an anti-human ovarian carcinomaxanti-human CD3 bispecific single-chain antibody with an albumin-original interlinker. Gynecol Oncol 92(1):135-146 (2004).
Harris et al. A bispecific antibody agonist of the IL-2 heterodimeric receptor preferentially promotes in vivo expansion of CD8 and NK cells. Sci Rep. 11(1):10592 (2021).
Lin et al. ProTriTAC: A Protease-Activatable T Cell Engager Platform that Links Half-Life Extension to Functional Masking Society for Immunotherapy of Cancer (SITC) Annual Meeting. Nov. 2018, Available at https://www.harpoontx.com/file.cfm/43/docs/SITC_2018_ProTriTAC_Poster.pdf.
Ma et al. Combination therapy with T cell engager and PD-L1 blockade enhances the antitumor potency of T cells as predicted by a QSP model. J Immunother Cancer. 8(2):e001141 (2020).
PCT/US2022/022871 International Search Report and Written Opinion dated Aug. 3, 2022.
PCT/US2022/031916 International Search Report and Written Opinion dated Sep. 29, 2022.
PCT/US2022/031919 International Search Report and Written Opinion dated Nov. 21, 2022.
U.S. Appl. No. 16/773,843 Office Action dated Aug. 11, 2022.
U.S. Appl. No. 16/802,007 Office Action dated Sep. 29, 2022.
Annual Report Pursuant to Section 13 or 15(d) of the Securities Exchange Act of 1934. 2019 22-24 [online]. [Retrieved on Aug. 5, 2021]. Retrieved from website URL:https://www.annualreports.com/HostedData/AnnualReportArchive/h/NASDAQ_HARP_2018.pdf.
Hassanzadeh-Ghassabeh et al. Nanobodies and their potential applications. Nanomedicine 8(6):1013-1026 (2013).
Krzywinska et al. CD45 Isoform Profile Identifies Natural Killer (NK) Subsets with Differential Activity. PLoS One 11(4):e0150434 (2016).
Leibl et al. Ovarian granulosa cell tumors frequently express EGFR (Her-1), Her-3, and Her-4: An immunohistochemical study. Gynecol Oncol 101(1):18-23 (2006).
Mason et al. CD79a: a novel marker for B-cell neoplasms in routinely processed tissue samples. Blood 86(4):1453-1459 (1995).
PCT/US2021/018853 International Search Report and Written Opinion dated Jul. 8, 2021.
PCT/US2021/031790 International Search Report and Written Opinion dated Sep. 16, 2021.
Sandler et al. Nondermatologic adverse events associated with anti-EGFR therapy. Oncology (Williston Park) 20(5 Suppl 2):35-40 (2006).
Thomas. Cetuximab: adverse event profile and recommendations for toxicity management. Clin J Oncol Nurs. 9(3):332-8 (2005).
UniProtKB Accession No. A0A3M1V7M7_9EURY, Ig-like_bact domain-containing protein, Feb. 13, 2019 [online] [Retrieved on Jun. 8, 2021]. Retrieved from the internet <url:<ahref="https://www.uniprotorg/uniprot/A0A3M1V7M7.bct">https://www.uniprotorg/uniprot/A0A3M1V7M7.bct</url:.<a>.
U.S. Appl. No. 16/161,986 Office Action dated Dec. 2, 2021.
Agata et al. Expression of the PD-1 antigen on the surface of stimulated mouse T and B lymphocytes. Int. Immunol 8:765-75 (1996).
Al-Lazikani et al. Standard conformations for the canonical structures of immunoglobulins. J. Mol Biology 273(4):927-948 (1997).

(56) References Cited

OTHER PUBLICATIONS

Almagro et al. Humanization of antibodies. Front Biosci 13:1619-1633 (2008).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1997).
Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Barrett et al. Treatment of advanced leukemia in mice with mRNA engineered T cells. Hum Gene Ther 22:1575-1586 (2011).
Batzer et al. Enhanced evolutionary PCR using oligonucleotides with inosine at the 3'-terminus. Nucleic Acids Res. 19(18):5081 (1991).
Baum et al. Antitumor activities of PSMAxCD3 diabodies by redirected T-cell lysis of prostate cancer cells. Immunotherapy 5(1):27-38 (2013).
Bedouelle et al. Diversity and junction residues as hotspots of binding energy in an antibody neutralizing the dengue virus. FEBS J 273(1):34-46 (2006).
Bendell et al. Abstract 5552: First-in-human phase I study of HPN424, a tri-specific half-life extended PSMA-targeting T-cell engager in patients with metastatic castration-resistant prostate cancer (mCRPC). J Clin Oncol 38(15):5552 (May 2020).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Bortoletto et al. Optimizing anti-CD3 affinity for effective T cell targeting against tumor cells. Eur J Immunol 32:3102-3107 (2002).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Brauchle et al. Characterization of a Novel FLT3 BiTE Molecule for the Treatment of Acute Myeloid Leukemia. Mol Cancer Ther 19:1875-88 (2020).
Brown et al. Tolerance of single, but not multiple, amino acid replacements in antibody VH CDR 2: a means of minimizing B cell wastage from somatic hypermutation? J Immunol 156(9):3285-3291 (1996).
Caldas et al. Design and synthesis of germline-based hemi-humanized single-chain Fv against the CD18 surface antigen. Protein Eng 13(5):353-360 (2000).
Caldas et al. Humanization of the anti-CD18 antibody 6.7: an unexpected effect of a framework residue in binding to antigen. Mol Immunol. 39(15):941-952 (2003).
Carter et al. Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Casset et al. A peptide mimetic of an anti-CD4 monoclonal antibody by rational design. Biochemical and Biophysical Research Communication 307:198-205 (2003).

Chang et al. Loop-sequence features and stability determinants in antibody variable domains by high-throughput experiments. Structure 22(1):9-21 (2014).
Chang et al. Molecular cloning of mesothelin, a differentiation antigen present on mesothelium, mesotheliomas, and ovarian cancers. PNAS USA 93:136-140 (1996).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Fusion protein linkers: Property, design and functionality. Advanced Drug Delivery Reviews 65:1357-1369 (2013).
Chen et al. Selection and analysis of an optimized anti-VEGF antibody: Crystal structure of an affinity-matured Fab in complex with antigen. J Mol Bio 293:865-881 (1999).
Chien et al. Significant structural and functional change of an antigen-binding site by a distant amino acid substitution: proposal of a structural mechanism. PNAS USA 86(14):5532-5536 (1989).
Cho et al. Targeting B Cell Maturation Antigen (BCMA) in Multiple Myeloma: Potential Uses of BCMA-Based Immunotherapy. Front Immunol 9:1821 (2018).
Choi et al. Engineering of Immunoglobulin Fc heterodimers using yeast surface-displayed combinatorial Fc library screening. PLOS One 10(12):e0145349 (2015).
Chothia et al. Canonical structures for the hypervariable regions of immunoglobulins. J Mol Biol 196(4):901-917 (1987).
Chothia, et al. Conformations of immunoglobulin hypervariable regions. Nature 342(6252):877-83 (1989).
Corso et al. Real-time detection of mesothelin in pancreatic cancer cell line supernatant using an acoustic wave immunosensor. Cancer Detect Prey 30:180-187 (2006).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
Dao et al. Targeting the intracellular WT1 oncogene product with a therapeutic human antibody. Sci Transl Med 5(176):176ra33 (2013).
De Genst et al. Antibody repertoire development in camelids. Dev Comp Immunol 30(1-2):187-198 (2006).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Dennis et al. Imaging Tumors with an Albumin-Binding Fab, a Novel Tumor-Targeting Agent. Cancer Res 67(1):254-61 (2007).
Document D28—Investigation of human CD3ε variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).
Dong et al. B7-H1 pathway and its role in the evasion of tumor immunity. J Mol Med 81:281-287 (2003).

(56) References Cited

OTHER PUBLICATIONS

Elango et al. Optimized transfection of mRNA transcribed from a d(A/T)100 tail-containing vector. Biochim Biophys Res Commun 330:958-966 (2005).
Foote et al. Antibody Framework Residues Affecting the Conformation of the Hypervariable Loops. J. Mol. Biol. 224(2):487-99 (1992).
Frankel et al. Targeting T cells to tumor cells using bispecific antibodies. Curr Opin Chem Biol 17(3):385-392 (2013).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Giusti et al. Somatic diversification of S107 from an antiphosphocholine to an anti-DNA autoantibody is due to a single base change in its heavy chain variable region. PNAS USA 84(9):2926-30 (1987).
Glaser et al. Novel antibody hinge regions for efficient production of CH2 domain-deleted antibodies. J. Biol. Chem. 280:41494-503 (2005).
Goldman et al. Enhancing Stability of Camelid and Shark Single Domain Antibodies: An Overview. Front. Immunol. 8:865 (2017).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Grupp et al. Chimeric antigen receptor-modified T cells for acute lymphoid leukemia. NEJM 368:1509-1518 (2013).
Gubbels et al. Mesothelin-MUC16 binding is a high affinity, N-glycan dependent interaction that facilitates peritoneal metastasis of ovarian tumors. Mol Cancer 5:50 (2006).
Gussow et al. Chapter 5: Humanization of Monoclonal Antibodies. Methods in Enzymology 203:99-121 (1991).
Haanen et al. Selective expansion of cross-reactive CD8(+) memory T cells by viral variants. J Exp Med 190(9):1319-1328 (1999).
Halaby et al. The immunoglobulin fold family: sequence analysis and 3D structure comparisons. Prot Eng 12(7):563-571 (1999).
Han et al. Masked Chimeric Antigen Receptor for Tumor-Specific Activation. Molecular Therapy 25(1):274-284 (2017).
Harding et al. The immunogenicity of humanized and fully human antibodies: residual immunogenicity resides in the CDR regions. MAbs 2(3):256-265 (2010).
Harmsen et al. Properties, production, and applications of camelid single-domain antibody fragments. Appl. Microbiol. Biotechnol. 77:13-22 (2007).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor- associated mesothelin. Cancer Immun. 7:20 (2007).
Hellstrom et al. Mesothelin variant 1 is released from tumor cells as a diagnostic marker. Cancer Epidemiol Biomarkers Prey 15:1014-1020 (2006).
Hipp et al. A novel BCMA/CD3 bispecific T-cell engager for the treatment of multiple myeloma induces selective lysis in vitro and in vivo. Leukemia 31(8):1743-1751 (2017).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Ho et al. Mesothelin is shed from tumor cells. Cancer Epidemiol Biomarkers Prey 15:1751 (2006).
Holliger, et al. "Diabodies": small bivalent and bispecific antibody fragments. Proc Natl Acad Sci USA. Jul. 15, 1993; 90(14): 6444-6448. doi: 10.1073/pnas.90.14.6444.
Holm et al. Functional mapping and single chain construction of the anti-cytokeratin 8 monoclonal antibody TS1. Mol Immunol 44(6):1075-1084 (2007).
Holt et al. Anti-serum albumin domain antibodies for extending the half-lives of short-lived drugs. Protein Eng Des Sel 21(5):283-288 (2008).
Hopp et al. The effects of affinity and valency of an albumin-binding domain (ABD) on the half-life of a single-chain diabody-ABD fusion protein. Protein Eng. Des. Sel. 23(11):827-34 (2010).
Huck et al. Sequence of a human immunoglobulin gamma 3 heavy chain constant region gene: comparison with the other human C gamma genes. Nucl. Acids Res. 14:1779-89 (1986).
Huston et al. Protein engineering of antibody binding sites: recovery of specific activity in an anti-digoxin single-chain Fv analogue produced in *Escherichia coli*. PNAS USA 85(16):5879-5883 (1988).
Hutchinson et al. Mutagenesis at a specific position in a DNA sequence. J Biol Chem 253:6551-6560 (1978).
Izumoto et al. Phase II clinical trial of Wilms tumor 1 peptide vaccination for patients with recurrent glioblastoma multiforme. J Neurosurg 108:963-971 (2008).
Janssen letter—Submission under Rule 116 EPC. Submitted by Janssen Biotech to the European Patent Register on Mar. 18, 2016 in connection with their opposition to the EP2155783 patent (6 pages) (2016).
Jones et al. Replacing the complementarity-determining regions in a human antibody with those from a mouse. Nature 321:522-525 (1986).
Julian et al. Efficient affinity maturation of antibody variable domains requires co-selection of compensatory mutations to maintain thermodynamic stability. Sci Rep 7:45259 (2017).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Škrlec et al. Non-immunoglobulin scaffolds: a focus on their targets. Trends in Biotechnol 33:408-418 (2015).
Laabi et al. The BCMA gene, preferentially expressed during B lymphoid maturation, is bidirectionally transcribed. Nucleic Acids Res 22(7):1147-1154 (1994).
Latchman et al. PD-L2 is a second ligand for PD-1 and inhibits T cell activation. Nat Immunol 2:261-268 (2001).
Le Gall et al. Immunosuppressive properties of anti-CD3 single-chain Fv and diabody. J Immunol Methods 285(1):111-127 (2004).
Li et al. Development of novel tetravalent anti-CD20 antibodies with potent antitumor activity. Cancer Res 68:2400-2408 (2008).
Liu et al. A New Format of Single Chain Tri-specific Antibody with Diminished Molecular Size Efficiently Induces Ovarian Tumor Cell Killing. Biotechnology Letters 27(22):1821-1827 (2005).
Liu et al. MGD011, a CD19 × CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Lowman et al. Monovalent phage display: A method for selecting variant proteins from random libraries. Methods 3:205-216 (1991).

(56) References Cited

OTHER PUBLICATIONS

Lu et al. In vitro and in vivo antitumor effect of a trivalent bispecific antibody targeting ErbB2 and CD16. Cancer Biol Ther. 7(11):1744-1750 (2008).
Lutterbuese et al. T cell-engaging BiTE antibodies specific for EGFR potently eliminate KRAS- and BRAF-mutated colorectal cancer cells. PNAS 107:12605-12610 (2007).
MacCallum et al. Antibody-antigen interactions: contact analysis and binding site topography. J Mol Biol. 262(5):732-745 (1996).
Mariuzza et al. The structural basis of antigen-antibody recognition. Annu Rev Biophys Biophys Chem 16:139-159 (1987).
Milone et al. Chimeric receptors containing CD137 signal transduction domains mediate enhanced survival of T cells and increased antileukemic efficacy in vivo. Mol Ther 17(8):1453-1464 (2009).
Mirsky et al. Antibody-Specific Model of Amino Acid Substitution for Immunological Inferences from Alignments of Antibody Sequences. Mol. Biol. Evol. 32(3):806-819 (2014).
Müller et al. Improved Pharmacokinetics of Recombinant Bispecific Antibody Molecules by Fusion to Human Serum Albumin. J. Biol. Chem. 282(17):12650-60 (2007).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muller et al. Improving the pharmacokinetic properties of biologics by fusion to an anti-HSA shark VNAR domain. MAbs 4(6):673-685 (2012).
Mumtaz et al. Design of liposomes for circumventing the reticuloendothelial cells. Glycobiology 5:505-10 (1991).
Muul et al. Persistence and expression of the adenosine deaminase gene for 12 years and immune reaction to gene transfer components: long-term results of the first clinical gene therapy trial. Blood 101(7):2563-2569 (2003).
Muyldermans. Nanobodies: natural single-domain antibodies. Annu Rev Biochem 82:775-797 (2013).
Nacheva et al. Preventing nondesired RNA-primed RNA extension catalyzed by T7 RNA polymerase. Eur J Biochem 270:1458-1465 (2003).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Needleman et al. A general method applicable to the search for similarities in the amino acid sequence of two proteins. J. Mol. Biol. 48:443-453 (1970).
Nelson et al. Antibody fragments Hope and Hype. mAbs 2(1):77-83 (2010).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Nunez-Prado et al. The coming of age of engineered multivalent antibodies. Drug Discovery Today 20(5):588-594 (2015).
Ohiro et al. A homogeneous and noncompetitive immunoassay based on the enhanced fluorescence resonance energy transfer by leucine zipper interaction. Anal Chem 74(22):5786-5792 (2002).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Padlan. Anatomy of the Antibody Molecule. Mol Immunol 31(3):169-217 (1994).
Padlan, et al., A possible procedure for reducing the immunogenicity of antibody variable domains while preserving their ligand-binding properties. Mol Immunol 28(4-5):489-498 (1991).
Padlan et al. Structure of an antibody-antigen complex: Crystal structure of the HyHEL-10 Fab-lysozyme complex. PNAS USA 86:5938-5942 (1989).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).
PCT/US2016/033644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
PCT/US2017/056530 International Search Report and Written Opinion dated Jan. 23, 2018.
PCT/US2017/063121 International Search Report and Written Opinion dated Mar. 26, 2018.
PCT/US2017/063126 International Search Report and Written Opinion dated Apr. 5, 2018.
PCT/US2018/014396 International Search Report and Written Opinion dated Jun. 14, 2018.
PCT/US2018/020185 International Search Report and Written Opinion dated Jun. 15, 2018.
PCT/US2018/020307 International Search Report and Written Opinion dated Aug. 24, 2018.
PCT/US2018/030983 International Search Report and Written Opinion dated Sep. 25, 2018.
PCT/US2018/032418 International Search Report and Written Opinion dated Sep. 24, 2018.
PCT/US2018/032427 International Search Report and Written Opinion dated Sep. 13, 2018.
PCT/US2018/055659 International Search Report and Written Opinion dated Feb. 21, 2019.
PCT/US2018/055682 International Search Report and Written Opinion dated Mar. 1, 2019.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
PCT/US2019/052206 International Search Report and Written Opinion dated Feb. 14, 2020.
PCT/US2019/052270 International Search Report and Written Opinion dated Mar. 5, 2020.
PCT/US2019/053017 International Search Report and Written Opinion dated Jan. 31, 2020.
PCT/US/2020/032985 International Search Report and Written Opinion dated Oct. 15, 2020.
PCT/US2020/060184 International Search Report and Written Opinion dated Mar. 4, 2021.
Pearson et al. Improved Tools for Biological Sequence Comparison. PNAS USA 85:2444-48 (1988).
Pedersen et al. Comparison of surface accessible residues in human and murine immunoglobulin Fv domains. Implication for humanization of murine antibodies. J Mol Biol 235(3):959-973 (1994).
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta. Antibody Engineering. Curr Op Struct Biol 2:593-596 (1992).

(56) References Cited

OTHER PUBLICATIONS

Presta et al. Humanization of an antibody directed against IgE. J Immunol 151:2623-2632 (1993).
Ramadoss et al. An Anti-B Cell Maturation Antigen Bispecific Antibody for Multiple Myeloma. J. Ann. Chem. Soc. 137(16):5288-91 (2015).
Riechmann et al. Reshaping human antibodies for therapy. Nature, 332.6162:323-7 (1988).
Riechmann et al. Single domain antibodies: comparison of camel VH and camelised human VH domains. J Immunol Methods 231(1-2):25-38 (1999).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rosok et al. A Combinatorial Library Strategy for the Rapid Humanization of Anticarcinoma BR96 Fab. J Biol Chem 271:22611-22618 (1996).
Rossolini et al. Use of deoxyinosine-containing primers vs degenerate primers for polymerase chain reaction based on ambiguous sequence information. Mol Cell Probes 8(2):91-98 (1994).
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Running Deer et al. High-level expression of proteins in mammalian cells using transcription regulatory sequences from the Chinese hamster EF-1alpha gene. Biotechnol Prog. 20:880-889 (2004).
Sadelain et al. Targeting tumours with genetically enhanced T lymphocytes. Nat Rev Cancer 3(1):35-45 (2003).
Sadelain et al. The basic principles of chimeric antigen receptor design. Cancer Discov. 3(4):388-98 (2013).
Saerens et al. Identification of a universal VHH framework to graft non-canonical antigen- binding loops of camel single-domain antibodies. J. Mol. Biol. 352(3):597-607 (2005).
Sandhu. A rapid procedure for the humanization of monoclonal antibodies. Gene 150(2):409-410 (1994).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Schmidt et al. Cloning and Characterization of Canine Prostate-Specific Membrane Antigen. The Prostate 73:642-650 (2013).
Schmittgen et al. Expression of prostate specific membrane antigen and three alternatively spliced variants of PSMA in prostate cancer patients. Int J Cancer 107:323-329 (2003).
Sergeeva et al. An anti-PR1/HLA-A2 T-cell receptor-like antibody mediates complement-dependent cytotoxicity against acute myeloid leukemia progenitor cells. Blood 117(16):4262-4272 (2011).
Sheng et al. Novel Transgenic Mouse Model for Studying Human Serum Albumin as a Biomarker of Carcinogenic Exposure. Chem. Res. Toxicol. 29(5):797-809 (2016).
Sims et al. A humanized CD18 antibody can block function without cell destruction. J Immunol. 151:2296-2308 (1993).
Smirnova et al. Identification of new splice variants of the genes BAFF and BCMA. Mol. Immunol. 45 (4):1179-83 (2008).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Spiess et al. Alternative molecular formats and therapeutic applications for bispecific antibodies. Mol. Immunol. 67(2 Pt A):95-106 (2015).
Stehle et al. Albumin-based drug carriers: comparison between serum albumins of different species on pharmacokinetics and tumor uptake of the conjugate. Anticancer Drugs. 10(8):785-90 (1999).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Stirewalt et al. The role of FLT3 in haematopoietic malignancies. Nat Rev Cancer 3:650-665 (2003).
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
STROP. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).
Su et al. PSMA specific single chain antibody-mediated targeted knockdown of Notch1 inhibits human prostate cancer cell proliferation and tumor growth. Cancer Lett. 338 (2): 282-291 (2013).
Tan et al. Influence of the hinge region on complement activation, C1q binding, and segmental flexibility in chimeric human immunoglobulins. PNAS USA 87:162-166 (1990).
Tan et al. "Superhumanized" antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Thomas et al. Mesothelin-specific CD8(+) T cell responses provide evidence of in vivo cross-priming by antigen-presenting cells in vaccinated pancreatic cancer patients. J Exp Med 200:297-306 (2004).
Tijink et al. Improved tumor targeting of anti-epidermal growth factor receptor nanobodies through albumin binding: taking advantage of modular Nanobody technology. Mol. Cancer Ther. 7(8):2288-97 (2008).
Tiller et al. Facile Affinity Maturation of Antibody Variable Domains Using Natural Diversity Mutagenesis. Front. Immunol. 8:986 (2017).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Ui-Tei et al. Sensitive assay of RNA interference in Drosophila and Chinese hamster cultured cells using firefly luciferase gene as target. FEBS Letters 479: 79-82 (2000).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 25, 2019.
U.S. Appl. No. 15/600,264 Office Action dated Apr. 26, 2018.
U.S. Appl. No. 15/600,264 Office Action dated Nov. 27, 2018.
U.S. Appl. No. 15/600,264 Office Action dated Oct. 3, 2017.
U.S. Appl. No. 15/600,582 Office Action dated Nov. 16, 2017.
U.S. Appl. No. 15/630,259 Office Action dated Dec. 30, 2019.
U.S. Appl. No. 15/630,259 Office Action dated Sep. 30, 2020.

(56) References Cited

OTHER PUBLICATIONS

U.S. Appl. No. 15/704,620 Office Action dated Oct. 26, 2017.
U.S. Appl. No. 15/821,498 Office Action dated Apr. 21, 2020.
U.S. Appl. No. 15/821,498 Office Action dated May 3, 2019.
U.S. Appl. No. 15/821,498 Office Action dated Oct. 26, 2018.
U.S. Appl. No. 15/821,530 Office Action dated Apr. 22, 2020.
U.S. Appl. No. 15/821,530 Office Action dated Apr. 3, 2019.
U.S. Appl. No. 15/821,530 Office Action dated Sep. 25, 2018.
U.S. Appl. No. 15/977,968 Office Action dated Feb. 21, 2019.
U.S. Appl. No. 15/977,988 Office Action dated Aug. 20, 2019.
U.S. Appl. No. 15/977,988 Office Action dated Mar. 26, 2019.
U.S. Appl. No. 15/977,988 Pre-Interview First Office Action dated Jan. 25, 2019.
U.S. Appl. No. 16/159,545 Office Action dated Aug. 6, 2019.
U.S. Appl. No. 16/159,545 Office Action dated Dec. 2, 2019.
U.S. Appl. No. 16/159,554 Office Action dated Jun. 7, 2019.
U.S. Appl. No. 16/159,554 Office Action dated Mar. 16, 2021.
U.S. Appl. No. 16/159,554 Office Action dated Oct. 1, 2019.
U.S. Appl. No. 16/159,554 Office Action dated Oct. 5, 2020.
U.S. Appl. No. 16/583,070 Office Action dated Mar. 3, 2020.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).
Van Der Linden et al. Induction of immune responses and molecular cloning of the heavy chain antibody repertoire of Lama glama. J Immunol Methods 240:185-195 (2000).
Vaughan et al. Human antibodies by design. Nature Biotech 16:535-539 (1998).
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells in Vitro Efficiently. Journal of Biochemistry 135(4):555-565 (2004).
Willemsen et al. A phage display selected fab fragment with MHC class I-restricted specificity for MAGE-A1 allows for retargeting of primary human T lymphocytes. Gene Ther 8(21):1601-1608 (2001).
Winkler et al. Changing the antigen binding specificity by single point mutations of an anti-p24 (HIV-1) antibody. J Immunol. 165(8):4505-4514 (2000).
Wu et al. Humanization of a murine monoclonal antibody by simultaneous optimization of framework and CDR residues. J. Mol. Biol. 294:151-162 (1999).
Yan et al. Engineering upper hinge improves stability and effector function of a human IgG1. J. Biol. Chem. 287:5891 (2012).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Yoshinaga et al. Ig L-chain shuffling for affinity maturation of phage library-derived human anti-human MCP-1 antibody blocking its chemotactic activity. J Biochem 143(5):593-601 (2008).
Yu et al. Rationalization and design of the complementarity determining region sequences in an antibody-antigen recognition interface. PLoS One 7(3):e33340 (2012).
Zabetakis et al. Contributions of the complementarity determining regions to the thermal stability of a single-domain antibody. PLoS One 8(10):e77678 (2013).
Zare et al. Production of nanobodies against prostate-specific membrane antigen (PSMA) recognizing LnCaP cells. Int. J. Biol. Markers 29(2):e169-e179 (2014).
Zhang et al. New High Affinity Monoclonal Antibodies Recognize Non-Overlapping Epitopes on Mesothelin for Monitoring and Treating Mesothelioma. Sci Rep 5:9928 (2015).
Zhu et al. COMBODY: one-domain antibody multimer with improved avidity. Immunology and Cell Biology 88(6):667-675 (2010).
Galsky et al. Phase I trial of the prostate-specific membrane antigen-directed immunoconjugate MLN2704 in patients with progressive metastatic castration-resistant prostate cancer. J Clin Oncol 26(13):2147-54 (2008).
Henry et al. A prostate-specific membrane antigen-targeted monoclonal antibody-chemotherapeutic conjugate designed for the treatment of prostate cancer. Cancer Res. 64(21):7995-8001 (2004).
Hupe et al. Expression of Prostate-Specific Membrane Antigen (PSMA) on Biopsies Is an Independent Risk Stratifier of Prostate Cancer Patients at Time of Initial Diagnosis. Front Oncol 8:623 (2018).
Jemaa et al. Co-expression and impact of prostate specific membrane antigen and prostate specific antigen in prostatic pathologies. J Exp Clin Cancer Res 29(1):171 (2010).
Korenchuk et al. VCaP, a cell-based model system of human prostate cancer. In Vivo. 15(2):163-8 (2001).
Loberg et al. Development of the VCaP androgen-independent model of prostate cancer. Urol Oncol 24(2):161-8 (2006).
McDevitt et al. An alpha-particle emitting antibody ([213Bi]J591) for radioimmunotherapy of prostate cancer. Cancer Res. 60:6095-6100 (2000).
Rabia, et al. Understanding and overcoming trade-offs between antibody affinity, specificity, stability and solubility. Biochem Eng J. 137:365-374. (2018).
Sramkoski et al. A new human prostate carcinoma cell line, 22Rv1. In Vitro Cell Dev Biol Anim 35(7):403-409 (1999).
U.S. Appl. No. 16/802,007 Office Action dated Apr. 14, 2023.
U.S. Appl. No. 16/999,773 Office Action dated Apr. 21, 2023.
U.S. Appl. No. 17/030,118 Office Action dated May 5, 2023.
U.S. Appl. No. 17/072,370 Office Action dated Jun. 2, 2023.
Ye et al. Androgen and epidermal growth factor down-regulate cyclin-dependent kinase inhibitor p27Kip1 and costimulate proliferation of MDA PCa 2a and MDA PCa 2b prostate cancer cells. Clin Cancer Res 5(8):2171-7 (1999).
Allard et al., The ectonucleotidases CD39 and CD73: Novel checkpoint inhibitor targets. Immunol Rev., 276(1):121-144 (2018).
Altenhofer et al., The NOX toolbox: validating the role of NADPH oxidases in physiology and disease. Cell Mol Life Sciences 69(14):2327-2343 (2012).
Austin et al. TriTACs, a Novel Class of T-Cell-Engaging Protein Constructs Designed for the Treatment of Solid Tumors. Mol Cancer Ther 20(1):109-120 (2021).
Ayers et al. IFN-γ-related mRNA profile predicts clinical response to PD-1 blockade. The Journal of Clinical Investigation 127(8):2930-2940 (Aug. 2017).
Balzar et al. Epidermal growth factor-like repeats mediate lateral and reciprocal interactions of Ep-CAM molecules in homophilic adhesions. Mol Cell Biol. 21(7):2570-80 (2001).
Balzar et al. The biology of the 17-1A antigen (Ep-CAM). J. Mol. Med. 77:699-712 (1999).
Bluemel et al. Epitope distance to the target cell membrane and antigen size determine the potency of T cell-mediated lysis by BiTE antibodies specific for a large melanoma surface antigen. Cancer Immunol Immunother 59(8):1197-209 (2010).
Chaubal et al. Ep-CAM—a marker for the detection of disseminated tumor cells in patients suffering from SCCHN. Anticancer Res 19:2237-2242 (1999).
Cheong et al., A patent review of IDO1 inhibitors for cancer. Expert Opin Ther Pat. 28(4):317-330 (2018).
Croso et al., Real-time detection of mesothelin in pancreatic cancer cell line supernatant using an acoustic wave immunosensor. Cancer Detect. Prev. 30:180-187 (2006).
Dickopf et al. Format and geometries matter: Structure-based design defines the functionality of bispecific antibodies. Comput Struct Biotechnol J 18:1221-1227 (2020).

(56) References Cited

OTHER PUBLICATIONS

Eyvazi et al. Antibody Based EpCAM Targeted Therapy of Cancer, Review and Update. Curr Cancer Drug Targets. 18(9):857-868 (2018).
Gastl et al. Ep-CAM overexpression in breast cancer as a predictor of survival. Lancet. 356:1981-1982 (2000).
Gautam et al., Dual Inhibition of NOX2 and Receptor Tyrosine Kinase by BJ-1301 Enhances Anticancer Therapy Efficacy via Suppression of Autocrine-Stimulatory Factors in Lung Cancer. Mol Cancer Ther 16(10):2144-2156 (2017).
Gianni et al., A novel and specific NADPH oxidase-1 (Nox1) small-molecule inhibitor blocks the formation of functional invadopodia in human colon cancer cells. ACS Chem Biol 5(10):981-93 (2010).
Goettlinger et al. The epithelial cell surface antigen 17-1A, a target for antibody-mediated tumor therapy: its biochemical nature, tissue distribution and recognition by different monoclonal antibodies. Int J Cancer. 38:47-53 (1986).
Gorshkova et al. Single domain antibodies and bioengineering drugs on their basis: new opportunities for diagnostics and therapy. Medical Immunology (Russia) 18(6):505-520 (2016) (English Abstract).
Jang et al. Human 4-1BB (CD137) signals are mediated by TRAF2 and activate nuclear factor-kappa B. Biochem. Biophys. Res. Commun. 242 (3):613-20 (1998).
Kakkad et al. Collagen 1 fiber content may predict for recurrence in non-small cell lung cancer. Cancer Research 78(13 Supplement):3691-3691 (2018).
Kauder et al., ALX148 blocks CD47 and enhances innate and adaptive antitumor immunity with a favorable safety profile. PLoS One 13(8):e0201832 (2019).
Kim et al., 2077—An oral dual inhibitor of IDO and TDO enhances anti-cancer immunity and synergizes with immune checkpoint blockade. Annals Oncol 29 (suppl_8):viii400-viii441 (2018) (Poster Abstract).
Koprowski et al. Colorectal carcinoma antigens detected by hybridoma antibodies. Somatic Cell Genet. 5:957-971 (1979).
Litvinov et al. Epithelial cell adhesion molecule (Ep-CAM) modulates cell-cell interactions mediated by classic cadherins. J Cell Biol. 139:1337-1348 (1997).
Litvinov et al. Expression of Ep-CAM in cervical squamous epithelia correlates with an increased proliferation and the disappearance of markers for terminal differentiation. Am. J. Pathol. 148:865-75 (1996).
Lu et al., Characterization of potent and selective iodonium-class inhibitors of NADPH oxidases. Biochem Pharmacol 143:25-38 (2017).
Lv et al. Mesothelin as a biomarker for targeted therapy. Biomark Res 7:18 (2019).
Magiera-Mularz et al. Bioactive macrocyclic inhibitors of the PD-1/PD-L1 immune checkpoint Angew. Chem. Int. Ed. 56(44):13732-13735 (2017).
Monney et al. Th1-specific cell surface protein Tim-3 regulates macrophage activation and severity of an autoimmune disease. Nature 415:536-41 (2002).
Nakae et al. Phenotypic differences between Th1 and Th17 cells and negative regulation of Th1 cell differentiation by IL-17. J Leukoc Biol 81:1258-68 (2007).
Nicolaou et al. Calicheamicin ⊖1 : a rationally designed molecule with extremely potent and selective DNA cleaving properties and apoptosis inducing activity. Angew. Chem. Intl. Ed. Engl., 33:183-186 (1994).
Osta et al. EpCAM is overexpressed in breast cancer and is a potential target for breast cancer gene therapy. Cancer Res 64:5818-24 (2004).
PCT/US2021/058108 International Search Report and Written Opinion dated Apr. 1, 2022.
PCT/US2022/019302 International Search Report and Written Opinion dated Jun. 27, 2022.

Perrot et al., Blocking Antibodies Targeting the CD39/CD73 Immunosuppressive Pathway Unleash Immune Responses in Combination Cancer Therapies. Cell Reports 8:2411-2425.E9 (2019).
Piyathilake et al. The expression of Ep-CAM (17-1A) in squamous cell cancers of the lung. Hum Pathol. 31:482-487 (2000).
Poczatek et al. Ep-Cam levels in prostatic adenocarcinoma and prostatic intraepithelial neoplasia. J Urol. 162:1462-1464 (1999).
Popoli et al., Effects of SCH 58261, an Adenosine A2A receptor antagonist, on quinpirole-induced turning in 6-Hydroxydopamine-lesioned rats: lack of tolerance after chronic caffeine intake. Neuropsychopharm 22:522-529 (2000).
Quak et al. Production of a monoclonal antibody (K 931) to a squamous cell carcinoma associated antigen identified as the 17-1A antigen. Hybridoma 9:377-387 (1990).
Roda-Navarro et al. Understanding the Spatial Topology of Artificial Immunological Synapses Assembled in T Cell-Redirecting Strategies: A Major Issue in Cancer Immunotherapy. Front Cell Dev Biol 7:370 (2020).
Schaer et al. Modulation of GITR for cancer immunotherapy. Curr Opin Immunol. 24(2): 217-224 (2012).
Sheridan. IDO inhibitors move center stage in immuno-oncology. Nat Biotechnol 33:321-322 (2015).
Simon et al. Epithelial glycoprotein is a member of a family of epithelial cell surface antigens homologous to nidogen, a matrix adhesion protein. PNAS USA 87:2755-2759 (1990).
Stasi et al., Animal models of Parkinson's disease: Effects of two adenosine A2A receptor antagonists ST4206 and ST3932, metabolites of 2-n-Butyl-9-methyl-8-[1,2,3]triazol-2-yl-9H-purin-6-ylamine (ST1535). Europ J Pharmacol 761:353-361 (2015).
Tang et al., NOX4, a new genetic target for anti-cancer therapy in digestive system cancer. J Dig Dis 19(10):578-585 (2018).
Trebak et al. Oligomeric state of the colon carcinoma-associated glycoprotein GA733-2 (Ep-CAM/EGP40) and its role in GA733-mediated homotypic cell-cell adhesion. J Biol Chem. 276:2299-2309 (2001).
U.S. Appl. No. 16/339,263 Office Action dated May 3, 2022.
Wang et al., A Small Molecule Antagonist of PD-1/PD-L1 Interactions Acts as an Immune Checkpoint Inhibitor for NSCLC and Melanoma Immunotherapy. Front. Immunol. 12:654463.
Wang et al., In vitro characterization of the anti-PD-1 antibody nivolumab, BMS-936558, and in vivo toxicology in non-human primates. Cancer Immunol. Res. 2(9):846-856 (2014).
Watt et al., Homophilic adhesion of human CEACAM1 involves N-terminal domain interactions: structural analysis of the binding site. Blood 98:1469-1479 (2001).
Weir et al., Colony stimulating factor-1 plays a role in osteoclast formation and function in bone resorption induced by parathyroid hormone and parathyroid hormone-related protein. J Bone Mineral Res 11:1474-1481 (1996).
Chen et al. Enhancement and destruction of antibody function U by somatic mutation: unequal occurrence is controlled by V gene combinatorial associations. The EMBO Journal 14(12):2784-2794 (1995).
Colman. Effects of amino acid sequence changes on antibody-antigen interactions. Res Immunol 145(1):33-36 (1994).
Jiang et al. Protritac: A protease cleavable T cell Engager Platform. Scientific Reports 6(Suppl 1):115 Available at https://calidibio.com/wp-content/uploads/2019/10/609-Abstract-_SITC-2018.pdf (2018).
Kelm et al., Functional groups of sialic acids involved in binding to siglecs (sialoadhesins) deduced from interactions with synthetic analogues. Eur. J. Biochem. 255:663-672 (1998).
Kelm et al., The Sialoadhesins—a family of sialic acid-dependent cellular recognition molecules within the immunoglobulin superfamily. Glycoconj. J. 13:913-926 (1996).
PCT/US2022/031917 International Search Report and Written Opinion dated Dec. 2, 2022.
PCT/US2022/034856 International Search Report and Written Opinion dated Dec. 8, 2022.
Stanciu-Herrera et al., Anti-CD19 and anti-CD22 monoclonal antibodies increase the effectiveness of chemotherapy in Pre-B acute lymphoblastic leukemia cell lines . Leuk Res. 32:625-32 (2008).

(56) References Cited

OTHER PUBLICATIONS

Tamura et al. Structural correlates of an anticarcinoma antibody: identification of specificity-determining residues (SDRs) and development of a minimally immunogenic antibody variant by retention of SDRs only. J Immunol. 164(3):1432-41 (2020).

U.S. Appl. No. 16/339,263 Office Action dated Jan. 18, 2023.

Davé et al. Fab-dsFv: A bispecific antibody format with extended serum half-life through albumin binding. MAbs 8(7):1319-1335 (2016).

Kim et al. Strategies and 1-17 Advancement in Antibody-Drug Conjugate Optimization for Targeted Cancer Therapeutics. Biomol Ther (Seoul) 23(6):493-509 (2015).

Lehmann et al. Stability engineering of anti-EGFR scFv antibodies by rational design of a lambda-to-kappa swap of the VL framework using a structure-guided approach. MAbs 7(6):1058-1071 (2015).

Lin et al. Improved affinity of a chicken single-chain antibody to avian infectious bronchitis virus by site-directed mutagenesis of complementarity-determining region H3. African Journal of Biotechnology 10(79):18294-18302 (2011).

Lucchi et al. The Masking Game: Design of Activatable Antibodies and Mimetics for Selective Thera-peutics Cell Control. ACS Cent Sci 7(5):724-738 (2021).

McCall et al. Isolation and characterization of an anti-CD16 single-chain Fv fragment and construction of an anti-HER2/neu/anti-CD16 bispecific scFv that triggers CD16-dependent tumor cytolysis Mol Immunol. 36(7):433-46 (1999).

McCarthy et al. Altering the fine specificity of an anti-Legionella single chain antibody by a single amino acid insertion. J Immunol Methods 251(1-2):137-49 (2001).

Trail et al. Antibody drug 1-17 conjugates for treatment of breast cancer: Novel targets and diverse approaches in ADC design. Pharmacol Ther 181:126-142 (2018).

U.S. Appl. No. 16/339,263 Office Action dated Jan. 11, 2022.

U.S. Appl. No. 16/489,523 Office Action dated Feb. 14, 2022.

U.S. Appl. No. 16/773,843 Office Action dated Feb. 8, 2022.

PCT/US2022/078178 International Search Report and Written Opinion dated Jul. 18, 2023.

\* cited by examiner

FIG. 2

SDS-PAGE OF PURIFIED BCMA TARGETING TRISPECIFIC PROTEINS

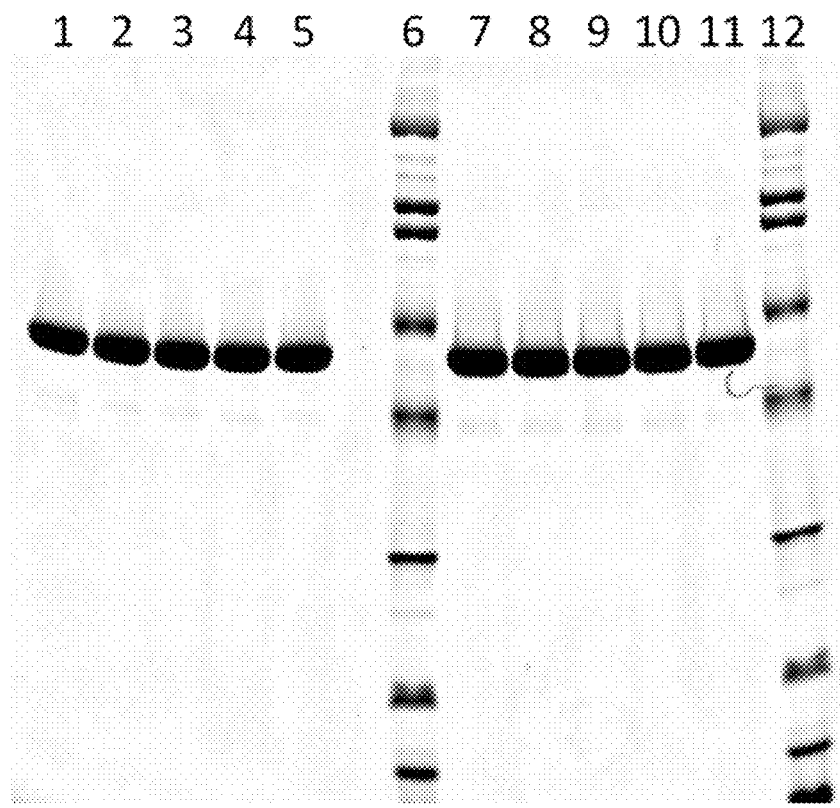

Lane 1: 01F07-M34Y TriTAC non-reduced
Lane 2: 01F07-M34G-TriTAC non-reduced
Lane 3: 02B05 TriTAC non-reduced
Lane 4: 02G02-M34Y TriTAC non-reduced
Lane 5: 02G02 M34G TriTAC non-reduced
Lane 6: Broad Range SDS-PAGE Standard (Bio-Rad #1610317)
Lane 7: 01F07-M34Y TriTAC non-reduced
Lane 8: 01F07-M34G-TriTAC non-reduced
Lane 9: 02B05 TriTAC non-reduced
Lane 10: 02G02-M34Y TriTAC non-reduced
Lane 11: 02G02 M34G TriTAC non-reduced
Lane 12: Broad Range SDS-PAGE Standard (Bio-Rad #1610317)

NCI-H929

BCMA RNA FPKM 1931

▒ BCMA Trispecific Protein
░ GFP Trispecific Protein

EJM

BCMA RNA FPKM 607

NCI-H510A

BCMA RNA RFPKM 0

▒ BCMA Trispecific Protein
░ GFP Trispecific Protein

OPM2

BCMA RNA FPKM 358

RPMI 8226

BCMA RNA FPKM 35

▒ BCMA Trispecific Protein
░ GFP Trispecific Protein

DMS 153

BCMA RNA FPKM 0

SEQUENCE LISTING

<160> NUMBER OF SEQ ID NOS: 475

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic

```
              peptide
<220> FEATURE:
<221> NAME/KEY: MOD_RES
<222> LOCATION: (1)..(1)
<223> OTHER INFORMATION: Thr or Ser
<220> FEATURE:
<221> NAME/KEY: MOD_RES
<222> LOCATION: (2)..(2)
<223> OTHER INFORMATION: Asn, Asp or Ser
<220> FEATURE:
<221> NAME/KEY: MOD_RES
<222> LOCATION: (3)..(3)
<223> OTHER INFORMATION: Ile, Asp, Gln, His, Val or Glu
<220> FEATURE:
<221> NAME/KEY: MOD_RES
<222> LOCATION: (4)..(4)
<223> OTHER INFORMATION: Phe, Ser, Glu, Ala, Thr, Met, Val, Ile, Asp,
      Gln, Pro, Arg or Gly
<220> FEATURE:
<221> NAME/KEY: MOD_RES
<222> LOCATION: (5)..(5)
<223> OTHER INFORMATION: Ser, Met, Arg or Asn
<220> FEATURE:
<221> NAME/KEY: MOD_RES
<222> LOCATION: (6)..(6)
<223> OTHER INFORMATION: Ile, Lys, Ser, Thr, Arg, Glu, Asp, Asn, Val,
      His, Leu, Ala, Gln or Gly
<220> FEATURE:
<221> NAME/KEY: MOD_RES
<222> LOCATION: (7)..(7)
<223> OTHER INFORMATION: Ser, Thr, Tyr, Arg or Asn
<220> FEATURE:
<221> NAME/KEY: MOD_RES
<222> LOCATION: (9)..(9)
<223> OTHER INFORMATION: Met, Gly or Tyr

<400> SEQUENCE: 1

Xaa Xaa Xaa Xaa Xaa Xaa Xaa Pro Xaa Gly
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: His, Asn or Ser
<220> FEATURE:
<221> NAME/KEY: MOD_RES
<222> LOCATION: (5)..(5)
<223> OTHER INFORMATION: Phe, Gly, Lys, Arg, Pro, Asp, Gln, His, Glu,
      Asn, Thr, Ser, Ala, Ile, Leu or Val
<220> FEATURE:
<221> NAME/KEY: MOD_RES
<222> LOCATION: (6)..(6)
<223> OTHER INFORMATION: Ser, Gln, Glu, Thr, Lys or Asp
<220> FEATURE:
<221> NAME/KEY: MOD_RES
<222> LOCATION: (8)..(8)
<223> OTHER INFORMATION: Leu, Val, Ile, Phe, Tyr or Trp

<400> SEQUENCE: 2

Ala Ile Xaa Gly Xaa Xaa Thr Xaa Tyr Ala Asp Ser Val Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (5)..(5)
<223> OTHER INFORMATION: Asp, Ile, Thr, Lys, Arg, Ala, Glu, Ser or Tyr
<220> FEATURE:
<221> NAME/KEY: MOD_RES
<222> LOCATION: (9)..(9)
<223> OTHER INFORMATION: Arg, Gly, Leu, Lys, Thr, Gln, Ser or Asn
<220> FEATURE:
<221> NAME/KEY: MOD_RES
<222> LOCATION: (10)..(10)
<223> OTHER INFORMATION: Asn, Lys, Glu, Val, Arg, Met or Asp
<220> FEATURE:
<221> NAME/KEY: MOD_RES
<222> LOCATION: (12)..(12)
<223> OTHER INFORMATION: Tyr, Ala, Val, Lys, His, Leu, Met, Thr, Arg,
      Gln, Cys, Ser or Asn

<400> SEQUENCE: 3

Val Pro Trp Gly Xaa Tyr His Pro Xaa Xaa Val Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Asp Ile Phe Ser Ile Ser Pro Met Gly
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Asn Ile Phe Ser Ser Ser Pro Met Gly
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Asn Ile Phe Ser Ile Ser Pro Gly Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Asn Ile Phe Met Ile Ser Pro Met Gly
1               5                   10
```

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Asn Ile Phe Ser Ser Ser Pro Met Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Asn Ile Phe Ser Ile Arg Pro Met Gly
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Asn Ile Ser Ser Ile Ser Pro Met Gly
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Asn Ile Phe Ser Ser Ser Pro Met Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Asn Ile Phe Ser Ile Thr Pro Met Gly
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Asn Ile Pro Ser Ile Ser Pro Met Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Asn Ile Thr Ser Ile Ser Pro Met Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Asn Ile Phe Ser Lys Ser Pro Met Gly
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Asn Asp Phe Ser Ile Ser Pro Met Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Asn Ile Thr Ser Ile Ser Pro Met Gly
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Asn Ile Phe Ser Ile Ser Pro Met Gly
1               5                   10

<210> SEQ ID NO 19
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Asn Ile Phe Ser Arg Ser Pro Met Gly
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Asn Ile Glu Ser Ile Ser Pro Met Gly
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Asn Ile Phe Ser Ile Ser Pro Met Gly
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Asn Ile Phe Ser Thr Ser Pro Met Gly
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Asn Ile Val Ser Ile Ser Pro Met Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Asn Ile Glu Ser Ile Ser Pro Met Gly
```

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Asn Ile Pro Ser Ile Ser Pro Met Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Asn Ile Phe Ser Ser Ser Pro Met Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Asn Ile Phe Ser Ile Ser Pro Met Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Asn Ile Phe Ser Ile Tyr Pro Met Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Asn Ile Phe Ser Asn Ser Pro Met Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Thr Asn Ile Ser Ser Ile Ser Pro Met Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Asn Ile Val Ser Ile Ser Pro Met Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Asn Ile Phe Ser Asn Ser Pro Met Gly
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Asn Ile Thr Ser Ile Ser Pro Met Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Asn Ile Phe Ser Asp Ser Pro Met Gly
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Asn Ile Phe Ser Arg Ser Pro Met Gly
1               5                   10

<210> SEQ ID NO 36

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Asn Ile Phe Ser Ala Ser Pro Met Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Asn Ile Phe Ser Ala Ser Pro Met Gly
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Asn Ile Thr Ser Ile Ser Pro Met Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Asn Ile Ala Ser Ile Ser Pro Met Gly
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Asn Ile Phe Ser Arg Ser Pro Met Gly
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

```
Thr Asn Ile Phe Ser Leu Ser Pro Met Gly
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Asn Ile Pro Ser Ile Ser Pro Met Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Asn Ile Phe Ser Gln Ser Pro Met Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Asn Ile Glu Ser Ile Ser Pro Met Gly
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Asn Ile Phe Ser His Ser Pro Met Gly
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Asn Ile Phe Ser Glu Ser Pro Met Gly
1               5                   10

<210> SEQ ID NO 47
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 47

Thr Asn Ile Asp Ser Ile Ser Pro Met Gly
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Asn Ile Phe Ser Ser Ser Pro Met Gly
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Asn Ile Phe Ser Thr Ser Pro Met Gly
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Asn Ile Thr Ser Val Ser Pro Met Gly
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Asn Ile Ser Ser Ile Ser Pro Met Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Asn Ile Phe Ser Ile Ser Pro Met Gly
1               5                   10
```

```
<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Asn Ile Phe Arg Ile Ser Pro Met Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Asn Ile Val Ser Ile Ser Pro Met Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Asn Ile Asp Ser Ile Ser Pro Met Gly
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Asn Ile Phe Ser Arg Ser Pro Met Gly
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Asn Ile Gln Ser Ile Ser Pro Met Gly
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58
```

Thr Asn Ile Phe Asn Ile Ser Pro Met Gly
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Asn Glu Phe Ser Ile Ser Pro Met Gly
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Asn Ile Pro Ser Ile Ser Pro Met Gly
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Asn Ile Gly Ser Ile Ser Pro Met Gly
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Asn Ile Phe Ser Lys Ser Pro Met Gly
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Asn Ile Phe Ser Ile Thr Pro Met Gly
1               5                   10

<210> SEQ ID NO 64
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 64

Thr Ser Asp Phe Ser Ile Ser Pro Met Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Asn Ile Met Ser Ile Ser Pro Met Gly
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Asn Ile Met Ser Ile Ser Pro Met Gly
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Asn Ile Pro Ser Ile Ser Pro Met Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Asn Ile Phe Ser Thr Ser Pro Met Gly
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Asn Ile Phe Ser Gln Ser Pro Met Gly
1               5                   10
```

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Asn Ile Ala Ser Ile Ser Pro Met Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Asn Ile Phe Ser Lys Ser Pro Met Gly
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Asn Ile Phe Ser Arg Ser Pro Met Gly
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Asn His Phe Ser Ile Ser Pro Met Gly
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Asn Ile Phe Ser Asn Ser Pro Met Gly
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 75

Thr Asn Ile Phe Ser Thr Ser Pro Met Gly
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Asn Ile Phe Ser Ile Ser Pro Tyr Gly
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Asn Ile Phe Ser Asn Ser Pro Met Gly
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Asn Ile Phe Ser Ser Ser Pro Met Gly
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Asn Ile Val Ser Ile Ser Pro Met Gly
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Asn Ile Ser Ser Ile Ser Pro Met Gly
1               5                   10

<210> SEQ ID NO 81
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 81

Thr Asn Ile Ile Ser Ile Ser Pro Met Gly
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Asn Ile Ala Ser Ile Ser Pro Met Gly
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Asn Ile Phe Ser Glu Ser Pro Met Gly
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Asn Ile Phe Ser Thr Ser Pro Met Gly
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Asn Ile Ser Ser Ile Ser Pro Met Gly
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Asn Val Val Ser Ile Ser Pro Met Gly
1               5                   10
```

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Asn Glu Phe Ser Ile Ser Pro Met Gly
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr Asn Ile Phe Ser Asn Ser Pro Met Gly
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Asn Ile Phe Ser Arg Ser Pro Met Gly
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Thr Asn Ile Phe Ser Asp Ser Pro Met Gly
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr Asn Asp Phe Ser Ile Ser Pro Met Gly
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 92

Thr Asn Ile Phe Ser Lys Ser Pro Met Gly
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Asn Ile Phe Ser Ile Tyr Pro Met Gly
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Asn Ile Phe Ser Ser Ser Pro Met Gly
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Thr Asn Ile Phe Ser Val Ser Pro Met Gly
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Asn Ile Phe Ser Ile Thr Pro Met Gly
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Asn Ile Glu Ser Ile Ser Pro Met Gly
1               5                   10

<210> SEQ ID NO 98
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Thr Asn Ile Phe Ser Thr Ser Pro Met Gly
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Asn Ile Glu Ser Ile Ser Pro Met Gly
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Asn Ile Phe Ser Ile Asn Pro Met Gly
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Asn Ile Phe Ser Ile Thr Pro Met Gly
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Asn Ile Thr Ser Ile Ser Pro Met Gly
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Asn Ile Phe Ser Gly Ser Pro Met Gly
```

```
<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Asn Ile Phe Ser Ile Thr Pro Met Gly
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Asn Ile Asp Ser Ile Ser Pro Met Gly
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Thr Asn Ile Phe Ser Asp Ser Pro Met Gly
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Asn Ile Asp Ser Ile Ser Pro Met Gly
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Thr Asn Ile Phe Ser Lys Ser Pro Met Gly
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 109

Thr Asn Ile Phe Ser Val Ser Pro Met Gly
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Thr Asn Gln Phe Ser Ile Ser Pro Met Gly
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Asn Ile Arg Ser Ile Ser Pro Met Gly
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Asn Ile Phe Ser Arg Ser Pro Met Gly
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Thr Asn Ile Thr Ser Ile Ser Pro Met Gly
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Asn Ile Phe Ser Thr Ser Pro Tyr Gly
1               5                   10

<210> SEQ ID NO 115

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Thr Asn Ile Phe Ser Thr Ser Pro Gly Gly
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Asn Ile Phe Ser Ile Thr Pro Tyr Gly
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr Asn Ile Phe Ser Ile Thr Pro Gly Gly
1               5                   10

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Ile His Gly Gly Ser Thr Leu Tyr Ala Asp Ser Val Lys
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Ile Asn Gly Phe Ser Thr Leu Tyr Ala Asp Ser Val Lys
1               5                   10

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120
```

Ala Ile His Gly Ser Ser Thr Leu Tyr Ala Asp Ser Val Lys
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Ile His Gly Asp Ser Thr Leu Tyr Ala Asp Ser Val Lys
1               5                   10

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Ile His Gly Phe Ser Thr Leu Tyr Ala Asp Ser Val Lys
1               5                   10

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Ile His Gly Phe Ser Thr Val Tyr Ala Asp Ser Val Lys
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Ile His Gly Thr Ser Thr Leu Tyr Ala Asp Ser Val Lys
1               5                   10

<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ile His Gly Glu Ser Thr Leu Tyr Ala Asp Ser Val Lys
1               5                   10

<210> SEQ ID NO 126
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 126

Ala Ile His Gly Arg Ser Thr Leu Tyr Ala Asp Ser Val Lys
1               5                   10

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Ile His Gly Glu Ser Thr Leu Tyr Ala Asp Ser Val Lys
1               5                   10

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Ile Ser Gly Phe Ser Thr Leu Tyr Ala Asp Ser Val Lys
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Ile His Gly Lys Ser Thr Leu Tyr Ala Asp Ser Val Lys
1               5                   10

<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Ile His Gly Lys Ser Thr Leu Tyr Ala Asp Ser Val Lys
1               5                   10

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Ile His Gly Phe Glu Thr Leu Tyr Ala Asp Ser Val Lys
1               5                   10

```
<210> SEQ ID NO 132
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Ile His Gly Asp Ser Thr Leu Tyr Ala Asp Ser Val Lys
1               5                   10

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ile His Gly Asn Ser Thr Leu Tyr Ala Asp Ser Val Lys
1               5                   10

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Ile His Gly Ser Ser Thr Leu Tyr Ala Asp Ser Val Lys
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Ile His Gly Ser Ser Thr Leu Tyr Ala Asp Ser Val Lys
1               5                   10

<210> SEQ ID NO 136
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Ile His Gly Phe Gln Thr Leu Tyr Ala Asp Ser Val Lys
1               5                   10

<210> SEQ ID NO 137
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137
```

```
Ala Ile His Gly His Ser Thr Leu Tyr Ala Asp Ser Val Lys
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ile His Gly Asn Ser Thr Leu Tyr Ala Asp Ser Val Lys
1               5                   10

<210> SEQ ID NO 139
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ala Ile His Gly Asp Ser Thr Leu Tyr Ala Asp Ser Val Lys
1               5                   10

<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ile His Gly Phe Lys Thr Leu Tyr Ala Asp Ser Val Lys
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Ile His Gly Asp Ser Thr Leu Tyr Ala Asp Ser Val Lys
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Ile His Gly Phe Ser Thr Tyr Tyr Ala Asp Ser Val Lys
1               5                   10

<210> SEQ ID NO 143
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 143

Ala Ile His Gly Gly Ser Thr Leu Tyr Ala Asp Ser Val Lys
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Ile His Gly Phe Ser Thr Leu Tyr Ala Asp Ser Val Lys
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Ile His Gly Lys Ser Thr Leu Tyr Ala Asp Ser Val Lys
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Ile His Gly Asp Ser Thr Leu Tyr Ala Asp Ser Val Lys
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Ile His Gly Val Ser Thr Leu Tyr Ala Asp Ser Val Lys
1               5                   10

<210> SEQ ID NO 148
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Ile His Gly Thr Ser Thr Leu Tyr Ala Asp Ser Val Lys
1               5                   10
```

<210> SEQ ID NO 149
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Ile His Gly Asp Ser Thr Leu Tyr Ala Asp Ser Val Lys
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Ile His Gly Ser Ser Thr Leu Tyr Ala Asp Ser Val Lys
1               5                   10

<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Ile His Gly Ser Ser Thr Leu Tyr Ala Asp Ser Val Lys
1               5                   10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Ile His Gly Asp Ser Thr Leu Tyr Ala Asp Ser Val Lys
1               5                   10

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Ile His Gly Thr Ser Thr Leu Tyr Ala Asp Ser Val Lys
1               5                   10

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 154

Ala Ile His Gly Thr Ser Thr Leu Tyr Ala Asp Ser Val Lys
1               5                   10

<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ala Ile His Gly Asp Ser Thr Leu Tyr Ala Asp Ser Val Lys
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Ile His Gly Gln Ser Thr Leu Tyr Ala Asp Ser Val Lys
1               5                   10

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Ile His Gly Asp Ser Thr Leu Tyr Ala Asp Ser Val Lys
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Ile His Gly Lys Ser Thr Leu Tyr Ala Asp Ser Val Lys
1               5                   10

<210> SEQ ID NO 159
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Ile His Gly Thr Ser Thr Leu Tyr Ala Asp Ser Val Lys
1               5                   10

<210> SEQ ID NO 160
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 160

Ala Ile His Gly Asn Ser Thr Leu Tyr Ala Asp Ser Val Lys
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Ile His Gly Phe Gln Thr Leu Tyr Ala Asp Ser Val Lys
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Ile His Gly Phe Ser Thr Trp Tyr Ala Asp Ser Val Lys
1               5                   10

<210> SEQ ID NO 163
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Ile His Gly Phe Ser Thr Ile Tyr Ala Asp Ser Val Lys
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ala Ile His Gly Pro Ser Thr Leu Tyr Ala Asp Ser Val Lys
1               5                   10

<210> SEQ ID NO 165
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Ile His Gly His Ser Thr Leu Tyr Ala Asp Ser Val Lys
1               5                   10
```

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Ile His Gly Glu Ser Thr Leu Tyr Ala Asp Ser Val Lys
1               5                   10

<210> SEQ ID NO 167
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ala Ile His Gly Asp Ser Thr Leu Tyr Ala Asp Ser Val Lys
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Ile His Gly Asp Ser Thr Leu Tyr Ala Asp Ser Val Lys
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Ile His Gly Asn Ser Thr Leu Tyr Ala Asp Ser Val Lys
1               5                   10

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Ile His Gly Phe Glu Thr Leu Tyr Ala Asp Ser Val Lys
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 171

Ala Ile His Gly Phe Glu Thr Leu Tyr Ala Asp Ser Val Lys
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Ile His Gly Phe Ser Thr Tyr Tyr Ala Asp Ser Val Lys
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Ile His Gly Leu Ser Thr Leu Tyr Ala Asp Ser Val Lys
1               5                   10

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Ile His Gly Ala Ser Thr Leu Tyr Ala Asp Ser Val Lys
1               5                   10

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Ile His Gly Gln Ser Thr Leu Tyr Ala Asp Ser Val Lys
1               5                   10

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Ile His Gly Gln Ser Thr Leu Tyr Ala Asp Ser Val Lys
1               5                   10

<210> SEQ ID NO 177
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ala Ile His Gly Thr Ser Thr Leu Tyr Ala Asp Ser Val Lys
1               5                   10

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Ile His Gly Phe Glu Thr Leu Tyr Ala Asp Ser Val Lys
1               5                   10

<210> SEQ ID NO 179
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Ile His Gly Phe Ser Thr Val Tyr Ala Asp Ser Val Lys
1               5                   10

<210> SEQ ID NO 180
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Ile His Gly Asn Ser Thr Leu Tyr Ala Asp Ser Val Lys
1               5                   10

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Ile His Gly Glu Ser Thr Leu Tyr Ala Asp Ser Val Lys
1               5                   10

<210> SEQ ID NO 182
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ala Ile His Gly Phe Ser Thr Leu Tyr Ala Asp Ser Val Lys
```

<210> SEQ ID NO 183
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Ile His Gly Lys Ser Thr Leu Tyr Ala Asp Ser Val Lys
1               5                   10

<210> SEQ ID NO 184
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Ile His Gly Lys Ser Thr Leu Tyr Ala Asp Ser Val Lys
1               5                   10

<210> SEQ ID NO 185
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Ile His Gly Asn Ser Thr Leu Tyr Ala Asp Ser Val Lys
1               5                   10

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ala Ile His Gly Glu Ser Thr Leu Tyr Ala Asp Ser Val Lys
1               5                   10

<210> SEQ ID NO 187
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Ile His Gly Ser Ser Thr Leu Tyr Ala Asp Ser Val Lys
1               5                   10

<210> SEQ ID NO 188
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Ala Ile His Gly Arg Ser Thr Leu Tyr Ala Asp Ser Val Lys
1               5                   10

<210> SEQ ID NO 189
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Ile His Gly Phe Ser Thr Ile Tyr Ala Asp Ser Val Lys
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Ile His Gly Thr Ser Thr Leu Tyr Ala Asp Ser Val Lys
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ala Ile His Gly Phe Ser Thr Leu Tyr Ala Asp Ser Val Lys
1               5                   10

<210> SEQ ID NO 192
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ala Ile His Gly His Ser Thr Leu Tyr Ala Asp Ser Val Lys
1               5                   10

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Ile His Gly Asp Ser Thr Leu Tyr Ala Asp Ser Val Lys
1               5                   10

<210> SEQ ID NO 194

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Ile His Gly Phe Asp Thr Leu Tyr Ala Asp Ser Val Lys
1               5                   10

<210> SEQ ID NO 195
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ala Ile His Gly Ala Ser Thr Leu Tyr Ala Asp Ser Val Lys
1               5                   10

<210> SEQ ID NO 196
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Ile His Gly Ser Ser Thr Leu Tyr Ala Asp Ser Val Lys
1               5                   10

<210> SEQ ID NO 197
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ala Ile His Gly Phe Thr Thr Leu Tyr Ala Asp Ser Val Lys
1               5                   10

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Ile His Gly Thr Ser Thr Leu Tyr Ala Asp Ser Val Lys
1               5                   10

<210> SEQ ID NO 199
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199
```

Ala Ile His Gly Phe Ser Thr Val Tyr Ala Asp Ser Val Lys
1               5                   10

<210> SEQ ID NO 200
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Ile His Gly Lys Ser Thr Leu Tyr Ala Asp Ser Val Lys
1               5                   10

<210> SEQ ID NO 201
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Ile His Gly Glu Ser Thr Leu Tyr Ala Asp Ser Val Lys
1               5                   10

<210> SEQ ID NO 202
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Ile His Gly Pro Ser Thr Leu Tyr Ala Asp Ser Val Lys
1               5                   10

<210> SEQ ID NO 203
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ala Ile His Gly Ile Ser Thr Leu Tyr Ala Asp Ser Val Lys
1               5                   10

<210> SEQ ID NO 204
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Ile His Gly Phe Ser Thr Phe Tyr Ala Asp Ser Val Lys
1               5                   10

<210> SEQ ID NO 205
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 205

Ala Ile His Gly Gly Ser Thr Leu Tyr Ala Asp Ser Val Lys
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ala Ile His Gly Ser Ser Thr Leu Tyr Ala Asp Ser Val Lys
1               5                   10

<210> SEQ ID NO 207
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ala Ile His Gly Ser Ser Thr Leu Tyr Ala Asp Ser Val Lys
1               5                   10

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala Ile His Gly Phe Ser Thr Leu Tyr Ala Asp Ser Val Lys
1               5                   10

<210> SEQ ID NO 209
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Ile His Gly Asn Ser Thr Leu Tyr Ala Asp Ser Val Lys
1               5                   10

<210> SEQ ID NO 210
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Ile His Gly Glu Ser Thr Leu Tyr Ala Asp Ser Val Lys
1               5                   10

```
<210> SEQ ID NO 211
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ala Ile His Gly Phe Ser Thr Leu Tyr Ala Asp Ser Val Lys
1               5                   10

<210> SEQ ID NO 212
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Ile His Gly Thr Ser Thr Leu Tyr Ala Asp Ser Val Lys
1               5                   10

<210> SEQ ID NO 213
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Ile His Gly Thr Ser Thr Leu Tyr Ala Asp Ser Val Lys
1               5                   10

<210> SEQ ID NO 214
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Ile His Gly Phe Asp Thr Leu Tyr Ala Asp Ser Val Lys
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ala Ile His Gly Ala Ser Thr Leu Tyr Ala Asp Ser Val Lys
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216
```

```
Ala Ile His Gly Asn Ser Thr Leu Tyr Ala Asp Ser Val Lys
1               5                   10
```

<210> SEQ ID NO 217
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Ala Ile His Gly Asn Ser Thr Leu Tyr Ala Asp Ser Val Lys
1               5                   10
```

<210> SEQ ID NO 218
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Ala Ile His Gly Glu Ser Thr Leu Tyr Ala Asp Ser Val Lys
1               5                   10
```

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

```
Ala Ile His Gly Glu Ser Thr Leu Tyr Ala Asp Ser Val Lys
1               5                   10
```

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

```
Ala Ile His Gly Phe Ser Thr Leu Tyr Ala Asp Ser Val Lys
1               5                   10
```

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

```
Ala Ile His Gly Ser Ser Thr Leu Tyr Ala Asp Ser Val Lys
1               5                   10
```

<210> SEQ ID NO 222
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 222

Ala Ile His Gly Ser Ser Thr Leu Tyr Ala Asp Ser Val Lys
1               5                   10

<210> SEQ ID NO 223
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Ile His Gly Asn Ser Thr Leu Tyr Ala Asp Ser Val Lys
1               5                   10

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Ile His Gly Lys Ser Thr Leu Tyr Ala Asp Ser Val Lys
1               5                   10

<210> SEQ ID NO 225
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Ile His Gly Ser Ser Thr Leu Tyr Ala Asp Ser Val Lys
1               5                   10

<210> SEQ ID NO 226
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ala Ile His Gly Ser Ser Thr Leu Tyr Ala Asp Ser Val Lys
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Ile His Gly Glu Ser Thr Leu Tyr Ala Asp Ser Val Lys
1               5                   10
```

```
<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Ile His Gly Phe Ser Thr Ile Tyr Ala Asp Ser Val Lys
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Ile His Gly Phe Ser Thr Ile Tyr Ala Asp Ser Val Lys
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Ile His Gly Ala Ser Thr Leu Tyr Ala Asp Ser Val Lys
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ala Ile His Gly Ala Ser Thr Leu Tyr Ala Asp Ser Val Lys
1               5                   10

<210> SEQ ID NO 232
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Val Pro Trp Gly Asp Tyr His Pro Arg Asn Val Ala
1               5                   10

<210> SEQ ID NO 233
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 233

Val Pro Trp Gly Asp Tyr His Pro Arg Asn Val His
1               5                   10

<210> SEQ ID NO 234
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Val Pro Trp Gly Asp Tyr His Pro Arg Asn Val Tyr
1               5                   10

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Val Pro Trp Gly Arg Tyr His Pro Arg Asn Val Tyr
1               5                   10

<210> SEQ ID NO 236
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Val Pro Trp Gly Asp Tyr His Pro Arg Asn Val Tyr
1               5                   10

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Val Pro Trp Gly Asp Tyr His Pro Arg Asn Val Tyr
1               5                   10

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Val Pro Trp Gly Asp Tyr His Pro Gly Asn Val Tyr
1               5                   10

<210> SEQ ID NO 239
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 239

Val Pro Trp Gly Asp Tyr His Pro Arg Lys Val Tyr
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Val Pro Trp Gly Ser Tyr His Pro Arg Asn Val Tyr
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Val Pro Trp Gly Asp Tyr His Pro Arg Asn Val Ala
1               5                   10

<210> SEQ ID NO 242
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Val Pro Trp Gly Asp Tyr His Pro Arg Asn Val Tyr
1               5                   10

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Val Pro Trp Gly Asp Tyr His Pro Arg Asn Val Val
1               5                   10

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Val Pro Trp Gly Asp Tyr His Pro Arg Asn Val Lys
1               5                   10
```

```
<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Val Pro Trp Gly Asp Tyr His Pro Gly Asn Val Tyr
1               5                   10

<210> SEQ ID NO 246
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Val Pro Trp Gly Glu Tyr His Pro Arg Asn Val Tyr
1               5                   10

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Val Pro Trp Gly Ile Tyr His Pro Arg Asn Val Tyr
1               5                   10

<210> SEQ ID NO 248
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Val Pro Trp Gly Arg Tyr His Pro Arg Asn Val Tyr
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Val Pro Trp Gly Asp Tyr His Pro Gly Asn Val Tyr
1               5                   10

<210> SEQ ID NO 250
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 250

Val Pro Trp Gly Asp Tyr His Pro Arg Asn Val Val
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Val Pro Trp Gly Asp Tyr His Pro Gly Asn Val Tyr
1               5                   10

<210> SEQ ID NO 252
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Val Pro Trp Gly Arg Tyr His Pro Arg Asn Val Tyr
1               5                   10

<210> SEQ ID NO 253
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Val Pro Trp Gly Asp Tyr His Pro Arg Asn Val Tyr
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Val Pro Trp Gly Asp Tyr His Pro Gly Asn Val Tyr
1               5                   10

<210> SEQ ID NO 255
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Val Pro Trp Gly Lys Tyr His Pro Arg Asn Val Tyr
1               5                   10

<210> SEQ ID NO 256
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Val Pro Trp Gly Ser Tyr His Pro Arg Asn Val Tyr
1               5                   10

<210> SEQ ID NO 257
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Val Pro Trp Gly Asp Tyr His Pro Arg Asn Val His
1               5                   10

<210> SEQ ID NO 258
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Val Pro Trp Gly Tyr Tyr His Pro Arg Asn Val Tyr
1               5                   10

<210> SEQ ID NO 259
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Val Pro Trp Gly Asp Tyr His Pro Gly Asn Val Tyr
1               5                   10

<210> SEQ ID NO 260
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val Pro Trp Gly Asp Tyr His Pro Arg Asn Val Arg
1               5                   10

<210> SEQ ID NO 261
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Val Pro Trp Gly Asp Tyr His Pro Arg Asn Val Gln
```

```
<210> SEQ ID NO 262
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Val Pro Trp Gly Asp Tyr His Pro Arg Asn Val Tyr
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Val Pro Trp Gly Asp Tyr His Pro Arg Asn Val Thr
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Val Pro Trp Gly Asp Tyr His Pro Arg Asn Val Asn
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Val Pro Trp Gly Arg Tyr His Pro Arg Asn Val Tyr
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Val Pro Trp Gly Asp Tyr His Pro Gly Asn Val Tyr
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 267

Val Pro Trp Gly Asp Tyr His Pro Gly Asn Val Tyr
1               5                   10

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Val Pro Trp Gly Lys Tyr His Pro Arg Asn Val Tyr
1               5                   10

<210> SEQ ID NO 269
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Val Pro Trp Gly Asp Tyr His Pro Arg Asn Val Tyr
1               5                   10

<210> SEQ ID NO 270
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Val Pro Trp Gly Asp Tyr His Pro Arg Asn Val Gln
1               5                   10

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Val Pro Trp Gly Asp Tyr His Pro Gly Asn Val Cys
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Val Pro Trp Gly Asp Tyr His Pro Arg Arg Val Tyr
1               5                   10

<210> SEQ ID NO 273
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Val Pro Trp Gly Arg Tyr His Pro Arg Asn Val Tyr
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Val Pro Trp Gly Thr Tyr His Pro Arg Asn Val Tyr
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Val Pro Trp Gly Asp Tyr His Pro Gly Asn Val Tyr
1               5                   10

<210> SEQ ID NO 276
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Val Pro Trp Gly Arg Tyr His Pro Arg Asn Val Tyr
1               5                   10

<210> SEQ ID NO 277
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Val Pro Trp Gly Asp Tyr His Pro Gly Asn Val Tyr
1               5                   10

<210> SEQ ID NO 278
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278
```

```
Val Pro Trp Gly Asp Tyr His Pro Thr Asn Val Tyr
1               5                  10
```

<210> SEQ ID NO 279
<211> LENGTH: 12
<212> TYPE: PRT
<213> ORGANIZM: Artificial Sequence
<220> FEATURE:
<223> OTHER INFORMATION: Description of Artificial Sequence: Synthetic
      peptide

<400> SEQUENCE: 279

```
Val Pro Trp Gly Arg Tyr His Pro Arg Asn Val Tyr
1               5                  10
```

<210> SEQ ID NO 280
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

```
Val Pro Trp Gly Asp Tyr His Pro Arg Asn Val Thr
1               5                  10
```

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

```
Val Pro Trp Gly Arg Tyr His Pro Arg Asn Val Tyr
1               5                  10
```

<210> SEQ ID NO 282
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

```
Val Pro Trp Gly Asp Tyr His Pro Arg Arg Val Tyr
1               5                  10
```

<210> SEQ ID NO 283
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

```
Val Pro Trp Gly Asp Tyr His Pro Arg Met Val Tyr
1               5                  10
```

<210> SEQ ID NO 284
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 284

Val Pro Trp Gly Asp Tyr His Pro Arg Asn Val Leu
1               5                   10

<210> SEQ ID NO 285
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Val Pro Trp Gly Asp Tyr His Pro Gly Asn Val Tyr
1               5                   10

<210> SEQ ID NO 286
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Val Pro Trp Gly Arg Tyr His Pro Arg Asn Val Tyr
1               5                   10

<210> SEQ ID NO 287
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Val Pro Trp Gly Ala Tyr His Pro Arg Asn Val Tyr
1               5                   10

<210> SEQ ID NO 288
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Val Pro Trp Gly Asp Tyr His Pro Arg Asn Val Ala
1               5                   10

<210> SEQ ID NO 289
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Val Pro Trp Gly Asp Tyr His Pro Gln Asn Val Tyr
1               5                   10

```
<210> SEQ ID NO 290
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Val Pro Trp Gly Asp Tyr His Pro Arg Asn Val Thr
1               5                   10

<210> SEQ ID NO 291
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Val Pro Trp Gly Arg Tyr His Pro Arg Asn Val Tyr
1               5                   10

<210> SEQ ID NO 292
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Val Pro Trp Gly Asp Tyr His Pro Gly Asn Val Tyr
1               5                   10

<210> SEQ ID NO 293
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Val Pro Trp Gly Asp Tyr His Pro Gly Asn Val Tyr
1               5                   10

<210> SEQ ID NO 294
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Val Pro Trp Gly Asp Tyr His Pro Gly Asn Val Tyr
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295
```

```
Val Pro Trp Gly Asp Tyr His Pro Arg Asn Val Tyr
1               5                   10

<210> SEQ ID NO 296
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Val Pro Trp Gly Asp Tyr His Pro Gly Asn Val Tyr
1               5                   10

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Val Pro Trp Gly Asp Tyr His Pro Ser Asn Val Tyr
1               5                   10

<210> SEQ ID NO 298
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Val Pro Trp Gly Asp Tyr His Pro Gly Asn Val Tyr
1               5                   10

<210> SEQ ID NO 299
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Val Pro Trp Gly Asp Tyr His Pro Arg Glu Val Tyr
1               5                   10

<210> SEQ ID NO 300
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Val Pro Trp Gly Arg Tyr His Pro Gly Asn Val Tyr
1               5                   10

<210> SEQ ID NO 301
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 301

Val Pro Trp Gly Asp Tyr His Pro Arg Val Val Tyr
1               5                   10

<210> SEQ ID NO 302
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Val Pro Trp Gly Asp Tyr His Pro Arg Asn Val Met
1               5                   10

<210> SEQ ID NO 303
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Val Pro Trp Gly Asp Tyr His Pro Leu Asn Val Tyr
1               5                   10

<210> SEQ ID NO 304
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Val Pro Trp Gly Asp Tyr His Pro Gly Asn Val Tyr
1               5                   10

<210> SEQ ID NO 305
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Val Pro Trp Gly Asp Tyr His Pro Gly Asn Val Tyr
1               5                   10

<210> SEQ ID NO 306
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Val Pro Trp Gly Asp Tyr His Pro Arg Asn Val Thr
1               5                   10
```

```
<210> SEQ ID NO 307
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Val Pro Trp Gly Asp Tyr His Pro Arg Asn Val Ser
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Val Pro Trp Gly Asp Tyr His Pro Arg Asn Val Tyr
1               5                   10

<210> SEQ ID NO 309
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Val Pro Trp Gly Asp Tyr His Pro Gly Asn Val Tyr
1               5                   10

<210> SEQ ID NO 310
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Val Pro Trp Gly Asp Tyr His Pro Gly Asn Val Tyr
1               5                   10

<210> SEQ ID NO 311
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Val Pro Trp Gly Asp Tyr His Pro Arg Asn Val Thr
1               5                   10

<210> SEQ ID NO 312
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 312

Val Pro Trp Gly Asp Tyr His Pro Gly Asn Val Tyr
1               5                   10

<210> SEQ ID NO 313
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Val Pro Trp Gly Arg Tyr His Pro Arg Asn Val Tyr
1               5                   10

<210> SEQ ID NO 314
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Val Pro Trp Gly Asp Tyr His Pro Asn Asn Val Tyr
1               5                   10

<210> SEQ ID NO 315
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Val Pro Trp Gly Asp Tyr His Pro Gly Asn Val Tyr
1               5                   10

<210> SEQ ID NO 316
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Val Pro Trp Gly Asp Tyr His Pro Arg Asn Val Thr
1               5                   10

<210> SEQ ID NO 317
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Val Pro Trp Gly Asp Tyr His Pro Gly Asn Val Tyr
1               5                   10

<210> SEQ ID NO 318
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 318

Val Pro Trp Gly Asp Tyr His Pro Gly Asn Val Tyr
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Val Pro Trp Gly Asp Tyr His Pro Arg Asn Val Ala
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Val Pro Trp Gly Asp Tyr His Pro Gly Asn Val Tyr
1               5                   10

<210> SEQ ID NO 321
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Val Pro Trp Gly Asp Tyr His Pro Lys Asn Val Tyr
1               5                   10

<210> SEQ ID NO 322
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Val Pro Trp Gly Asp Tyr His Pro Gly Asn Val Tyr
1               5                   10

<210> SEQ ID NO 323
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Val Pro Trp Gly Lys Tyr His Pro Arg Asn Val Tyr
1               5                   10
```

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Val Pro Trp Gly Arg Tyr His Pro Arg Asn Val Tyr
1               5                   10

<210> SEQ ID NO 325
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Val Pro Trp Gly Asp Tyr His Pro Gly Asn Val Tyr
1               5                   10

<210> SEQ ID NO 326
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Val Pro Trp Gly Asp Tyr His Pro Arg Asn Val Gln
1               5                   10

<210> SEQ ID NO 327
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Val Pro Trp Gly Asp Tyr His Pro Gly Asn Val Tyr
1               5                   10

<210> SEQ ID NO 328
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Val Pro Trp Gly Asp Tyr His Pro Arg Asn Val Ser
1               5                   10

<210> SEQ ID NO 329
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 329

Val Pro Trp Gly Asp Tyr His Pro Gly Asn Val Tyr
1               5                   10

<210> SEQ ID NO 330
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Val Pro Trp Gly Asp Tyr His Pro Gly Asn Val Tyr
1               5                   10

<210> SEQ ID NO 331
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Val Pro Trp Gly Asp Tyr His Pro Gly Asn Val Tyr
1               5                   10

<210> SEQ ID NO 332
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Val Pro Trp Gly Asp Tyr His Pro Arg Asp Val Tyr
1               5                   10

<210> SEQ ID NO 333
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Val Pro Trp Gly Asp Tyr His Pro Arg Asn Val Thr
1               5                   10

<210> SEQ ID NO 334
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Val Pro Trp Gly Asp Tyr His Pro Arg Asn Val Ala
1               5                   10

<210> SEQ ID NO 335
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Val Pro Trp Gly Asp Tyr His Pro Arg Asn Val Thr
1               5                   10

<210> SEQ ID NO 336
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Val Pro Trp Gly Asp Tyr His Pro Arg Asn Val Tyr
1               5                   10

<210> SEQ ID NO 337
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Val Pro Trp Gly Asp Tyr His Pro Arg Asn Val Tyr
1               5                   10

<210> SEQ ID NO 338
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Val Pro Trp Gly Asp Tyr His Pro Arg Asn Val Val
1               5                   10

<210> SEQ ID NO 339
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Val Pro Trp Gly Asp Tyr His Pro Arg Asn Val Val
1               5                   10

<210> SEQ ID NO 340
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Val Pro Trp Gly Asp Tyr His Pro Gly Asn Val Tyr
```

```
1               5                   10
```

```
<210> SEQ ID NO 341
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Val Pro Trp Gly Asp Tyr His Pro Arg Asn Val Tyr
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Val Pro Trp Gly Asp Tyr His Pro Gly Asn Val Tyr
1               5                   10

<210> SEQ ID NO 343
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Val Pro Trp Gly Asp Tyr His Pro Gly Asn Val Tyr
1               5                   10

<210> SEQ ID NO 344
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Val Pro Trp Gly Asp Tyr His Pro Gly Asn Val Tyr
1               5                   10

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Val Pro Trp Gly Asp Tyr His Pro Gly Asn Val Tyr
1               5                   10

<210> SEQ ID NO 346
<211> LENGTH: 119
<212> TYPE: PRT
<213> ORGANISM: Artificial Sequence
<220> FEATURE:
<223> OTHER INFORMATION: Description of Artificial Sequence: Synthetic
```

-continued

<400> SEQUENCE: 346

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 347
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Glu Val Gln Leu Val Glu Ser Gly Gly Gly Leu Val Gln Pro Gly Arg
1               5                   10                  15

Ser Leu Thr Leu Ser Cys Ala Ala Ser Thr Asp Ile Phe Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Gly Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Ala Trp Gly Gln Gly
            100                 105                 110

Thr Gln Val Thr Val Ser Ser
        115

<210> SEQ ID NO 348
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Asp Phe Ser Ile Ser
            20                  25                  30

```
Pro Met Gly Trp Tyr Arg Gln Ala Pro Gly Lys Gln Arg Glu Leu Val
            35                  40                  45

Ala Ala Ile His Gly Gly Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Ala Trp Gly Gln Gly
                100                 105                 110

Thr Gln Val Thr Val Ser Ser
            115

<210> SEQ ID NO 349
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Lys Ser
                20                  25                  30

Pro Met Gly Trp Tyr Arg Gln Ala Pro Gly Lys Gln Arg Glu Leu Val
            35                  40                  45

Ala Ala Ile His Gly Lys Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Val Trp Gly Gln Gly
                100                 105                 110

Thr Gln Val Thr Val Ser Ser
            115

<210> SEQ ID NO 350
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Asp Phe Ser Ile Ser
                20                  25                  30

Pro Met Gly Trp Tyr Arg Gln Ala Pro Gly Lys Gln Arg Glu Leu Val
            35                  40                  45

Ala Ala Ile His Gly Lys Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80
```

```
Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Lys Trp Gly Gln Gly
            100                 105                 110

Thr Gln Val Thr Val Ser Ser
        115

<210> SEQ ID NO 351
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Gln Phe Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Lys Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Val Trp Gly Gln Gly
            100                 105                 110

Thr Gln Val Thr Val Ser Ser
        115

<210> SEQ ID NO 352
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ser Ser
            20                  25                  30

Pro Met Gly Trp Tyr Arg Gln Ala Pro Gly Lys Gln Arg Glu Leu Val
        35                  40                  45

Ala Ala Ile Asn Gly Phe Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val His Trp Gly Gln Gly
            100                 105                 110

Thr Gln Val Thr Val Ser Ser
        115
```

<210> SEQ ID NO 353
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ser Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 354
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Thr Ser
            20                  25                  30

Pro Met Gly Trp Tyr Arg Gln Ala Pro Gly Lys Gln Arg Glu Leu Val
        35                  40                  45

Ala Ala Ile His Gly Phe Gln Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Val Trp Gly Gln Gly
            100                 105                 110

Thr Gln Val Thr Val Ser Ser
        115

<210> SEQ ID NO 355
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Arg Ser
            20                  25                  30

Pro Met Gly Trp Tyr Arg Gln Ala Pro Gly Lys Gln Arg Glu Leu Val
        35                  40                  45

Ala Ala Ile His Gly Phe Glu Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Leu Trp Gly Gln Gly
            100                 105                 110

Thr Gln Val Thr Val Ser Ser
        115

<210> SEQ ID NO 356
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Glu Ser
            20                  25                  30

Pro Met Gly Trp Tyr Arg Gln Ala Pro Gly Lys Gln Arg Glu Leu Val
        35                  40                  45

Ala Ala Ile His Gly Phe Thr Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Thr Trp Gly Gln Gly
            100                 105                 110

Thr Gln Val Thr Val Ser Ser
        115

<210> SEQ ID NO 357
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Asp Ser
            20                  25                  30

Pro Met Gly Trp Tyr Arg Gln Ala Pro Gly Lys Gln Arg Glu Leu Val
            35                  40                  45

Ala Ala Ile His Gly Phe Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Ala Trp Gly Gln Gly
            100                 105                 110

Thr Gln Val Thr Val Ser Ser
            115

<210> SEQ ID NO 358
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Phe Ser Asn Ser
                20                  25                  30

Pro Met Gly Trp Tyr Arg Gln Ala Pro Gly Lys Gln Arg Glu Leu Val
            35                  40                  45

Ala Ala Ile His Gly Gly Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val His Trp Gly Gln Gly
            100                 105                 110

Thr Gln Val Thr Val Ser Ser
            115

<210> SEQ ID NO 359
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Phe Ser Asn Ser
                20                  25                  30

Pro Met Gly Trp Tyr Arg Gln Ala Pro Gly Lys Gln Arg Glu Leu Val
            35                  40                  45

Ala Ala Ile His Gly Arg Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Met Trp Gly Gln Gly
            100                 105                 110

Thr Gln Val Thr Val Ser Ser
        115

<210> SEQ ID NO 360
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Asn Ser
            20                  25                  30

Pro Met Gly Trp Tyr Arg Gln Ala Pro Gly Lys Gln Arg Glu Leu Val
        35                  40                  45

Ala Ala Ile His Gly Pro Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Thr Trp Gly Gln Gly
            100                 105                 110

Thr Gln Val Thr Val Ser Ser
        115

<210> SEQ ID NO 361
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Asn Ser
            20                  25                  30

Pro Met Gly Trp Tyr Arg Gln Ala Pro Gly Lys Gln Arg Glu Leu Val
        35                  40                  45

Ala Ala Ile His Gly Asp Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Arg Trp Gly Gln Gly
            100                 105                 110

Thr Gln Val Thr Val Ser Ser
        115

<210> SEQ ID NO 362
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Arg Ser
            20                  25                  30

Pro Met Gly Trp Tyr Arg Gln Ala Pro Gly Lys Gln Arg Glu Leu Val
        35                  40                  45

Ala Ala Ile His Gly Asp Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Thr Trp Gly Gln Gly
            100                 105                 110

Thr Gln Val Thr Val Ser Ser
        115

<210> SEQ ID NO 363
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Lys Ser
            20                  25                  30

Pro Met Gly Trp Tyr Arg Gln Ala Pro Gly Lys Gln Arg Glu Leu Val
        35                  40                  45

Ala Ala Ile His Gly Gln Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Thr Trp Gly Gln Gly
            100                 105                 110

Thr Gln Val Thr Val Ser Ser
        115

<210> SEQ ID NO 364
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ser Ser
            20                  25                  30

Pro Met Gly Trp Tyr Arg Gln Ala Pro Gly Lys Gln Arg Glu Leu Val
        35                  40                  45

Ala Ala Ile His Gly His Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Thr Gly Gln Gly
            100                 105                 110

Thr Gln Val Thr Val Ser Ser
        115

<210> SEQ ID NO 365
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ser Ser
            20                  25                  30

Pro Met Gly Trp Tyr Arg Gln Ala Pro Gly Lys Gln Arg Glu Leu Val
        35                  40                  45

Ala Ala Ile His Gly Glu Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Lys Val Tyr Trp Gly Gln Gly
            100                 105                 110

Thr Gln Val Thr Val Ser Ser
        115

<210> SEQ ID NO 366
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Arg Ser
            20                  25                  30

Pro Met Gly Trp Tyr Arg Gln Ala Pro Gly Lys Gln Arg Glu Leu Val

```
                    35                  40                  45

Ala Ala Ile His Gly Asn Ser Thr Leu Tyr Ala Asp Ser Val Lys Gly
        50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Ile Tyr His Pro Arg Asn Val Tyr Trp Gly Gln Gly
            100                 105                 110

Thr Gln Val Thr Val Ser Ser
            115

<210> SEQ ID NO 367
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Glu Ser
            20                  25                  30

Pro Met Gly Trp Tyr Arg Gln Ala Pro Gly Lys Gln Arg Glu Leu Val
        35                  40                  45

Ala Ala Ile His Gly Asn Ser Thr Leu Tyr Ala Asp Ser Val Lys Gly
        50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Thr Tyr His Pro Arg Asn Val Tyr Trp Gly Gln Gly
            100                 105                 110

Thr Gln Val Thr Val Ser Ser
            115

<210> SEQ ID NO 368
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Val Ser
            20                  25                  30

Pro Met Gly Trp Tyr Arg Gln Ala Pro Gly Lys Gln Arg Glu Leu Val
        35                  40                  45

Ala Ala Ile His Gly Asn Ser Thr Leu Tyr Ala Asp Ser Val Lys Gly
        50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
```

85                  90                  95

Val Pro Trp Gly Lys Tyr His Pro Arg Asn Val Tyr Trp Gly Gln Gly
            100                 105                 110

Thr Gln Val Thr Val Ser Ser
        115

<210> SEQ ID NO 369
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Val Ser
            20                  25                  30

Pro Met Gly Trp Tyr Arg Gln Ala Pro Gly Lys Gln Arg Glu Leu Val
        35                  40                  45

Ala Ala Ile His Gly Asn Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 370
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Lys Ser
            20                  25                  30

Pro Met Gly Trp Tyr Arg Gln Ala Pro Gly Lys Gln Arg Glu Leu Val
        35                  40                  45

Ala Ala Ile His Gly Asn Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Glu Val Tyr Trp Gly Gln Gly
            100                 105                 110

Thr Gln Val Thr Val Ser Ser
        115

```
<210> SEQ ID NO 371
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371
```

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Asp Ser
            20                  25                  30

Pro Met Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser
        115

```
<210> SEQ ID NO 372
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372
```

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Arg Ser
            20                  25                  30

Pro Met Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Lys Tyr His Pro Arg Asn Val Tyr Trp Gly Gln Gly
            100                 105                 110

Thr Gln Val Thr Val Ser Ser
        115

```
<210> SEQ ID NO 373
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373
```

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser His Ser
            20                  25                  30

Pro Met Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Arg Tyr His Pro Arg Asn Val Tyr Trp Gly Gln Gly
            100                 105                 110

Thr Gln Val Thr Val Ser Ser
            115

<210> SEQ ID NO 374
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Thr Ser
            20                  25                  30

Pro Met Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
            115

<210> SEQ ID NO 375
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Thr Ser
            20                  25                  30

Pro Met Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
            50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
            85                  90                  95

Val Pro Trp Gly Asp Tyr His Pro Arg Asn Val Gln Trp Gly Gln Gly
            100                 105                 110

Thr Gln Val Thr Val Ser Ser
        115

<210> SEQ ID NO 376
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Leu Ser
            20                  25                  30

Pro Met Gly Trp Tyr Arg Gln Ala Pro Gly Lys Gln Arg Glu Leu Val
            35                  40                  45

Ala Ala Ile His Gly Asp Ser Thr Leu Tyr Ala Asp Ser Val Lys Gly
            50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
            85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 377
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Ser
            20                  25                  30

Pro Gly Gly Trp Tyr Arg Gln Ala Pro Gly Lys Gln Arg Glu Leu Val
            35                  40                  45

Ala Ala Ile His Gly Ser Ser Thr Leu Tyr Ala Asp Ser Val Lys Gly
            50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
            85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 378
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn His Phe Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Val Val Tyr Trp Gly Gln Gly
            100                 105                 110

Thr Gln Val Thr Val Ser Ser
        115

<210> SEQ ID NO 379
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ala Ser
            20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Asn Trp Gly Gln Gly
            100                 105                 110

Thr Gln Val Thr Val Ser Ser
        115

<210> SEQ ID NO 380

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ala Ser
            20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Arg Tyr His Pro Arg Asn Val Tyr Trp Gly Gln Gly
            100                 105                 110

Thr Gln Val Thr Val Ser Ser
        115

<210> SEQ ID NO 381
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Ser Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 382
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382
```

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Glu Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 383
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Ser
            20                  25                  30

Pro Tyr Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 384
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Ala Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 385
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Ala Ser Ile Ser
                20                  25                  30

Pro Met Gly Trp Tyr Arg Gln Ala Pro Gly Lys Gln Arg Glu Leu Val
            35                  40                  45

Ala Ala Ile His Gly Lys Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 386
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Ala Ser Ile Ser
                20                  25                  30

Pro Met Gly Trp Tyr Arg Gln Ala Pro Gly Lys Gln Arg Glu Leu Val
            35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

-continued

Val Pro Trp Gly Asp Tyr His Pro Gly Asn Val Tyr Trp Gln Gly
            100                 105                 110

Thr Gln Val Thr Val Ser Ser
        115

<210> SEQ ID NO 387
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Thr Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Asp Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 388
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Met Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Asn Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 389
<211> LENGTH: 119

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Thr Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Asn Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 390
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Val Ser Ile Ser
            20                  25                  30

Pro Met Gly Trp Tyr Arg Gln Ala Pro Gly Lys Gln Arg Glu Leu Val
        35                  40                  45

Ala Ala Ile His Gly His Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 391
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Glu Val Gln Leu Val Glu Ser Gly Gly Gly Leu Val Gln Pro Gly Arg

```
1               5                   10                  15
Ser Leu Thr Leu Ser Cys Ala Ala Ser Thr Asn Ile Val Ser Ile Ser
            20                  25                  30

Pro Met Gly Trp Tyr Arg Gln Ala Pro Gly Lys Gln Arg Glu Leu Val
            35                  40                  45

Ala Ala Ile His Gly Lys Ser Thr Leu Tyr Ala Asp Ser Val Lys Gly
            50                  55                  60

Arg Phe Thr Ile Ser Arg Asp Asn Ala Lys Asn Ser Ile Tyr Leu Gln
65                      70                  75                  80

Met Asn Ser Leu Arg Pro Glu Asp Thr Ala Leu Tyr Tyr Cys Asn Lys
            85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 392
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Val Val Ser Ile Ser
            20                  25                  30

Pro Met Gly Trp Tyr Arg Gln Ala Pro Gly Lys Gln Arg Glu Leu Val
            35                  40                  45

Ala Ala Ile His Gly Lys Ser Thr Leu Tyr Ala Asp Ser Val Lys Gly
            50                  55                  60

Arg Phe Thr Ile Ser Arg Asp Asn Ala Lys Asn Ser Ile Tyr Leu Gln
65                      70                  75                  80

Met Asn Ser Leu Arg Pro Glu Asp Thr Ala Leu Tyr Tyr Cys Asn Lys
            85                  90                  95

Val Pro Trp Gly Asp Tyr His Pro Asn Asn Val Tyr Trp Gly Gln Gly
            100                 105                 110

Thr Gln Val Thr Val Ser Ser
        115

<210> SEQ ID NO 393
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Ile Ser Ile Ser
            20                  25                  30

Pro Met Gly Trp Tyr Arg Gln Ala Pro Gly Lys Gln Arg Glu Leu Val
            35                  40                  45

Ala Ala Ile His Gly Ala Ser Thr Leu Tyr Ala Asp Ser Val Lys Gly
```

```
                50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Gly Asn Val Tyr Trp Gly Gln Gly
                100                 105                 110

Thr Gln Val Thr Val Ser Ser
            115

<210> SEQ ID NO 394
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Phe Ser Ile Thr
                20                  25                  30

Pro Met Gly Trp Tyr Arg Gln Ala Pro Gly Lys Gln Arg Glu Leu Val
            35                  40                  45

Ala Ala Ile His Gly Ala Ser Thr Leu Tyr Ala Asp Ser Val Lys Gly
        50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Gly Asn Val Tyr Trp Gly Gln Gly
                100                 105                 110

Thr Gln Val Thr Val Ser Ser
            115

<210> SEQ ID NO 395
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Thr Ser Ile Ser
                20                  25                  30

Pro Met Gly Trp Tyr Arg Gln Ala Pro Gly Lys Gln Arg Glu Leu Val
            35                  40                  45

Ala Ala Ile His Gly Phe Glu Thr Leu Tyr Ala Asp Ser Val Lys Gly
        50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Gly Asn Val Tyr Trp Gly Gln Gly
```

-continued

```
                100                 105                 110
Thr Gln Val Thr Val Ser Ser
        115

<210> SEQ ID NO 396
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Gln Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Phe Glu Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 397
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

Glu Val Gln Leu Val Glu Ser Gly Gly Gly Leu Val Gln Pro Gly Arg
1               5                   10                  15

Ser Leu Thr Leu Ser Cys Ala Ala Ser Thr Ser Asp Phe Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Phe Glu Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 398
<211> LENGTH: 119
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 398

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Asp Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Phe Gln Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 399
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Met Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Val Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 400
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Glu Val Gln Leu Val Glu Ser Gly Gly Gly Leu Val Gln Pro Gly Arg
1               5                   10                  15
```

Ser Leu Thr Leu Ser Cys Ala Ala Ser Thr Asn Ile Glu Ser Ile Ser
            20                  25                  30

Pro Met Gly Trp Tyr Arg Gln Ala Pro Gly Lys Gln Arg Glu Leu Val
            35                  40                  45

Ala Ala Ile His Gly Phe Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 401
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ser Ser
            20                  25                  30

Pro Met Gly Trp Tyr Arg Gln Ala Pro Gly Lys Gln Arg Glu Leu Val
            35                  40                  45

Ala Ala Ile His Gly Phe Lys Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Arg Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 402
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ser Ser
            20                  25                  30

Pro Met Gly Trp Tyr Arg Gln Ala Pro Gly Lys Gln Arg Glu Leu Val
            35                  40                  45

Ala Ala Ile His Gly Phe Ser Thr Leu Tyr Ala Asp Ser Val Lys Gly
    50                  55                  60

```
Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Gly Asn Val Tyr Trp Gly Gln Gly
                100                 105                 110

Thr Gln Val Thr Val Ser Ser
            115

<210> SEQ ID NO 403
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Glu Val Gln Leu Val Glu Ser Gly Gly Gly Leu Val Gln Pro Gly Arg
  1               5                  10                  15

Ser Leu Thr Leu Ser Cys Ala Ala Ser Thr Asn Ile Phe Ser Asn Ser
                 20                  25                  30

Pro Met Gly Trp Tyr Arg Gln Ala Pro Gly Lys Gln Arg Glu Leu Val
                 35                  40                  45

Ala Ala Ile His Gly Phe Ser Thr Leu Tyr Ala Asp Ser Val Lys Gly
             50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Gly Asn Val Tyr Trp Gly Gln Gly
                100                 105                 110

Thr Gln Val Thr Val Ser Ser
            115

<210> SEQ ID NO 404
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Glu Val Gln Leu Val Glu Ser Gly Gly Gly Leu Val Gln Pro Gly Arg
  1               5                  10                  15

Ser Leu Thr Leu Ser Cys Ala Ala Ser Thr Asn Ile Phe Ser Thr Ser
                 20                  25                  30

Pro Met Gly Trp Tyr Arg Gln Ala Pro Gly Lys Gln Arg Glu Leu Val
                 35                  40                  45

Ala Ala Ile His Gly Phe Ser Thr Ile Tyr Ala Asp Ser Val Lys Gly
             50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Gly Asn Val Tyr Trp Gly Gln Gly
                100                 105                 110
```

Thr Gln Val Thr Val Ser Ser
        115

<210> SEQ ID NO 405
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Thr Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Ile Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Leu Asn Val Tyr Trp Gly Gln Gly
            100                 105                 110

Thr Gln Val Thr Val Ser Ser
        115

<210> SEQ ID NO 406
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Glu Val Gln Leu Val Glu Ser Gly Gly Gly Leu Val Gln Pro Gly Arg
1               5                   10                  15

Ser Leu Thr Leu Ser Cys Val Ala Ser Thr Asn Ile Phe Ser Thr Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 407
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Asp Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Phe Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 408
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Gln Ser
            20                  25                  30

Pro Met Gly Trp Tyr Arg Gln Ala Pro Gly Lys Gln Arg Glu Leu Val
        35                  40                  45

Ala Ala Ile His Gly Asp Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Cys Trp Gly Gln Gly
            100                 105                 110

Thr Gln Val Thr Val Ser Ser
        115

<210> SEQ ID NO 409
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Glu Val Gln Leu Val Glu Ser Gly Gly Gly Leu Val Gln Pro Gly Arg
1               5                   10                  15

```
Ser Leu Thr Leu Ser Cys Ala Ala Ser Thr Asn Ile Phe Ser Gln Ser
            20                  25                  30

Pro Met Gly Trp Tyr Arg Gln Ala Pro Gly Lys Gln Arg Glu Leu Val
        35                  40                  45

Ala Ala Ile His Gly Lys Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Ser Asn Val Tyr Trp Gly Lys Gly
            100                 105                 110

Thr Gln Val Thr Val Ser Ser
            115
```

<210> SEQ ID NO 410
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

```
Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Arg Ser
            20                  25                  30

Pro Met Gly Trp Tyr Arg Gln Ala Pro Gly Lys Gln Arg Glu Leu Val
        35                  40                  45

Ala Ala Ile His Gly Glu Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Arg Tyr His Pro Gly Asn Val Tyr Trp Gly Gln Gly
            100                 105                 110

Thr Gln Val Thr Val Ser Ser
            115
```

<210> SEQ ID NO 411
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

```
Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Arg Ser
            20                  25                  30

Pro Met Gly Trp Tyr Arg Gln Ala Pro Gly Lys Gln Arg Glu Leu Val
        35                  40                  45

Ala Ala Ile His Gly Ile Ser Thr Leu Tyr Ala Asp Ser Val Lys Gly
    50                  55                  60
```

```
Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 412
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Phe Ser Arg Ser
             20                  25                  30

Pro Met Gly Trp Tyr Arg Gln Ala Pro Gly Lys Gln Arg Glu Leu Val
             35                  40                  45

Ala Ala Ile His Gly Ser Ser Thr Leu Tyr Ala Asp Ser Val Lys Gly
         50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 413
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Phe Ser Gly Ser
             20                  25                  30

Pro Met Gly Trp Tyr Arg Gln Ala Pro Gly Lys Gln Arg Glu Leu Val
             35                  40                  45

Ala Ala Ile His Gly Asn Ser Thr Leu Tyr Ala Asp Ser Val Lys Gly
         50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Gly Asn Val Tyr Trp Gly Gln Gly
            100                 105                 110
```

```
Thr Gln Val Thr Val Ser Ser
        115

<210> SEQ ID NO 414
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Glu Val Gln Leu Val Glu Ser Gly Gly Gly Leu Val Gln Pro Gly Arg
1               5                   10                  15

Ser Leu Thr Leu Ser Cys Ala Ala Ser Ser Asn Ile Phe Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 415
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Tyr
            20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Lys Asn Val Tyr Trp Gly Gln Gly
            100                 105                 110

Thr Gln Val Thr Val Ser Ser
        115

<210> SEQ ID NO 416
<211> LENGTH: 119
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 416

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Lys Ser
            20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 417
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Lys Ser
            20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 418
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Glu Phe Ser Ile Ser

```
                    20                  25                  30
Pro Met Gly Trp Tyr Arg Gln Ala Pro Gly Lys Gln Arg Glu Leu Val
            35                  40                  45

Ala Ala Ile His Gly Leu Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Ala Tyr His Pro Arg Asn Val Tyr Trp Gly Gln Gly
            100                 105                 110

Thr Gln Val Thr Val Ser Ser
        115
```

<210> SEQ ID NO 419
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

```
Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Glu Phe Ser Ile Ser
            20                  25                  30

Pro Met Gly Trp Tyr Arg Gln Ala Pro Gly Lys Gln Arg Glu Leu Val
            35                  40                  45

Ala Ala Ile His Gly Glu Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115
```

<210> SEQ ID NO 420
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

```
Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Pro Ser Ile Ser
            20                  25                  30

Pro Met Gly Trp Tyr Arg Gln Ala Pro Gly Lys Gln Arg Glu Leu Val
            35                  40                  45

Ala Ala Ile His Gly Glu Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
```

```
                65                  70                  75                  80
Met Asn Ser Leu Arg Pro Glu Asp Thr Ala Leu Tyr Tyr Cys Asn Lys
                    85                  90                  95

Val Pro Trp Gly Asp Tyr His Pro Arg Asn Val Ala Trp Gly Gln Gly
                100                 105                 110

Thr Gln Val Thr Val Ser Ser
        115

<210> SEQ ID NO 421
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Pro Ser Ile Ser
                20                  25                  30

Pro Met Gly Trp Tyr Arg Gln Ala Pro Gly Lys Gln Arg Glu Leu Val
            35                  40                  45

Ala Ala Ile His Gly Ala Ser Thr Leu Tyr Ala Asp Ser Val Lys Gly
        50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                    85                  90                  95

Val Pro Trp Gly Asp Tyr His Pro Arg Asn Val Ala Trp Gly Gln Gly
                100                 105                 110

Thr Gln Val Thr Val Ser Ser
        115

<210> SEQ ID NO 422
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Pro Ser Ile Ser
                20                  25                  30

Pro Met Gly Trp Tyr Arg Gln Ala Pro Gly Lys Gln Arg Glu Leu Val
            35                  40                  45

Ala Ala Ile His Gly Glu Ser Thr Leu Tyr Ala Asp Ser Val Lys Gly
        50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                    85                  90                  95

Val Pro Trp Gly Asp Tyr His Pro Arg Asn Val Tyr Trp Gly Gln Gly
                100                 105                 110

Thr Gln Val Thr Val Ser Ser
```

115

<210> SEQ ID NO 423
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Pro Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Asp Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 424
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Thr Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Val Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Gln Trp Gly Gln Gly
            100                 105                 110

Thr Gln Val Thr Val Ser Ser
        115

<210> SEQ ID NO 425
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 425

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Pro Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Gln Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Gln Trp Gly Gln Gly
            100                 105                 110

Thr Gln Val Thr Val Ser Ser
        115

<210> SEQ ID NO 426
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Val Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Asp Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Ser Trp Gly Gln Gly
            100                 105                 110

Thr Gln Val Thr Val Ser Ser
        115

<210> SEQ ID NO 427
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Glu Val Gln Leu Val Glu Ser Gly Gly Gly Leu Val Gln Pro Gly Arg
1               5                   10                  15

Ser Leu Thr Leu Ser Cys Ala Ala Ser Ser Asn Ile Phe Ser Ile Ser
            20                  25                  30

```
Pro Met Gly Trp Tyr Arg Gln Ala Pro Gly Lys Gln Arg Glu Leu Val
        35                  40                  45

Ala Ala Ile His Gly Glu Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Arg Asn Val Thr Trp Gly Gln Gly
            100                 105                 110

Thr Gln Val Thr Val Ser Ser
        115
```

<210> SEQ ID NO 428
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

```
Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Asp Ser Ile Ser
                20                  25                  30

Pro Met Gly Trp Tyr Arg Gln Ala Pro Gly Lys Gln Arg Glu Leu Val
        35                  40                  45

Ala Ala Ile His Gly Glu Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Arg Asn Val Thr Trp Gly Gln Gly
            100                 105                 110

Thr Gln Val Thr Val Ser Ser
        115
```

<210> SEQ ID NO 429
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

```
Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Asp Ser Ile Ser
                20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80
```

```
Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Thr Trp Gly Gln Gly
            100                 105                 110

Thr Gln Val Thr Val Ser Ser
        115

<210> SEQ ID NO 430
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Arg Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Val Trp Gly Gln Gly
            100                 105                 110

Thr Gln Val Thr Val Ser Ser
        115

<210> SEQ ID NO 431
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Thr Ser Ile Ser
            20                  25                  30

Pro Met Gly Trp Tyr Arg Gln Ala Pro Gly Lys Gln Arg Glu Leu Val
        35                  40                  45

Ala Ala Ile Ser Gly Phe Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Glu
                85                  90                  95

Val Pro Trp Gly Asp Tyr His Pro Arg Asn Val Tyr Trp Gly Gln Gly
            100                 105                 110

Thr Gln Val Thr Val Ser Ser
        115
```

<210> SEQ ID NO 432
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Thr Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Glu Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 433
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Thr Ser Val Ser
            20                  25                  30

Pro Met Gly Trp Tyr Arg Gln Ala Pro Gly Lys Gln Arg Glu Leu Val
        35                  40                  45

Ala Ala Ile His Gly Pro Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Thr Asn Val Tyr Trp Gly Gln Gly
            100                 105                 110

Thr Gln Val Thr Val Ser Ser
        115

<210> SEQ ID NO 434
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Gly Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Gln Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
            85                  90                  95

Val Pro Trp Gly Asp Tyr His Pro Gln Asn Val Tyr Trp Gly Gln Gly
            100                 105                 110

Thr Gln Val Thr Val Ser Ser
        115

<210> SEQ ID NO 435
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Glu Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Lys Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
            85                  90                  95

Val Pro Trp Gly Asp Tyr His Pro Arg Arg Val Tyr Trp Gly Gln Gly
            100                 105                 110

Thr Gln Val Thr Val Ser Ser
        115

<210> SEQ ID NO 436
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Val Ser Ile Ser
            20                  25                  30

Pro Met Gly Trp Tyr Arg Gln Ala Pro Gly Lys Gln Arg Glu Leu Val
            35                  40                  45

Ala Ala Ile His Gly Asp Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Arg Arg Val Tyr Trp Gly Gln Gly
            100                 105                 110

Thr Gln Val Thr Val Ser Ser
            115

<210> SEQ ID NO 437
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Asp Ser Ile Ser
            20                  25                  30

Pro Met Gly Trp Tyr Arg Gln Ala Pro Gly Lys Gln Arg Glu Leu Val
            35                  40                  45

Ala Ala Ile His Gly Asn Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Arg Met Val Tyr Trp Gly Gln Gly
            100                 105                 110

Thr Gln Val Thr Val Ser Ser
            115

<210> SEQ ID NO 438
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Phe Met Ile Ser
            20                  25                  30

Pro Met Gly Trp Tyr Arg Gln Ala Pro Gly Lys Gln Arg Glu Leu Val
            35                  40                  45

Ala Ala Ile His Gly Asp Ser Thr Leu Tyr Ala Asp Ser Val Lys Gly
 50                  55                  60

Arg Phe Thr Ile Ser Arg Asp Asn Ala Lys Asn Ser Ile Tyr Leu Gln
 65                  70                  75                  80

```
Met Asn Ser Leu Arg Pro Glu Asp Thr Ala Leu Tyr Tyr Cys Asn Lys
                85                  90                  95

Val Pro Trp Gly Arg Tyr His Pro Arg Asn Val Tyr Trp Gly Gln Gly
            100                 105                 110

Thr Gln Val Thr Val Ser Ser
        115

<210> SEQ ID NO 439
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Arg Ile Ser
            20                  25                  30

Pro Met Gly Trp Tyr Arg Gln Ala Pro Gly Lys Gln Arg Glu Leu Val
        35                  40                  45

Ala Ala Ile His Gly Asp Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Arg Tyr His Pro Arg Asn Val Tyr Trp Gly Gln Gly
            100                 105                 110

Thr Gln Val Thr Val Ser Ser
        115

<210> SEQ ID NO 440
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Asp Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Glu Tyr His Pro Arg Asn Val Tyr Trp Gly Gln Gly
            100                 105                 110

Thr Gln Val Thr Val Ser Ser
        115
```

<210> SEQ ID NO 441
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 441

```
Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Asp Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Lys Tyr His Pro Arg Asn Val Tyr Trp Gly Gln Gly
            100                 105                 110

Thr Gln Val Thr Val Ser Ser
        115
```

<210> SEQ ID NO 442
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 442

```
Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Glu Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Ser Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Arg Tyr His Pro Arg Asn Val Tyr Trp Gly Gln Gly
            100                 105                 110

Thr Gln Val Thr Val Ser Ser
        115
```

<210> SEQ ID NO 443
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 443

Glu Val Gln Leu Val Glu Ser Gly Gly Leu Val Gln Pro Gly Arg
1               5                   10                  15

Ser Leu Thr Leu Ser Cys Ala Ala Ser Thr Asn Ile Glu Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Asn Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Arg Tyr His Pro Arg Asn Val Tyr Trp Gly Gln Gly
            100                 105                 110

Thr Gln Val Thr Val Ser Ser
            115

<210> SEQ ID NO 444
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Glu Val Gln Leu Val Glu Ser Gly Gly Leu Val Gln Pro Gly Arg
1               5                   10                  15

Ser Leu Thr Leu Ser Cys Ala Ala Ser Thr Asn Ile Ser Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Tyr Tyr His Pro Arg Asn Val Tyr Trp Gly Gln Gly
            100                 105                 110

Thr Gln Val Thr Val Ser Ser
            115

<210> SEQ ID NO 445
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

Glu Val Gln Leu Val Glu Ser Gly Gly Leu Val Gln Pro Gly Arg
1               5                   10                  15

Ser Leu Thr Leu Ser Cys Ala Ala Ser Thr Asn Ile Ser Ser Ile Ser
            20                  25                  30

Pro Met Gly Trp Tyr Arg Gln Ala Pro Gly Lys Gln Arg Glu Leu Val

```
                35                  40                  45
Ala Ala Ile His Gly His Ser Thr Leu Tyr Ala Asp Ser Val Lys Gly
         50                  55                  60
Arg Phe Thr Ile Ser Arg Asp Asn Ala Lys Asn Ser Ile Tyr Leu Gln
65                  70                  75                  80
Met Asn Ser Leu Arg Pro Glu Asp Thr Ala Leu Tyr Tyr Cys Asn Lys
                 85                  90                  95
Val Pro Trp Gly Arg Tyr His Pro Arg Asn Val Tyr Trp Gly Gln Gly
                100                 105                 110
Thr Gln Val Thr Val Ser Ser
            115

<210> SEQ ID NO 446
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Glu Val Gln Leu Val Glu Ser Gly Gly Gly Leu Val Gln Pro Gly Arg
1               5                  10                  15
Ser Leu Thr Leu Ser Cys Ala Ala Ser Thr Asn Ile Ser Ser Ile Ser
            20                  25                  30
Pro Met Gly Trp Tyr Arg Gln Ala Pro Gly Lys Gln Arg Glu Leu Val
        35                  40                  45
Ala Ala Ile His Gly Phe Ser Thr Val Tyr Ala Asp Ser Val Lys Gly
    50                  55                  60
Arg Phe Thr Ile Ser Arg Asp Asn Ala Lys Asn Ser Ile Tyr Leu Gln
65                  70                  75                  80
Met Asn Ser Leu Arg Pro Glu Asp Thr Ala Leu Tyr Tyr Cys Asn Lys
                 85                  90                  95
Val Pro Trp Gly Arg Tyr His Pro Arg Asn Val Tyr Trp Gly Gln Gly
                100                 105                 110
Thr Gln Val Thr Val Ser Ser
            115

<210> SEQ ID NO 447
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Glu Val Gln Leu Val Glu Ser Gly Gly Gly Leu Val Gln Pro Gly Arg
1               5                  10                  15
Ser Leu Thr Leu Ser Cys Ala Ala Ser Thr Asn Ile Phe Ser Ile Arg
            20                  25                  30
Pro Met Gly Trp Tyr Arg Gln Ala Pro Gly Lys Gln Arg Glu Leu Val
        35                  40                  45
Ala Ala Ile His Gly Phe Ser Thr Val Tyr Ala Asp Ser Val Lys Gly
    50                  55                  60
Arg Phe Thr Ile Ser Arg Asp Asn Ala Lys Asn Ser Ile Tyr Leu Gln
65                  70                  75                  80
Met Asn Ser Leu Arg Pro Glu Asp Thr Ala Leu Tyr Tyr Cys Asn Lys
```

-continued

```
                    85                  90                  95

Val Pro Trp Gly Asp Tyr His Pro Arg Asn Val Tyr Trp Gly Gln Gly
                100                 105                 110

Thr Gln Val Thr Val Ser Ser
        115

<210> SEQ ID NO 448
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Tyr
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Tyr Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Ser Tyr His Pro Arg Asn Val Tyr Trp Gly Gln Gly
                100                 105                 110

Thr Gln Val Thr Val Ser Ser
        115

<210> SEQ ID NO 449
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Asn Ile Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Tyr Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Arg Tyr His Pro Arg Asn Val Tyr Trp Gly Gln Gly
                100                 105                 110

Thr Gln Val Thr Val Ser Ser
        115
```

```
<210> SEQ ID NO 450
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ser Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Trp Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Arg Tyr His Pro Arg Asn Val Tyr Trp Gly Gln Gly
            100                 105                 110

Thr Gln Val Thr Val Ser Ser
        115

<210> SEQ ID NO 451
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Ser Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Phe Asp Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 452
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452
```

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Asn
            20                  25                  30

Pro Met Gly Trp Tyr Arg Gln Ala Pro Gly Lys Gln Arg Glu Leu Val
        35                  40                  45

Ala Ala Ile His Gly Phe Asp Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Arg Asn Val Ser Trp Gly Gln Gly
            100                 105                 110

Thr Gln Val Thr Val Ser Ser
            115

<210> SEQ ID NO 453
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Thr
            20                  25                  30

Pro Met Gly Trp Tyr Arg Gln Ala Pro Gly Lys Gln Arg Glu Leu Val
        35                  40                  45

Ala Ala Ile His Gly Arg Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Ser Tyr His Pro Arg Asn Val Tyr Trp Gly Gln Gly
            100                 105                 110

Thr Gln Val Thr Val Ser Ser
            115

<210> SEQ ID NO 454
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Thr
            20                  25                  30

Pro Met Gly Trp Tyr Arg Gln Ala Pro Gly Lys Gln Arg Glu Leu Val
        35                  40                  45

Ala Ala Ile His Gly Thr Ser Thr Leu Tyr Ala Asp Ser Val Lys Gly
            50                   55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Arg Tyr His Pro Arg Asn Val Tyr Trp Gly Gln Gly
                100                 105                 110

Thr Gln Val Thr Val Ser Ser
            115

<210> SEQ ID NO 455
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Phe Ser Ile Thr
            20                  25                  30

Pro Met Gly Trp Tyr Arg Gln Ala Pro Gly Lys Gln Arg Glu Leu Val
         35                  40                  45

Ala Ala Ile His Gly Glu Ser Thr Leu Tyr Ala Asp Ser Val Lys Gly
            50                   55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Arg Tyr His Pro Arg Asn Val Tyr Trp Gly Gln Gly
                100                 105                 110

Thr Gln Val Thr Val Ser Ser
            115

<210> SEQ ID NO 456
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Glu Val Gln Leu Val Glu Ser Gly Gly Gly Leu Val Gln Pro Gly Arg
 1               5                  10                  15

Ser Leu Thr Leu Ser Cys Ala Ala Ser Thr Asn Ile Phe Ser Ile Thr
            20                  25                  30

Pro Met Gly Trp Tyr Arg Gln Ala Pro Gly Lys Gln Arg Glu Leu Val
         35                  40                  45

Ala Ala Ile His Gly Glu Ser Thr Leu Tyr Ala Asp Ser Val Lys Gly
            50                   55                  60

Arg Phe Thr Ile Ser Arg Asp Asn Ala Lys Asn Ser Ile Tyr Leu Gln
 65                  70                  75                  80

Met Asn Ser Leu Arg Pro Glu Asp Thr Ala Leu Tyr Tyr Cys Asn Lys
                 85                  90                  95

Val Pro Trp Gly Asp Tyr His Pro Arg Asp Val Tyr Trp Gly Gln Gly
                100                 105                 110

Thr Gln Val Thr Val Ser Ser
        115

<210> SEQ ID NO 457
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Thr Ser
            20                  25                  30

Pro Tyr Gly Trp Tyr Arg Gln Ala Pro Gly Lys Gln Arg Glu Leu Val
        35                  40                  45

Ala Ala Ile His Gly Phe Ser Thr Ile Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
                100                 105                 110

Thr Gln Val Thr Val Ser Ser
        115

<210> SEQ ID NO 458
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Thr Ser
            20                  25                  30

Pro Gly Gly Trp Tyr Arg Gln Ala Pro Gly Lys Gln Arg Glu Leu Val
        35                  40                  45

Ala Ala Ile His Gly Phe Ser Thr Ile Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
                100                 105                 110

Thr Gln Val Thr Val Ser Ser
        115

<210> SEQ ID NO 459

<211> LENGTH: 119
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 459

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Thr
            20                  25                  30

Pro Tyr Gly Trp Tyr Arg Gln Ala Pro Gly Lys Gln Arg Glu Leu Val
        35                  40                  45

Ala Ala Ile His Gly Ala Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 460
<211> LENGTH: 119
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 460

Glu Val Gln Leu Val Glu Ser Gly Gly Gly Leu Val Gln Pro Gly Arg
1               5                   10                  15

Ser Leu Thr Leu Ser Cys Ala Ala Ser Thr Asn Ile Phe Ser Ile Thr
            20                  25                  30

Pro Gly Gly Trp Tyr Arg Gln Ala Pro Gly Lys Gln Arg Glu Leu Val
        35                  40                  45

Ala Ala Ile His Gly Ala Ser Thr Leu Tyr Ala Asp Ser Val Lys Gly
    50                  55                  60

Arg Phe Thr Ile Ser Arg Asp Asn Ala Lys Asn Ser Ile Tyr Leu Gln
65                  70                  75                  80

Met Asn Ser Leu Arg Pro Glu Asp Thr Ala Leu Tyr Tyr Cys Asn Lys
                85                  90                  95

Val Pro Trp Gly Asp Tyr His Pro Gly Asn Val Tyr Trp Gly Gln Gly
            100                 105                 110

Thr Gln Val Thr Val Ser Ser
        115

<210> SEQ ID NO 461
<211> LENGTH: 25
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 461

Glu Val Gln Leu Val Glu Ser Gly Gly Gly Leu Val Gln Pro Gly Arg
1               5                   10                  15

Ser Leu Thr Leu Ser Cys Ala Ala Ser
            20                  25

<210> SEQ ID NO 462
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Glu Val Gln Leu Val Glu Ser Gly Gly Gly Leu Val Gln Pro Gly Arg
1               5                   10                  15

Ser Leu Thr Leu Ser Cys Val Ala Ser
            20                  25

<210> SEQ ID NO 463
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Trp Tyr Arg Gln Ala Pro Gly Lys Gln Arg Glu Leu Val Ala
1               5                   10

<210> SEQ ID NO 464
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Gly Arg Phe Thr Ile Ser Arg Asp Asn Ala Lys Asn Ser Ile Tyr Leu
1               5                   10                  15

Gln Met Asn Ser Leu Arg Pro Glu Asp Thr Ala Leu Tyr Tyr Cys Asn
            20                  25                  30

Lys

<210> SEQ ID NO 465
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

Gly Arg Phe Thr Ile Ser Arg Asp Asn Ala Lys Asn Ser Ile Tyr Leu
1               5                   10                  15

Gln Met Asn Ser Leu Arg Pro Glu Asp Thr Ala Leu Tyr Tyr Cys Asn
            20                  25                  30

Glu

<210> SEQ ID NO 466
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 466

Trp Gly Gln Gly Thr Gln Val Thr Val Ser Ser
1               5                   10

<210> SEQ ID NO 467
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Trp Gly Lys Gly Thr Gln Val Thr Val Ser Ser
1               5                   10

<210> SEQ ID NO 468
<211> LENGTH: 184
<212> TYPE: PRT
<213> ORGANISM: Homo sapiens

<400> SEQUENCE: 468

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 469
<211> LENGTH: 185
<212> TYPE: PRT
<213> ORGANISM: Mus sp.

<400> SEQUENCE: 469

Met Ala Gln Gln Cys Phe His Ser Glu Tyr Phe Asp Ser Leu Leu His
1               5                   10                  15
```

```
Ala Cys Lys Pro Cys His Leu Arg Cys Ser Asn Pro Ala Thr Cys
            20                  25                  30

Gln Pro Tyr Cys Asp Pro Ser Val Thr Ser Ser Val Lys Gly Thr Tyr
        35                  40                  45

Thr Val Leu Trp Ile Phe Leu Gly Leu Thr Leu Val Leu Ser Leu Ala
 50                  55                  60

Leu Phe Thr Ile Ser Phe Leu Leu Arg Lys Met Asn Pro Glu Ala Leu
 65                  70                  75                  80

Lys Asp Glu Pro Gln Ser Pro Gly Gln Leu Asp Gly Ser Ala Gln Leu
                    85                  90                  95

Asp Lys Ala Asp Thr Glu Leu Thr Arg Ile Arg Ala Gly Asp Asp Arg
                100                 105                 110

Ile Phe Pro Arg Ser Leu Glu Tyr Thr Val Glu Glu Cys Thr Cys Glu
                115                 120                 125

Asp Cys Val Lys Ser Lys Pro Lys Gly Asp Ser Asp His Phe Phe Pro
            130                 135                 140

Leu Pro Ala Met Glu Glu Gly Ala Thr Ile Leu Val Thr Thr Lys Thr
145                 150                 155                 160

Gly Asp Tyr Gly Lys Ser Ser Val Pro Thr Ala Leu Gln Ser Val Met
                165                 170                 175

Gly Met Glu Lys Pro Thr His Thr Arg
                180                 185

<210> SEQ ID NO 470
<211> LENGTH: 183
<212> TYPE: PRT
<213> ORGANISM: Macaca fascicularis

<400> SEQUENCE: 470

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
                20                  25                  30

Pro Leu Thr Cys Gln Arg Tyr Cys Asn Ala Ser Met Thr Asn Ser Val
        35                  40                  45

Lys Gly Met Asn Ala Ile Leu Trp Thr Cys Leu Gly Leu Ser Leu Ile
 50                  55                  60

Ile Ser Leu Ala Val Phe Val Leu Thr Phe Leu Leu Arg Lys Met Ser
 65                  70                  75                  80

Ser Glu Pro Leu Lys Asp Glu Phe Lys Asn Thr Gly Ser Gly Leu Leu
                85                  90                  95

Gly Met Ala Asn Ile Asp Leu Glu Lys Gly Arg Thr Gly Asp Glu Ile
                100                 105                 110

Val Leu Pro Arg Gly Leu Glu Tyr Thr Val Glu Glu Cys Thr Cys Glu
                115                 120                 125

Asp Cys Ile Lys Asn Lys Pro Lys Val Asp Ser Asp His Cys Phe Pro
            130                 135                 140

Leu Pro Ala Met Glu Glu Gly Ala Thr Ile Leu Val Thr Thr Lys Thr
145                 150                 155                 160

Asn Asp Tyr Cys Asn Ser Leu Ser Ala Ala Leu Ser Val Thr Glu Ile
                165                 170                 175

Glu Lys Ser Ile Ser Ala Arg
                180

<210> SEQ ID NO 471
```

-continued

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 471

His His His His His His
1               5

<210> SEQ ID NO 472
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Gln Val Gln Leu Val Glu Ser Gly Gly Gly Leu Val Gln Pro Gly Glu
1               5                   10                  15

Ser Leu Arg Leu Ser Cys Ala Ala Ser Thr Asn Ile Phe Ser Ile Ser
            20                  25                  30

Pro Met Gly Trp Tyr Arg Gln Ala Pro Gly Lys Gln Arg Glu Leu Val
        35                  40                  45

Ala Ala Ile His Gly Phe Ser Thr Leu Tyr Ala Asp Ser Val Lys Gly
    50                  55                  60

Arg Phe Thr Ile Ser Arg Asp Asn Ala Lys Asn Thr Ile Tyr Leu Gln
65                  70                  75                  80

Met Asn Ser Leu Lys Pro Glu Asp Thr Ala Val Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser
        115

<210> SEQ ID NO 473
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Thr Asn Ile Phe Ser Ile Ser Pro Met Gly
1               5                   10

<210> SEQ ID NO 474
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Ala Ile His Gly Phe Ser Thr Leu Tyr Ala Asp Ser Val Lys
1               5                   10

<210> SEQ ID NO 475
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 475

Val Pro Trp Gly Asp Tyr His Pro Arg Asn Val Tyr
1               5                   10
```

B CELL MATURATION ANTIGEN BINDING PROTEINS

CROSS-REFERENCE

This application is a divisional application of U.S. patent application Ser. No. 16/159,545, filed Oct. 12, 2018, and claims the benefit of U.S. Provisional Application No. 62/572,375 filed Oct. 13, 2017 all of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Oct. 11, 2018, is named 47517-722_201_SL.txt and is 232,688 bytes in size.

BACKGROUND OF THE INVENTION

Cancer is the second leading cause of human death next to coronary disease. Worldwide, millions of people die from cancer every year. In the United States alone, cancer causes the death of well over a half-million people each year, with some 1.4 million new cases diagnosed per year. While deaths from heart disease have been declining significantly, those resulting from cancer generally are on the rise. In the early part of the next century, cancer is predicted to become the leading cause of death.

Moreover, even for those cancer patients that initially survive their primary cancers, common experience has shown that their lives are dramatically altered. Many cancer patients experience strong anxieties driven by the awareness of the potential for recurrence or treatment failure. Many cancer patients experience significant physical debilitations following treatment.

Generally speaking, the fundamental problem in the management of the deadliest cancers is the lack of effective and non-toxic systemic therapies. Cancer is a complex disease characterized by genetic mutations that lead to uncontrolled cell growth. Cancerous cells are present in all organisms and, under normal circumstances, their excessive growth is tightly regulated by various physiological factors.

SUMMARY OF THE INVENTION

The present disclosure provides single domain B cell maturation antigen (BCMA) binding proteins which can be used for diagnosing and treating indications correlated to the expression of BCMA.

Provided herein is a single domain B cell maturation agent (BCMA) binding protein, comprising complementarity determining regions CDR1, CDR2, and CDR3, wherein (a) the amino acid sequence of CDR1 is as set forth in $X_1X_2X_3X_4X_5X_6X_7PX_8G$ (SEQ ID NO: 1), wherein $X_1$ is T or S; $X_2$ is N, D, or S; $X_3$ is I, D, Q, H, V, or E; $X_4$ is F, S, E, A, T, M, V, I, D, Q, P, R, or G; $X_5$ is S, M, R, or N; $X_6$ is I, K, S, T, R, E, D, N, V, H, L, A, Q, or G; $X_7$ is S, T, Y, R, or N; and $X_8$ is M, G, or Y; (b) the amino acid sequence of CDR2 is as set forth in $AIX_9GX_{10}X_{11}TX_{12}YADSVK$ (SEQ ID NO: 2), wherein $X_9$ is H, N, or S; $X_{10}$ is F, G, K, R, P, D, Q, H, E, N, T, S, A, I, L, or V; $X_{11}$ is S, Q, E, T, K, or D; and $X_{12}$ is L, V, I, F, Y, or W; and (c) the amino acid sequence of CDR3 is as set forth in $VPWGX_{13}YHPX_{14}X_{15}VX_{16}$ (SEQ ID NO: 3), wherein $X_{13}$ is D, I, T, K, R, A, E, S, or Y; $X_{14}$ is R, G, L, K, T, Q, S, or N; $X_{15}$ is N, K, E, V, R, M, or D; and $X_{16}$ is Y, A, V, K, H, L, M, T, R, Q, C, S, or N.

In one embodiment, the CDR1 does not comprise an amino acid sequence of SEQ ID NO: 473. In one embodiment, the CDR2 does not comprise an amino acid sequence of SEQ ID NO: 474. In one embodiment, the CDR3 does not comprise an amino acid sequence of SEQ ID NO: 475. In one embodiment, the CDR1 and CDR2 do not comprise amino acid sequences of SEQ ID NO: 473 and 474, respectively. In one embodiment, the CDR1 and CDR3 do not comprise amino acid sequences of SEQ ID NO: 473 and 475, respectively. In one embodiment, the CDR2 and CDR3 do not comprise amino acid sequences of SEQ ID NO: 474 and 475, respectively. In one embodiment, the CDR1, CDR2 and CDR3 do not comprise amino acid sequences of SEQ ID NO: 473, 474 and 475, respectively.

Provided herein is a single domain BCMA binding protein wherein said protein comprises the following formula: f1-r1-f2-r2-f3-r3-f4, wherein, r1 is SEQ ID NO: 1; r2 is SEQ ID NO: 2; and r3 is SEQ ID NO: 3; and wherein f1, f2, f3 and f4 are framework residues selected so that said protein is from about eighty percent (80%) to about 99% identical to the amino acid sequence set forth in SEQ ID NO: 346 or 472. Provided herein is a single domain BCMA binding protein wherein said protein comprises the following formula: f1-r1-f2-r2-f3-r3-f4, wherein, r1 is SEQ ID NO: 1; r2 is SEQ ID NO: 2; and r3 is SEQ ID NO: 3; and wherein f1, f2, f3 and f4 are framework residues selected so that said protein is from about 80% to about 90% identical to the amino acid sequence set forth in SEQ ID NO: 346 or 472. In one embodiment, the amino acid sequence of the single domain BCMA binding protein does not comprise SEQ ID NO: 472.

In some non-limiting examples, r1 comprises an amino acid sequence set forth as any one of SEQ ID NOS: 4-117.

In some non-limiting examples, r2 comprises an amino acid sequence set forth as any one of SEQ ID NO 118-231.

In some non-limiting examples, r3 comprises an amino acid sequence set forth as any one of SEQ ID NOS: 232-345.

In other non-limiting examples, the protein comprises an amino sequence set forth as any one of SEQ ID NOS: 346-460.

In a single domain BCMA binding protein, f1 can comprise SEQ ID NO: 461 or 462.

In a single domain BCMA binding protein, f2 can comprise SEQ ID NO: 463.

In a single domain BCMA binding protein, f3 can comprise SEQ ID NO: 464 or 465.

In a single domain BCMA binding protein, wherein f4 can comprise SEQ ID NO: 466 or 467.

In one non-limiting example, r1 comprises SEQ ID NO: 76, 114, 115, 116 or 117. In one non-limiting example, r1 comprises SEQ ID NO: 76.

In one non-limiting example, r1 comprises SEQ ID NO: 76, r2 is SEQ ID NO: 190, and r3 is SEQ ID NO: 304.

In one non-limiting example, r1 comprises SEQ ID NO: 114, r2 comprises SEQ ID NO: 228 and r3 comprises SEQ ID NO: 342.

In one non-limiting example, r1 comprises SEQ ID NO: 115, r2 comprises SEQ ID NO: 229 and r3 comprises SEQ ID NO: 343.

In one non-limiting example, r1 comprises SEQ ID NO: 117, r2 comprises SEQ ID NO: 231 and r3 comprises SEQ ID NO: 345.

In one non-limiting example, r1 comprises SEQ ID NO: 116, r2 comprises SEQ ID NO: 230 and r3 comprises SEQ ID NO: 344.

One embodiment provides a single domain B cell maturation agent (BCMA) binding protein, comprising complementarity determining regions CDR1, CDR2, and CDR3, wherein CDR1 comprises an amino acid sequence set forth as any one of SEQ ID NOS: 4-117, CDR2 comprises an amino acid sequence set forth as any one of SEQ ID NOS: 118-231, and CDR3 comprises an amino acid sequence set forth as any one of SEQ ID NOS: 232-345.

A single domain BCMA binding protein can have an elimination half-time of at least 12 hours, at least 20 hours, at least 25 hours, at least 30 hours, at least 35 hours, at least 40 hours, at least 45 hours, at least 50 hours, at least 100 hours or more. In some embodiments, the single domain BCMA binding protein further comprises a Fc domain. In some embodiments, the single domain BCMA binding protein further comprises an anti-cancer agent.

Provided herein is a single domain BCMA binding protein parental llama anti-BCMA 253BH10 SEQ ID NO: 472 or a humanized version of this llama sequence, BH2T, SEQ ID NO 346, wherein one or more amino acid residues selected from amino acid positions 26, 27, 28, 29, 30, 31, 32 and 34 of CDR1; positions 52, 54, 55 and 57 of CDR2; and positions 101, 105, 106 and 108 of CDR3 are substituted, wherein amino acid position 26, if substituted, is substituted with S; amino acid position 27, if substituted, is substituted with D or S; amino acid position 28, if substituted, is substituted with D, Q, H, V, or E; amino acid position 29, if substituted, is substituted with S, E, A, T, M, V, I, D, Q, P, R, or G; amino acid position 30, if substituted, is substituted with M, R, or N; amino acid position 31, if substituted, is substituted with K, S, T, R, E, D, N, V, H, L, A, Q, or G; amino acid position 32, if substituted, is substituted with T, Y, R, or N; amino acid position 34, if substituted, is substituted with G or Y; amino acid position 52, if substituted, is substituted with N or S; amino acid position 54, if substituted, is substituted with G, K, R, P, D, Q, H, E, N, T, S, A, I, L, or V; amino acid position 55, if substituted, is substituted with Q, E, T, K, or D; amino acid position 57, if substituted, is substituted with V, I, F, Y, or W; amino acid position 101, if substituted, is substituted with I, T, K, R, A, E, S, or Y; amino acid position 105, if substituted, is substituted with G, L, K, T, Q, S, or N; amino acid position 106, if substituted, is substituted with K, E, V, R, M, or D; and amino acid position 108, if substituted, is substituted with A, V, K, H, L, M, T, R, Q, C, S, or N.

Such a single domain BCMA binding protein can be human, humanized, affinity matured, or a combination thereof.

Provided herein is a method for the treatment or amelioration of a B cell lineage cancer in a subject in need thereof, comprising administering to the subject a single domain BCMA binding protein described herein. One embodiment provides a method for the treatment or amelioration of a B cell lineage cancer in a subject in need thereof, comprising administering to the subject a single domain BCMA binding protein complementarity determining regions CDR1, CDR2, and CDR3, wherein (a) the amino acid sequence of CDR1 is as set forth in X1X2X3X4X5X6X7PX8G (SEQ ID NO: 1), wherein X1 is T or S; X2 is N, D, or S; X3 is I, D, Q, H, V, or E; X4 is F, S, E, A, T, M, V, I, D, Q, P, R, or G; X5 is S, M, R, or N; X6 is I, K, S, T, R, E, D, N, V, H, L, A, Q, or G; X7 is S, T, Y, R, or N; and X8 is M, G, or Y; (b) the amino acid sequence of CDR2 is as set forth in AIX9GX10X11TX12YADSVK (SEQ ID NO: 2), wherein X9 is H, N, or S; X10 is F, G, K, R, P, D, Q, H, E, N, T, S, A, I, L, or V; X11 is S, Q, E, T, K, or D; and X12 is L, V, I, F, Y, or W; and (c) the amino acid sequence of CDR3 is as set forth in VPWGX13YHPX14X15VX16 (SEQ ID NO: 3), wherein X13 is D, I, T, K, R, A, E, S, or Y; X14 is R, G, L, K, T, Q, S, or N; X15 is N, K, E, V, R, M, or D; and X16 is Y, A, V, K, H, L, M, T, R, Q, C, S, or N; and wherein CDR1 is not SEQ ID NO: 473, wherein CDR2 is not SEQ ID NO: 474, and wherein CDR3 is not SEQ ID NO: 475.

Provided herein is a multispecific binding protein comprising the single domain BCMA binding protein described herein.

Provided herein is a method for the treatment or amelioration of a B cell lineage cancer in a subject in need thereof, comprising administering to the subject a multispecific binding protein described herein.

The B cell lineage cancer can be a primary cancer or a metastatic cancer.

A B cell lineage cancer to be treated with the methods described herein can be a multiple myeloma, a leukemia, a lymphoma.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 is an image of an SDS-PAGE of representative purified BCMA trispecific molecules. Lane 1: 01F07-M34Y TriTAC non-reduced; Lane 2:01F07-M34G-TriTAC non-reduced; Lane 3: 02B05 TriTAC non-reduced; Lane 4: 02G02-M34Y TriTAC non-reduced; Lane 5: 02G02 M34G TriTAC non-reduced; Lane 6: Broad Range SDS-PAGE Standard (Bio-Rad #1610317); Lane 7: 01F07-M34Y TriTAC non-reduced; Lane 8:01F07-M34G-TriTAC non-reduced; Lane 9: 02B05 TriTAC non-reduced; Lane 10: 02G02-M34Y TriTAC non-reduced; Lane 11: 02G02 M34G TriTAC non-reduced; and Lane 12: Broad Range SDS-PAGE Standard (Bio-Rad #1610317).

DETAILED DESCRIPTION OF THE INVENTION

Figure 1:
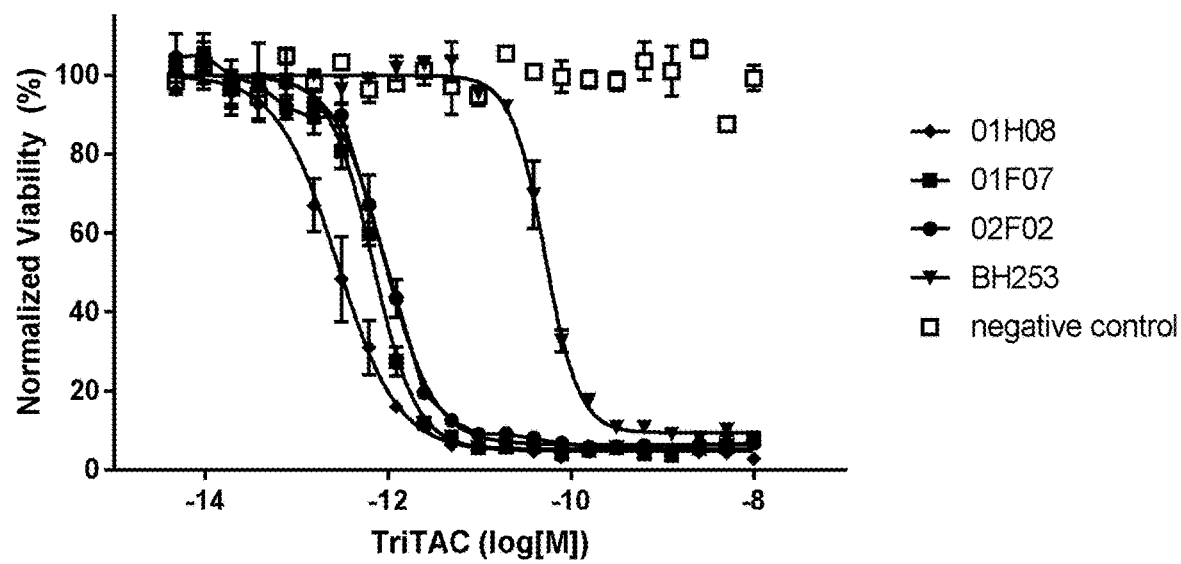
FIG. 1 illustrates the effect of exemplary BCMA targeting molecules (01H08, 01F07, 02F02, and BH253), containing an anti-BCMA binding protein according to the present disclosure in killing of EJM cells that express BCMA compared to a negative control.
Figure 3A:
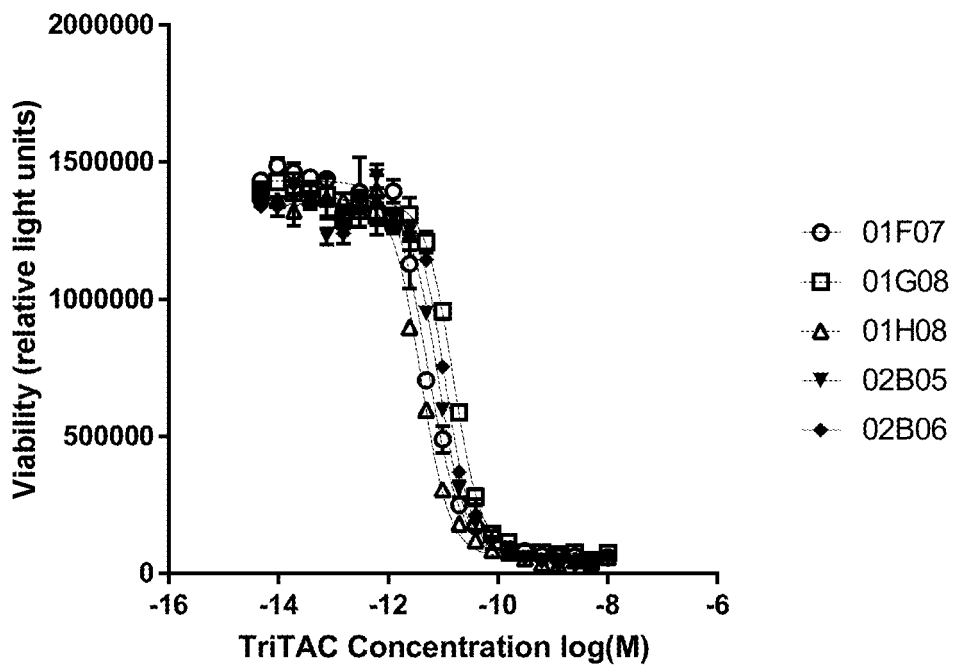
FIGS. 3A-3I illustrate the effect of exemplary BCMA trispecific targeting molecules containing an anti-BCMA binding protein according to the present disclosure in killing of Jeko1 (FIGS. 3A-3C), MOLP-8 (FIGS. 3D-3F) or OPM-2 (FIGS. 3G-3I) cells that express BCMA compared to a negative control.
Figure 3B:
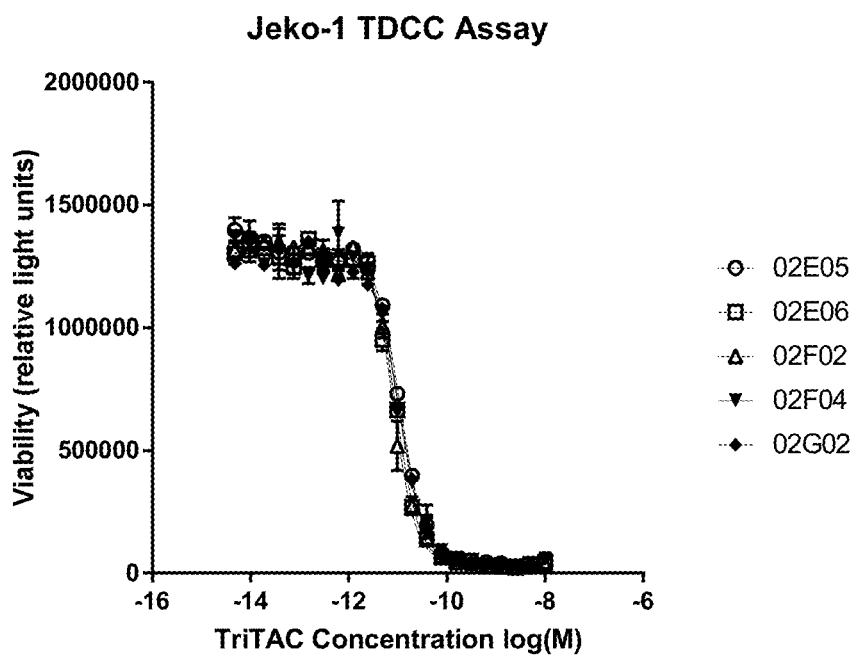
Figure 3C:
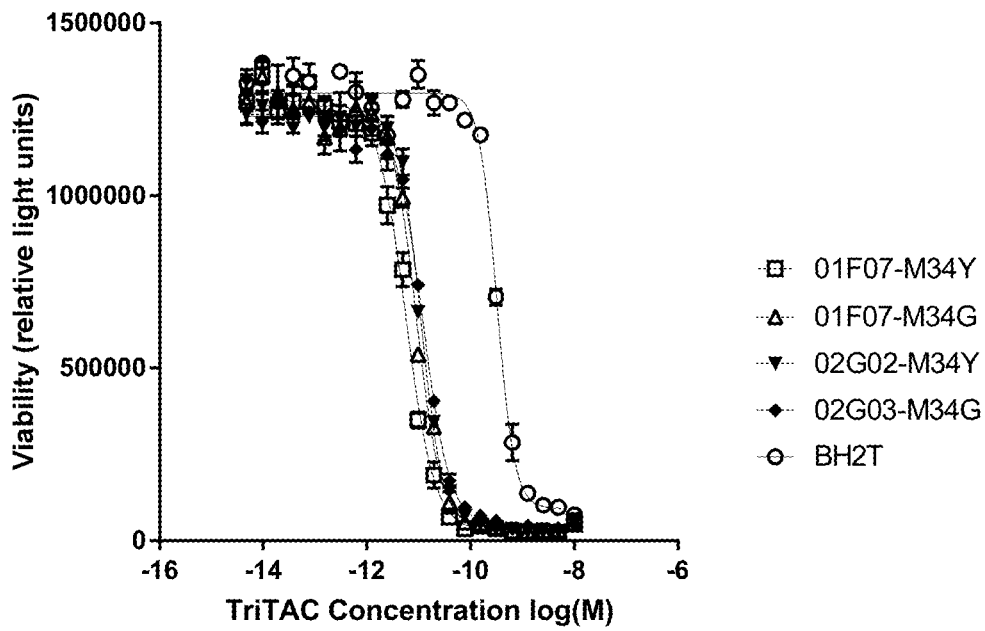
Figure 3D:
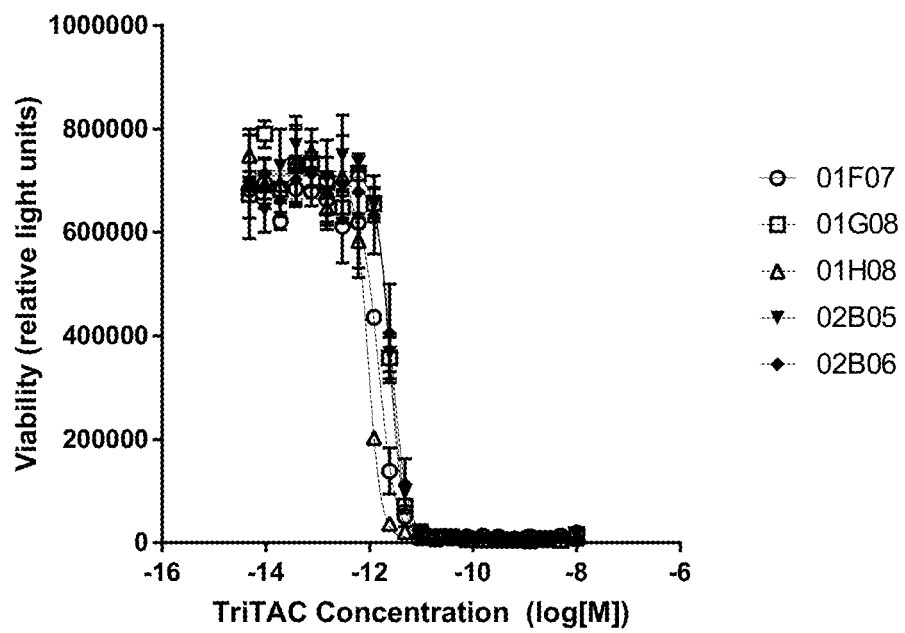
Figure 3E:
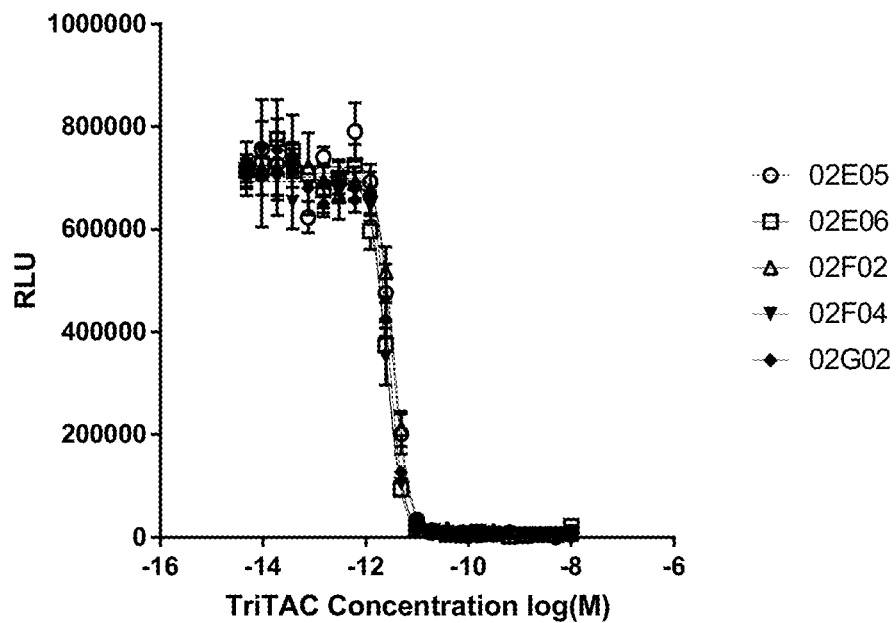
Figure 3F:
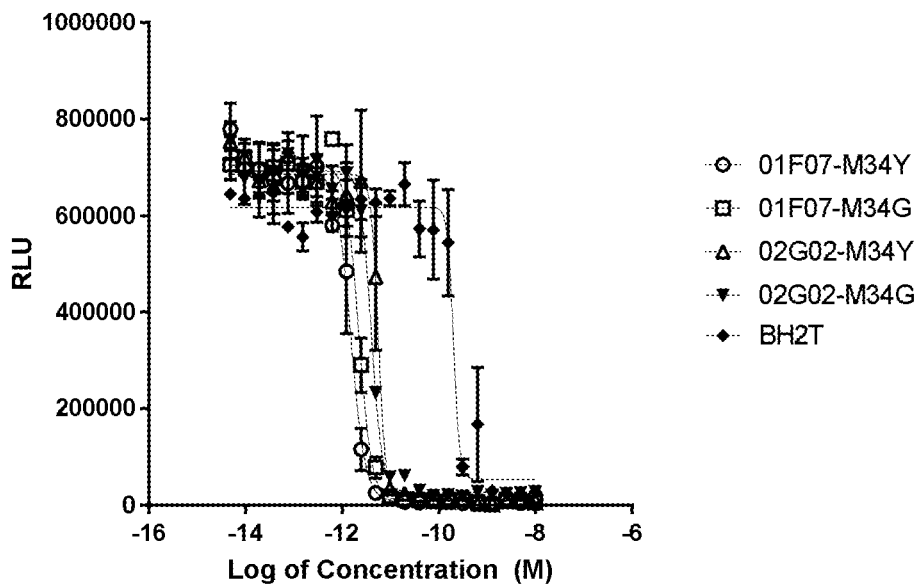
Figure 3G:
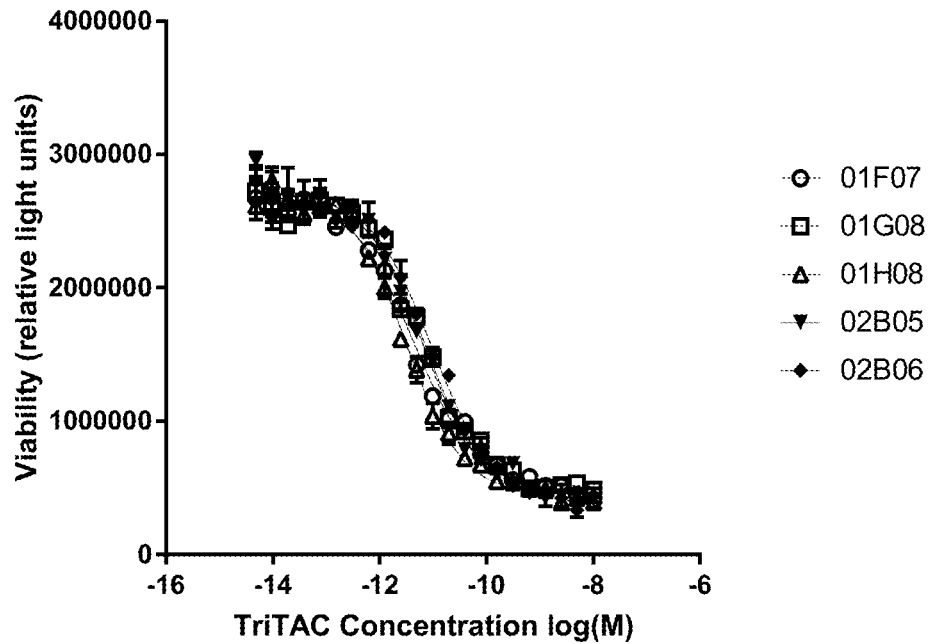
Figure 3H:
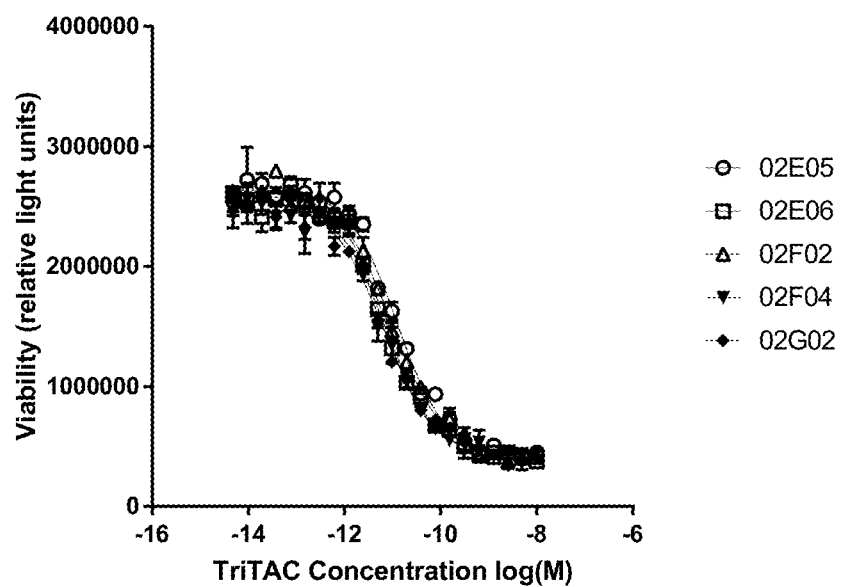
Figure 3I:
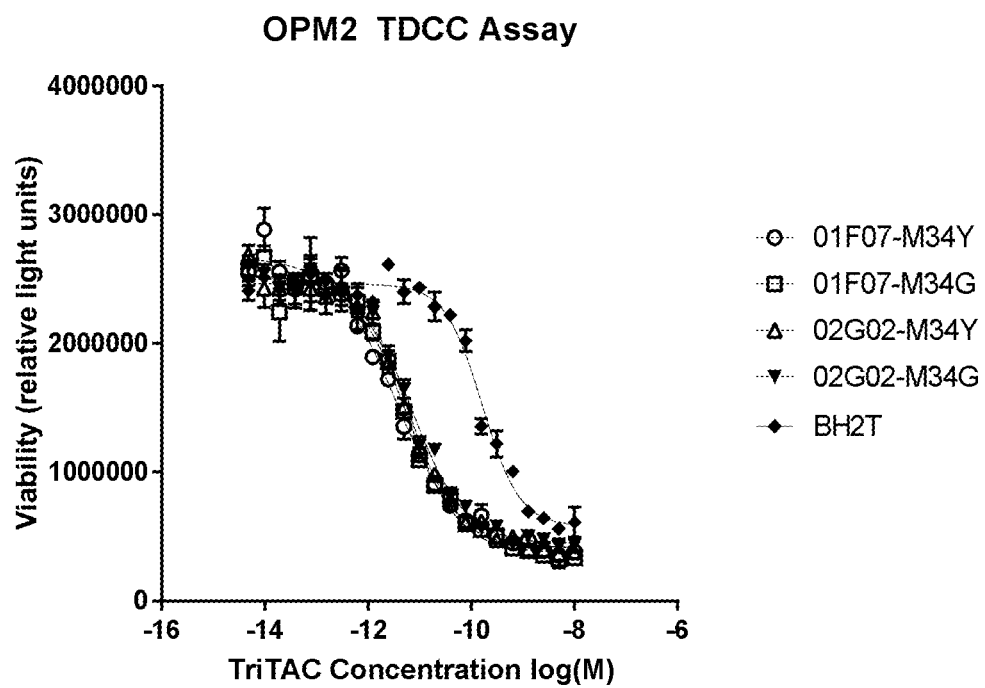
Figure 4A:
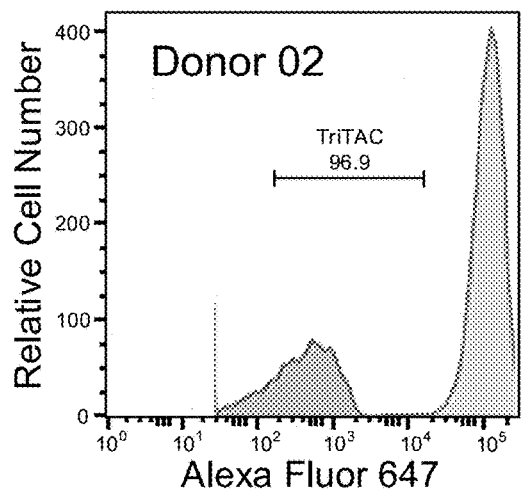
FIGS. 4A-4D illustrate binding of an exemplary BCMA trispecific targeting protein containing a BCMA binding protein of this disclosure (02B05) to purified T Cells from four different human donors, donor 02 (FIG. 4A), donor 35 (FIG. 4B), donor 81 (FIG. 4C), donor 86 (FIG. 4D).
Figure 4B:
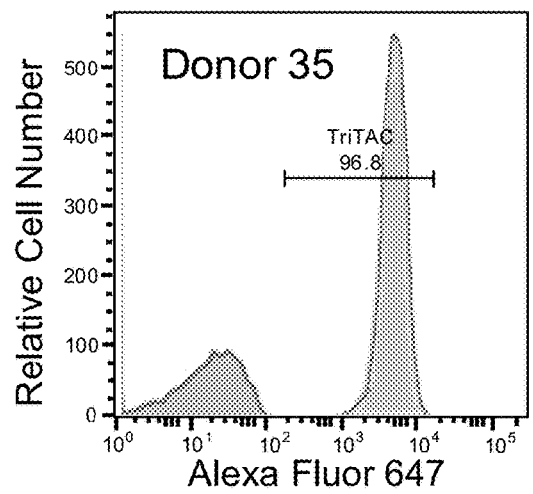
Figure 4C:
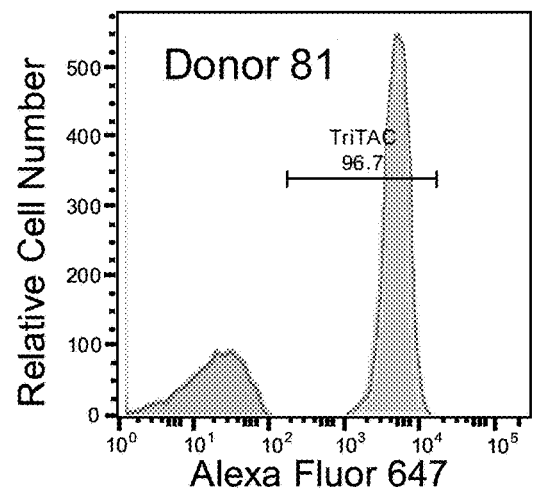
Figure 4D:
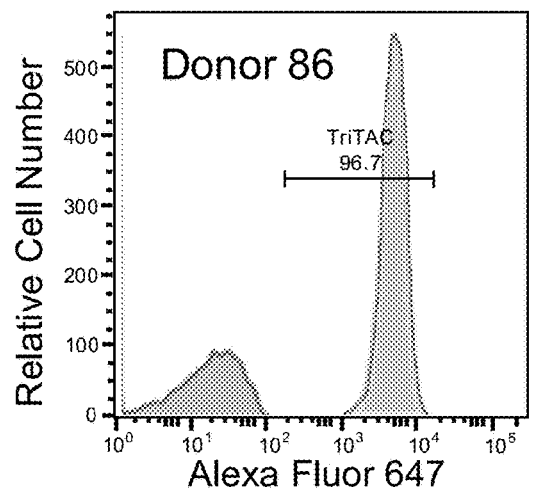

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

An "antibody" typically refers to a Y-shaped tetrameric protein comprising two heavy (H) and two light (L) polypeptide chains held together by covalent disulfide bonds and non-covalent interactions. Human light chains comprise a variable domain (VL) and a constant domain (CL) wherein the constant domain may be readily classified as kappa or lambda based on amino acid sequence and gene loci. Each heavy chain comprises one variable domain (VH) and a constant region, which in the case of IgG, IgA, and IgD comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (generally from about 10 to about 60 amino acids in IgG). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues. There are two types of native disulfide bridges or bonds in immunoglobulin molecules: inter-chain and intra-chain disulfide bonds. The location and number of inter-chain disulfide bonds vary according to the immunoglobulin class and species. Inter-chain disulfide bonds are located on the surface of the immunoglobulin, are accessible to solvent and are usually relatively easily reduced. In the human IgG1 isotype there are four inter-chain disulfide bonds, one from each heavy chain to the light chain and two between the heavy chains. The inter-chain disulfide bonds are not required for chain association. As is well known the cysteine rich IgG1 hinge region of the heavy chain has generally been held to consist of three parts: an upper hinge, a core hinge, and a lower hinge. Those skilled in the art will appreciate that the IgG1 hinge region contain the cysteines in the heavy chain that comprise the inter-chain disulfide bonds (two heavy/heavy, two heavy/light), which provide structural flexibility that facilitates Fab movements. The inter-chain disulfide bond between the light and heavy chain of IgG1 are formed between C214 of the kappa or lambda light chain and C220 in the upper hinge region of the heavy chain. The inter-chain disulfide bonds between the heavy chains are at positions C226 and C229 (all numbered per the EU index according to Kabat, et al., infra.)

As used herein the term "antibody" includes polyclonal antibodies, multiclonal antibodies, monoclonal antibodies, chimeric antibodies, humanized and primatized antibodies, CDR grafted antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof, immunospecific antibody fragments such as Fd, Fab, F(ab')2, F(ab') fragments, single-chain fragments (e.g., ScFv and ScFvFc), disulfide-linked Fvs (sdFv), a Fd fragment consisting of the VH and CH1 domains, linear antibodies, single domain antibodies such as sdAb (VH, VL, or VHH domains (such as a heavy chain only antibody devoid of a light chain)); and derivatives thereof including Fc fusions and other modifications, and any other immunoreactive molecule so long as it comprises a domain having a binding site for preferential association or binding with a BCMA protein. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter alpha, delta, epsilon, gamma, and mu, respectively. Light chains of the antibodies from any vertebrate species can be assigned to one of two clearly distinct types, called kappa (kappa) and lambda (lambda), based on the amino acid sequences of their constant domains.

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the βsheet structure. The CDRs in each chain are held together in close proximity by the FR regions and, with the CDRs from the other chain, contribute to the formation of the antigen-binding site of antibodies (see, Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. "Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. It is not intended that CDRs of the present disclosure necessarily correspond to the Kabat numbering convention.

In some embodiments, the BCMA binding proteins comprise a heavy chain only antibody, such as a VH or a VHH domain. In some cases, the BCMA binding proteins comprise a heavy chain only antibody that is an engineered human VH domain. In some examples, the engineered human VH domain is produced by panning of phage display libraries. In some embodiments, the BCMA binding proteins comprise a VHH. The term "VHH," as used herein, refers to single chain antibody binding domain devoid of light chain. In some cases, a VHH is derived from an antibody of the type that can be found in Camelidae or cartilaginous fish which are naturally devoid of light chains or to a synthetic and non-immunized VHH which can be constructed accordingly. Each heavy chain comprises a variable region encoded by V-, D- and J exons. A VHH, in some cases, is a natural VHH, such as a Camelid-derived VHH, or a recombinant protein comprising a heavy chain variable domain. In some embodiments, the VHH is derived from a species selected from the group consisting of camels, llamas, vicugnas, guanacos, and cartilaginous fish (such as, but not limited to, sharks). In another embodiment, the VHH is derived from an alpaca (such as, but not limited to, a Huacaya Alpaca or a Suri alpaca).

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software programs such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

As used herein, "elimination half-time" is used in its ordinary sense, as is described in *Goodman and Gillman's The Pharmaceutical Basis of Therapeutics* 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t_{1/2}$ the time required for 50% completion of the process. The units of these two constants are $time^{-1}$ and time, respectively. A first-order rate constant and the half-time of the reaction are simply related ($k \times t_{1/2}=0.693$) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

As used herein, the term "binding affinity" refers to the affinity of the proteins described in the disclosure to their binding targets, and is expressed numerically using "Kd" values. If two or more proteins are indicated to have comparable binding affinities towards their binding targets, then the Kd values for binding of the respective proteins towards their binding targets, are within ±2-fold of each other. If two or more proteins are indicated to have comparable binding affinities towards single binding target, then the Kd values for binding of the respective proteins towards said single binding target, are within ±2-fold of each other. If a protein is indicated to bind two or more targets with comparable binding affinities, then the Kd values for binding of said protein to the two or more targets are within ±2-fold of each other. In general, a higher Kd value corresponds to a weaker binding. In some embodiments, the "Kd" is measured by a radiolabeled antigen binding assay (MA) or surface plasmon resonance assays using a BIACORE®-2000 or a BIACORE®-3000 (BIAcore, Inc., Piscataway, N.J.). In certain embodiments, an "on-rate" or "rate of association" or "association rate" or "kon" and an "off-rate" or "rate of dissociation" or "dissociation rate" or "koff" are also determined with the surface plasmon resonance technique using a BIACORE®-2000 or a BIACORE®-3000 (BIAcore, Inc., Piscataway, N.J.). In additional embodiments, the "Kd", "kon", and "koff" are measured using the OCTET® Systems (Pall Life Sciences). In an exemplary method for measuring binding affinity using the OCTET® Systems, the ligand, e.g., biotinylated human BCMA, is immobilized on the OCTET® streptavidin capillary sensor tip surface which streptavidin tips are then activated according to manufacturer's instructions using about 20-50 µg/ml human BCMA protein. A solution of PBS/Casein is also introduced as a blocking agent. For association kinetic measurements, BCMA binding protein variants are introduced at a concentration ranging from about 10 ng/mL to about 100 µg/mL, about 50 ng/mL to about 5 µg/mL, or about 2 ng/mL to about 20 µg/mL. In some embodiments, the BCMA binding single domain proteins are used at a concentration ranging from about 2 ng/mL to about 20 µg/mL. Complete dissociation is observed in case of the negative control, assay buffer without the binding proteins. The kinetic parameters of the binding reactions are then determined using an appropriate tool, e.g., ForteBio software.

Described herein are BCMA binding proteins, pharmaceutical compositions as well as nucleic acids, recombinant expression vectors, and host cells for making such BCMA binding proteins. Also provided are methods of using the disclosed BCMA binding proteins in the prevention, and/or treatment of diseases, conditions and disorders. The BCMA binding proteins are capable of specifically binding to BCMA. In some embodiments, the BCMA binding proteins include additional domains, such as a CD3 binding domain and an albumin binding domain.

B Cell Maturation Antigen (BCMA)

B cell maturation antigen (BCMA, TNFRSF17, CD269) is a transmembrane protein belonging to the tumor necrosis family receptor (TNFR) super family that is primarily expressed on terminally differentiated B cells. BCMA expression is restricted to the B cell lineage and mainly present on plasma cells and plasmablasts and to some extent on memory B cells, but virtually absent on peripheral and naive B cells. BCMA is also expressed on multiple myeloma (MM) cells, on leukemia cells and lymphoma cells.

BCMA was identified through molecular analysis of a t(4;16)(q26;p13) translocation found in a human intestinal T cell lymphoma and an in-frame sequence was mapped to the 16p13.1 chromosome band.

Human BCMA cDNA has an open reading frame of 552 bp that encodes a 184 amino acid polypeptide. The BCMA gene is organized into three exons that are separated by two introns, each flanked by GT donor and AG acceptor consensus splicing sites, and codes for a transcript of 1.2 kb. The structure of BCMA protein includes an integral transmembrane protein based on a central 24 amino acid hydrophobic region in an alpha-helix structure.

The murine BCMA gene is located on chromosome 16 syntenic to the human 16p13 region, and also includes three exons that are separated by two introns. The gene encodes a 185 amino acid protein. Murine BCMA mRNA is expressed as a 404 bp transcript at the highest levels in plasmacytoma cells (J558) and at modest levels in the A20 B cell lymphoma line. Murine BCMA mRNA transcripts have also been detected at low levels in T cell lymphoma (EL4, BW5147) and dendritic cell (CB1D6, D2SC1) lines in contrast to human cell lines of T cell and dendritic cell origin. The murine BCMA cDNA sequence has 69.3% nucleotide identity with the human BCMA cDNA sequence and slightly higher identity (73.7%) when comparing the coding regions between these two cDNA sequences. Mouse BCMA protein is 62% identical to human BCMA protein and, like human BCMA, contains a single hydrophobic region, which may be an internal transmembrane segment. The N-terminal 40 amino acid domain of both murine and human BCMA protein have six conserved cysteine residues, consistent with the formation of a cysteine repeat motif found in the extracellular domain of TNFRs. Similar to members of the TNFR superfamily, BCMA protein contains a conserved aromatic residue four to six residues C-terminal from the first cysteine.

BCMA is not expressed at the cell surface, but rather, is located on the Golgi apparatus. The amount of BCMA expression is proportional to the stage of cellular differentiation (highest in plasma cells).

BCMA is involved in B cell development and homeostasis due to its interaction with its ligands BAFF (B cell activating factor, also designated as TALL-1 or TNFSF13B) and APRIL (A proliferation inducing ligand).

BCMA regulates different aspects of humoral immunity, B cell development and homeostasis along with its family members TACI (transmembrane activator and cyclophylin ligand interactor) and BAFF-R (B cell activation factor receptor, also known as tumor necrosis factor receptor superfamily member 13C). Expression of BCMA appears rather late in B cell differentiation and contributes to the long term survival of plasmablasts and plasma cells in the bone marrow. BCMA also supports growth and survival of multiple myeloma (MM) cells.

BCMA is mostly known for its functional activity in mediating the survival of plasma cells that maintain long-term humoral immunity.

There is a need for having treatment options for solid tumor diseases related to the overexpression of BCMA, such as cancer multiple myeloma, leukemias and lymphomas. The present disclosure provides, in certain embodiments, single domain proteins which specifically bind to BCMA on the surface of tumor target cells.

BCMA Binding Proteins

Contemplated herein are BCMA binding proteins. Provided herein in certain embodiments are binding proteins, such as anti-BCMA single domain antibodies or antibody variants, which bind to an epitope in the BCMA protein. In some embodiments, the BCMA binding protein binds to a human BCMA protein comprising the sequence of SEQ ID NO: 468. In some embodiments, the BCMA binding protein binds to a human BCMA protein comprising a truncated sequence compared to SEQ ID NO: 468. In one non-limiting example, the BCMA binding protein binds to a human BCMA protein comprising amino acid residues 5-51 of SEQ ID NO: 468.

In some embodiments, the BCMA binding proteins of the present disclosure can be expressed within a multidomain protein that includes additional immunoglobulin domains. Such multidomain proteins can act via immunotoxin-based inhibition of tumor growth and induction of antibody-dependent cellular cytotoxicity (ADCC). In some embodiments, the multidomain proteins containing the BCMA binding proteins of the present disclosure exhibit complement-dependent cytotoxicity (CDC) activity. In some embodiments, the multidomain proteins containing the BCMA binding proteins of the present disclosure exhibit both ADCC and CDC activity, against cancer cells expressing BCMA. An amino acid sequence of a Fc domain can be added on to the BCMA binding proteins described herein to induce ACDD or CDC. Amino acid sequences of Fc domains are known in the art and are contemplated herein.

A BCMA binding protein described herein binds to the extracellular domain of BCMA. In one instance, a BCMA binding protein described herein binds to amino acid residues 5-51 of human BCMA.

In some embodiments, the BCMA binding protein is an anti-BCMA antibody or an antibody variant. As used herein, the term "antibody variant" refers to variants and derivatives of an antibody described herein. In certain embodiments, amino acid sequence variants of the anti-BCMA antibodies described herein are contemplated. For example, in certain embodiments amino acid sequence variants of anti-BCMA antibodies described herein are contemplated to improve the binding affinity and/or other biological properties of the antibodies. Exemplary methods for preparing amino acid variants include, but are not limited to, introducing appropriate modifications into the nucleotide sequence encoding the antibody, or by peptide synthesis. Such modifications include, for example, deletions from, and/or insertions into and/or substitutions of residues within the amino acid sequences of the antibody.

Any combination of deletion, insertion, and substitution can be made to arrive at the final construct, provided that the final construct possesses the desired characteristics, e.g., antigen-binding. In certain embodiments, antibody variants having one or more amino acid substitutions are provided. Sites of interest for substitution mutagenesis include the CDRs and framework regions. Examples of such substitutions are described below. Amino acid substitutions may be introduced into an antibody of interest and the products screened for a desired activity, e.g., retained/improved antigen binding, decreased immunogenicity, or improved antibody-dependent cell mediated cytotoxicity (ADCC) or complement dependent cytotoxicity (CDC). Both conservative and non-conservative amino acid substitutions are contemplated for preparing the antibody variants.

In another example of a substitution to create a variant anti-BCMA antibody, one or more hypervariable region residues of a parent antibody are substituted. In general, variants are then selected based on improvements in desired properties compared to a parent antibody, for example, increased affinity, reduced affinity, reduced immunogenicity, increased pH dependence of binding. For example, an affinity matured variant antibody can be generated, e.g., using phage display-based affinity maturation techniques such as those described herein and known in the field.

In some embodiments, the BCMA binding protein described herein is a single domain antibody such as a heavy chain variable domain (VH), a variable domain (VHH) of llama derived sdAb, peptide, ligand or a small molecule entity specific for BCMA. In some embodiments, the BCMA binding domain of the BCMA binding protein described herein is any domain that binds to BCMA including, but not limited to, domains from a monoclonal antibody, a polyclonal antibody, a recombinant antibody, a human antibody, a humanized antibody. In certain embodiments, the BCMA binding protein is a single-domain antibody. In other embodiments, the BCMA binding protein is a peptide. In further embodiments, the BCMA binding protein is a small molecule.

Generally, it should be noted that the term single domain antibody as used herein in its broadest sense is not limited to a specific biological source or to a specific method of preparation. Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, and bovine. For example, in some embodiments, the single domain antibodies of the disclosure are obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a species of mammal, such as from a human being, or by expression of a nucleic acid encoding such a camelized VH domain; (5) by "camelisation" of a "domain antibody" or "Dab", or by expression of a nucleic acid encoding such a camelized VH domain; (6) by using synthetic or semi-synthetic techniques for preparing proteins, polypeptides or other amino acid sequences; (7) by preparing a nucleic acid encoding a single domain antibody using techniques for nucleic acid synthesis known in the field, followed by expression of the nucleic acid thus obtained; and/or (8) by any combination of one or more of the foregoing.

In one embodiment, a single domain antibody corresponds to the VHH domains of naturally occurring heavy chain antibodies directed against BCMA. As further described herein, such VHH sequences can generally be generated or obtained by suitably immunizing a species of Llama with BCMA, (i.e., so as to raise an immune response and/or heavy chain antibodies directed against BCMA), by obtaining a suitable biological sample from said Llama (such as a blood sample, serum sample or sample of B-cells), and by generating VHH sequences directed against BCMA, starting from said sample, using any suitable technique known in the field.

In another embodiment, such naturally occurring VHH domains against BCMA, are obtained from naïve libraries of Camelid VHH sequences, for example by screening such a library using BCMA, or at least one part, fragment, antigenic determinant or epitope thereof using one or more screening techniques known in the field. Such libraries and techniques are, for example, described in WO 99/37681, WO 01/90190, WO 03/025020 and WO 03/035694. Alternatively, improved synthetic or semi-synthetic libraries derived from naïve VHH libraries are used, such as VHH libraries obtained from naïve VHH libraries by techniques such as random mutagenesis and/or CDR shuffling, as for example, described in WO 00/43507.

In a further embodiment, yet another technique for obtaining VHH sequences directed against BCMA, involves suitably immunizing a transgenic mammal that is capable of expressing heavy chain antibodies (i.e., so as to raise an immune response and/or heavy chain antibodies directed against BCMA), obtaining a suitable biological sample from said transgenic mammal (such as a blood sample, serum sample or sample of B-cells), and then generating VHH sequences directed against BCMA, starting from said sample, using any suitable technique known in the field. For example, for this purpose, the heavy chain antibody-expressing rats or mice and the further methods and techniques described in WO 02/085945 and in WO 04/049794 can be used.

In some embodiments, an anti-BCMA antibody, as described herein comprises single domain antibody with an amino acid sequence that corresponds to the amino acid sequence of a naturally occurring VHH domain, but that has been "humanized", i.e., by replacing one or more amino acid residues in the amino acid sequence of said naturally occurring VHH sequence (and in particular in the framework sequences) by one or more of the amino acid residues that occur at the corresponding position(s) in a VH domain from a conventional 4-chain antibody from a human being (e.g., as indicated above). This can be performed in a manner known in the field, which will be clear to the skilled person, for example on the basis of the further description herein. Again, it should be noted that such humanized anti-BCMA single domain antibodies of the disclosure are obtained in any suitable manner known per se (i.e., as indicated under points (1)-(8) above) and thus are not strictly limited to polypeptides that have been obtained using a polypeptide that comprises a naturally occurring VHH domain as a starting material. In some additional embodiments, a single domain BCMA antibody, as described herein, comprises a single domain antibody with an amino acid sequence that corresponds to the amino acid sequence of a naturally occurring VH domain, but that has been "camelized", i.e., by replacing one or more amino acid residues in the amino acid sequence of a naturally occurring VH domain from a conventional 4-chain antibody by one or more of the amino acid residues that occur at the corresponding position(s) in a VHH domain of a heavy chain antibody. Such "camelizing" substitutions are preferably inserted at amino acid positions that form and/or are present at the VH-VL interface, and/or at the so-called Camelidae hallmark residues (see for example WO 94/04678 and Davies and Riechmann (1994 and 1996)). Preferably, the VH sequence that is used as a starting material or starting point for generating or designing the camelized single domain is preferably a VH sequence from a mammal, more preferably the VH sequence of a human being, such as a VH3 sequence. However, it should be noted that such camelized anti-BCMA single domain antibodies of the disclosure, in certain embodiments, are obtained in any suitable manner known in the field (i.e., as indicated under points (1)-(8) above) and thus are not strictly limited to polypeptides that have been obtained using a polypeptide that comprises a naturally occurring VH domain as a starting material. For example, as further described herein, both "humanization" and "camelization" are performed by providing a nucleotide sequence that encodes a naturally occurring VHH domain or VH domain, respectively, and then changing, one or more codons in said nucleotide sequence in such a way that the new nucleotide sequence encodes a "humanized" or "camelized" single domain antibody, respectively. This nucleic acid can then be expressed, so as to provide the desired anti-BCMA single domain antibody of the disclosure. Alternatively, in other embodiments, based on the amino acid sequence of a naturally occurring VHH domain or VH domain, respectively, the amino acid sequence of the desired humanized or camelized anti-BCMA single domain antibody of the disclosure, respectively, are designed and then synthesized de novo using known techniques for peptide synthesis. In some embodiments, based on the amino acid sequence or nucleotide sequence of a naturally occurring VHH domain or VH domain, respectively, a nucleotide sequence encoding the desired humanized or camelized anti-BCMA single domain antibody of the disclosure, respectively, is designed and then synthesized de novo using known techniques for nucleic acid synthesis, after which the nucleic acid thus obtained is expressed in using known expression techniques, so as to provide the desired anti-BCMA single domain antibody of the disclosure.

Other suitable methods and techniques for obtaining the anti-BCMA single domain antibody of the disclosure and/or nucleic acids encoding the same, starting from naturally occurring VH sequences or VHH sequences for example comprises combining one or more parts of one or more naturally occurring VH sequences (such as one or more framework (FR) sequences and/or complementarity determining region (CDR) sequences), one or more parts of one or more naturally occurring VHH sequences (such as one or more FR sequences or CDR sequences), and/or one or more synthetic or semi-synthetic sequences, in a suitable manner, so as to provide an anti-BCMA single domain antibody of the disclosure or a nucleotide sequence or nucleic acid encoding the same.

It is contemplated that in some embodiments the BCMA binding protein is fairly small and no more than 25 kD, no more than 20 kD, no more than 15 kD, or no more than 10 kD in some embodiments. In certain instances, the BCMA binding protein is 5 kD or less if it is a peptide or small molecule entity.

In some embodiments, the BCMA binding protein is an anti-BCMA specific antibody comprising a heavy chain variable complementarity determining region CDR1, a heavy chain variable CDR2, a heavy chain variable CDR3, a light chain variable CDR1, a light chain variable CDR2, and a light chain variable CDR3. In some embodiments, the BCMA binding protein comprises any domain that binds to BCMA including but not limited to domains from a monoclonal antibody, a polyclonal antibody, a recombinant antibody, a human antibody, a humanized antibody, or antigen binding fragments such as single domain antibodies (sdAb), Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some embodiments, the BCMA binding protein is a single domain antibody. In some embodiments, the anti-BCMA single domain antibody comprises heavy chain variable complementarity determining regions (CDR), CDR1, CDR2, and CDR3.

In some embodiments, the BCMA binding protein of the present disclosure is a polypeptide comprising an amino acid sequence that is comprised of four framework regions/sequences (f1-f4) interrupted by three complementarity determining regions/sequences, as represented by the formula: f1-r1-f2-r2-f3-r3-f4, wherein r1, r2, and r3 are complementarity determining regions CDR1, CDR2, and CDR3, respectively, and f1, f2, f3, and f4 are framework residues. The r1 residues of the BCMA binding protein of the present disclosure comprise, for example, amino acid residues 26, 27, 28, 29, 30, 31, 32, 33 and 34; the r2 residues of the BCMA binding protein of the present disclosure comprise, for example, amino acid residues, for example, 50, 51, 52, 53, 54, 55, 56, 57, 58, 59, 60, 61, 62 and 63; and the r3 residues of the BCMA binding protein of the present disclosure comprise, for example, amino acid residues, for example, 97, 98, 99, 100, 101, 102, 103, 104, 105, 106, 107 and 108. In some embodiments, the BCMA binding protein comprises an amino acid sequence selected from SEQ ID NOs: 346-460.

In one embodiment, the CDR1 does not comprise an amino acid sequence of SEQ ID NO: 473. In one embodiment, the CDR2 does not comprise an amino acid sequence of SEQ ID NO: 474. In one embodiment, the CDR3 does not comprise an amino acid sequence of SEQ ID NO: 475.

In some embodiments, the CDR1 comprises the amino acid sequence as set forth in SEQ ID NO: 1 or a variant thereof having one, two, three, four, five, six, seven, eight, nine, or ten amino acid substitutions. An exemplary CDR1 comprises the amino acid sequence as set forth in SEQ ID NO: 4. Another exemplary CDR1 comprises the amino acid sequence as set forth in SEQ ID NO: 5. Another exemplary CDR1 comprises the amino acid sequence as set forth in SEQ ID NO: 6. Another exemplary CDR1 comprises the amino acid sequence as set forth in SEQ ID NO: 7. Another exemplary CDR1 comprises the amino acid sequence as set forth in SEQ ID NO: 8. Another exemplary CDR1 comprises the amino acid sequence as set forth in SEQ ID NO: 9. Another exemplary CDR1 comprises the amino acid sequence as set forth in SEQ ID NO: 10. Another exemplary CDR1 comprises the amino acid sequence as set forth in SEQ ID NO: 11. Another exemplary CDR1 comprises the amino acid sequence as set forth in SEQ ID NO: 12. Another exemplary CDR1 comprises the amino acid sequence as set forth in SEQ ID NO: 13. Another exemplary CDR1 comprises the amino acid sequence as set forth in SEQ ID NO: 14. Another exemplary CDR1 comprises the amino acid sequence as set forth in SEQ ID NO: 15. Another exemplary CDR1 comprises the amino acid sequence as set forth in SEQ ID NO: 16. Another exemplary CDR1 comprises the amino acid sequence as set forth in SEQ ID NO: 17. Another exemplary CDR1 comprises the amino acid sequence as set forth in SEQ ID NO: 18. Another exemplary CDR1 comprises the amino acid sequence as set forth in SEQ ID NO: 19. Another exemplary CDR1 comprises the amino acid sequence as set forth in SEQ ID NO: 20. Another exemplary CDR1 comprises the amino acid sequence as set forth in SEQ ID NO: 21. Another exemplary CDR1 comprises the amino acid sequence as set forth in SEQ ID NO: 22. Another exemplary CDR1 comprises the amino acid sequence as set forth in SEQ ID NO: 23. Another exemplary CDR1 comprises the amino acid sequence as set forth in SEQ ID NO: 24. Another exemplary CDR1 comprises the amino acid sequence as set forth in SEQ ID NO: 25. Another exemplary CDR1 comprises the amino acid sequence as set forth in SEQ ID NO: 26. Another exemplary CDR1 comprises the amino acid sequence as set forth in SEQ ID NO: 27. Another exemplary CDR1 comprises the amino acid sequence as set forth in SEQ ID NO: 28. Another exemplary CDR1 comprises the amino acid sequence as set forth in SEQ ID NO: 29. Another exemplary CDR1 comprises the amino acid sequence as set forth in SEQ ID NO: 30. Another exemplary CDR1 comprises the amino acid sequence as set forth in SEQ ID NO: 31. Another exemplary CDR1 comprises the amino acid sequence as set forth in SEQ ID NO: 32. Another exemplary CDR1 comprises the amino acid sequence as set forth in SEQ ID NO: 33. Another exemplary CDR1 comprises the amino acid sequence as set forth in SEQ ID NO: 34. Another exemplary CDR1 comprises the amino acid sequence as set forth in SEQ ID NO: 35. Another exemplary CDR1 comprises the amino acid sequence as set forth in SEQ ID NO: 36. Another exemplary CDR1 comprises the amino acid sequence as set forth in SEQ ID NO: 37. Another exemplary CDR1 comprises the amino acid sequence as set forth in SEQ ID NO: 38. Another exemplary CDR1 comprises the amino acid sequence as set forth in SEQ ID NO: 39. Another exemplary CDR1 comprises the amino acid sequence as set forth in SEQ ID NO: 40. Another exemplary CDR1 comprises the amino acid sequence as set forth in SEQ ID NO: 41. Another exemplary CDR1 comprises the amino acid sequence as set forth in SEQ ID NO: 42. Another exemplary CDR1 comprises the amino acid sequence as set forth in SEQ ID NO: 43. Another exemplary CDR1 comprises the amino acid sequence as set forth in SEQ ID NO: 44. Another exemplary CDR1 comprises the amino acid sequence as set forth in SEQ ID NO: 45. Another exemplary CDR1 comprises the amino acid sequence as set forth in SEQ ID NO: 46. Another exemplary CDR1 comprises the amino acid sequence as set forth in SEQ ID NO: 47. Another exemplary CDR1 comprises the amino acid sequence as set forth in SEQ ID NO: 48. Another exemplary CDR1 comprises the amino acid sequence as set forth in SEQ ID NO: 49. Another exemplary CDR1 comprises the amino acid sequence as set forth in SEQ ID NO: 50. Another exemplary CDR1 comprises the amino acid sequence as set forth in SEQ ID NO: 51. Another exemplary CDR1 comprises the amino acid sequence as set forth in SEQ ID NO: 52. Another exemplary CDR1 comprises the amino acid sequence as set forth in SEQ ID NO: 53. Another exemplary CDR1 comprises the amino acid sequence as set forth in SEQ ID NO: 54. Another exemplary CDR1 comprises the amino acid sequence as set forth in SEQ ID NO: 55. Another exemplary CDR1 comprises the amino acid sequence as set forth in SEQ ID NO: 56. Another exemplary CDR1 comprises the amino acid sequence as set forth in SEQ ID NO: 57. Another exemplary CDR1 comprises the amino acid sequence as set forth in SEQ ID NO: 58. Another exemplary CDR1 comprises the amino acid sequence as set forth in SEQ ID NO: 59. Another exemplary CDR1 comprises the amino acid sequence as set forth in SEQ ID NO: 60. Another exemplary CDR1 comprises the amino acid sequence as set forth in SEQ ID NO: 61. Another exemplary CDR1 comprises the amino acid sequence as set forth in SEQ ID NO: 62. Another exemplary CDR1 comprises the amino acid sequence as set forth in SEQ ID NO: 63. Another exemplary CDR1 comprises the amino acid sequence as set forth in SEQ ID NO: 64. Another exemplary CDR1 comprises the amino acid sequence as set forth in SEQ ID NO: 65. Another exemplary CDR1 comprises the amino acid sequence as set forth in SEQ ID NO: 66. Another exemplary CDR1 comprises the amino acid sequence as set forth in SEQ ID NO: 67. Another exemplary CDR1 comprises the amino acid sequence as set forth in SEQ ID NO: 68. Another exemplary CDR1 comprises the amino acid sequence as set forth in SEQ ID NO: 69. Another exemplary CDR1 comprises the amino acid sequence as set forth in SEQ ID NO: 70. Another exemplary CDR1 comprises the amino acid sequence as set forth in SEQ ID NO: 71. Another exemplary CDR1 comprises the amino acid sequence as set forth in SEQ ID NO: 72. Another exemplary CDR1 comprises the amino acid sequence as set forth in SEQ ID NO: 73. Another exemplary CDR1 comprises the amino acid sequence as set forth in SEQ ID NO: 74. Another exemplary CDR1 comprises the amino acid sequence as set forth in SEQ ID NO: 75. Another exemplary CDR1 comprises the amino acid sequence as set forth in SEQ ID NO: 76. Another exemplary CDR1 comprises the amino acid sequence as set forth in SEQ ID NO: 77. Another exemplary CDR1 comprises the amino acid sequence as set forth in SEQ ID NO: 78. Another exemplary CDR1 comprises the amino acid sequence as set forth in SEQ ID NO: 79. Another exemplary CDR1 comprises the amino acid sequence as set forth in SEQ ID NO: 80. Another exemplary CDR1 comprises the amino acid sequence as set forth in SEQ ID NO: 81. Another exemplary CDR1 comprises the amino acid sequence as set forth in SEQ ID NO: 82. Another exemplary CDR1 comprises the amino acid sequence as set forth in SEQ ID NO: 83. Another exemplary CDR1 comprises the amino acid sequence as set forth in SEQ ID NO: 84. Another exemplary CDR1 comprises the amino acid sequence as set forth in SEQ ID NO: 85. Another exemplary CDR1 comprises the amino acid sequence as set forth in SEQ ID NO: 86. Another exemplary CDR1 comprises the amino acid sequence as set forth in SEQ ID NO: 87. Another exemplary CDR1 comprises the amino acid sequence as set forth in SEQ ID NO: 88. Another exemplary CDR1 comprises the amino acid sequence as set forth in SEQ ID NO: 89. Another exemplary CDR1 comprises the amino acid sequence as set forth in SEQ ID NO: 90. Another exemplary CDR1 comprises the amino acid sequence as set forth in SEQ ID NO: 91. Another exemplary CDR1 comprises the amino acid sequence as set forth in SEQ ID NO: 92. Another exemplary CDR1 comprises the amino acid sequence as set forth in SEQ ID NO: 93. Another exemplary CDR1 comprises the amino acid sequence as set forth in SEQ ID NO: 94. Another exemplary CDR1 comprises the amino acid sequence as set forth in SEQ ID NO: 95. Another exemplary CDR1 comprises the amino acid sequence as set forth in SEQ ID NO: 96. Another exemplary CDR1 comprises the amino acid sequence as set forth in SEQ ID NO: 97. Another exemplary CDR1 comprises the amino acid sequence as set forth in SEQ ID NO: 98. Another exemplary CDR1 comprises the amino acid sequence as set forth in SEQ ID NO: 99. Another exemplary CDR1 comprises the amino acid sequence as set forth in SEQ ID NO: 100. Another exemplary CDR1 comprises the amino acid sequence as set forth in SEQ ID NO: 101. Another exemplary CDR1 comprises the amino acid sequence as set forth in SEQ ID NO: 102. Another exemplary CDR1 comprises the amino acid sequence as set forth in SEQ ID NO: 103. Another exemplary CDR1 comprises the amino acid sequence as set forth in SEQ ID NO: 104. Another exemplary CDR1 comprises the amino acid sequence as set forth in SEQ ID NO: 105. Another exemplary CDR1 comprises the amino acid sequence as set forth in SEQ ID NO: 106. Another exemplary CDR1 comprises the amino acid sequence as set forth in SEQ ID NO: 107. Another exemplary CDR1 comprises the amino acid sequence as set forth in SEQ ID NO: 108. Another exemplary CDR1 comprises the amino acid sequence as set forth in SEQ ID NO: 109. Another exemplary CDR1 comprises the amino acid sequence as set forth in SEQ ID NO: 110. Another exemplary CDR1 comprises the amino acid sequence as set forth in SEQ ID NO: 111. Another exemplary CDR1 comprises the amino acid sequence as set forth in SEQ ID NO: 112. Another exemplary CDR1 comprises the amino acid sequence as set forth in SEQ ID NO: 113. Another exemplary CDR1 comprises the amino acid sequence as set forth in SEQ ID NO: 114. Another exemplary CDR1 comprises the amino acid sequence as set forth in SEQ ID NO: 115. Another exemplary CDR1 comprises the amino acid sequence as set forth in SEQ ID NO: 116. Another exemplary CDR1 comprises the amino acid sequence as set forth in SEQ ID NO: 117.

In some embodiments, the CDR2 comprises a sequence as set forth in SEQ ID NO: 2 or a variant having one, two, three, four, five, six, seven, eight, nine, or ten amino acid substitutions in SEQ ID NO: 2. Another exemplary CDR2 comprises the amino acid sequence as set forth in SEQ ID NO: 118. Another exemplary CDR2 comprises the amino acid sequence as set forth in SEQ ID NO: 119. Another exemplary CDR2 comprises the amino acid sequence as set forth in SEQ ID NO: 120. Another exemplary CDR2 comprises the amino acid sequence as set forth in SEQ ID NO: 121. Another exemplary CDR2 comprises the amino acid sequence as set forth in SEQ ID NO: 122. Another exemplary CDR2 comprises the amino acid sequence as set forth in SEQ ID NO: 123. Another exemplary CDR2 comprises the amino acid sequence as set forth in SEQ ID NO: 124. Another exemplary CDR2 comprises the amino acid sequence as set forth in SEQ ID NO: 125. Another exemplary CDR2 comprises the amino acid sequence as set forth in SEQ ID NO: 126. Another exemplary CDR2 comprises the amino acid sequence as set forth in SEQ ID NO: 127. Another exemplary CDR2 comprises the amino acid sequence as set forth in SEQ ID NO: 128. Another exemplary CDR2 comprises the amino acid sequence as set forth in SEQ ID NO: 129. Another exemplary CDR2 comprises the amino acid sequence as set forth in SEQ ID NO: 130. Another exemplary CDR2 comprises the amino acid sequence as set forth in SEQ ID NO: 131. Another exemplary CDR2 comprises the amino acid sequence as set forth in SEQ ID NO: 132. Another exemplary CDR2 comprises the amino acid sequence as set forth in SEQ ID NO: 133. Another exemplary CDR2 comprises the amino acid sequence as set forth in SEQ ID NO: 134. Another exemplary CDR2 comprises the amino acid sequence as set forth in SEQ ID NO: 135. Another exemplary CDR2 comprises the amino acid sequence as set forth in SEQ ID NO: 136. Another exemplary CDR2 comprises the amino acid sequence as set forth in SEQ ID NO: 137. Another exemplary CDR2 comprises the amino acid sequence as set forth in SEQ ID NO: 138. Another exemplary CDR2 comprises the amino acid sequence as set forth in SEQ ID NO: 139. Another exemplary CDR2 comprises the amino acid sequence as set forth in SEQ ID NO: 140. Another exemplary CDR2 comprises the amino acid sequence as set forth in SEQ ID NO: 141. Another exemplary CDR2 comprises the amino acid sequence as set forth in SEQ ID NO: 142. Another exemplary CDR2 comprises the amino acid sequence as set forth in SEQ ID NO: 143. Another exemplary CDR2 comprises the amino acid sequence as set forth in SEQ ID NO: 144. Another exemplary CDR2 comprises the amino acid sequence as set forth in SEQ ID NO: 145. Another exemplary CDR2 comprises the amino acid sequence as set forth in SEQ ID NO: 146. Another exemplary CDR2 comprises the amino acid sequence as set forth in SEQ ID NO: 147. Another exemplary CDR2 comprises the amino acid sequence as set forth in SEQ ID NO: 148. Another exemplary CDR2 comprises the amino acid sequence as set forth in SEQ ID NO: 149. Another exemplary CDR2 comprises the amino acid sequence as set forth in SEQ ID NO: 150. Another exemplary CDR2 comprises the amino acid sequence as set forth in SEQ ID NO: 151. Another exemplary CDR2 comprises the amino acid sequence as set forth in SEQ ID NO: 152. Another exemplary CDR2 comprises the amino acid sequence as set forth in SEQ ID NO: 153. Another exemplary CDR2 comprises the amino acid sequence as set forth in SEQ ID NO: 154. Another exemplary CDR2 comprises the amino acid sequence as set forth in SEQ ID NO: 155. Another exemplary CDR2 comprises the amino acid sequence as set forth in SEQ ID NO: 156. Another exemplary CDR2 comprises the amino acid sequence as set forth in SEQ ID NO: 157. Another exemplary CDR2 comprises the amino acid sequence as set forth in SEQ ID NO: 158. Another exemplary CDR2 comprises the amino acid sequence as set forth in SEQ ID NO: 159. Another exemplary CDR2 comprises the amino acid sequence as set forth in SEQ ID NO: 160. Another exemplary CDR2 comprises the amino acid sequence as set forth in SEQ ID NO: 161. Another exemplary CDR2 comprises the amino acid sequence as set forth in SEQ ID NO: 162. Another exemplary CDR2 comprises the amino acid sequence as set forth in SEQ ID NO: 163. Another exemplary CDR2 comprises the amino acid sequence as set forth in SEQ ID NO: 164. Another exemplary CDR2 comprises the amino acid sequence as set forth in SEQ ID NO: 165. Another exemplary CDR2 comprises the amino acid sequence as set forth in SEQ ID NO: 166. Another exemplary CDR2 comprises the amino acid sequence as set forth in SEQ ID NO: 167. Another exemplary CDR2 comprises the amino acid sequence as set forth in SEQ ID NO: 168. Another exemplary CDR2 comprises the amino acid sequence as set forth in SEQ ID NO: 169. Another exemplary CDR2 comprises the amino acid sequence as set forth in SEQ ID NO: 170. Another exemplary CDR2 comprises the amino acid sequence as set forth in SEQ ID NO: 171. Another exemplary CDR2 comprises the amino acid sequence as set forth in SEQ ID NO: 172. Another exemplary CDR2 comprises the amino acid sequence as set forth in SEQ ID NO: 173. Another exemplary CDR2 comprises the amino acid sequence as set forth in SEQ ID NO: 174. Another exemplary CDR2 comprises the amino acid sequence as set forth in SEQ ID NO: 175. Another exemplary CDR2 comprises the amino acid sequence as set forth in SEQ ID NO: 176. Another exemplary CDR2 comprises the amino acid sequence as set forth in SEQ ID NO: 177. Another exemplary CDR2 comprises the amino acid sequence as set forth in SEQ ID NO: 178. Another exemplary CDR2 comprises the amino acid sequence as set forth in SEQ ID NO: 179. Another exemplary CDR2 comprises the amino acid sequence as set forth in SEQ ID NO: 180. Another exemplary CDR2 comprises the amino acid sequence as set forth in SEQ ID NO: 181. Another exemplary CDR2 comprises the amino acid sequence as set forth in SEQ ID NO: 182. Another exemplary CDR2 comprises the amino acid sequence as set forth in SEQ ID NO: 183. Another exemplary CDR2 comprises the amino acid sequence as set forth in SEQ ID NO: 184. Another exemplary CDR2 comprises the amino acid sequence as set forth in SEQ ID NO: 185. Another exemplary CDR2 comprises the amino acid sequence as set forth in SEQ ID NO: 186. Another exemplary CDR2 comprises the amino acid sequence as set forth in SEQ ID NO: 187. Another exemplary CDR2 comprises the amino acid sequence as set forth in SEQ ID NO: 188. Another exemplary CDR2 comprises the amino acid sequence as set forth in SEQ ID NO: 189. Another exemplary CDR2 comprises the amino acid sequence as set forth in SEQ ID NO: 190. Another exemplary CDR2 comprises the amino acid sequence as set forth in SEQ ID NO: 191. Another exemplary CDR2 comprises the amino acid sequence as set forth in SEQ ID NO: 192. Another exemplary CDR2 comprises the amino acid sequence as set forth in SEQ ID NO: 193. Another exemplary CDR2 comprises the amino acid sequence as set forth in SEQ ID NO: 194. Another exemplary CDR2 comprises the amino acid sequence as set forth in SEQ ID NO: 195. Another exemplary CDR2 comprises the amino acid sequence as set forth in SEQ ID NO: 196. Another exemplary CDR2 comprises the amino acid sequence as set forth in SEQ ID NO: 197. Another exemplary CDR2 comprises the amino acid sequence as set forth in SEQ ID NO: 198. Another exemplary CDR2 comprises the amino acid sequence as set forth in SEQ ID NO: 199. Another exemplary CDR2 comprises the amino acid sequence as set forth in SEQ ID NO: 200. Another exemplary CDR2 comprises the amino acid sequence as set forth in SEQ ID NO: 201. Another exemplary CDR2 comprises the amino acid sequence as set forth in SEQ ID NO: 202. Another exemplary CDR2 comprises the amino acid sequence as set forth in SEQ ID NO: 203. Another exemplary CDR2 comprises the amino acid sequence as set forth in SEQ ID NO: 204. Another exemplary CDR2 comprises the amino acid sequence as set forth in SEQ ID NO: 205. Another exemplary CDR2 comprises the amino acid sequence as set forth in SEQ ID NO: 206. Another exemplary CDR2 comprises the amino acid sequence as set forth in SEQ ID NO: 207. Another exemplary CDR2 comprises the amino acid sequence as set forth in SEQ ID NO: 208. Another exemplary CDR2 comprises the amino acid sequence as set forth in SEQ ID NO: 209. Another exemplary CDR2 comprises the amino acid sequence as set forth in SEQ ID NO: 210. Another exemplary CDR2 comprises the amino acid sequence as set forth in SEQ ID NO: 211. Another exemplary CDR2 comprises the amino acid sequence as set forth in SEQ ID NO: 212. Another exemplary CDR2 comprises the amino acid sequence as set forth in SEQ ID NO: 213. Another exemplary CDR2 comprises the amino acid sequence as set forth in SEQ ID NO: 214. Another exemplary CDR2 comprises the amino acid sequence as set forth in SEQ ID NO: 215. Another exemplary CDR2 comprises the amino acid sequence as set forth in SEQ ID NO: 216. Another exemplary CDR2 comprises the amino acid sequence as set forth in SEQ ID NO: 217. Another exemplary CDR2 comprises the amino acid sequence as set forth in SEQ ID NO: 218. Another exemplary CDR2 comprises the amino acid sequence as set forth in SEQ ID NO: 219. Another exemplary CDR2 comprises the amino acid sequence as set forth in SEQ ID NO: 220. Another exemplary CDR2 comprises the amino acid sequence as set forth in SEQ ID NO: 221. Another exemplary CDR2 comprises the amino acid sequence as set forth in SEQ ID NO: 222. Another exemplary CDR2 comprises the amino acid sequence as set forth in SEQ ID NO: 223. Another exemplary CDR2 comprises the amino acid sequence as set forth in SEQ ID NO: 224. Another exemplary CDR2 comprises the amino acid sequence as set forth in SEQ ID NO: 225. Another exemplary CDR2 comprises the amino acid sequence as set forth in SEQ ID NO: 226. Another exemplary CDR2 comprises the amino acid sequence as set forth in SEQ ID NO: 227. Another exemplary CDR2 comprises the amino acid sequence as set forth in SEQ ID NO: 228. Another exemplary CDR2 comprises the amino acid sequence as set forth in SEQ ID NO: 229. Another exemplary CDR2 comprises the amino acid sequence as set forth in SEQ ID NO: 230. Another exemplary CDR2 comprises the amino acid sequence as set forth in SEQ ID NO: 231.

In some embodiments, the CDR3 comprises a sequence as set forth in SEQ ID NO: 3 or a variant having one, two, three, four, five, six, seven, eight, nine, or ten amino acid substitutions in SEQ ID NO: 3. Another exemplary CDR3 comprises the amino acid sequence as set forth in SEQ ID NO: 232. Another exemplary CDR3 comprises the amino acid sequence as set forth in SEQ ID NO: 233. Another exemplary CDR3 comprises the amino acid sequence as set forth in SEQ ID NO: 234. Another exemplary CDR3 comprises the amino acid sequence as set forth in SEQ ID NO: 235. Another exemplary CDR3 comprises the amino acid sequence as set forth in SEQ ID NO: 236. Another exemplary CDR3 comprises the amino acid sequence as set forth in SEQ ID NO: 237. Another exemplary CDR3 comprises the amino acid sequence as set forth in SEQ ID NO: 238. Another exemplary CDR3 comprises the amino acid sequence as set forth in SEQ ID NO: 239. Another exemplary CDR3 comprises the amino acid sequence as set forth in SEQ ID NO: 240. Another exemplary CDR3 comprises the amino acid sequence as set forth in SEQ ID NO: 241. Another exemplary CDR3 comprises the amino acid sequence as set forth in SEQ ID NO: 242. Another exemplary CDR3 comprises the amino acid sequence as set forth in SEQ ID NO: 243. Another exemplary CDR3 comprises the amino acid sequence as set forth in SEQ ID NO: 244. Another exemplary CDR3 comprises the amino acid sequence as set forth in SEQ ID NO: 245. Another exemplary CDR3 comprises the amino acid sequence as set forth in SEQ ID NO: 246. Another exemplary CDR3 comprises the amino acid sequence as set forth in SEQ ID NO: 247. Another exemplary CDR3 comprises the amino acid sequence as set forth in SEQ ID NO: 248. Another exemplary CDR3 comprises the amino acid sequence as set forth in SEQ ID NO: 249. Another exemplary CDR3 comprises the amino acid sequence as set forth in SEQ ID NO: 250. Another exemplary CDR3 comprises the amino acid sequence as set forth in SEQ ID NO: 251. Another exemplary CDR3 comprises the amino acid sequence as set forth in SEQ ID NO: 252. Another exemplary CDR3 comprises the amino acid sequence as set forth in SEQ ID NO: 253. Another exemplary CDR3 comprises the amino acid sequence as set forth in SEQ ID NO: 254. Another exemplary CDR3 comprises the amino acid sequence as set forth in SEQ ID NO: 255. Another exemplary CDR3 comprises the amino acid sequence as set forth in SEQ ID NO: 256. Another exemplary CDR3 comprises the amino acid sequence as set forth in SEQ ID NO: 257. Another exemplary CDR3 comprises the amino acid sequence as set forth in SEQ ID NO: 258. Another exemplary CDR3 comprises the amino acid sequence as set forth in SEQ ID NO: 259. Another exemplary CDR3 comprises the amino acid sequence as set forth in SEQ ID NO: 260. Another exemplary CDR3 comprises the amino acid sequence as set forth in SEQ ID NO: 261. Another exemplary CDR3 comprises the amino acid sequence as set forth in SEQ ID NO: 262. Another exemplary CDR3 comprises the amino acid sequence as set forth in SEQ ID NO: 263. Another exemplary CDR3 comprises the amino acid sequence as set forth in SEQ ID NO: 264. Another exemplary CDR3 comprises the amino acid sequence as set forth in SEQ ID NO: 265. Another exemplary CDR3 comprises the amino acid sequence as set forth in SEQ ID NO: 266. Another exemplary CDR3 comprises the amino acid sequence as set forth in SEQ ID NO: 267. Another exemplary CDR3 comprises the amino acid sequence as set forth in SEQ ID NO: 268. Another exemplary CDR3 comprises the amino acid sequence as set forth in SEQ ID NO: 269. Another exemplary CDR3 comprises the amino acid sequence as set forth in SEQ ID NO: 270. Another exemplary CDR3 comprises the amino acid sequence as set forth in SEQ ID NO: 271. Another exemplary CDR3 comprises the amino acid sequence as set forth in SEQ ID NO: 272. Another exemplary CDR3 comprises the amino acid sequence as set forth in SEQ ID NO: 273. Another exemplary CDR3 comprises the amino acid sequence as set forth in SEQ ID NO: 274. Another exemplary CDR3 comprises the amino acid sequence as set forth in SEQ ID NO: 275. Another exemplary CDR3 comprises the amino acid sequence as set forth in SEQ ID NO: 276. Another exemplary CDR3 comprises the amino acid sequence as set forth in SEQ ID NO: 277. Another exemplary CDR3 comprises the amino acid sequence as set forth in SEQ ID NO: 278. Another exemplary CDR3 comprises the amino acid sequence as set forth in SEQ ID NO: 279. Another exemplary CDR3 comprises the amino acid sequence as set forth in SEQ ID NO: 280. Another exemplary CDR3 comprises the amino acid sequence as set forth in SEQ ID NO: 281. Another exemplary CDR3 comprises the amino acid sequence as set forth in SEQ ID NO: 282. Another exemplary CDR3 comprises the amino acid sequence as set forth in SEQ ID NO: 283. Another exemplary CDR3 comprises the amino acid sequence as set forth in SEQ ID NO: 284. Another exemplary CDR3 comprises the amino acid sequence as set forth in SEQ ID NO: 285. Another exemplary CDR3 comprises the amino acid sequence as set forth in SEQ ID NO: 286. Another exemplary CDR3 comprises the amino acid sequence as set forth in SEQ ID NO: 287. Another exemplary CDR3 comprises the amino acid sequence as set forth in SEQ ID NO: 288. Another exemplary CDR3 comprises the amino acid sequence as set forth in SEQ ID NO: 289. Another exemplary CDR3 comprises the amino acid sequence as set forth in SEQ ID NO: 290. Another exemplary CDR3 comprises the amino acid sequence as set forth in SEQ ID NO: 291. Another exemplary CDR3 comprises the amino acid sequence as set forth in SEQ ID NO: 292. Another exemplary CDR3 comprises the amino acid sequence as set forth in SEQ ID NO: 293. Another exemplary CDR3 comprises the amino acid sequence as set forth in SEQ ID NO: 294. Another exemplary CDR3 comprises the amino acid sequence as set forth in SEQ ID NO: 295. Another exemplary CDR3 comprises the amino acid sequence as set forth in SEQ ID NO: 296. Another exemplary CDR3 comprises the amino acid sequence as set forth in SEQ ID NO: 297. Another exemplary CDR3 comprises the amino acid sequence as set forth in SEQ ID NO: 298. Another exemplary CDR3 comprises the amino acid sequence as set forth in SEQ ID NO: 299. Another exemplary CDR3 comprises the amino acid sequence as set forth in SEQ ID NO: 300. Another exemplary CDR3 comprises the amino acid sequence as set forth in SEQ ID NO: 301. Another exemplary CDR3 comprises the amino acid sequence as set forth in SEQ ID NO: 302. Another exemplary CDR3 comprises the amino acid sequence as set forth in SEQ ID NO: 303. Another exemplary CDR3 comprises the amino acid sequence as set forth in SEQ ID NO: 304. Another exemplary CDR3 comprises the amino acid sequence as set forth in SEQ ID NO: 305. Another exemplary CDR3 comprises the amino acid sequence as set forth in SEQ ID NO: 306. Another exemplary CDR3 comprises the amino acid sequence as set forth in SEQ ID NO: 307. Another exemplary CDR3 comprises the amino acid sequence as set forth in SEQ ID NO: 308. Another exemplary CDR3 comprises the amino acid sequence as set forth in SEQ ID NO: 309. Another exemplary CDR3 comprises the amino acid sequence as set forth in SEQ ID NO: 310. Another exemplary CDR3 comprises the amino acid sequence as set forth in SEQ ID NO: 311. Another exemplary CDR3 comprises the amino acid sequence as set forth in SEQ ID NO: 312. Another exemplary CDR3 comprises the amino acid sequence as set forth in SEQ ID NO: 313. Another exemplary CDR3 comprises the amino acid sequence as set forth in SEQ ID NO: 314. Another exemplary CDR3 comprises the amino acid sequence as set forth in SEQ ID NO: 315. Another exemplary CDR3 comprises the amino acid sequence as set forth in SEQ ID NO: 316. Another exemplary CDR3 comprises the amino acid sequence as set forth in SEQ ID NO: 317. Another exemplary CDR3 comprises the amino acid sequence as set forth in SEQ ID NO: 318. Another exemplary CDR3 comprises the amino acid sequence as set forth in SEQ ID NO: 319. Another exemplary CDR3 comprises the amino acid sequence as set forth in SEQ ID NO: 320. Another exemplary CDR3 comprises the amino acid sequence as set forth in SEQ ID NO: 321. Another exemplary CDR3 comprises the amino acid sequence as set forth in SEQ ID NO: 322. Another exemplary CDR3 comprises the amino acid sequence as set forth in SEQ ID NO: 323. Another exemplary CDR3 comprises the amino acid sequence as set forth in SEQ ID NO: 324. Another exemplary CDR3 comprises the amino acid sequence as set forth in SEQ ID NO: 325. Another exemplary CDR3 comprises the amino acid sequence as set forth in SEQ ID NO: 326. Another exemplary CDR3 comprises the amino acid sequence as set forth in SEQ ID NO: 327. Another exemplary CDR3 comprises the amino acid sequence as set forth in SEQ ID NO: 328. Another exemplary CDR3 comprises the amino acid sequence as set forth in SEQ ID NO: 329. Another exemplary CDR3 comprises the amino acid sequence as set forth in SEQ ID NO: 330. Another exemplary CDR3 comprises the amino acid sequence as set forth in SEQ ID NO: 331. Another exemplary CDR3 comprises the amino acid sequence as set forth in SEQ ID NO: 332. Another exemplary CDR3 comprises the amino acid sequence as set forth in SEQ ID NO: 333. Another exemplary CDR3 comprises the amino acid sequence as set forth in SEQ ID NO: 334. Another exemplary CDR3 comprises the amino acid sequence as set forth in SEQ ID NO: 335. Another exemplary CDR3 comprises the amino acid sequence as set forth in SEQ ID NO: 336. Another exemplary CDR3 comprises the amino acid sequence as set forth in SEQ ID NO: 337. Another exemplary CDR3 comprises the amino acid sequence as set forth in SEQ ID NO: 338. Another exemplary CDR3 comprises the amino acid sequence as set forth in SEQ ID NO: 339. Another exemplary CDR3 comprises the amino acid sequence as set forth in SEQ ID NO: 340. Another exemplary CDR3 comprises the amino acid sequence as set forth in SEQ ID NO: 341. Another exemplary CDR3 comprises the amino acid sequence as set forth in SEQ ID NO: 342. Another exemplary CDR3 comprises the amino acid sequence as set forth in SEQ ID NO: 343. Another exemplary CDR3 comprises the amino acid sequence as set forth in SEQ ID NO: 344. Another exemplary CDR3 comprises the amino acid sequence as set forth in SEQ ID NO: 345.

In various embodiments, the BCMA binding protein of the present disclosure has a CDR1 that has an amino acid sequence that is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID NOs: 4-117.

In various embodiments, the BCMA binding protein of the present disclosure has a CDR2 that has an amino acid sequence that is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID NOs: 118-231.

In various embodiments, a complementarity determining region of the BCMA binding protein of the present disclosure has a CDR3 that has an amino acid sequence that is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID NOs: 232-345.

In various embodiments, a BCMA binding protein of the present disclosure has an amino acid sequence that is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID NOs: 346-460.

In various embodiments, a BCMA binding protein of the present disclosure has a framework 1 (f1) that has an amino acid sequence that is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 461 or SEQ ID NO: 462.

In various embodiments, a BCMA binding protein of the present disclosure has a framework 2 (f2) that has an amino acid sequence that is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 463.

In various embodiments, a BCMA binding protein of the present disclosure has a framework 3 (f3) that has an amino acid sequence that is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 464 or SEQ ID NO: 465.

In various embodiments, a BCMA binding protein of the present disclosure has a framework 4 (f4) that has an amino acid sequence that is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 466 or SEQ ID NO: 467.

In some embodiments, the BCMA binding protein is a single domain antibody comprising the sequence of SEQ ID NO: 346. In some embodiments, the BCMA binding protein is a single domain antibody comprising the sequence of SEQ ID NO: 347. In some embodiments, the BCMA binding protein is a single domain antibody comprising the sequence of SEQ ID NO: 348. In some embodiments, the BCMA binding protein is a single domain antibody comprising the sequence of SEQ ID NO: 349. In some embodiments, the BCMA binding protein is a single domain antibody comprising the sequence of SEQ ID NO: 350. In some embodiments, the BCMA binding protein is a single domain antibody comprising the sequence of SEQ ID NO: 351. In some embodiments, the BCMA binding protein is a single domain antibody comprising the sequence of SEQ ID NO: 352. In some embodiments, the BCMA binding protein is a single domain antibody comprising the sequence of SEQ ID NO: 353. In some embodiments, the BCMA binding protein is a single domain antibody comprising the sequence of SEQ ID NO: 354. In some embodiments, the BCMA binding protein is a single domain antibody comprising the sequence of SEQ ID NO: 355. In some embodiments, the BCMA binding protein is a single domain antibody comprising the sequence of SEQ ID NO: 356. In some embodiments, the BCMA binding protein is a single domain antibody comprising the sequence of SEQ ID NO: 357. In some embodiments, the BCMA binding protein is a single domain antibody comprising the sequence of SEQ ID NO: 358. In some embodiments, the BCMA binding protein is a single domain antibody comprising the sequence of SEQ ID NO: 359.

In some embodiments, the BCMA binding protein is a single domain antibody comprising the sequence of SEQ ID NO: 360. In some embodiments, the BCMA binding protein is a single domain antibody comprising the sequence of SEQ ID NO: 361. In some embodiments, the BCMA binding protein is a single domain antibody comprising the sequence of SEQ ID NO: 362. In some embodiments, the BCMA binding protein is a single domain antibody comprising the sequence of SEQ ID NO: 363. In some embodiments, the BCMA binding protein is a single domain antibody comprising the sequence of SEQ ID NO: 364. In some embodiments, the BCMA binding protein is a single domain antibody comprising the sequence of SEQ ID NO: 365. In some embodiments, the BCMA binding protein is a single domain antibody comprising the sequence of SEQ ID NO: 366. In some embodiments, the BCMA binding protein is a single domain antibody comprising the sequence of SEQ ID NO: 367. In some embodiments, the BCMA binding protein is a single domain antibody comprising the sequence of SEQ ID NO: 368. In some embodiments, the BCMA binding protein is a single domain antibody comprising the sequence of SEQ ID NO: 369.

In some embodiments, the BCMA binding protein is a single domain antibody comprising the sequence of SEQ ID NO: 370. In some embodiments, the BCMA binding protein is a single domain antibody comprising the sequence of SEQ ID NO: 371. In some embodiments, the BCMA binding protein is a single domain antibody comprising the sequence of SEQ ID NO: 372. In some embodiments, the BCMA binding protein is a single domain antibody comprising the sequence of SEQ ID NO: 373. In some embodiments, the BCMA binding protein is a single domain antibody comprising the sequence of SEQ ID NO: 374. In some embodiments, the BCMA binding protein is a single domain antibody comprising the sequence of SEQ ID NO: 375. In some embodiments, the BCMA binding protein is a single domain antibody comprising the sequence of SEQ ID NO: 376. In some embodiments, the BCMA binding protein is a single domain antibody comprising the sequence of SEQ ID NO: 377. In some embodiments, the BCMA binding protein is a single domain antibody comprising the sequence of SEQ ID NO: 378. In some embodiments, the BCMA binding protein is a single domain antibody comprising the sequence of SEQ ID NO: 379.

In some embodiments, the BCMA binding protein is a single domain antibody comprising the sequence of SEQ ID NO: 380. In some embodiments, the BCMA binding protein is a single domain antibody comprising the sequence of SEQ ID NO: 381. In some embodiments, the BCMA binding protein is a single domain antibody comprising the sequence of SEQ ID NO: 382. In some embodiments, the BCMA binding protein is a single domain antibody comprising the sequence of SEQ ID NO: 383. In some embodiments, the BCMA binding protein is a single domain antibody comprising the sequence of SEQ ID NO: 384. In some embodiments, the BCMA binding protein is a single domain antibody comprising the sequence of SEQ ID NO: 385. In some embodiments, the BCMA binding protein is a single domain antibody comprising the sequence of SEQ ID NO: 386. In some embodiments, the BCMA binding protein is a single domain antibody comprising the sequence of SEQ ID NO: 387. In some embodiments, the BCMA binding protein is a single domain antibody comprising the sequence of SEQ ID NO: 388. In some embodiments, the BCMA binding protein is a single domain antibody comprising the sequence of SEQ ID NO: 389.

In some embodiments, the BCMA binding protein is a single domain antibody comprising the sequence of SEQ ID NO: 390. In some embodiments, the BCMA binding protein is a single domain antibody comprising the sequence of SEQ ID NO: 391. In some embodiments, the BCMA binding protein is a single domain antibody comprising the sequence of SEQ ID NO: 392. In some embodiments, the BCMA binding protein is a single domain antibody comprising the sequence of SEQ ID NO: 393. In some embodiments, the BCMA binding protein is a single domain antibody comprising the sequence of SEQ ID NO: 394. In some embodiments, the BCMA binding protein is a single domain antibody comprising the sequence of SEQ ID NO: 395. In some embodiments, the BCMA binding protein is a single domain antibody comprising the sequence of SEQ ID NO: 396. In some embodiments, the BCMA binding protein is a single domain antibody comprising the sequence of SEQ ID NO: 397. In some embodiments, the BCMA binding protein is a single domain antibody comprising the sequence of SEQ ID NO: 398. In some embodiments, the BCMA binding protein is a single domain antibody comprising the sequence of SEQ ID NO: 399.

In some embodiments, the BCMA binding protein is a single domain antibody comprising the sequence of SEQ ID NO: 400. In some embodiments, the BCMA binding protein is a single domain antibody comprising the sequence of SEQ ID NO: 401. In some embodiments, the BCMA binding protein is a single domain antibody comprising the sequence of SEQ ID NO: 402. In some embodiments, the BCMA binding protein is a single domain antibody comprising the sequence of SEQ ID NO: 403. In some embodiments, the BCMA binding protein is a single domain antibody comprising the sequence of SEQ ID NO: 404. In some embodiments, the BCMA binding protein is a single domain antibody comprising the sequence of SEQ ID NO: 405. In some embodiments, the BCMA binding protein is a single domain antibody comprising the sequence of SEQ ID NO: 406. In some embodiments, the BCMA binding protein is a single domain antibody comprising the sequence of SEQ ID NO: 407. In some embodiments, the BCMA binding protein is a single domain antibody comprising the sequence of SEQ ID NO: 408. In some embodiments, the BCMA binding protein is a single domain antibody comprising the sequence of SEQ ID NO: 409.

In some embodiments, the BCMA binding protein is a humanized single domain antibody comprising the sequence of SEQ ID NO: 410. In some embodiments, the BCMA binding protein is a single domain antibody comprising the sequence of SEQ ID NO: 411. In some embodiments, the BCMA binding protein is a single domain antibody comprising the sequence of SEQ ID NO: 412. In some embodiments, the BCMA binding protein is a single domain antibody comprising the sequence of SEQ ID NO: 413. In some embodiments, the BCMA binding protein is a single domain antibody comprising the sequence of SEQ ID NO: 414. In some embodiments, the BCMA binding protein is a single domain antibody comprising the sequence of SEQ ID NO: 415. In some embodiments, the BCMA binding protein is a single domain antibody comprising the sequence of SEQ ID NO: 416. In some embodiments, the BCMA binding protein is a single domain antibody comprising the sequence of SEQ ID NO: 417. In some embodiments, the BCMA binding protein is a single domain antibody comprising the sequence of SEQ ID NO: 418. In some embodiments, the BCMA binding protein is a single domain antibody comprising the sequence of SEQ ID NO: 419.

In some embodiments, the BCMA binding protein is a humanized single domain antibody comprising the sequence of SEQ ID NO: 420. In some embodiments, the BCMA binding protein is a humanized single domain antibody comprising the sequence of SEQ ID NO: 421. In some embodiments, the BCMA binding protein is a single domain antibody comprising the sequence of SEQ ID NO: 422. In some embodiments, the BCMA binding protein is a single domain antibody comprising the sequence of SEQ ID NO: 423. In some embodiments, the BCMA binding protein is a single domain antibody comprising the sequence of SEQ ID NO: 424. In some embodiments, the BCMA binding protein is a single domain antibody comprising the sequence of SEQ ID NO: 425. In some embodiments, the BCMA binding protein is a single domain antibody comprising the sequence of SEQ ID NO: 426. In some embodiments, the BCMA binding protein is a single domain antibody comprising the sequence of SEQ ID NO: 427. In some embodiments, the BCMA binding protein is a single domain antibody comprising the sequence of SEQ ID NO: 428. In some embodiments, the BCMA binding protein is a single domain antibody comprising the sequence of SEQ ID NO: 429.

In some embodiments, the BCMA binding protein is a single domain antibody comprising the sequence of SEQ ID NO: 430. In some embodiments, the BCMA binding protein is a single domain antibody comprising the sequence of SEQ ID NO: 431. In some embodiments, the BCMA binding protein is a single domain antibody comprising the sequence of SEQ ID NO: 432. In some embodiments, the BCMA binding protein is a single domain antibody comprising the sequence of SEQ ID NO: 433. In some embodiments, the BCMA binding protein is a single domain antibody comprising the sequence of SEQ ID NO: 434. In some embodiments, the BCMA binding protein is a single domain antibody comprising the sequence of SEQ ID NO: 435. In some embodiments, the BCMA binding protein is a single domain antibody comprising the sequence of SEQ ID NO: 436. In some embodiments, the BCMA binding protein is a single domain antibody comprising the sequence of SEQ ID NO: 437. In some embodiments, the BCMA binding protein is a single domain antibody comprising the sequence of SEQ ID NO: 438. In some embodiments, the BCMA binding protein is a single domain antibody comprising the sequence of SEQ ID NO: 439.

In some embodiments, the BCMA binding protein is a single domain antibody comprising the sequence of SEQ ID NO: 440. In some embodiments, the BCMA binding protein is a single domain antibody comprising the sequence of SEQ ID NO: 441. In some embodiments, the BCMA binding protein is a single domain antibody comprising the sequence of SEQ ID NO: 442. In some embodiments, the BCMA binding protein is a single domain antibody comprising the sequence of SEQ ID NO: 443. In some embodiments, the BCMA binding protein is a single domain antibody comprising the sequence of SEQ ID NO: 444. In some embodiments, the BCMA binding protein is a single domain antibody comprising the sequence of SEQ ID NO: 445. In some embodiments, the BCMA binding protein is a single domain antibody comprising the sequence of SEQ ID NO: 446. In some embodiments, the BCMA binding protein is a single domain antibody comprising the sequence of SEQ ID NO: 447. In some embodiments, the BCMA binding protein is a single domain antibody comprising the sequence of SEQ ID NO: 448. In some embodiments, the BCMA binding protein is a single domain antibody comprising the sequence of SEQ ID NO: 449. In some embodiments, the BCMA binding protein is a single domain antibody comprising the sequence of SEQ ID NO: 450.

In some embodiments, the BCMA binding protein is a single domain antibody comprising the sequence of SEQ ID NO: 451. In some embodiments, the BCMA binding protein is a single domain antibody comprising the sequence of SEQ ID NO: 452. In some embodiments, the BCMA binding protein is a single domain antibody comprising the sequence of SEQ ID NO: 453. In some embodiments, the BCMA binding protein is a single domain antibody comprising the sequence of SEQ ID NO: 454. In some embodiments, the BCMA binding protein is a single domain antibody comprising the sequence of SEQ ID NO: 455. In some embodiments, the BCMA binding protein is a single domain antibody comprising the sequence of SEQ ID NO: 456. In some embodiments, the BCMA binding protein is a single domain antibody comprising the sequence of SEQ ID NO: 457. In some embodiments, the BCMA binding protein is a single domain antibody comprising the sequence of SEQ ID NO: 458. In some embodiments, the BCMA binding protein is a single domain antibody comprising the sequence of SEQ ID NO: 459. In some embodiments, the BCMA binding protein is a single domain antibody comprising the sequence of SEQ ID NO: 460.

A BCMA binding protein described herein can bind to human BCMA with a Kd ranges from about 0.1 nM to about 500 nM. In some embodiments, the hKd ranges from about 0.1 nM to about 450 nM. In some embodiments, the hKd ranges from about 0.1 nM to about 400 nM. In some embodiments, the hKd ranges from about 0.1 nM to about 350 nM. In some embodiments, the hKd and ranges from about 0.1 nM to about 300 nM. In some embodiments, the hKd ranges from about 0.1 nM to about 250 nM. In some embodiments, the hKd ranges from about 0.1 nM to about 200 nM. In some embodiments, the hKd ranges from about 0.1 nM to about 150 nM. In some embodiments, the hKd ranges from about 0.1 nM to about 100 nM. In some embodiments, the hKd ranges from about 0.1 nM to about 90 nM. In some embodiments, the hKd range from about 0.2 nM to about 80 nM. In some embodiments, the hKd ranges from about 0.3 nM to about 70 nM. In some embodiments, the hKd ranges from about 0.4 nM to about 50 nM. In some embodiments, the hKd ranges from about 0.5 nM to about 30 nM. In some embodiments, the hKd ranges from about 0.6 nM to about 10 nM. In some embodiments, the hKd ranges from about 0.7 nM to about 8 nM. In some embodiments, the hKd ranges from about 0.8 nM to about 6 nM. In some embodiments, the hKd ranges from about 0.9 nM to about 4 nM. In some embodiments, the hKd ranges from about 1 nM to about 2 nM.

In some embodiments, any of the foregoing BCMA binding proteins are affinity peptide tagged for ease of purification. In some embodiments, the affinity peptide tag is six consecutive histidine residues, also referred to as a His tag or a 6×-His tag (e.g., SEQ ID NO: 471).

In certain embodiments, the BCMA binding proteins according to the present disclosure may be incorporated into BCMA targeting trispecific proteins. In some examples, the trispecific binding protein comprises a CD3 binding domain, a human serum albumin (HSA) binding domain and an anti-BCMA binding domain according to the present disclosure. In some instances, the trispecific binding protein comprises the domains described above in the following orientation: BCMA-HSA-CD3.

In certain embodiments, the BCMA binding proteins of the present disclosure preferentially bind membrane bound BCMA over soluble BCMA. Membrane bound BCMA refers to the presence of BCMA in or on the cell membrane surface of a cell that expresses BCMA. Soluble BCMA refers to BCMA that is no longer on in or on the cell membrane surface of a cell that expresses or expressed BCMA. In certain instances, the soluble BCMA is present in the blood and/or lymphatic circulation in a subject. In one embodiment, the BCMA binding proteins bind membrane-bound BCMA at least 5 fold, 10 fold, 15 fold, 20 fold, 25 fold, 30 fold, 40 fold, 50 fold, 100 fold, 500 fold, or 1000 fold greater than soluble BCMA. In one embodiment, the antigen binding proteins of the present disclosure preferentially bind membrane-bound BCMA 30 fold greater than soluble BCMA. Determining the preferential binding of an antigen binding protein to membrane bound BCMA over soluble BCMA can be readily determined using assays well known in the art.

Integration into Chimeric Antigen Receptors (CAR)

The BCMA binding proteins of the present disclosure, e.g., an anti-BCMA single domain antibody, can, in certain examples, be incorporated into a chimeric antigen receptor (CAR). An engineered immune effector cell, e.g., a T cell or NK cell, can be used to express a CAR that includes an anti-BCMA single domain antibody as described herein. In one embodiments, the CAR including an anti-BCMA single domain antibody as described herein is connected to a transmembrane domain via a hinge region, and further a costimulatory domain, e.g., a functional signaling domain obtained from OX40, CD27, CD28, CDS, ICAM-1, LFA-1 (CD11a/CD18), ICOS (CD278), or 4-1BB. In some embodiments, the CAR further comprises a sequence encoding an intracellular signaling domain, such as 4-1BB and/or CD3 zeta.

Multispecific Protein Targeting BCMA

One embodiment provides a multispecific protein comprising a BCMA binding domain, wherein the BCMA binding domain is according to any one of above embodiments. In some embodiments, the multispecific protein comprises the BCMA binding domain according to any one of above embodiments (anti-BCMA domain), a CD3 binding domain (anti-CD3 domain), and an albumin binding domain (anti-ALB domain). In some embodiments, the BCMA targeting multispecific protein is a trispecific protein, wherein the trispecific protein has a domain order of $H_2N$-(C)-(A)-(B)-COOH. In some embodiments, the anti-BCMA domain (the anti-target domain, T), the anti-CD3 domain (C), and the anti-ALB domain (A) are in an anti-CD3: anti-ALB: anti-BCMA (CAT) orientation. In some embodiments, the anti-BCMA domain (the anti-target domain, T) the anti-CD3 domain (C), and the anti-ALB domain (A) are in an anti-BCMA: anti-ALB: anti-CD3 (TAC) orientation.

Tumor Growth Reduction Properties

In certain embodiments, the BCMA binding proteins of the disclosure reduces the growth of tumor cells in vivo when administered to a subject who has tumor cells that express BCMA. Measurement of the reduction of the growth of tumor cells can be determined by multiple different methodologies well known in the art. Non-limiting examples include direct measurement of tumor dimension, measurement of excised tumor mass and comparison to control subjects, measurement via imaging techniques (e.g., CT or MRI) that may or may not use isotopes or luminescent molecules (e.g., luciferase) for enhanced analysis, and the like. In specific embodiments, administration of the antigen binding agents of the disclosure results in a reduction of in vivo growth of tumor cells as compared to a control antigen binding agent by at least about 10%, 20%, 30%, 40%, 50%, 60%, 70%, 80%, 90% or 100%, with an about 100% reduction in tumor growth indicating a complete response and disappearance of the tumor. In further embodiments, administration of the antigen binding agents of the disclosure results in a reduction of in vivo growth of tumor cells as compared to a control antigen binding agent by about 50-100%, about 75-100% or about 90-100%. In further embodiments, administration of the antigen binding agents of the disclosure results in a reduction of in vivo growth of tumor cells as compared to a control antigen binding agent by about 50-60%, about 60-70%, about 70-80%, about 80-90%, or about 90-100%.

BCMA Binding Protein Modifications

The BCMA binding proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence to block an immunogenic domain and/or for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in the BCMA binding proteins described herein, including the peptide backbone, the amino acid side-chains, and the amino or carboxyl termini. Certain common peptide modifications that are useful for modification of BCMA binding proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

Polynucleotides Encoding BCMA Binding Proteins

Also provided, in some embodiments, are polynucleotide molecules encoding a BCMA binding protein as described herein. In some embodiments, the polynucleotide molecules are provided as DNA constructs. In other embodiments, the polynucleotide molecules are provided as messenger RNA transcripts.

The polynucleotide molecules are constructed by known methods such as by combining the genes encoding the anti-BCMA binding protein, operably linked to a suitable promoter, and optionally a suitable transcription terminator, and expressing it in bacteria or other appropriate expression system such as, for example CHO cells.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described BCMA binding protein. Examples of expression vectors for expression in *E. coli* are pSKK (Le Gall et al., *J Immunol Methods*. (2004) 285(1): 111-27), pcDNA5 (Invitrogen) for expression in mammalian cells, PICHIAPINK™ Yeast Expression Systems (Invitrogen), BACUVANCE™ Baculovirus Expression System (GenScript).

Thus, the BCMA binding proteins as described herein, in some embodiments, are produced by introducing a vector encoding the protein as described above into a host cell and culturing said host cell under conditions whereby the protein domains are expressed, may be isolated and, optionally, further purified.

Pharmaceutical Compositions

Also provided, in some embodiments, are pharmaceutical compositions comprising a BCMA binding protein described herein, a vector comprising the polynucleotide encoding the polypeptide of the BCMA binding proteins or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents. A further embodiment provides one or more of the above described binding proteins, such as anti-BCMA single domain antibodies or antigen-binding fragments thereof packaged in lyophilized form, or packaged in an aqueous medium.

In some embodiments of the pharmaceutical compositions, the BCMA binding protein described herein is encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the BCMA binding protein is attached to liposomes. In some instances, the BCMA binding protein is conjugated to the surface of liposomes. In some instances, the BCMA binding protein is encapsulated within the shell of a liposome. In some instances, the liposome is a cationic liposome.

The BCMA binding proteins described herein are contemplated for use as a medicament. Administration is effected by different ways, e.g., by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

In some embodiments, the BCMA binding proteins of this disclosure are administered at a dosage of up to 10 mg/kg at a frequency of once a week. In some cases, the dosage ranges from about 1 ng/kg to about 10 mg/kg. In some embodiments, the dose is from about 1 ng/kg to about 10 ng/kg, about 5 ng/kg to about 15 ng/kg, about 12 ng/kg to about 20 ng/kg, about 18 ng/kg to about 30 ng/kg, about 25 ng/kg to about 50 ng/kg, about 35 ng/kg to about 60 ng/kg, about 45 ng/kg to about 70 ng/kg, about 65 ng/kg to about 85 ng/kg, about 80 ng/kg to about 1 µg/kg, about 0.5 µg/kg to about 5 µg/kg, about 2 µg/kg to about 10 µg/kg, about 7 µg/kg to about 15 µg/kg, about 12 µg/kg to about 25 µg/kg, about 20 µg/kg to about 50 µg/kg, about 35 µg/kg to about 70 µg/kg, about 45 µg/kg to about 80 µg/kg, about 65 µg/kg to about 90 µg/kg, about 85 µg/kg to about 0.1 mg/kg, about 0.095 mg/kg to about 10 mg/kg. In some cases, the dosage is about 0.1 mg/kg to about 0.2 mg/kg; about 0.25 mg/kg to about 0.5 mg/kg, about 0.45 mg/kg to about 1 mg/kg, about 0.75 mg/kg to about 3 mg/kg, about 2.5 mg/kg to about 4 mg/kg, about 3.5 mg/kg to about 5 mg/kg, about 4.5 mg/kg to about 6 mg/kg, about 5.5 mg/kg to about 7 mg/kg, about 6.5 mg/kg to about 8 mg/kg, about 7.5 mg/kg to about 9 mg/kg, or about 8.5 mg/kg to about 10 mg/kg. The frequency of administration, in some embodiments, is about less than daily, every other day, less than once a day, twice a week, weekly, once in 7 days, once in two weeks, once in two weeks, once in three weeks, once in four weeks, or once a month. In some cases, the frequency of administration is weekly. In some cases, the frequency of administration is weekly and the dosage is up to 10 mg/kg. In some cases, duration of administration is from about 1 day to about 4 weeks or longer.

Methods of Treatment

Also provided herein, in some embodiments, are methods and uses for stimulating the immune system of an individual in need thereof comprising administration of a BCMA binding protein as described herein. In some instances, the administration of a BCMA binding protein described herein induces and/or sustains cytotoxicity towards a cell expressing a target antigen. In some instances, the cell expressing a target antigen is a terminally differentiated B cell that is a cancer or tumor cell, or a metastatic cancer or tumor cell.

Also provided herein are methods and uses for a treatment of a disease, disorder or condition associated with BCMA comprising administering to an individual in need thereof a BCMA binding protein or a multispecific binding protein comprising the BCMA binding protein described herein.

Diseases, disorders or conditions associated with BCMA include, but are not limited to, a cancer or a metastasis that is of a B cell lineage.

Cancers that can be treated, prevented, or managed by the BCMA binding proteins of the present disclosure, and methods of using them, include but are not limited to a primary cancer or a metastatic cancer.

Examples of such leukemias include, but are not limited to: acute lymphoblastic leukemia (ALL), acute myeloid leukemia (AML), chronic lymphocytic leukemia (CLL) and chronic myeloid leukemia (CML), as well as a number of less common types such as, for example, Hairy cell leukemia (HCL), T-cell prolymphocytic leukemia (T-PLL), Large granular lymphocytic leukemia and Adult T-cell leukemia, etc. Acute lymphoblastic leukemia (ALL) subtypes to be treated include, but are not limited to, precursor B acute lymphoblastic leukemia, precursor T acute lymphoblastic leukemia, Burkitt's leukemia, and acute biphenotypic leukemia. Chronic lymphocytic leukemia (CLL) subtypes to be treated include, but are not limited to, B-cell prolymphocytic leukemia. Acute myelogenous leukemia (AML) subtypes to be treated include, but are not limited to, acute promyelocytic leukemia, acute myeloblastic leukemia, and acute megakaryoblastic leukemia. Chronic myelogenous leukemia (CML) subtypes to be treated include, but are not limited to, chronic myelomonocytic leukemia.

Examples of a lymphoma to be treated with the subject methods include, but not limited to Hodgkin's disease, non-Hodgkin's disease, or any subtype of lymphoma.

Examples of such multiple myelomas include, but are not limited to, a multiple myeloma of the bone or other tissues including, for example, a smoldering multiple myeloma, a non-secretory myeloma, a osteosclerotic myeloma, etc.

For a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

In some embodiments of the methods described herein, the BCMA binding proteins as described herein are administered in combination with an agent for treatment of the particular disease, disorder or condition. Agents include, but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, a BCMA binding protein as described herein is administered in combination with anti-diarrheal agents, anti-emetic agents, analgesics, opioids and/or non-steroidal anti-inflammatory agents. In some embodiments, a BCMA binding protein as described herein is administered in combination with anti-cancer agents. Non-limiting examples of anti-cancer agents that can be used in the various embodiments of the disclosure, including pharmaceutical compositions and dosage forms and kits of the disclosure, include: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1 interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; zorubicin hydrochloride. Other examples of anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; VITAXIN®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In some embodiments, the anti-BCMA single domain binding protein of the present disclosure is used in combination with gemcitabine.

In some embodiments, a BCMA binding proteins as described herein is administered before, during, or after surgery.

In some embodiments, the anti-cancer agent is conjugated via any suitable means to the trispecific protein.

Methods of Detection of BCMA Expression and Diagnosis of BCMA Associated Cancer

According to another embodiment of the disclosure, kits for detecting expression of BCMA in vitro or in vivo are provided. The kits include the foregoing BCMA binding proteins (e.g., a labeled anti-BCMA single domain antibody or antigen binding fragments thereof), and one or more compounds for detecting the label. In some embodiments, the label is selected from the group consisting of a fluorescent label, an enzyme label, a radioactive label, a nuclear magnetic resonance active label, a luminescent label, and a chromophore label.

In some cases, BCMA expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has cancer by contacting a sample from the subject with an anti-BCMA single domain antibody as disclosed herein; and detecting binding of the single domain antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with an anti-BCMA single domain antibody as disclosed herein; and detecting binding of the antibody to the sample. An increase in binding of the antibody to the sample as compared to binding of the antibody to a control sample confirms the diagnosis of cancer in the subject.

In some examples of the disclosed methods, the single domain antibody is directly labeled.

In some examples, the methods further include contacting a second antibody that specifically binds the single domain antibody with the sample; and detecting the binding of the second antibody. An increase in binding of the second antibody to the sample as compared to binding of the second antibody to a control sample detects cancer in the subject or confirms the diagnosis of cancer in the subject.

In some cases, the cancer is a lymphoma, a leukemia or a multiple myeloma.

In some examples, the control sample is a sample from a subject without cancer. In particular examples, the sample is a blood or tissue sample.

In some cases, the antibody that binds (for example specifically binds) BCMA is directly labeled with a detectable label. In another embodiment, the antibody that binds (for example, specifically binds) BCMA (the first antibody) is unlabeled and a second antibody or other molecule that can bind the antibody that specifically binds BCMA is labeled. A second antibody is chosen such that it is able to specifically bind the specific species and class of the first antibody. For example, if the first antibody is a llama IgG, then the secondary antibody may be an anti-llama-IgG. Other molecules that can bind to antibodies include, without limitation, Protein A and Protein G, both of which are available commercially. Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include 125I, 131I, 35S or 3H.

In an alternative embodiment, BCMA can be assayed in a biological sample by a competition immunoassay utilizing BCMA standards labeled with a detectable substance and an unlabeled antibody that specifically binds BCMA. In this assay, the biological sample, the labeled BCMA standards and the antibody that specifically bind BCMA are combined and the amount of labeled BCMA standard bound to the unlabeled antibody is determined. The amount of BCMA in the biological sample is inversely proportional to the amount of labeled BCMA standard bound to the antibody that specifically binds BCMA.

The immunoassays and method disclosed herein can be used for a number of purposes. In one embodiment, the antibody that specifically binds BCMA may be used to detect the production of BCMA in cells in cell culture. In another embodiment, the antibody can be used to detect the amount of BCMA in a biological sample, such as a tissue sample, or a blood or serum sample. In some examples, the BCMA is cell-surface BCMA. In other examples, the BCMA is soluble BCMA (e.g., BCMA in a cell culture supernatant or soluble BCMA in a body fluid sample, such as a blood or serum sample).

In one embodiment, a kit is provided for detecting BCMA in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble BCMA protein or fragment. Kits for detecting a polypeptide will typically comprise a single domain antibody, according to the present disclosure, that specifically binds BCMA. In some embodiments, an antibody fragment, such as a scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds BCMA. The instructional materials may be written, in an electronic form (such as a computer diskette or compact disk) or may be visual (such as video files), or provided through an electronic network, for example, over the internet, World Wide Web, an intranet, or other network. The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting BCMA in a biological sample generally includes the steps of contacting the biological sample with an antibody which specifically reacts, under immunologically reactive conditions, to a BCMA polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the single domain antibodies that bind BCMA, as disclosed herein, can be used in these assays. Thus, the antibodies can be used in a conventional immunoassay, including, without limitation, an ELISA, an RIA, FACS, tissue immunohistochemistry, Western blot or immunoprecipitation.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application.

Example 1

Ability of an Exemplar Anti-BCMA Trispecific Domain Antibody Containing a BCMA Binding Protein of the Present Disclosure to Mediate T Cell Killing of Cancer Cells Expressing BCMA, in TDCC (T Cell Dependent Cell Cytotoxic) Assays Protein Production Sequences of BCMA targeting trispecific molecules, containing a BCMA binding protein according to the present disclosure, were cloned into mammalian expression vector pcDNA 3.4 (Invitrogen) preceded by a leader sequence and followed by a 6× Histidine Tag (SEQ ID NO: 471). Expi293 cells (Life Technologies A14527) were maintained in suspension in Optimum Growth Flasks (Thomson) between 0.2 to 8×1e6 cells/mL in Expi293 media. Purified plasmid DNA was transfected into Expi293 cells in accordance with Expi293 Expression System Kit (Life Technologies, A14635) protocols, and maintained for 4-6 days post transfection. The amount of the exemplary trispecific proteins being tested, in the conditioned media, from the transfected Expi293 cells was quantitated using an Octet instrument with Protein A tips and using a control trispecific protein for a standard curve.

T Cell Dependent Cellular Cytotoxicity Assays

Titrations of conditioned media was added to TDCC assays (T cell Dependent Cell Cytotoxicity assays) to assess whether the anti-BCMA single domain antibody is capable of forming a synapse between T cells and a BCMA-expressing cell line and direct the T cells to kill the BCMA-expressing cell line. In this assay (Nazarian et al., 2015. *J. Biomol. Screen.*, 20:519-27), T cells and target cancer cell line cells were mixed together at a 10:1 ratio in a 384-well plate, and varying amounts of the trispecific proteins being tested were added. The tumor cell lines were engineered to express luciferase protein. After 48 hours, to quantitate the remaining viable tumor cells, STEADY-GLO® Luminescent Assay (Promega) was used.

In this example EJM cells were used, which is a cell line that serves as an in vitro model for multiple myeloma and plasma cell leukemia. Viability of the EJM cells is measured after 48 hours. It was seen that the trispecific proteins mediated T cell killing. FIG. 1 shows an example cell viability assay with test proteins 01H08, 01F07, 02F02 and BH253 compared to a negative control. The $EC_{50}$ for the TDCC activity of several other test trispecific proteins are listed below in Table 1.

Binding Affinity

In the instant study, the binding affinity to human BCMA protein of the BCMA targeting trispecific proteins containing a BCMA binding protein according to the present disclosure was determined. The affinity measurements are listed in Table 1.

TABLE 1

Binding affinity and TDCC Activity of several BCMA targeting trispecific proteins.

| Construct Name | Human BCMA $K_D$ (M) | TDCC EC50 (M) |
|---|---|---|
| 253BH10 | 2.77E−08 | 5.29E−11 |
| 01H08 | 2.86E−09 | 3.41E−13 |
| 01F07 | 4.18E−09 | 7.02E−13 |
| 01H06 | ND | 1.00E−12 |
| 02G02 | 5.26E−09 | 1.08E−12 |
| 02B05 | 5.39E−09 | 1.22E−12 |
| 01C01 | 6.52E−09 | 1.33E−12 |
| 02F02 | 6.73E−09 | 1.36E−12 |
| 02E05 | 6.53E−09 | 1.37E−12 |
| 01E08 | 5.56E−09 | 1.50E−12 |
| 02C01 | 5.31E−09 | 1.55E−12 |
| 02E06 | 6.31E−09 | 1.57E−12 |
| 02B06 | 6.77E−09 | 1.65E−12 |
| 02F04 | 6.75E−09 | 1.72E−12 |
| 01G08 | 6.27E−09 | 1.91E−12 |
| 02C06 | 6.90E−09 | 1.95E−12 |
| 01H09 | 5.44E−09 | 2.21E−12 |
| 01F04 | 6.55E−09 | 2.21E−12 |
| 01D02 | 7.35E−09 | 2.25E−12 |
| 02D11 | 6.71E−09 | 2.35E−12 |
| 01A07 | 6.95E−09 | 2.49E−12 |
| 02C03 | 7.09E−09 | 2.52E−12 |
| 02F07 | 7.06E−09 | 2.59E−12 |
| 01E04 | 7.29E−09 | 2.67E−12 |
| 02H09 | 6.83E−09 | 2.88E−12 |
| 01E03 | 6.36E−09 | 2.98E−12 |
| 02F05 | 7.15E−09 | 3.00E−12 |
| 01B05 | 6.52E−09 | 3.01E−12 |
| 01C05 | 6.09E−09 | 3.07E−12 |
| 02F12 | 7.76E−09 | 3.14E−12 |
| 01H11 | 7.06E−09 | 3.17E−12 |
| 02G06 | 7.50E−09 | 3.39E−12 |

TABLE 1-continued

Binding affinity and TDCC Activity of several BCMA targeting trispecific proteins.

| Construct Name | Human BCMA $K_D$ (M) | TDCC EC50 (M) |
| --- | --- | --- |
| 01E06 | 8.91E-09 | 3.77E-12 |
| 01G11 | 9.70E-09 | 3.98E-12 |
| 02A05 | 7.06E-09 | 4.21E-12 |
| 01A08 | 1.17E-08 | 4.25E-12 |
| 02G05 | 7.12E-09 | 4.33E-12 |
| 01B09 | 1.12E-08 | 5.27E-12 |
| 01G01 | 1.46E-08 | 5.83E-12 |
| 01B06 | 9.10E-09 | 6.97E-12 |
| 01F10 | 1.44E-08 | 7.44E-12 |
| 01E05 | 1.17E-08 | 1.08E-11 |
| 02G01 | 1.63E-08 | 1.08E-11 |
| 01A06 | 1.58E-08 | 1.10E-11 |
| 02B04 | 1.52E-08 | 1.13E-11 |
| 01D06 | 1.49E-08 | 1.35E-11 |
| 02B07 | 1.58E-08 | 1.42E-11 |
| 02B11 | 1.33E-08 | 1.44E-11 |
| 01H04 | 1.74E-08 | 1.47E-11 |
| 01D03 | 2.09E-08 | 1.49E-11 |
| 01A05 | 1.70E-08 | 1.51E-11 |
| 02F11 | 2.00E-08 | 1.52E-11 |
| 01D04 | 1.89E-08 | 1.60E-11 |
| 01B04 | 1.86E-08 | 1.61E-11 |
| 02C05 | 1.56E-08 | 1.62E-11 |
| 02E03 | 1.68E-08 | 1.65E-11 |
| 01D05 | 1.78E-08 | 1.66E-11 |
| 01C04 | 2.16E-08 | 1.75E-11 |
| 01E07 | 1.99E-08 | 1.92E-11 |
| 01G06 | 1.70E-08 | 1.92E-11 |
| 02F06 | 2.19E-08 | 1.93E-11 |
| 01B01 | 1.99E-08 | 1.95E-11 |
| 01D07 | 1.93E-08 | 1.96E-11 |
| 02A08 | 9.51E-09 | 2.01E-11 |
| 01A02 | 2.15E-08 | 2.18E-11 |
| 02G11 | 2.05E-08 | 2.38E-11 |
| 01G04 | 1.17E-08 | 2.41E-11 |
| 02F03 | 2.57E-08 | 2.45E-11 |
| 01C06 | 1.88E-08 | 2.51E-11 |
| 01A01 | 2.13E-08 | 2.64E-11 |
| 01B12 | 2.07E-08 | 2.73E-11 |
| 02A07 | 1.84E-08 | 2.79E-11 |
| 02G08 | 1.80E-08 | 2.86E-11 |
| 02E09 | 2.09E-08 | 3.11E-11 |
| 02H06 | 2.33E-08 | 3.19E-11 |
| 01H10 | 2.48E-08 | 3.52E-11 |
| 01F05 | 1.67E-08 | 3.72E-11 |
| 01C02 | 2.00E-08 | 3.73E-11 |
| 02A04 | 1.76E-08 | 3.82E-11 |
| 02H05 | 1.96E-08 | 3.89E-11 |
| 02G09 | 3.44E-08 | 3.96E-11 |
| 02D06 | 2.33E-08 | 4.28E-11 |
| 02G07 | 1.93E-08 | 4.46E-11 |
| 01H05 | 2.74E-08 | 4.54E-11 |
| 01C08 | 2.83E-08 | 4.57E-11 |
| 01A03 | 3.08E-08 | 4.61E-11 |
| 01A09 | 2.39E-08 | 4.84E-11 |
| 02B01 | 2.14E-08 | 5.18E-11 |
| 02H01 | 3.56E-08 | 5.42E-11 |
| 02H04 | 3.11E-08 | 5.99E-11 |
| 02A11 | 2.52E-08 | 6.06E-11 |
| 01E10 | 1.85E-08 | 6.23E-11 |
| 02D09 | 2.89E-08 | 6.73E-11 |
| 01F08 | 2.14E-08 | 7.12E-11 |
| 01F03 | 1.50E-08 | 7.64E-11 |
| 02H11 | 2.75E-08 | 7.75E-11 |
| 01C07 | 1.98E-08 | 8.33E-11 |
| 01B08 | 2.56E-08 | 8.76E-11 |
| 01B03 | 2.62E-08 | 9.64E-11 |
| 01H01 | 3.59E-08 | 1.18E-10 |
| 02B12 | 2.52E-08 | 1.24E-10 |
| 01G10 | 4.19E-08 | 1.43E-10 |
| 01A04 | 3.75E-08 | 1.59E-10 |
| 01B07 | 4.39E-08 | 1.74E-10 |
| 01C10 | 4.64E-08 | 2.08E-10 |
| 01F02 | 4.13E-08 | 2.25E-10 |
| 01B02 | 1.88E-08 | 3.59E-10 |
| 01F12 | 4.05E-08 | 3.92E-10 |
| 01G09 | 8.78E-08 | 4.41E-10 |
| 01D10 | 5.39E-08 | 4.53E-10 |
| 01F09 | 5.28E-08 | 9.45E-10 |

ND: Not determined.

Molecules 01H08, 01F07, 01H06, 02G02, 02B05, 01C01, 02F02, 02E05, 01E08, 02C01, 02E06, 02B06, 02F04, 01G08, 02C06, 01H09, 01F04, 01D02, 02D11, 01A07, 02C03, 02F07, 01E04, 02H09, 01E03, 02F05, 01B05, 01C05, 02F12, 01H11, 02G06, 01E06, 01G11, 02A05, 01A08, 02G05, 01B09, 01G01, 01B06, 01F10, 01E05, 02G01, 01A06, 02B04, 01D06, 02B07, 02B11, 01H04, 01D03, 01A05, 02F11, 01D04, 01B04, 02C05, 02E03, 01D05, 01C04, 01E07, 01G06, 02F06, 01B01, 01D07, 02A08, 01A02, 02G11, 01G04, 02F03, 01C06, 01A01 have at least two fold increase TDCC potency and also show increase affinity compared to a molecule with the parental CDRs, 253BH10.

Molecules 01H08, 01F07, 01H06, 02G02, 02B05, 01C01, 02F02, 02E05, 01E08, 02C01, 02E06, 02B06, 02F04, 01G08, 02C06, 01H09, 01F04, 01D02, 02D11, 01A07, 02C03, 02F07, 01E04, 02H09, 01E03, 02F05, 01B05, 01C05, 02F12, 01H11, 02G06, 01E06, 01G11, 02A05, 01A08, 02G05, 01B09 have at least ten-fold increase TDCC potency and also show increase affinity compared to a molecule with the parental CDRs, 253BH10.

An anti-GFP trispecific molecule, included in these assays as a negative control, had no detectable BCMA binding and no effect on cell viability in the TDCC assay (data not shown).

Example 2

Methods to Assess Binding and Cytotoxic Activities of Exemplary Purified Trispecific Antigen Binding Proteins Containing a BCMA Binding Domain According to the Present Disclosure Against Jeko1, MOLP8 and OPM2 Cells Protein Production Sequences of BCMA targeting trispecific molecules, containing a BCMA binding protein according to the present disclosure, preceded by a leader sequence and followed by a 6× Histidine Tag (SEQ ID NO: 471), were expressed using the vectors and methods previously described (Running Deer and Allison, 2004. *Biotechnol Prog.* 20:880-9) except lipid based reagents and non-linearized plasmid DNA were used for cell transfection. Recombinant trispecific proteins were purified using affinity chromatography, ion exchange, and/or size exclusion chromatography. Purified protein was quantitated using theoretical extinction coefficients and absorption spectroscopy. An image of a Coomassie stained SDS-PAGE demonstrates the purity of the proteins (FIG. 2).

Cytotoxicity Assays

A human T-cell dependent cellular cytotoxicity (TDCC) assay was used to measure the ability of T cell engagers, including trispecific molecules, to direct T cells to kill tumor cells (Nazarian et al., 2015. *J. Biomol. Screen.*, 20:519-27). In this assay, T cells and target cancer cell line cells are mixed together at a 10:1 ratio in a 384-well plate, and varying amounts of the trispecific proteins being tested are added. The tumor cell lines are engineered to express a luciferase protein. After 48 hours, to quantitate the remaining viable tumor cells, STEADY-GLO® Luminescent Assay (Promega) was used.

In the instant study, titrations of purified protein were added to TDCC assays (T cell Dependent Cell Cytotoxicity assays) to assess whether the anti-BCMA single domain antibody was capable of forming a synapse between T cells and BCMA-expressing Jeko1, MOLP8 and OPM2 cancer cell lines. Jeko1 is a B cell lymphoma cell line. MOLP-8 is a myeloma cell line. OPM-2 is a human myeloma cell line.

Viability of the cells was measured after 48 hours. It was seen that the trispecific proteins mediated T cell killing. FIG. 3 shows an example cell viability assay with test proteins compared to a negative control. The $EC_{50}$ for the TDCC activity of several other test trispecific proteins are listed below in Table 2. An anti-GFP trispecific molecule, included in these assays as a negative control, had no effect on cell viability (data not shown).

TABLE 2

TDCC $EC_{50}$ Values for 3 Cell Lines for
Select Binder Sequences in TriTAC format

| Construct name | Jeko1 EC50 (M) | MOLP-8 EC50 (M) | OPM-2 EC50 (M) |
| --- | --- | --- | --- |
| BH2T TriTAC | 3.2E−10 | 2.0E−10 | 1.6E−10 |
| 01F07 TriTAC | 5.3E−12 | 1.5E−12 | 4.4E−12 |
| 01F07-M34Y TriTAC | 5.6E−12 | 1.5E−12 | 3.6E−12 |
| 01F07-M34G TriTAC | 9.0E−12 | 2.2E−12 | 5.6E−12 |
| 01G08 TriTAC | 1.5E−11 | 2.5E−12 | 6.9E−12 |
| 01H08 TriTAC | 4.0E−12 | 9.4E−13 | 3.1E−12 |
| 02B05 TriTAC | 8.3E−12 | 2.5E−12 | 6.5E−12 |
| 02B06 TriTAC | 1.1E−11 | 2.8E−12 | 9.7E−12 |
| 02E05 TriTAC | 1.1E−11 | 3.3E−12 | 1.2E−11 |
| 02E06 TriTAC | 9.1E−12 | 2.4E−12 | 7.4E−12 |
| 02F02 TriTAC | 8.2E−12 | 3.5E−12 | 1.0E−11 |
| 02F04 TriTAC | 1.0E−11 | 2.5E−12 | 7.3E−12 |
| 02G02 TriTAC | 1.1E−11 | 2.8E−12 | 6.6E−12 |
| 02G02-M34Y TriTAC | 1.1E−11 | 5.6E−12 | 6.2E−12 |
| 02G02-M34G TriTAC | 1.2E−11 | 4.0E−12 | 7.1E−12 |

Binding Affinity

In the instant study, the binding affinity to human BCMA protein of the BCMA targeting trispecific proteins containing a BCMA binding protein according to the present disclosure was determined.

TABLE 3

Binding affinity of purified targeting trispecific
proteins containing a BCMA binding protein
according to the present disclosure.

| Construct name | Human BCMA KD (M) |
| --- | --- |
| 01F07-M34Y TriTAC | 3.0E−09 |
| 01F07-M34G TriTAC | 6.0E−09 |
| 02B05 TriTAC | 6.0E−09 |
| 02G02-M34Y TriTAC | 5.0E−09 |
| 02G02-M34G TriTAC | 7.0E−09 |

Example 3

ADCC Activity of an Exemplar Anti-BCMA Multidomain Antibody of the Present Disclosure This study is directed to determining the ability of an exemplary anti-BCMA multidomain antibody of the present disclosure to mediate ADCC as compared to a parental llama anti-BCMA antibody which does not have sequence modifications or substitutions as the exemplary antibody of the disclosure. Both antibodies are expressed as multidomain proteins which include an additional immunoglobulin Fc domain.

Materials

Donors are leukophoresed, and NK cells are isolated from the leukopack by the Cell Purification Group using the Milteni AUTOMACS® Pro negative selection system. NK cells are held overnight at 4° C. on a rocker, then washed, counted and resuspended at $4 \times 10^6$ cells/mL in complete RPMI for use in the ADCC assay.

Targets: Tumor cell targets are selected based on BCMA expression. Targets are washed and counted. $6 \times 10^6$ targets are resuspended in complete RPMI and labeled in a final concentration of 10 µM calcein (Sigma #C1359-00UL calcein am 4 mm in anhydrous DMSO) for 40 minutes at 37° C., 5% $CO_2$. Cells are washed twice in PBS, resuspended in complete RPMI and incubated at 37° C., 5% $CO_2$ for 2 hrs. After labeling, target cells are washed, recounted and resuspended at $0.2 \times 10^6$ cells/mL in complete RPMI for use in the ADCC assay.

Methods

The ADCC assay is performed in a 96-well round bottom tissue culture plate (Corning 3799). The test proteins are titrated from 20 µg/mL to 0.0002 µg/mL by carrying 10 µL in 1000 µL of complete RPMI containing 10% FCS (a 1:10 dilution). Calcein labeled targets are added, 50 µL to contain 10,000 cells. Target cells and various concentrations of the multidomain proteins containing either the exemplar anti-BCMA single domain antibody or the comparator antibody are incubated for 40 minutes at 4° C., then NK cell effectors added, 50 µL to contain 100,000 cells (10:1 E:T ratio). Cultures are incubated for 4 hrs at 37° C. then supernatants pulled and assayed for calcein release by measuring fluorescence at 485-535 nm on a Wallac Victor II 1420 Multilable HTS counter. 100% lysis values are determined by lysing six wells of labeled targets with IGEPAL® 630 detergent (3 µL per well) and spontaneous lysis values determined by measuring the fluorescence in supernatants from targets alone.

Statistical Analysis

Percent (%) specific lysis is defined as (sample fluorescence)−(spontaneous lysis fluorescence)/(100% lysis−spontaneous lysis fluorescence). Spontaneous lysis is determined by wells containing only targets and 100% lysis is determined by wells where targets are lysed with IGEPAL CA 630 detergent. Raw data is entered in an Excel spreadsheet with embedded formulae to calculate % specific lysis and resultant values transferred to graphic program (GraphPad Prism) where the data is transformed in a curve fit graph. Subsequent analyses (linear regression calculations) are done in GraphPad to generate $EC_{50}$ values.

Example 4

CDC Activity of an Exemplar Anti-BCMA Single Domain Antibody of the Present Disclosure To evaluate the anti-tumor activity of exemplar anti-BCMA single domain antibody, according to the present disclosure, against cancer cells, the cytotoxic activity in A431/H9 and NCI-H226 cell models in the presence of human serum as a source of complement is tested. The exemplar anti-BCMA single domain antibody is expressed as a multidomain protein containing a Fc domain.

A multidomain protein containing the exemplar anti-BCMA single domain antibody of the present disclosure exerts potent CDC activity by killing cancer cell lines, and shows no activity on a BCMA-negative cell line.

Example 5

Xenograft Tumor Model

An exemplary BCMA targeting trispecific protein containing an exemplary BCMA binding protein of this disclosure, 02B05 (SEQ ID NO: 383), was evaluated in a xenograft model.

Figure 29:
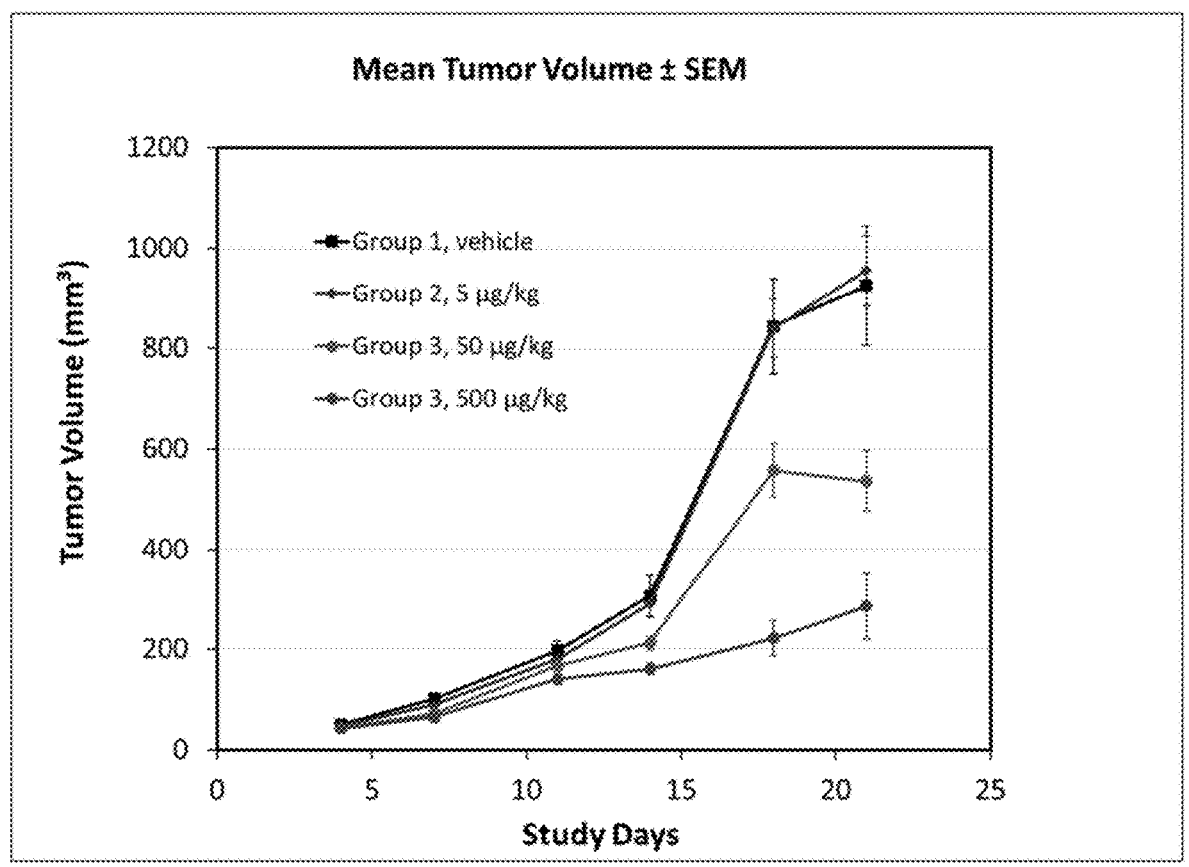
FIG. 29 illustrates tumor growth reduction in RPMI8226 xenograft model, treated with an exemplary BCMA targeting trispecific protein containing a BCMA binding protein of this disclosure (02B05), at varying concentrations, or with a control vehicle.

On day 0, NCG mice were subcutaneously inoculated with RPMI-8226 cells, and also intraperitoneally implanted with normal human peripheral blood mononuclear cells (PBMCs). Treatment with the exemplary BCMA targeting trispecific protein was also started on day 0 (qd×10) (once daily for 10 days). The dosage of administration was 5 μg/kg, 50 μg/kg, or 500 μg/kg of the BCMA targeting trispecific protein 02B05, or a vehicle as control. Tumor volumes were determined for 25 days. As shown in FIG. 29, the mean tumor volumes were significantly lower in mice treated with the exemplary BCMA targeting trispecific protein (02B05) (at 50 μg/kg, or 500 μg/kg), as compared to the mice treated with the vehicle or the lower dose of BCMA targeting trispecific protein (02B05) (at 5 μg/kg).

Figure 30:
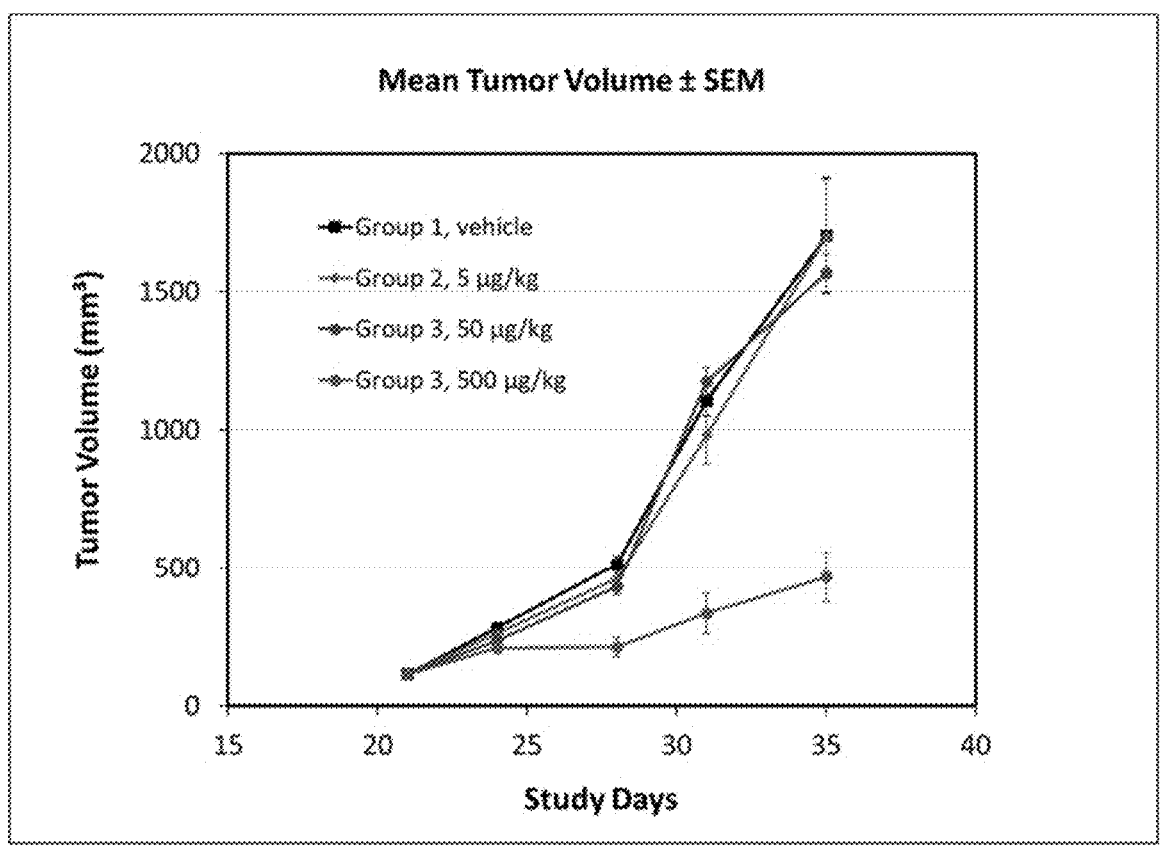
FIG. 30 illustrates tumor growth reduction in Jeko1 xenograft model, treated with an exemplary BCMA targeting trispecific protein containing a BCMA binding protein of this disclosure (02B05), at varying concentrations, or with a control vehicle.

On day 0, NCG mice were subcutaneously inoculated with Jeko 1 cells, and also intraperitoneally implanted with normal human peripheral blood mononuclear cells (PBMCs). Treatment with the exemplary BCMA targeting trispecific protein was started on day 3 (qd×10) (once daily for 10 days). The dosage of administration was 5 μg/kg, 50 μg/kg, or 500 μg/kg of the BCMA targeting trispecific protein 02B05, or a vehicle as control. Tumor volumes were determined for 25 days. As shown in FIG. 30, the mean tumor volumes were significantly lower in mice treated with the exemplary BCMA targeting trispecific protein (02B05) (at 500 μg/kg), as compared to the mice treated with the vehicle or the lower doses of BCMA targeting trispecific protein (02B05) (at 5 μg/kg or 50 μg/kg).

Example 6

Affinity Measurements for Human and Cynomolgus BCMA, CD3ε, and Albumin, Using an Exemplary BCMA Targeting Trispecific Containing a BCMA Binding Protein of this Disclosure Protein of this Disclosure The aim of this study was to assess the affinity of an exemplary BCMA targeting trispecific protein containing a BCMA binding protein of this disclosure (02B05) (SEQ ID NO: 383), toward human BCMA, cynomolgus BCMA, human CD3ε, cynomolgus CD3ε, human albumin, cynomolgus albumin, and mouse albumin. The affinities were measured using an Octet instrument. For these measurements, streptavidin tips were first loaded with 2.5 nM human BCMA-Fc, 2.5 nM cynomolgus BCMA-Fc, 2.5 nM CD3ε-Fc, 2.5 nM cynomolgus CDR3ε-Fc, 50 nM human serum albumin (HSA), 50 nM cynomolgus serum albumin, or 50 nM mouse serum albumin. Subsequently, the exemplary BCMA targeting trispecific protein containing a BCMA binding protein of this disclosure 02B05 was incubated with the tips, and following an association period, the tips were moved to a buffer solution to allow the exemplary BCMA targeting trispecific protein containing a BCMA binding protein of this disclosure (02B05) to disassociate. The affinities for binding to human and cynomolgus BCMA and CD3ε were measured in the presence of 15 mg/ml human serum albumin. Average calculated $K_D$ values from these studies are provided in Table 4 (n indicates the number of independent measurements, n/d indicates no binding detected under the conditions tested). Binding was detected to human BCMA, human CD3ε, cynomolgus CD3ε, human serum albumin, cynomolgus serum albumin, and mouse serum albumin. Under the conditions tested, no binding was detected to cynomolgus BCMA.

TABLE 4

Measured $K_D$ values for exemplary BCMA targeting trispecific protein containing a BCMA binding protein of this disclosure, 02B05, to protein ligands.

| Protein ligand | Species | $K_D$ (nM) | n |
|---|---|---|---|
| BCMA | human | 2.4 ± 0.2 | 2 |
|  | cynomolgus | n/d | 2 |
| CD3ε | human | 8 ± 1 | 2 |
|  | cynomolgus | 7.8 ± 0.4 | 2 |
| Albumin | human | 6 ± 1 | 3 |
|  | cynomolgus | 7.5 | 1 |
|  | mouse | 76 | 1 |

Example 7

Human T Cell Binding Ability of an Exemplary BCMA Targeting Trispecific Protein Containing a BCMA Binding Protein of this Disclosure of this Disclosure Exemplary BCMA targeting trispecific protein containing a BCMA binding protein of this disclosure, 02B05 (SEQ ID NO: 383) was tested for its ability to bind to purified T cells. Briefly, the BCMA trispecific protein or phosphate buffered saline (PBS) were incubated with purified T cells from 4 different anonymous human donors. After washing unbound protein, the T cells were then incubated with an Alexa Fluor 647 conjugated antibody that recognizes the anti-albumin domain in the 02B05 BCMA trispecific antigen-binding protein. The T cells were then analyzed by flow cytometry. It was observed that human T cells incubated with the 02B05 BCMA trispecific antigen-binding protein had notable shifts associated with Alexa Fluor 647 staining compared to cells that were incubated with PBS. The results are shown in FIGS. 4A, 4B, 4C, and 4D. In conclusion, this study indicated that the exemplary BCMA targeting trispecific protein containing a BCMA binding protein of this disclosure was able to bind human T cells.

Example 8

Figure 5A:
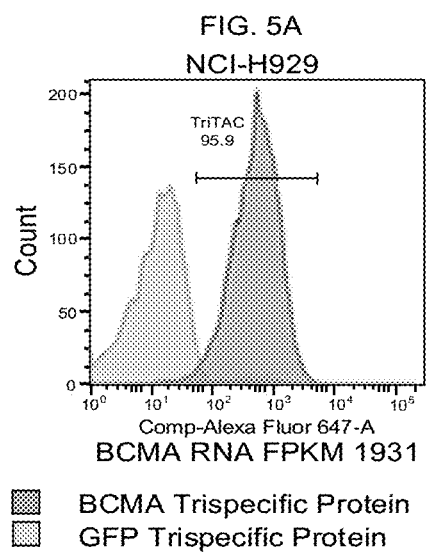
FIGS. 5A-5F illustrate binding of an exemplary BCMA trispecific targeting protein (02B05) to cells expressing BCMA, NCI-H929 (FIG. 5A), EJM (FIG. 5B), OPM2 (FIG. 5D), RPMI8226 (FIG. 5E); or cell lines lacking expression of BCMA, NCI-H510A (FIG. 5C), and DMS-153 (FIG. 5F).
Figure 5B:
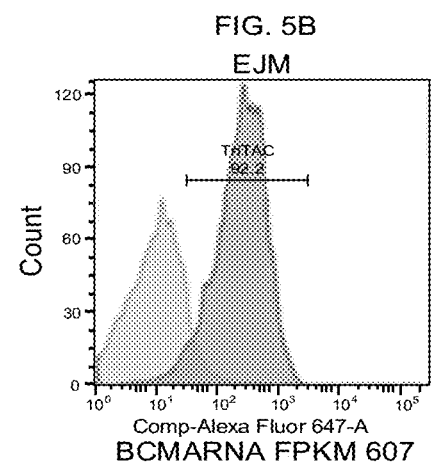
Figure 5C:
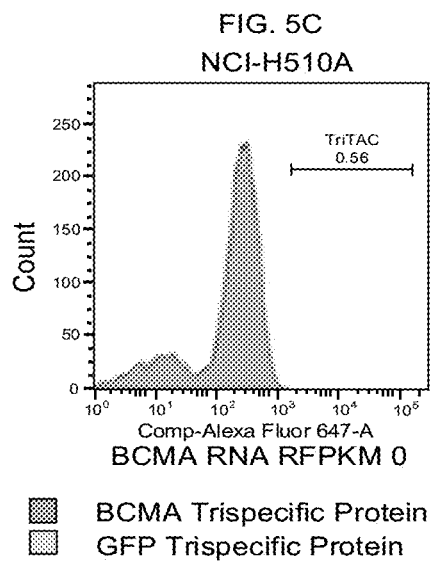
Figure 5D:
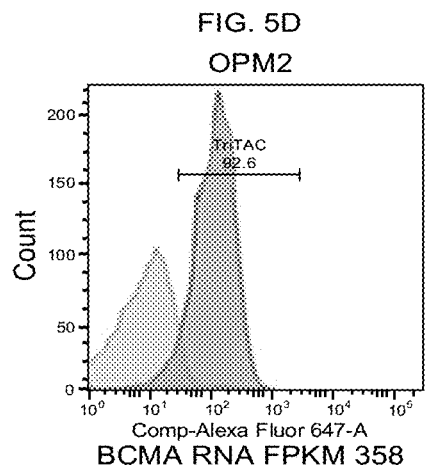
Figure 5E:
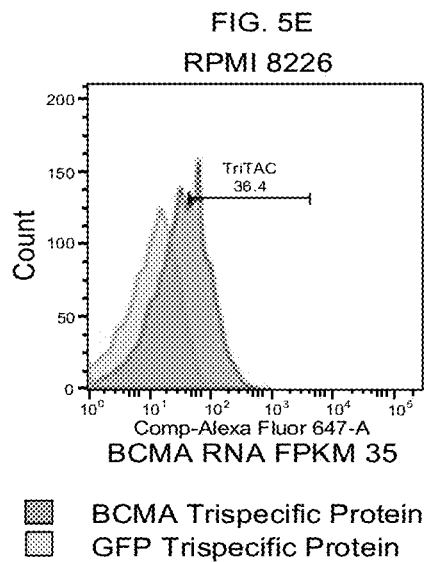
Figure 5F:
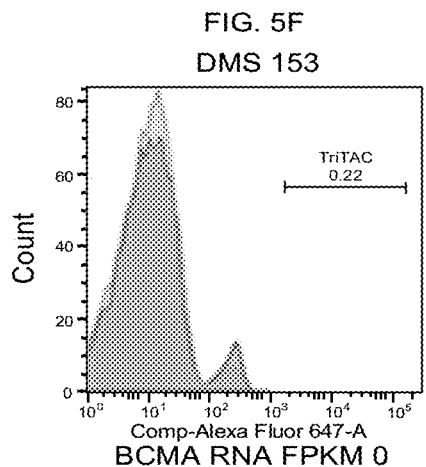

Ability of an Exemplary BCMA Targeting Trispecific Protein of this Disclosure to Bind BCMA Expressing Cells Exemplary BCMA targeting trispecific protein containing a BCMA binding protein of this disclosure 02B05 (SEQ ID NO: 383) was tested for its ability to bind to BCMA expressing cells. Briefly, the 02B05 BCMA trispecific antigen-binding protein was incubated with cell lines expressing BCMA (NCI-H929; EJM; RPMI-8226; OPM2) or lacking BCMA (NCI-H510A; DMS-153). Expression of BCMA RNA in these cells is indicated by the FPKM (fragments per kilobase million) values listed in FIGS. 5A-F: the RNA FPKM values are from the Cancer Cell Line Encyclopedia (Broad Institute, Cambridge, MA USA). After washing unbound protein, the cells were then incubated with an Alexa Fluor 647 conjugated antibody that recognizes the anti-albumin domain in the 02B05 BCMA trispecific antigen-binding protein. The cells were then analyzed by flow cytometry. As a negative control, cells were incubated with a trispecific protein targeting GFP. Cells expressing BCMA RNA and incubated with the BCMA trispecific protein had notable shifts associated with Alexa Fluor 647 staining compared to cells that were incubated with GFP trispecific protein (as in FIGS. 5A, 5B, 5D, and 5E). Whereas, cells lacking BCMA RNA produced equivalent Alexa Fluor 647 staining with the BCMA trispecific protein and the GFP trispecific protein (as seen in FIGS. 5C, and 5F). Thus, this study indicated that the exemplary BCMA trispecific antigen-binding was able to selectively bind to cells expressing BCMA.

Example 9

Figure 6:
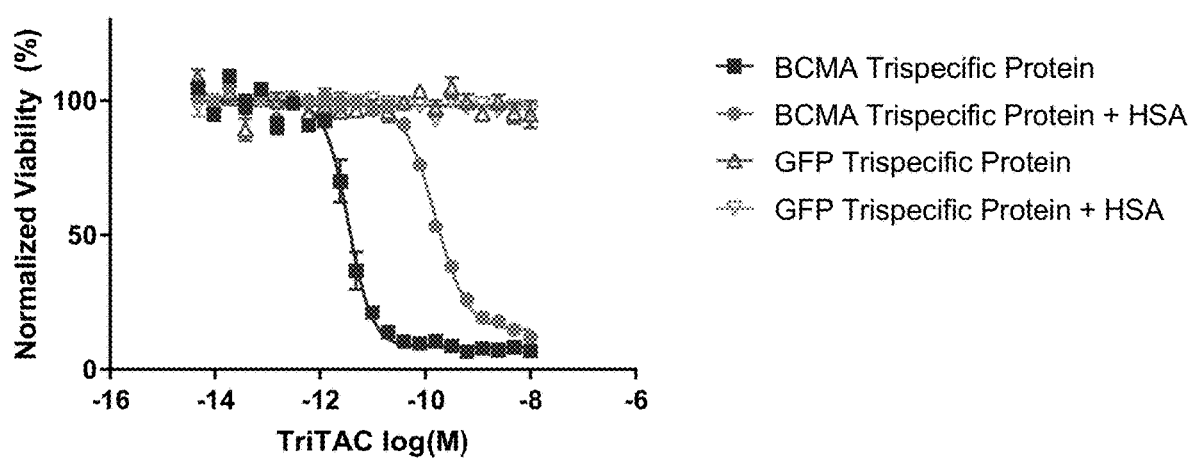
FIG. 6 illustrates the results of a TDCC assay using an exemplary BCMA trispecific targeting protein (02B05) and BCMA expressing EJM cells, in presence or absence of human serum albumin (HSA).

Ability of an Exemplary BCMA Targeting Trispecific Protein Containing a BCMA Binding Protein of this Disclosure to Mediate T Cell Killing of Cancer Cells Expressing BCMA Exemplary BCMA trispecific protein containing a BCMA binding protein of this disclosure 02B05 (SEQ ID NO: 383) was tested for its ability to direct T cells to kill BCMA expressing cells in the presence and absence of human serum albumin (HSA) using a standard TDCC assay as described in Example 1. Because the exemplary BCMA trispecific protein contains an anti-albumin domain, this experiment was performed to confirm that binding to albumin would not prevent the BCMA trispecific antigen-binding protein from directing T cells to kill BCMA expressing cells. Five BCMA expressing cell lines were tested: EJM, Jeko, OPM2, MOLP8, and NCI-H929. Representative data for an experiment with the EJM cells are shown in FIG. 6. It was observed that viability of the EJM cells decreased with increasing amount of the exemplary 02B05 BCMA trispecific antigen-binding protein in the presence or absence of human serum albumin (HSA), whereas a control GFP targeting trispecific protein did not affect cell viability. In the presence of albumin, higher concentrations of BCMA trispecific protein were needed to reduce viability of the EJM cells. The $EC_{50}$ values for cell killing by BCMA trispecific protein for the EJM cells as well as the Jeko, OPM2, MOLE, and NCI-H929 cells in the absence or presence of HSA are provided in Table 5. With all five cell lines, the exemplary 02B05 BCMA trispecific antigen-binding protein directed T cells to kill target cells in the presence of HSA.

TABLE 5

TDCC $EC_{50}$ Values for an exemplary BCMA targeting trispecific protein containing a BCMA binding protein of this disclosure in the presence or absence of human serum albumin with five different BCMA expressing cell lines

| Cell Line | $EC_{50}$ without HSA (PM) | $EC_{50}$ with HSA (pM) |
|---|---|---|
| EJM | 1.0 | 53 |
| Jeko | 8.3 | 662 |
| OPM2 | 6.5 | 328 |
| MOLP8 | 2.5 | 388 |
| NCI-11929 | 6.7 | 194 |

Example 10

Figure 7:
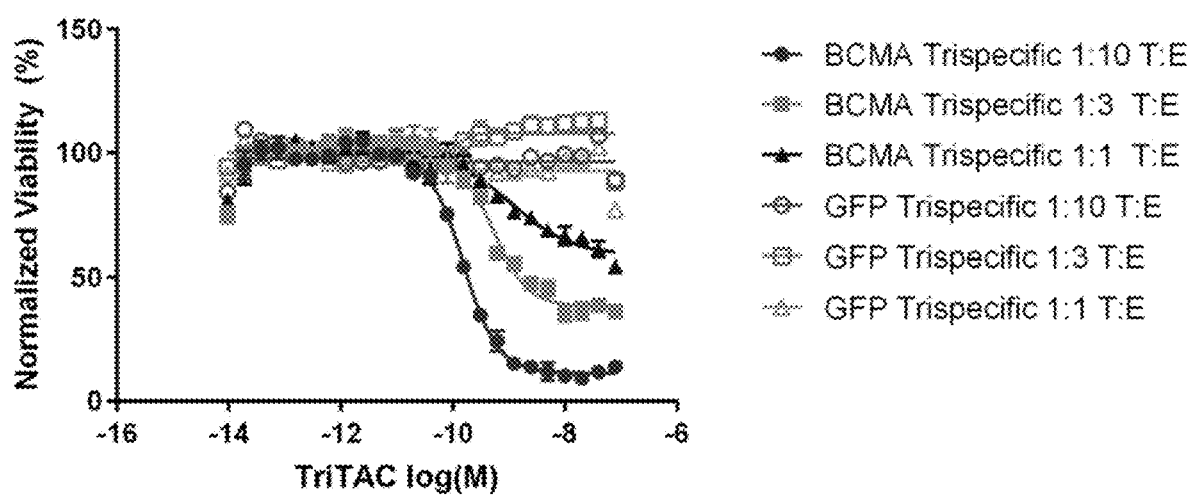
FIG. 7 illustrates the results of a TDCC assay using an exemplary BCMA trispecific targeting protein (02B05) and BCMA expressing EJM cells, using varying effector cells to target cells ratio.
Figure 8:
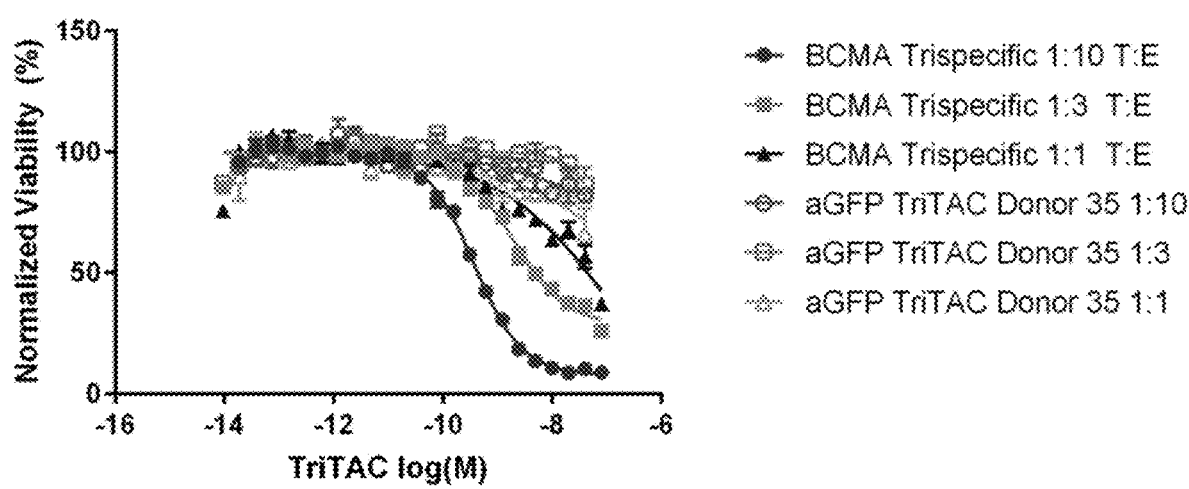
FIG. 8 illustrates the results of a TDCC assay using an exemplary BCMA trispecific targeting protein (02B05) and BCMA expressing OPM2 cells, using varying effector cells to target cells ratio.

Ability of an Exemplary BCMA Targeting Trispecific Protein Containing a BCMA Binding Protein of this Disclosure to Mediate T Cell Killing of Cancer Cells Expressing BCMA, Using a Smaller Target Cell to Effector Cell Ratio In the standard TDCC assay (as described in Example 1), a ratio 1 target cell (EJM cells or OPM2 cells) per 10 effector cells (T cells) is used in a 48 hour assay. In this experiment, the ability of exemplary BCMA targeting trispecific protein containing an exemplary BCMA binding protein of this disclosure 02B05 (SEQ ID NO: 383) to direct T cells to kill target cells with smaller target cell to effector ratios was tested. The expectation was that less killing would be observed when fewer effector cells were used. Two BCMA expressing cell lines were tested, EJM and OPM2, using target to effector cell ratios of 1:1, 1:3, and 1:10, and the experiment was performed in the presence of 15 mg/ml HSA. A GFP targeting trispecific protein was used as a negative control. Data from this experiment is shown in FIG. 7 (TDCC assay with EJM cells) and FIG. 8 (TDCC assay with OPM2 cells). As expected, near complete killing of the target cells was observed with a 1:10 target to effector cell ratio. The amount of killing was reduced with decreasing effector cells. The $EC_{50}$ values for cell killing with each ratio are listed in Table 6 (n/d indicates insufficient killing was observed to calculate an $EC_{50}$ value). The $EC_{50}$ values increased when fewer effector cells were present. Thus, as expected, reducing the number of effector cells to target cells reduced TDCC activity of the BCMA trispecific protein.

TABLE 6

TDCC $EC_{50}$ values for an exemplary BCMA targeting trispecific protein containing a BCMA binding protein of this disclosure (02B05) with varied target cell (EJM cells) to effector cell (T cells) ratios (tested in presence of 15 mg/ml HSA)

| Target cell: T Cell ratio | EJM $EC_{50}$ (pM) | OPM2 $EC_{50}$ (pM) |
|---|---|---|
| 1:10 | 154 | 371 |
| 1:3 | 523 | 1896 |
| 1 | 1147 | n/d |

Example 11

Figure 9:
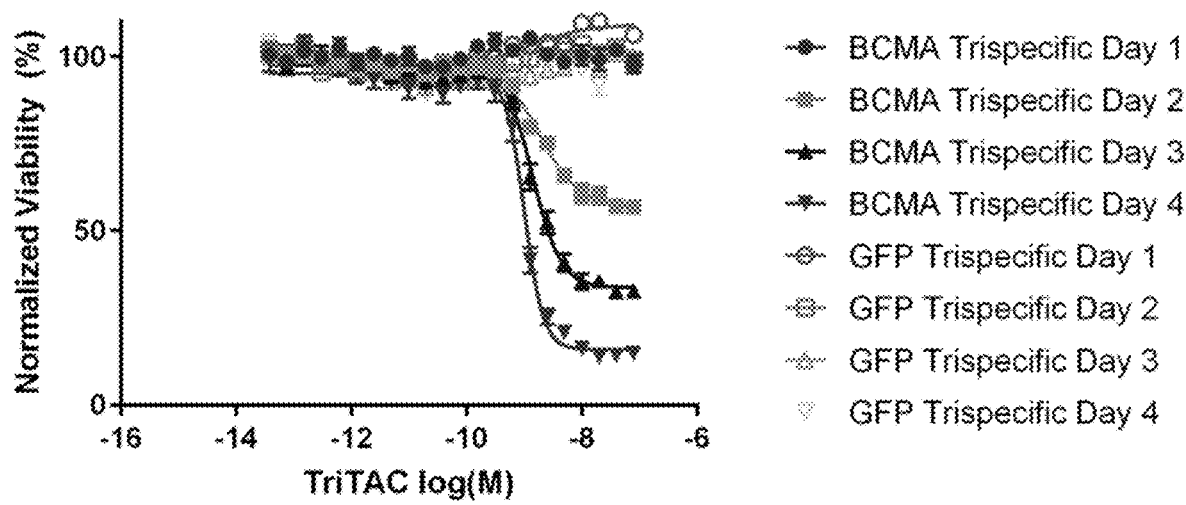
FIG. 9 illustrates the results of a TDCC assay using an exemplary BCMA trispecific targeting protein (02B05) and BCMA expressing NCI-H929 cells, using varying timepoints and a 1:1 effector cells to target cells ratio.
Figure 10:
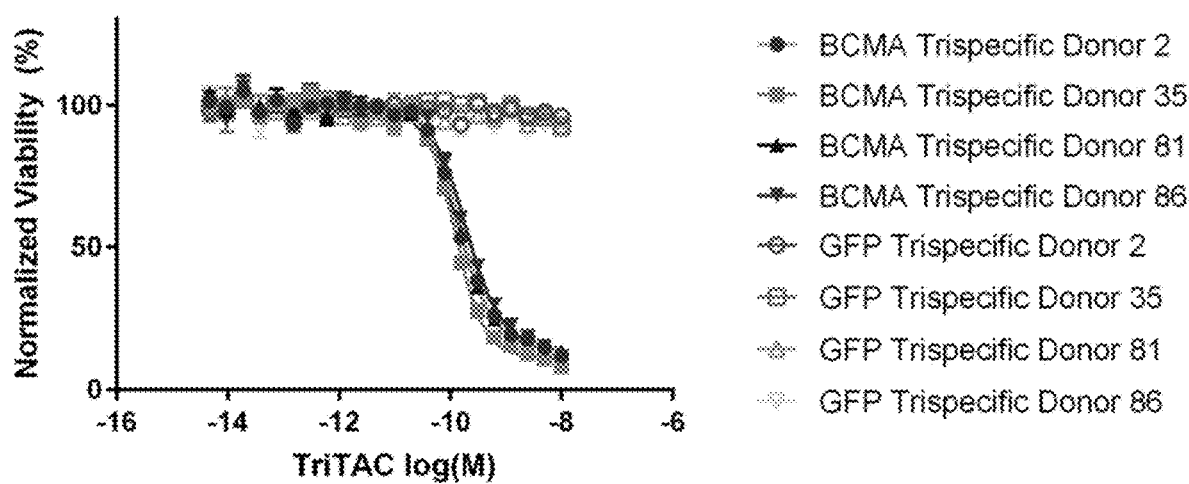
FIG. 10 illustrates the results of a TDCC assay using an exemplary BCMA trispecific targeting protein (02B05), BCMA expressing EJM cells, and T cells from four different donors, in presence of human serum albumin (HSA).
Figure 11:
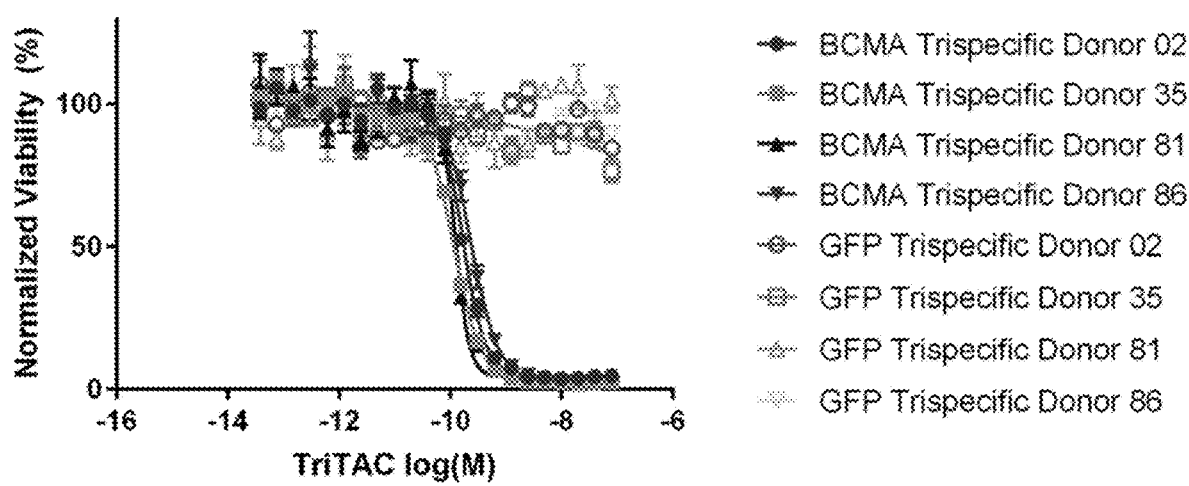
FIG. 11 illustrates the results of a TDCC assay using an exemplary BCMA trispecific targeting protein (02B05), BCMA expressing NCI-H929 cells, and T cells from four different donors, in presence of human serum albumin (HSA).
Figure 12:
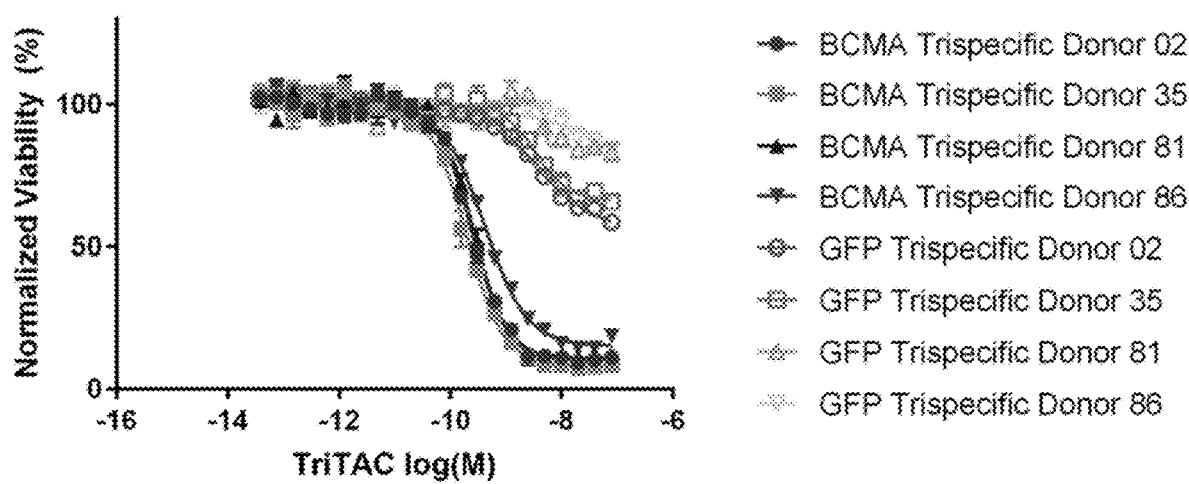
FIG. 12 illustrates the results of a TDCC assay using an exemplary BCMA trispecific targeting protein (02B05), BCMA expressing OPM2 cells, and T cells from four different donors, in presence of human serum albumin (HSA).
Figure 13:
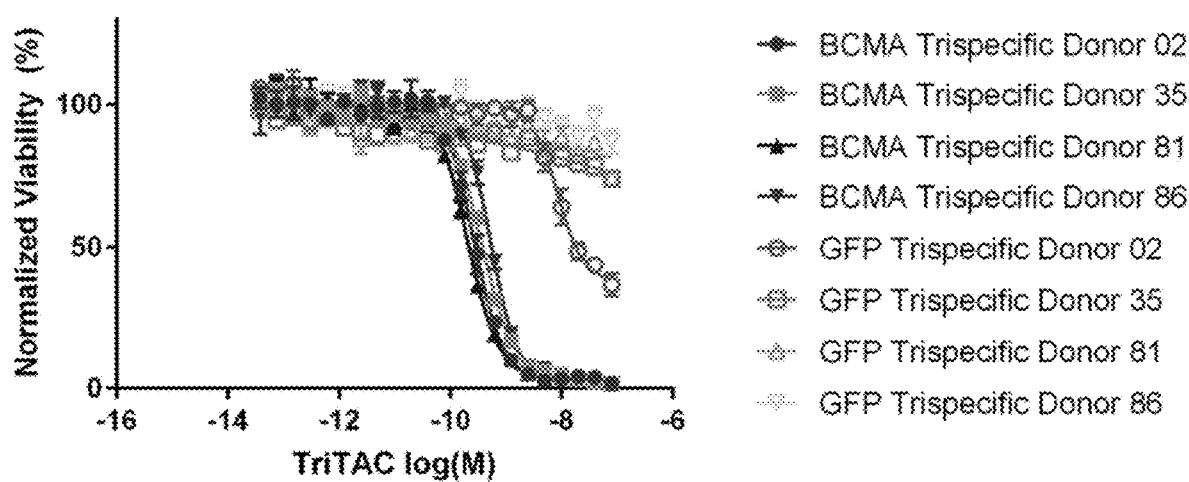
FIG. 13 illustrates the results of a TDCC assay using an exemplary BCMA trispecific targeting protein (02B05), BCMA expressing RPMI8226 cells, and T cells from four different donors, in presence of human serum albumin (HSA).

Ability of an Exemplary BCMA Targeting Trispecific Protein Containing a BCMA Binding Protein of this Disclosure to Mediate T Cell Killing of Cancer Cells Expressing BCMA, in a Time Course Study, Using a Smaller Target Cell to Effector Cell Ratio In the standard TDCC assay (Example 1), a ratio 1 target cell per 10 effector cells (T cells) is used in a 48 hour assay. In this experiment, a time course was performed using a 1 to 1 ratio of target cells (EJM cells) to effector cells (T cells). The expectation was that with increased time, a 1 to 1 ratio would result in target cell killing. The TDCC assay was performed using EJM and a 1:1 target to effector cell ratio, and the experiment was performed in the presence of 15 mg/ml HSA. A GFP targeting trispecific protein was used as a negative control. Target cell viability was measured on days 1, 2, 3, and 4 following incubation of the target cells and effector cells, at a 1:1 ratio, in presence of the exemplary 02B05 BCMA trispecific antigen-binding protein and 15 mg/ml HSA, or the GFP targeting trispecific protein and 15 mg/ml HSA. While no target cell killing was observed on day 1, killing was observed at all other time points with the 02B05 BCMA trispecific-antigen-binding protein, with the amount of killing increasing with time (FIG. 9). No target cell killing was observed with the GFP targeting trispecific protein. The $EC_{50}$ values calculated for cell killing on each day are provided in Table 7 (n/d indicates insufficient killing to determine an $EC_{50}$ value). From this study it was concluded that the exemplary 02B05 BCMA trispecific protein was able to direct T cell killing with lower numbers of effector cells, but more time was needed to achieve more complete killing.

TABLE 7

TDCC $EC_{50}$ values for an exemplary BCMA targeting trispecific protein containing a BCMA binding protein of this disclosure (02B05) with a 1 to 1 target cell (EJM cells) to effector cell (T cells) ratios (tested in presence of 15 mg/ml HSA), at varied time points

| | $EC_{50}$ (pM) |
|---|---|
| Day 1 | n/d |
| Day 2 | 1859 |
| Day 3 | 1420 |
| Day 4 | 1012 |

Example 12

Figure 14:
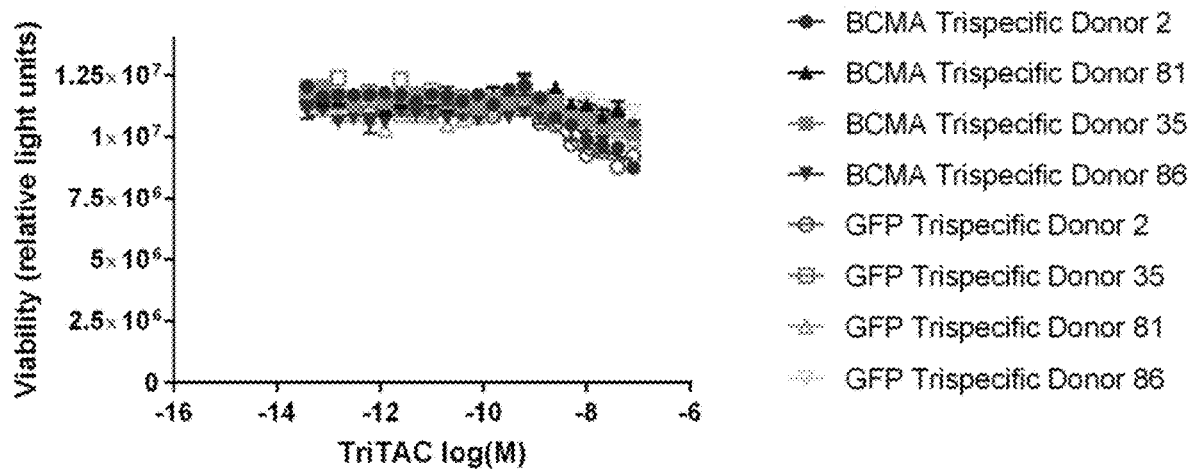
FIG. 14 illustrates the results of a TDCC assay using an exemplary BCMA trispecific targeting protein (02B05), BCMA non-expressing OVCAR8 cells, and T cells from four different donors, in presence of human serum albumin (HSA).
Figure 15:
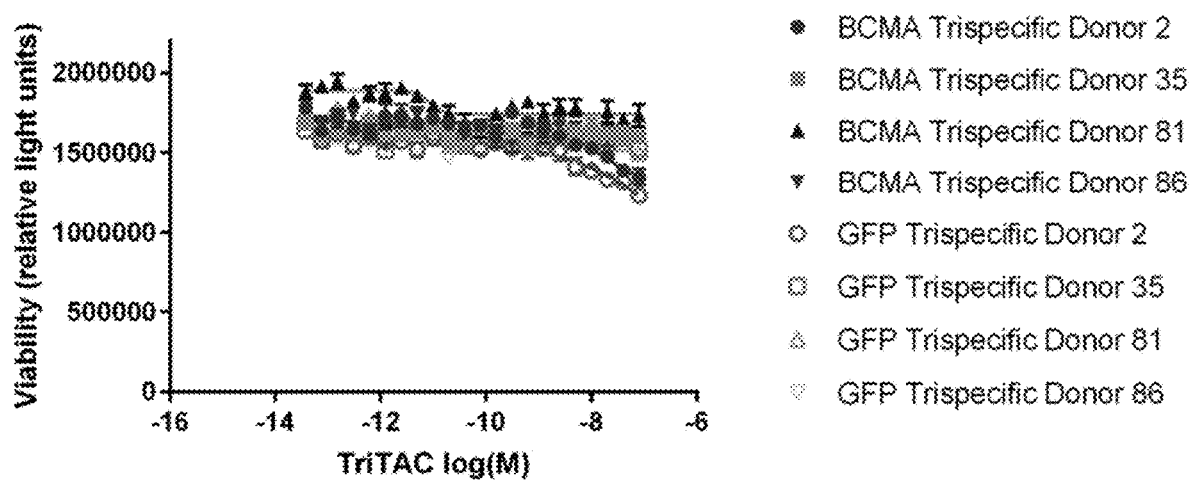
FIG. 15 illustrates the results of a TDCC assay using an exemplary BCMA trispecific targeting protein (02B05), BCMA non-expressing NCI-H510A cells, and T cells from four different donors, in presence of human serum albumin (HSA).

Ability of an Exemplary BCMA Targeting Trispecific Protein Containing a BCMA Binding Protein of this Disclosure to Direct Human T Cells to Kill BCMA Expressing Cells Exemplary BCMA trispecific protein containing a BCMA binding protein of this disclosure 02B05 (SEQ ID NO: 383) was tested for its ability to direct T cells from four different anonymous human donors to kill four different BCMA expressing cells in the presence of 15 mg/ml human serum albumin (HSA) using a standard TDCC assay as described in Example 1. The BCMA expressing cell lines were EJM, NCI-H929, OPM2, and RPMI8226. As negative controls, two cell lines that lack BCMA expression, OVCAR8 and NCI-H510A, were also tested in the TDCC assays. A control GFP targeting trispecific protein was also used as a negative control. With the four BCMA expressing cell lines and all four T cell donors, cell viability decreased with increasing amounts of the BCMA trispecific protein but not with the GFP trispecific protein (FIGS. 10, 11, 12, and 13). The $EC_{50}$ values for cell killing are provided in Table 8. The exemplary 02B05 BCMA trispecific antigen-binding protein did not direct killing of the cell lines lacking BCMA expression (FIGS. 14 and 15). Thus, it was inferred that the exemplary 02B05 BCMA trispecific antigen-binding protein was able to direct T cells from multiple donors to kill a spectrum of BCMA expressing cell lines.

TABLE 8

Exemplary BCMA trispecific protein $EC_{50}$ values from TDCC assays with four BCMA expressing cell lines and four T cell donors in presence of 15 mg/ml HSA

| | EC50 (pM) | | | |
|---|---|---|---|---|
| | H929 | OPM2 | RPMI8226 | EJM |
| Donor 02 | 169 | 250 | 275 | 151 |
| Donor 35 | 113 | 199 | 371 | 121 |
| Donor 81 | 124 | 265 | 211 | 143 |
| Donor 86 | 239 | 416 | 543 | 191 |

Example 13

Figure 16:
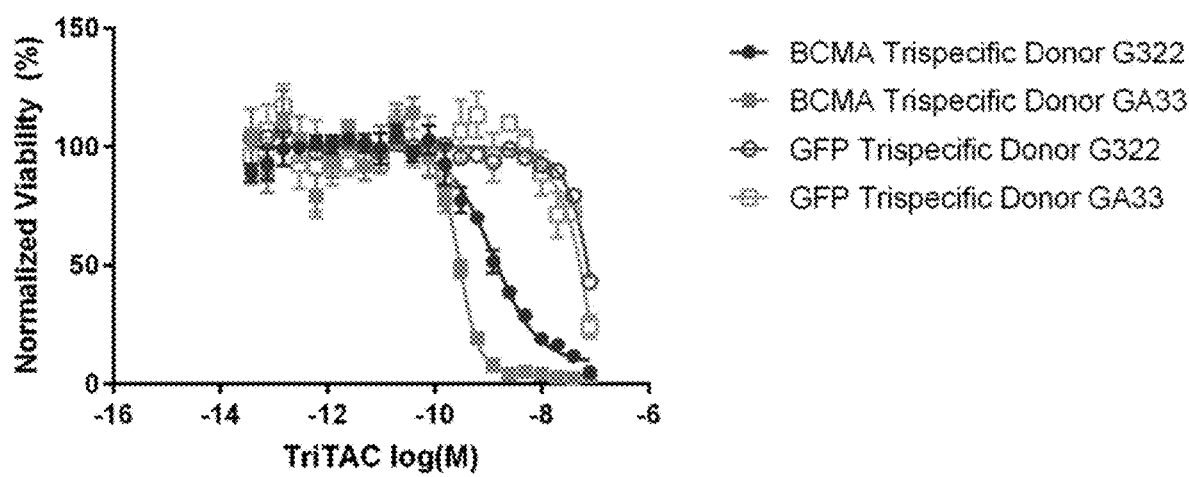
FIG. 16 illustrates the results of a TDCC assay using an exemplary BCMA trispecific targeting protein (02B05), BCMA expressing NCI-H929 cells, and peripheral blood mononuclear cells (PBMC) from two different cynomolgus, in presence of human serum albumin (HSA).
Figure 17:
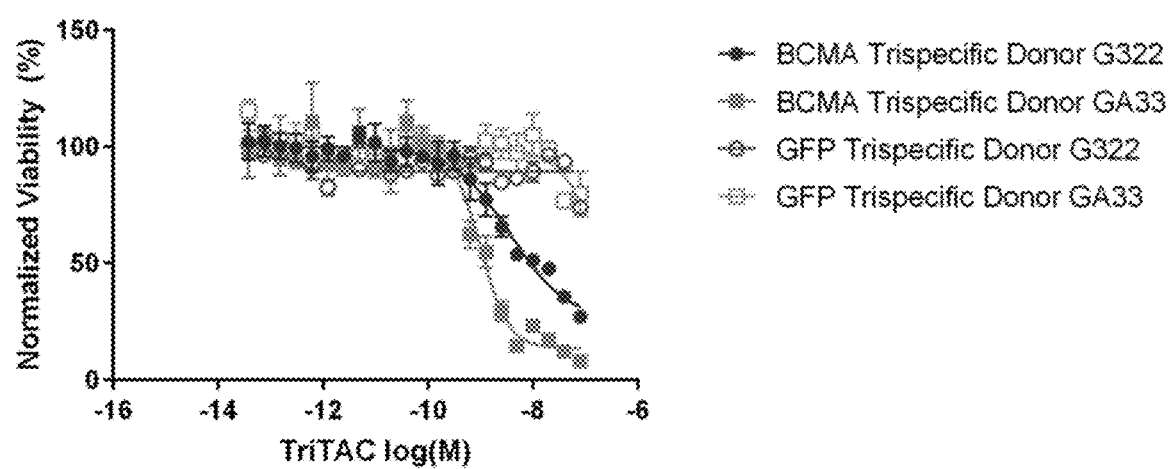
FIG. 17 illustrates the results of a TDCC assay using an exemplary BCMA trispecific targeting protein containing a BCMA binding protein of this disclosure (02B05), BCMA expressing RPMI8226 cells, and peripheral blood mononuclear cells (PBMC) from two different cynomolgus donors, in presence of human serum albumin (HSA).
Figure 18:
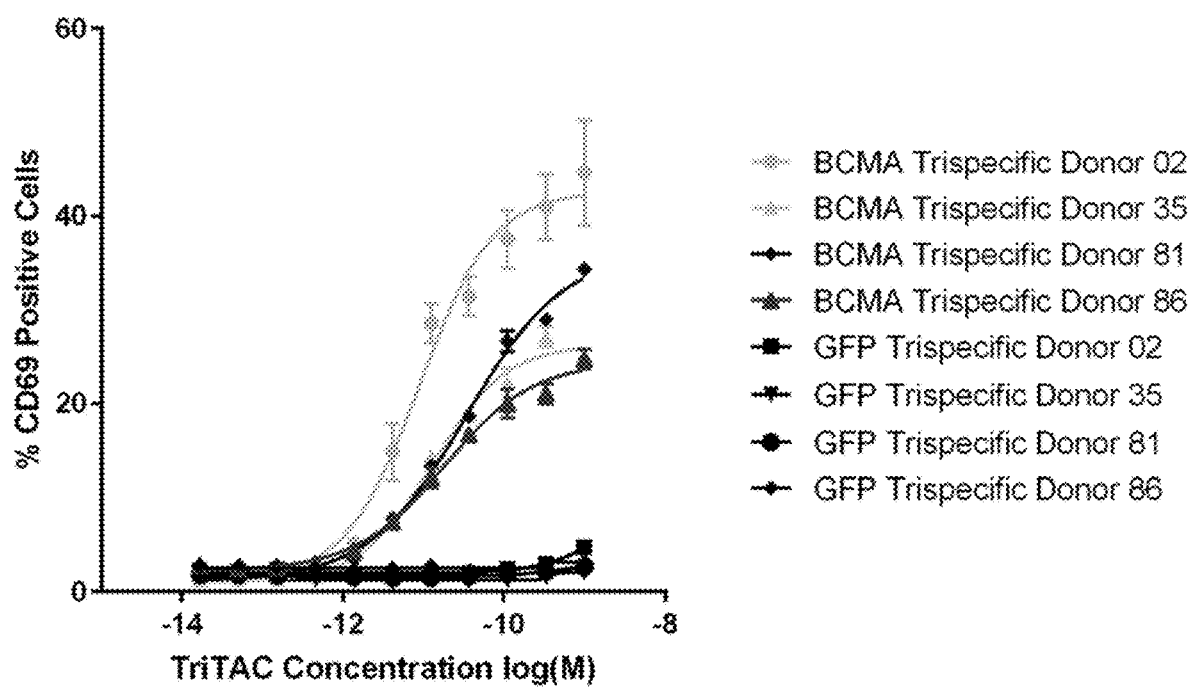
FIG. 18 illustrates the expression level of T cell activation biomarker CD69, following a TDCC assay using an exemplary BCMA targeting trispecific protein containing a BCMA binding protein of this disclosure (02B05) and BCMA expressing cells EJM.
Figure 19:
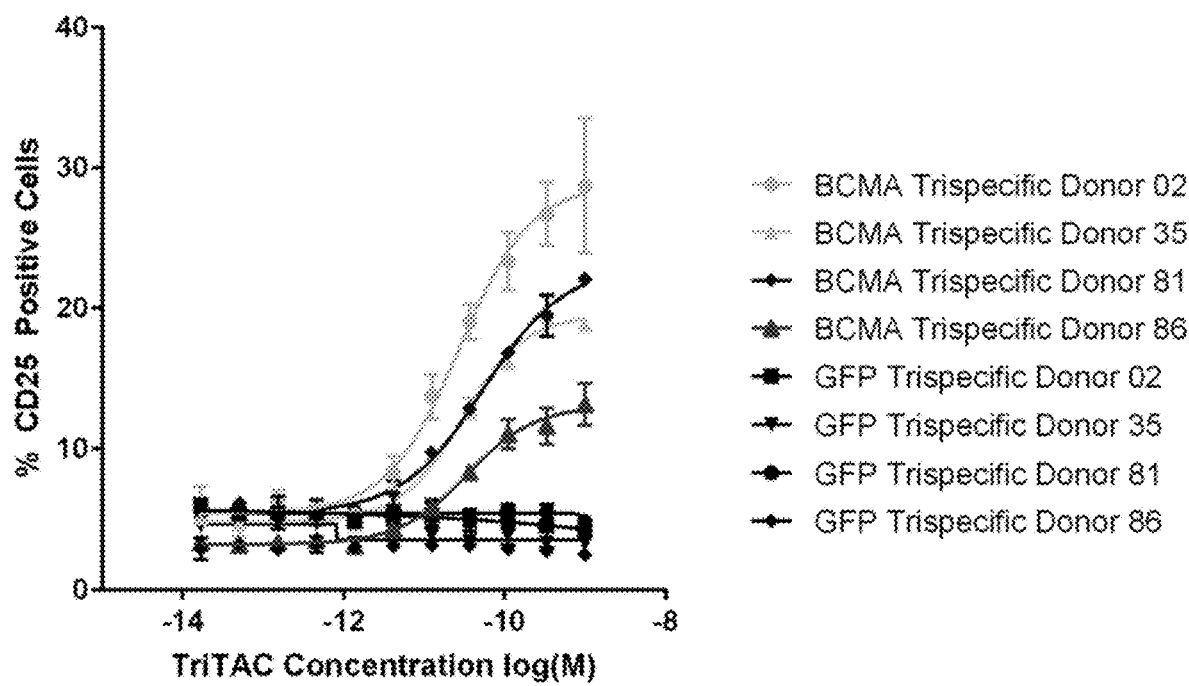
FIG. 19 illustrates the expression level of T cell activation biomarker CD25, following a TDCC assay using an exemplary BCMA targeting trispecific protein containing a BCMA binding protein of this disclosure (02B05) and BCMA expressing cells EJM.
Figure 20:
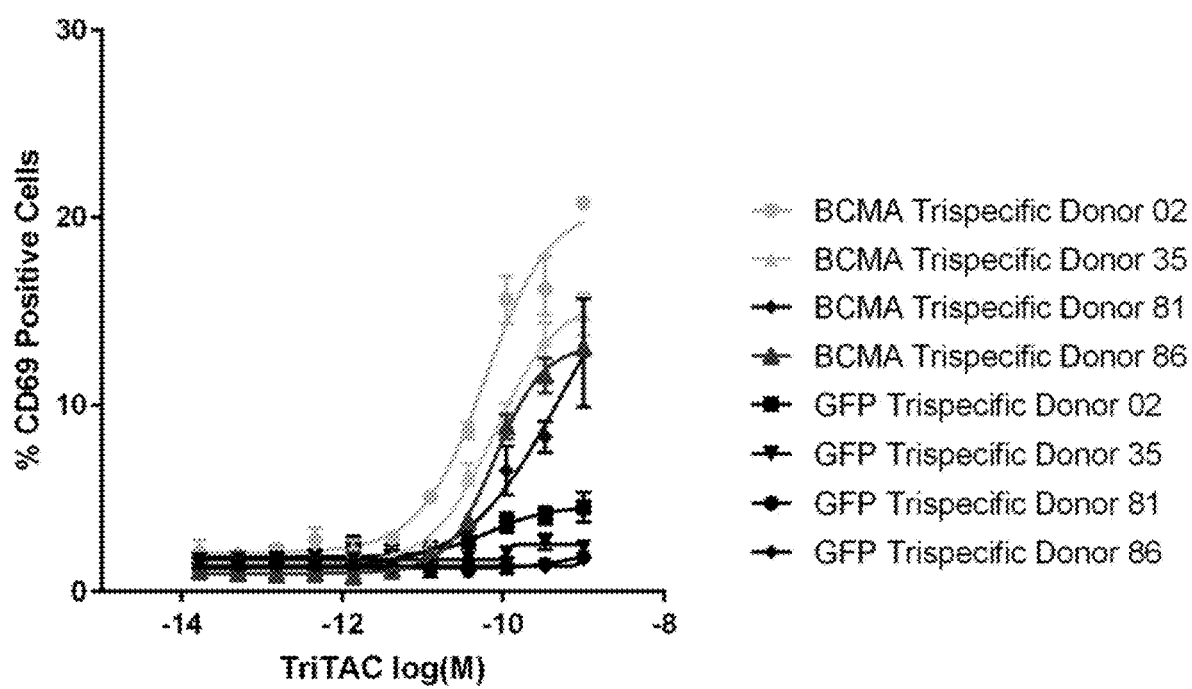
FIG. 20 illustrates the expression level of T cell activation biomarker CD69, following a TDCC assay using an exemplary BCMA targeting trispecific protein containing a BCMA binding protein of this disclosure (02B05) and BCMA expressing cells OPM2.
Figure 21:
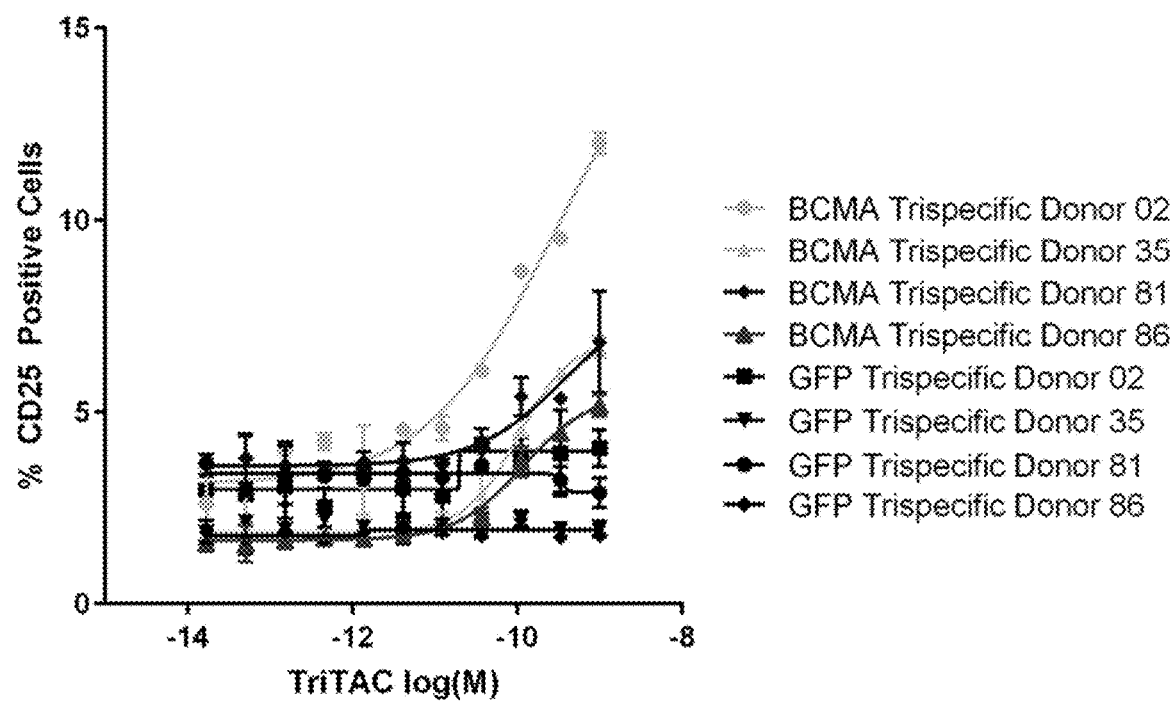
FIG. 21 illustrates the expression level of T cell activation biomarker CD25, following a TDCC assay using an exemplary BCMA targeting trispecific protein containing a BCMA binding protein of this disclosure (02B05) and BCMA expressing cells OPM2.
Figure 22:
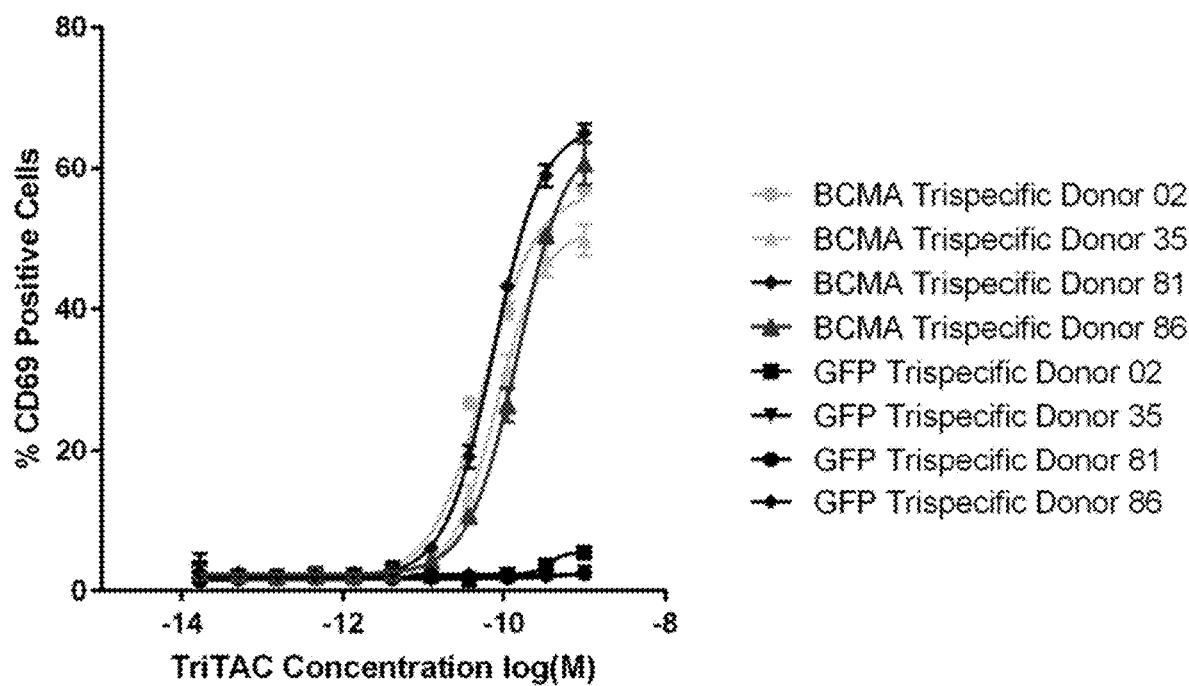
FIG. 22 illustrates the expression level of T cell activation biomarker CD69, following a TDCC assay using an exemplary BCMA targeting trispecific protein containing a BCMA binding protein of this disclosure (02B05) and BCMA expressing cells RPMI8226.
Figure 23:
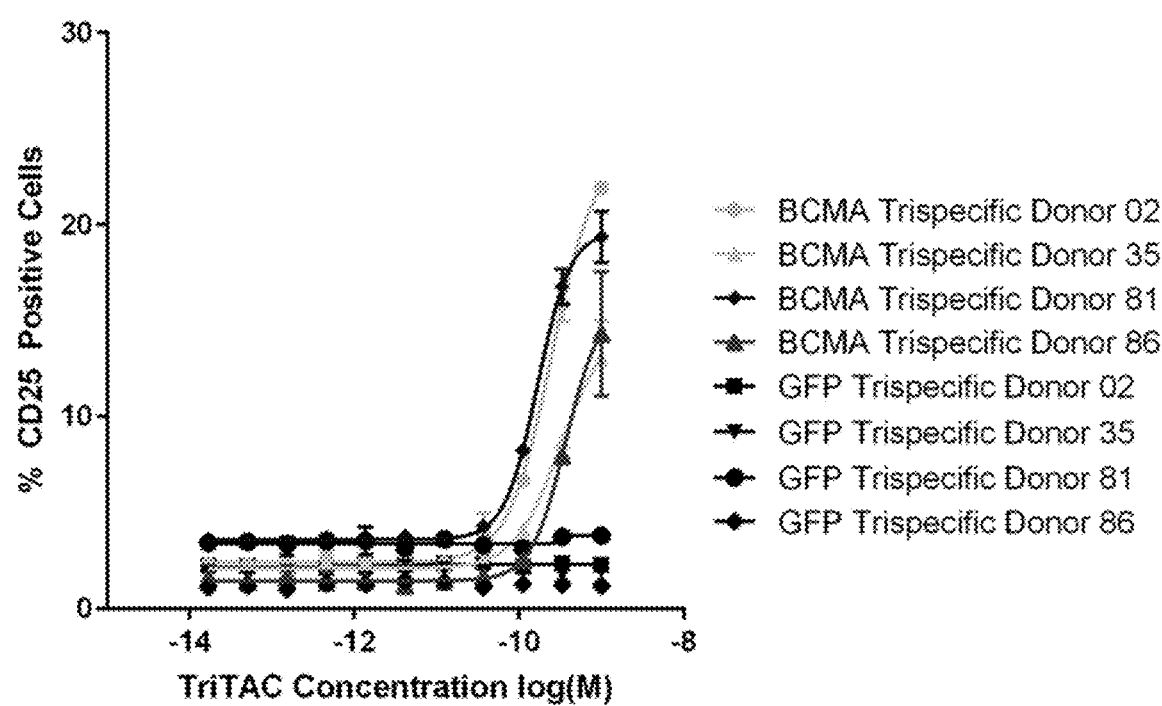
FIG. 23 illustrates the expression level of T cell activation biomarker CD25, following a TDCC assay using an exemplary BCMA targeting trispecific protein containing a BCMA binding protein of this disclosure (02B05) and BCMA expressing cells RPMI8226.
Figure 24:
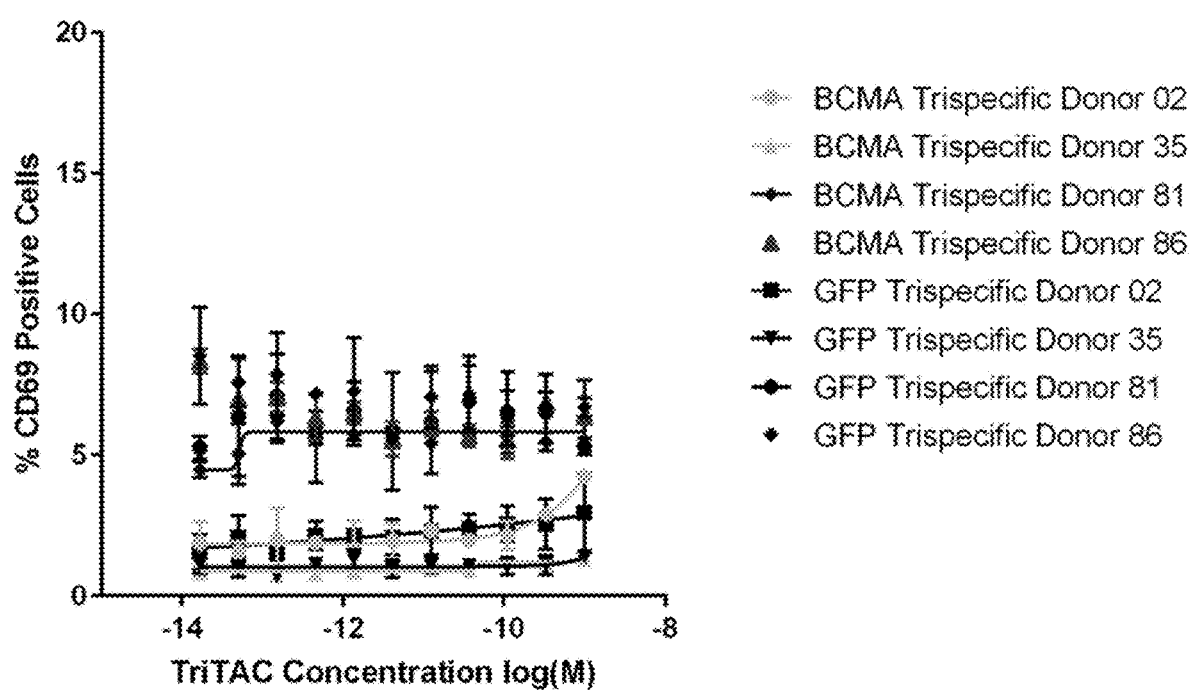
FIG. 24 illustrates the expression level of T cell activation biomarker CD69, following a TDCC assay using an exemplary BCMA targeting trispecific protein containing a BCMA binding protein of this disclosure (02B05) and BCMA non-expressing cells OVCAR8.
Figure 25:
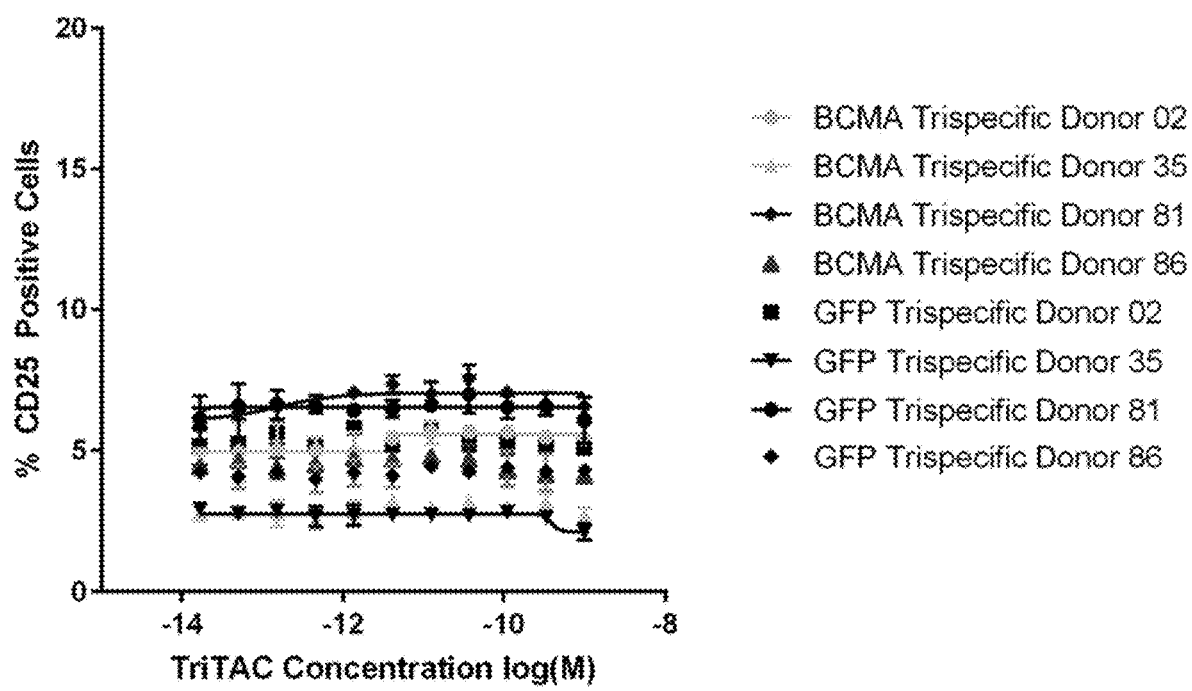
FIG. 25 illustrates the expression level of T cell activation biomarker CD25, following a TDCC assay using an exemplary BCMA targeting trispecific protein containing a BCMA binding protein of this disclosure (02B05) and BCMA non-expressing cells OVCAR8.
Figure 26:
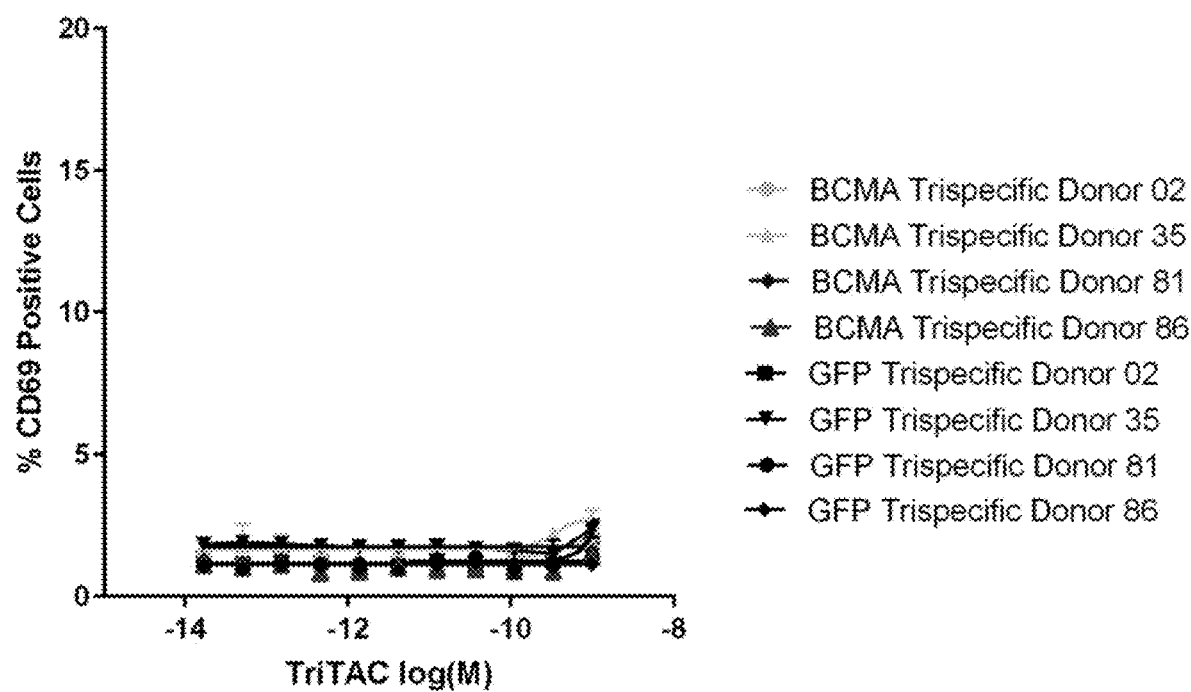
FIG. 26 illustrates the expression level of T cell activation biomarker CD69, following a TDCC assay using an exemplary BCMA targeting trispecific protein containing a BCMA binding protein of this disclosure (02B05) and BCMA non-expressing cells NCI-H510A.
Figure 27:
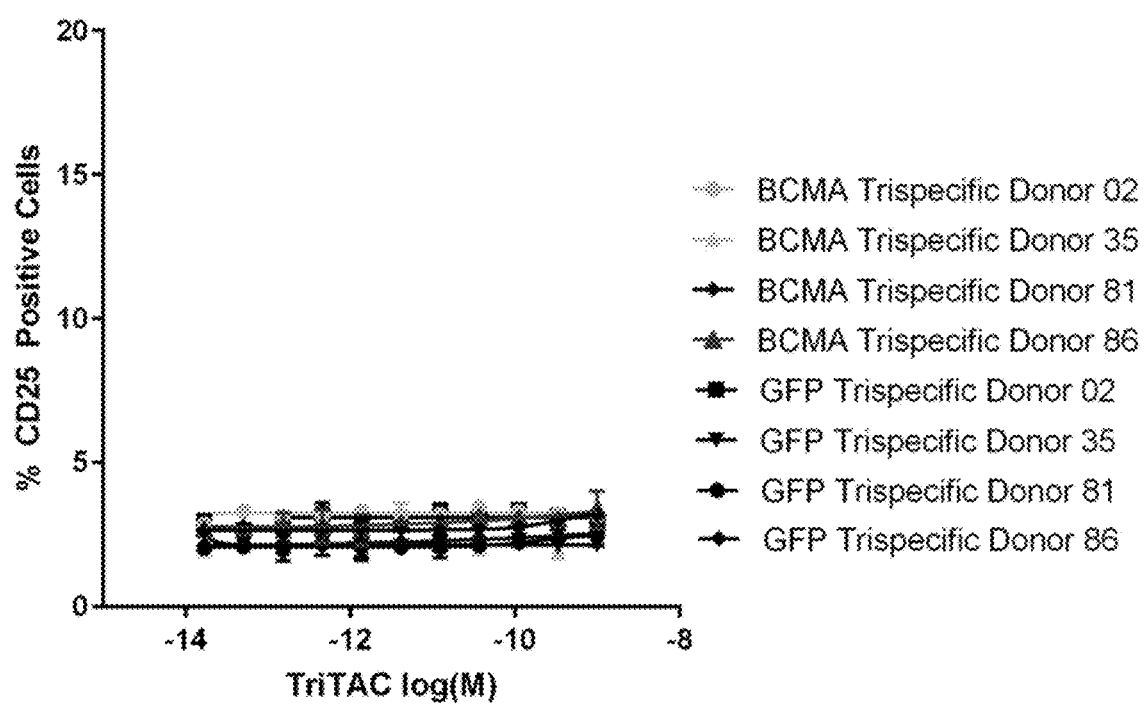
FIG. 27 illustrates the expression level of T cell activation biomarker CD25, following a TDCC assay using an exemplary BCMA targeting trispecific protein containing a BCMA binding protein of this disclosure (02B05) and BCMA non-expressing cells NCI-H510A.

Ability of an Exemplary BCMA Targeting Trispecific Protein Containing a BCMA Binding Protein of this Disclosure to Direct Cynomolgus T Cells to Kill BCMA Expressing Cells Exemplary BCMA targeting trispecific protein containing a BCMA binding protein of this disclosure 02B05 (SEQ ID NO: 383) was tested for its ability to direct T cells from cynomolgus monkeys to kill BCMA expressing cells in the presence of 15 mg/ml human serum albumin (HSA). The experimental conditions were the same as described in Example 1 except peripheral blood mononuclear cells (PBMC) from cynomolgus monkeys were used as a source of T cells. Two BCMA expressing cell lines were tested, RPMI8226 and NCI-H929. As shown in FIGS. 16 and 17, the BCMA trispecific protein was able to direct T cells present in the cynomolgus PBMCs to kill the two BCMA expressing cell lines. The $EC_{50}$ values for the cell killing are listed in Table 9. A GFP trispecific protein did not affect viability of the BCMA expressing cells. Thus, the BCMA expressing trispecific protein, which can bind cynomolgus CD3ε (as shown in Example 6), can direct cynomolgus T cells to kill cells expressing human BCMA.

TABLE 9

BCMA trispecific protein $EC_{50}$ values from TDCC Assays with two cell lines and two cynomolgus PMBC donors in the presence of 15 mg/ml HSA

| | $EC_{50}$ (pM) | |
|---|---|---|
| | RPMI8226 | NCI-H929 |
| Donor G322 | 3654 | 1258 |
| Donor GA33 | 1003 | 288 |

Example 14

Figure 28:
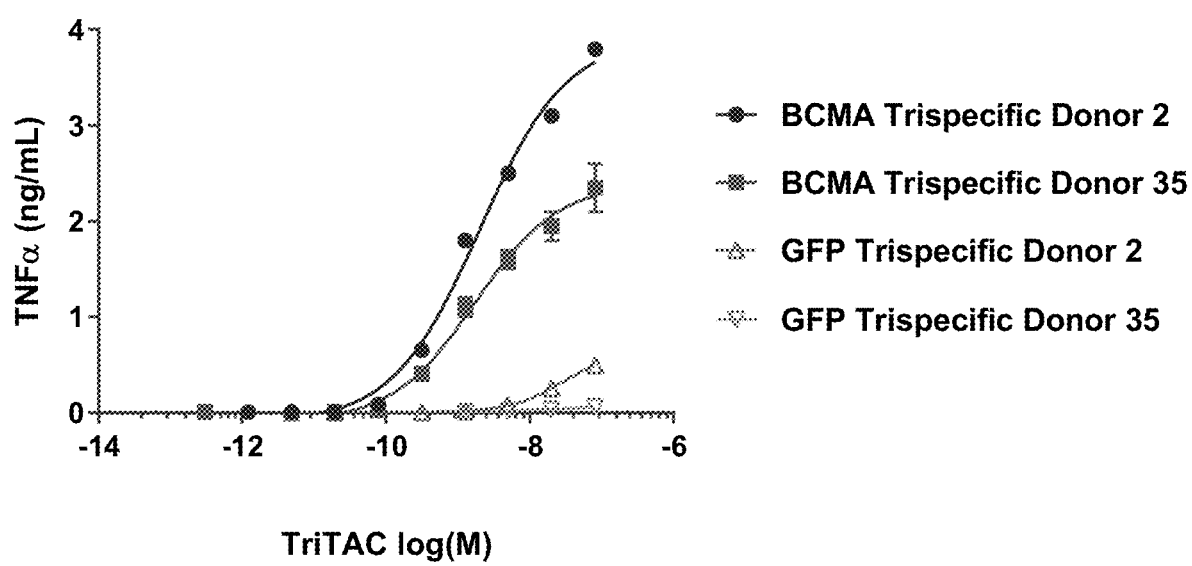
FIG. 28 illustrates the expression level a cytokine, TNF-α, in co-cultures of T cells and BCMA expressing target cells (EJM cells) treated with increasing concentrations of an exemplary BCMA targeting trispecific protein containing a BCMA binding protein of this disclosure (02B05) or with a negative control GFP trispecific protein.

Exemplary BCMA Targeting Trispecific Protein Containing a BCMA Binding Protein of this Disclosure in Mediating Induction of T Cell Activation Exemplary BCMA targeting trispecific protein containing a BCMA binding protein of this disclosure 02B05 (SEQ ID NO: 383) was tested for its ability to activate T cells in the presence of BCMA expressing cells. The BCMA expressing cell lines were EJM, OPM2, and RPMI8226. As negative controls, two cells lines that lack BCMA expression were also included, OVCAR8 and NCI-H510A. T cells were obtained from four different anonymous human donors. The assays were set up using the conditions of a standard TDCC assay as described in Example 1 except the assay was adapted to 96-well format and the assay was carried out in the presence of 15 mg/ml HSA. After the 48 hour assay, T cell activation was assessed by using flow cytometry to measure expression of T cell activation biomarkers CD25 and CD69 on the surface of the T cells. With increasing concentrations of the exemplary 02B05 BCMA trispecific antigen-binding protein increased expression of CD69 and CD25 was observed on T cells when co-cultured with the BCMA expressing cells (as shown in FIGS. 18-23). Thus, the observed interaction was dependent on interaction of the BCMA binding sequence within the exemplary BCMA targeting trispecific protein, as little to no activation was observed with a control GFP trispecific protein (as shown in FIGS. 18-23) or with target cells with no BCMA expression (as shown in FIGS. 24-27). Therefore the exemplary BCMA targeting trispecific protein activated T cells in co-cultures containing BCMA expressing cells. This conclusion is bolstered by additional data. For instance, expression of a cytokine, TNFα, was measured in the medium collected from a co-culture of T cells and BCMA expressing target cells treated with increasing concentrations of the exemplary BCMA targeting trispecific protein or with the negative control GFP trispecific protein. The co-cultures were set up using the conditions of a standard TDCC assay (as described in Example 1) supplemented with 15 mg/ml HSA. TNFα was measured using an electrochemiluminescent assay (Meso Scale Discovery). Robust induction of TNFα expression was observed with the exemplary BCMA targeting trispecific protein containing a BCMA binding protein of this disclosure 02B05 (SEQ ID NO: 383) and not the GFP trispecific protein (FIG. 28). This result further supports that the exemplary BCMA targeting trispecific protein activated T cells in co-cultures containing BCMA expressing cells.

Example 15

Figure 31:
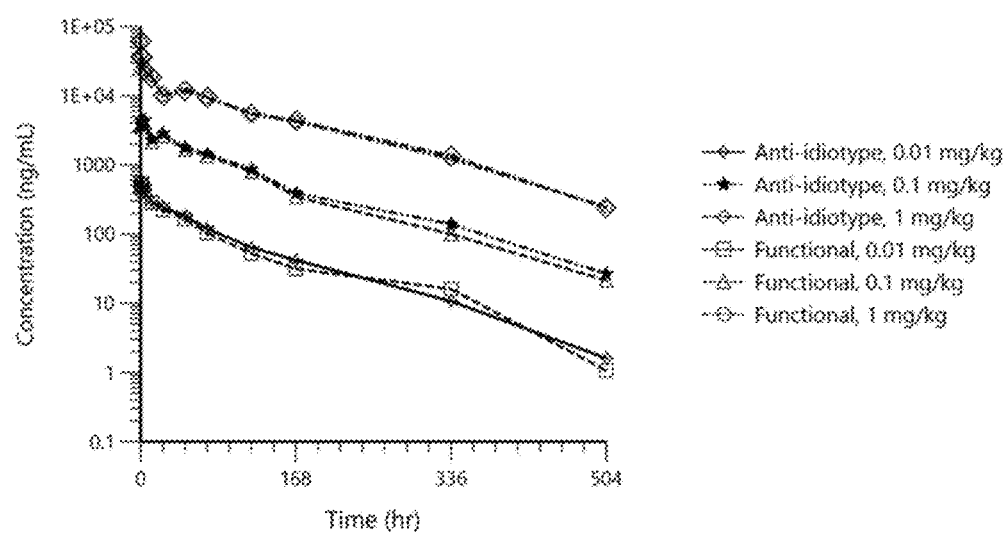
FIG. 31 illustrates concentration of BCMA targeting trispecific protein in serum samples from cynomolgus monkeys dosed with varying concentrations of an exemplary BCMA targeting trispecific protein containing a BCMA binding protein of this disclosure (02B05).

Pharmacokinetics of an Exemplary BCMA Targeting Trispecific Protein Containing a BCMA Binding Protein of this Disclosure Cynomolgus monkeys were administered single intravenous doses of an exemplary BCMA targeting trispecific protein containing a BCMA binding protein of this disclosure (02B05) (SEQ ID NO: 383), at 0.01 mg/kg, 0.1 mg/kg, or 1 mg/kg. Two animals were included per dose group. Following the administration, serum samples were collected and analyzed by two different electrochemiluminescent assays. One assay used biotinylated CD3ε as a capture reagent and detected with sulfo tagged BCMA (termed the functional assay). Another assay used as a capture reagent a biotinylated antibody recognizing the anti-albumin domain in the exemplary BCMA targeting trispecific protein containing a BCMA binding protein of this disclosure 02B05 (SEQ ID NO: 383) and used as a detection reagent a sulfo tagged antibody recognizing the anti-CD3 binding domain in the exemplary BCMA targeting trispecific protein containing a BCMA binding protein of this disclosure (i.e., an anti-idiotype antibody). The results from the electrochemiluminescent assays are plotted in FIG. 31. As seen in FIG. 31, the exemplary BCMA targeting trispecific protein was detected in the cynomolgus serum samples, even after 504 hours after the administration. The exemplary BCMA targeting trispecific protein was identified using both the sulfo-tagged BCMA (lines labeled using the term "functional" in FIG. 31) and by the anti-idiotype antibody (lines labeled using the term "anti-idiotype" in FIG. 31).

Figure 32:
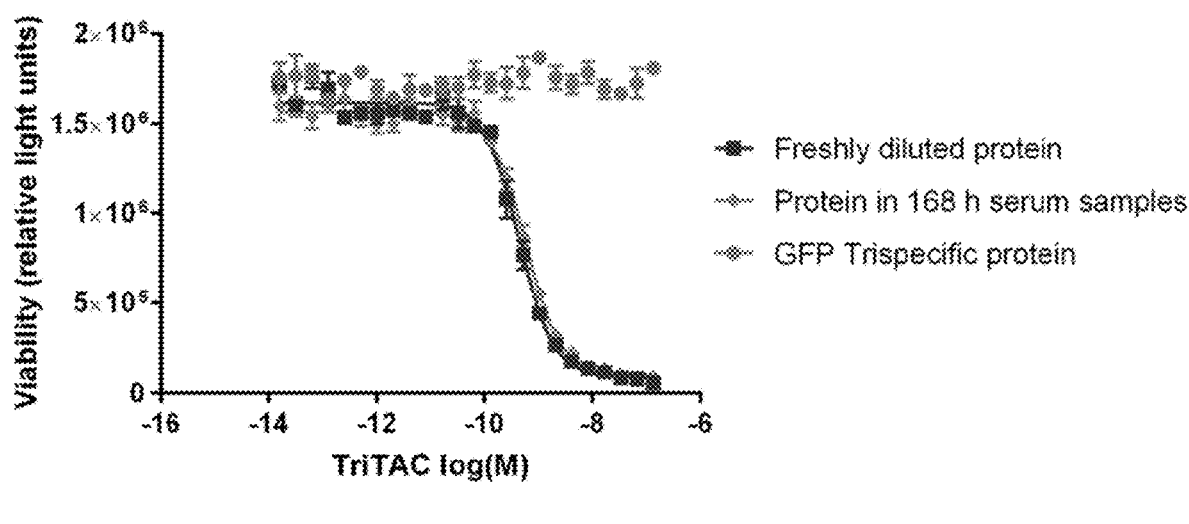
FIG. 32 the results of a TDCC assay using BCMA trispecific targeting protein obtained from serum samples of cynomolgus monkeys dosed with varying concentrations of an exemplary BCMA targeting trispecific protein containing a BCMA binding protein of this disclosure (02B05), BCMA expressing EJM cells, and purified human T cells, in presence of serum from cynomolgus monkeys that were not exposed to a BCMA targeting trispecific protein.

To confirm that the exemplary BCMA targeting trispecific protein retained the ability to direct T cells to kill BCMA expressing EJM cells, after in vivo administration, serum samples from the 168 hour time point were tested in a TDCC assay (as described in Example 1) in the presence of 16.7% serum from a cynomolgus monkey that has not been exposed to a BCMA targeting trispecific protein, titrating the exemplary BCMA targeting trispecific protein using the protein concentrations determined using the electrochemiluminescent assays (shown in FIG. 32). Fresh diluted exemplary BCMA targeting trispecific protein containing a BCMA binding protein of this disclosure 02B05 (SEQ ID NO: 383) was compared to the BCMA trispecific protein collected from the test cynomolgus monkeys at 168 h. A GFP trispecific protein was included as a negative control. This study demonstrated that the exemplary BCMA targeting trispecific protein collected from the test cynomolgus monkeys' serum had identical activity as freshly diluted protein, and that the protein in the serum samples retained the ability to direct T cells to kill BCMA expressing EJM cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Sequence Table

| SEQ ID NO: | Description | Sequence |
|---|---|---|
| 1 | Exemplary CDR1 | $X_1X_2X_3X_4X_5X_6X_7PX_8G$ where $X_1$ is T or S; $X_2$ is N, D, or S; $X_3$ is I, D, Q, H, V, or E; $X_4$ is F, S, E, A, T, M, V, I, D, Q, P, R, or G; $X_5$ is S, M, R, or N; $X_6$ is I, K, S, T, R, E, D, N, V, |

| | | Sequence Table |
|---|---|---|
| | | H, L, A, Q, or G; $X_7$ is S, T, Y, R, or N; and $X_8$ is M, G, or Y |
| 2 | Exemplary CDR2 | $AIX_9GX_{10}X_{11}TX_{12}YADSVK$ where $X_9$ is H, N, or S; $X_{10}$ is F, G, K, R, P, D, Q, H, E, N, T, S, A, I, L, or V; $X_{11}$ is S, Q, E, T, K, or D; and $X_{12}$ is L, V, I, F, Y, or W |
| 3 | Exemplary CDR3 | $VPWGX_{13}YHPX_{14}X_{15}VX_{16}$ where $X_{13}$ is D, I, T, K, R, A, E, S, or Y; $X_{14}$ is R, G, L, K, T, Q, S, or N; $X_{15}$ is N, K, E, V, R, M, or D; and $X_{16}$ is Y, A, V, K, H, L, M, T, R, Q, C, S, or N |

| SEQ ID NO: | Name | HCDR1 |
|---|---|---|
| 4. | 01A01 | TDIFSISPMG |
| 5. | 01A02 | TNIFSSSPMG |
| 6. | 01A03 | TNIFSISPGG |
| 7. | 01A04 | TNIFMISPMG |
| 8. | 01A05 | TNIFSSSPMG |
| 9. | 01A06 | TNIFSIRPMG |
| 10. | 01A07 | TNISSISPMG |
| 11. | 01A08 | TNIFSSSPMG |
| 12. | 01A09 | TNIFSITPMG |
| 13. | 01B01 | TNIPSISPMG |
| 14. | 01B02 | TNITSISPMG |
| 15. | 01B03 | TNIFSKSPMG |
| 16. | 01B04 | TNDFSISPMG |
| 17. | 01B05 | TNITSISPMG |
| 18. | 01B06 | TNIFSISPMG |
| 19. | 01B07 | TNIFSRSPMG |
| 20. | 01B08 | TNIESISPMG |
| 21. | 01B09 | SNIFSISPMG |
| 22. | 01B12 | TNIFSTSPMG |
| 23. | 01C01 | TNIVSISPMG |
| 24. | 01C02 | TNIESISPMG |
| 25. | 01C04 | TNIPSISPMG |
| 26. | 01C05 | TNIFSSSPMG |
| 27. | 01C06 | TNIFSISPMG |
| 28. | 01C07 | TNIFSIYPMG |
| 29. | 01C08 | TNIFSNSPMG |
| 30. | 01C10 | TNISSISPMG |
| 31. | 01D02 | TNIVSISPMG |
| 32. | 01D03 | TNIFSNSPMG |
| 33. | 01D04 | TNITSISPMG |
| 34. | 01D05 | TNIFSDSPMG |

| | | Sequence Table |
|---|---|---|
| 35. | 01D06 | TNIFSRSPMG |
| 36. | 01D07 | TNIFSASPMG |
| 37. | 01D10 | TNIFSASPMG |
| 38. | 01E03 | TNITSISPMG |
| 39. | 01E04 | TNIASISPMG |
| 40. | 01E05 | TNIFSRSPMG |
| 41. | 01E06 | TNIFSLSPMG |
| 42. | 01E07 | TNIPSISPMG |
| 43. | 01E08 | TNIFSQSPMG |
| 44. | 01E10 | TNIESISPMG |
| 45. | 01F02 | TNIFSHSPMG |
| 46. | 01F03 | TNIFSESPMG |
| 47. | 01F04 | TNIDSISPMG |
| 48. | 01F05 | TNIFSSSPMG |
| 49. | 01F07 | TNIFSTSPMG |
| 50. | 01F08 | TNITSVSPMG |
| 51. | 01F09 | TNISSISPMG |
| 52. | 01F10 | SNIFSISPMG |
| 53. | 01F12 | TNIFRISPMG |
| 54. | 01G01 | TNIVSISPMG |
| 55. | 01G04 | TNIDSISPMG |
| 56. | 01G06 | TNIFSRSPMG |
| 57. | 01G08 | TNIQSISPMG |
| 58. | 01G09 | TNIFNISPMG |
| 59. | 01G10 | TNEFSISPMG |
| 60. | 01G11 | TNIPSISPMG |
| 61. | 01H01 | TNIGSISPMG |
| 62. | 01H04 | TNIFSKSPMG |
| 63. | 01H05 | TNIFSITPMG |
| 64. | 01H06 | TSDFSISPMG |
| 65. | 01H08 | TNIMSISPMG |
| 66. | 01H09 | TNIMSISPMG |
| 67. | 01H10 | TNIPSISPMG |
| 68. | 01H11 | TNIFSTSPMG |
| 69. | 02A04 | TNIFSQSPMG |
| 70. | 02A05 | TNIASISPMG |
| 71. | 02A07 | TNIFSKSPMG |
| 72. | 02A08 | TNIFSRSPMG |
| 73. | 02A11 | TNHFSISPMG |

-continued

| | | Sequence Table |
|---|---|---|
| 74. | 02B01 | TNIFSNSPMG |
| 75. | 02B04 | TNIFSTSPMG |
| 76. | 02B05 | TNIFSISPYG |
| 77. | 02B06 | TNIFSNSPMG |
| 78. | 02B07 | TNIFSSSPMG |
| 79. | 02B11 | TNIVSISPMG |
| 80. | 02B12 | TNISSISPMG |
| 81. | 02C01 | TNIISISPMG |
| 82. | 02C03 | TNIASISPMG |
| 83. | 02C05 | TNIFSESPMG |
| 84. | 02C06 | TNIFSTSPMG |
| 85. | 02D06 | TNISSISPMG |
| 86. | 02D09 | TNVVSISPMG |
| 87. | 02D11 | TNEFSISPMG |
| 88. | 02E03 | TNIFSNSPMG |
| 89. | 02E05 | TNIFSRSPMG |
| 90. | 02E06 | TNIFSDSPMG |
| 91. | 02E09 | TNDFSISPMG |
| 92. | 02F02 | TNIFSKSPMG |
| 93. | 02F03 | TNIFSIYPMG |
| 94. | 02F04 | TNIFSSSPMG |
| 95. | 02F05 | TNIFSVSPMG |
| 96. | 02F06 | TNIFSITPMG |
| 97. | 02F07 | TNIESISPMG |
| 98. | 02F11 | TNIFSTSPMG |
| 99. | 02F12 | TNIESISPMG |
| 100. | 02G01 | TNIFSINPMG |
| 101. | 02G02 | TNIFSITPMG |
| 102. | 02G05 | TNITSISPMG |
| 103. | 02G06 | TNIFSGSPMG |
| 104. | 02G07 | TNIFSITPMG |
| 105. | 02G08 | TNIDSISPMG |
| 106. | 02G09 | TNIFSDSPMG |
| 107. | 02G11 | TNIDSISPMG |
| 108. | 02H01 | TNIFSKSPMG |
| 109. | 02H04 | TNIFSVSPMG |
| 110. | 02H05 | TNQFSISPMG |
| 111. | 02H06 | TNIRSISPMG |

-continued

| | | Sequence Table |
|---|---|---|
| 112. | 02H09 | TNIFSRSPMG |
| 113. | 02H11 | TNITSISPMG |
| 114. | 01F07-M34Y | TNIFSTSPYG |
| 115. | 01F01-M34G | TNIFSTSPGG |
| 116. | 02G02-M34Y | TNIFSITPYG |
| 117. | 02G02-M34G | TNIFSITPGG |
| SEQ ID NO: | Name | CDR2 |
| 118. | 01A01 | AIHGGSTLYADSVK |
| 119. | 01A02 | AINGFSTLYADSVK |
| 120. | 01A03 | AIHGSSTLYADSVK |
| 121. | 01A04 | AIHGDSTLYADSVK |
| 122. | 01A05 | AIHGFSTLYADSVK |
| 123. | 01A06 | AIHGFSTVYADSVK |
| 124. | 01A07 | AIHGTSTLYADSVK |
| 125. | 01A08 | AIHGESTLYADSVK |
| 126. | 01A09 | AIHGRSTLYADSVK |
| 127. | 01B01 | AIHGESTLYADSVK |
| 128. | 01B02 | AISGFSTLYADSVK |
| 129. | 01B03 | AIHGKSTLYADSVK |
| 130. | 01B04 | AIHGKSTLYADSVK |
| 131. | 01B05 | AIHGFETLYADSVK |
| 132. | 01B06 | AIHGDSTLYADSVK |
| 133. | 01B07 | AIHGNSTLYADSVK |
| 134. | 01B08 | AIHGSSTLYADSVK |
| 135. | 01B09 | AIHGSSTLYADSVK |
| 136. | 01B12 | AIHGFQTLYADSVK |
| 137. | 01C01 | AIHGHSTLYADSVK |
| 138. | 01C02 | AIHGNSTLYADSVK |
| 139. | 01C04 | AIHGDSTLYADSVK |
| 140. | 01C05 | AIHGEKTLYADSVK |
| 141. | 01C06 | AIHGDSTLYADSVK |
| 142. | 01C07 | AIHGESTYYADSVK |
| 143. | 01C08 | AIHGGSTLYADSVK |
| 144. | 01C10 | AIHGESTLYADSVK |
| 145. | 01D02 | AIHGKSTLYADSVK |
| 146. | 01D03 | AIHGDSTLYADSVK |
| 147. | 01D04 | AIHGVSTLYADSVK |
| 148. | 01D05 | AIHGTSTLYADSVK |
| 149. | 01D06 | AIHGDSTLYADSVK |

-continued

| | | Sequence Table |
|---|---|---|
| 150. | 01D07 | AIHGSSTLYADSVK |
| 151. | 01D10 | AIHGSSTLYADSVK |
| 152. | 01E03 | AIHGDSTLYADSVK |
| 153. | 01E04 | AIHGTSTLYADSVK |
| 154. | 01E05 | AIHGTSTLYADSVK |
| 155. | 01E06 | AIHGDSTLYADSVK |
| 156. | 01E07 | AIHGQSTLYADSVK |
| 157. | 01E08 | AIHGDSTLYADSVK |
| 158. | 01E10 | AIHGKSTLYADSVK |
| 159. | 01E02 | AIHGTSTLYADSVK |
| 160. | 01E03 | AIHGNSTLYADSVK |
| 161. | 01F04 | AIHGFQTLYADSVK |
| 162. | 01F05 | AIHGFSTWYADSVK |
| 163. | 01F07 | AIHGFSTIYADSVK |
| 164. | 01F08 | AIHGPSTLYADSVK |
| 165. | 01F09 | AIHGHSTLYADSVK |
| 166. | 01F10 | AIHGESTLYADSVK |
| 167. | 01F12 | AIHGDSTLYADSVK |
| 168. | 01G01 | AIHGDSTLYADSVK |
| 169. | 01G04 | AIHGNSTLYADSVK |
| 170. | 01G06 | AIHGFETLYADSVK |
| 171. | 01G08 | AIHGFETLYADSVK |
| 172. | 01G09 | AIHGFSTYYADSVK |
| 173. | 01G10 | AIHGLSTLYADSVK |
| 174. | 01G11 | AIHGASTLYADSVK |
| 175. | 01H01 | AIHGQSTLYADSVK |
| 176. | 01H04 | AIHGQSTLYADSVK |
| 177. | 01H05 | AIHGTSTLYADSVK |
| 178. | 01H06 | AIHGFETLYADSVK |
| 179. | 01H08 | AIHGFSTVYADSVK |
| 180. | 01H09 | AIHGNSTLYADSVK |
| 181. | 01H10 | AIHGESTLYADSVK |
| 182. | 01H11 | AIHGFSTLYADSVK |
| 183. | 02A04 | AIHGKSTLYADSVK |
| 184. | 02A05 | AIHGKSTLYADSVK |
| 185. | 02A07 | AIHGNSTLYADSVK |
| 186. | 02A08 | AIHGESTLYADSVK |
| 187. | 02A11 | AIHGSSTLYADSVK |

| | | Sequence Table |
|---|---|---|
| 188. | 02B01 | AIHGRSTLYADSVK |
| 189. | 02B04 | AIHGFSTIYADSVK |
| 190. | 02B05 | AIHGTSTLYADSVK |
| 191. | 02B06 | AIHGFSTLYADSVK |
| 192. | 02B07 | AIHGHSTLYADSVK |
| 193. | 02B11 | AIHGDSTLYADSVK |
| 194. | 02B12 | AIHGFDTLYADSVK |
| 195. | 02C01 | AIHGASTLYADSVK |
| 196. | 02C03 | AIHGSSTLYADSVK |
| 197. | 02C05 | AIHGFTTLYADSVK |
| 198. | 02C06 | AIHGTSTLYADSVK |
| 199. | 02D06 | AIHGFSTVYADSVK |
| 200. | 02D09 | AIHGKSTLYADSVK |
| 201. | 02D11 | AIHGESTLYADSVK |
| 202. | 02E03 | AIHGPSTLYADSVK |
| 203. | 02E05 | AIHGISTLYADSVK |
| 204. | 02E06 | AIHGFSTFYADSVK |
| 205. | 02E09 | AIHGGSTLYADSVK |
| 206. | 02F02 | AIHGSSTLYADSVK |
| 207. | 02F03 | AIHGSSTLYADSVK |
| 208. | 02F04 | AIHGFSTLYADSVK |
| 209. | 02F05 | AIHGNSTLYADSVK |
| 210. | 02F06 | AIHGESTLYADSVK |
| 211. | 02F07 | AIHGFSTLYADSVK |
| 212. | 02F11 | AIHGTSTLYADSVK |
| 213. | 02F12 | AIHGTSTLYADSVK |
| 214. | 02G01 | AIHGFDTLYADSVK |
| 215. | 02G02 | AIHGASTLYADSVK |
| 216. | 02G05 | AIHGNSTLYADSVK |
| 217. | 02G06 | AIHGNSTLYADSVK |
| 218. | 02G07 | AIHGESTLYADSVK |
| 219. | 02G08 | AIHGESTLYADSVK |
| 220. | 02G09 | AIHGFSTLYADSVK |
| 221. | 02G11 | AIHGSSTLYADSVK |
| 222. | 02H01 | AIHGSSTLYADSVK |
| 223. | 02H04 | AIHGNSTLYADSVK |
| 224. | 02H05 | AIHGKSTLYADSVK |
| 225. | 02H06 | AIHGSSTLYADSVK |
| 226. | 02H09 | AIHGSSTLYADSVK |

-continued

| | | Sequence Table |
|---|---|---|
| 227. | 02H11 | AIHGESTLYADSVK |
| 228. | 01F07-M34Y | AIHGFSTIYADSVK |
| 229. | 01F01-M34G | AIHGFSTIYADSVK |
| 230. | 02G02-M34Y | AIHGASTLYADSVK |
| 231. | 02G02-M34G | AIHGASTLYADSVK |
| SEQ ID NO: | Name | CDR3 |
| 232. | 01A01 | VPWGDYHPRNVA |
| 233. | 01A02 | VPWGDYHPRNVH |
| 234. | 01A03 | VPWGDYHPRNVY |
| 235. | 01A04 | VPWGRYHPRNVY |
| 236. | 01A05 | VPWGDYHPRNVY |
| 237. | 01A06 | VPWGDYHPRNVY |
| 238. | 01A07 | VPWGDYHPGNVY |
| 239. | 01A08 | VPWGDYHPRKVY |
| 240. | 01A09 | VPWGSYHPRNVY |
| 241. | 01B01 | VPWGDYHPRNVA |
| 242. | 01B02 | VPWGDYHPRNVY |
| 243. | 01B03 | VPWGDYHPRNVV |
| 244. | 01B04 | VPWGDYHPRNVK |
| 245. | 01B05 | VPWGDYHPGNVY |
| 246. | 01B06 | VPWGEYHPRNVY |
| 247. | 01B07 | VPWGIYHPRNVY |
| 248. | 01B08 | VPWGRYHPRNVY |
| 249. | 01B09 | VPWGDYHPGNVY |
| 250. | 01B12 | VPWGDYHPRNVV |
| 251. | 01C01 | VPWGDYHPGNVY |
| 252. | 01C02 | VPWGRYHPRNVY |
| 253. | 01C04 | VPWGDYHPRNVY |
| 254. | 01C05 | VPWGDYHPGNVY |
| 255. | 01C06 | VPWGKYHPRNVY |
| 256. | 01C07 | VPWGSYHPRNVY |
| 257. | 01C08 | VPWGDYHPRNVH |
| 258. | 01C10 | VPWGYYHPRNVY |
| 259. | 01D02 | VPWGDYHPGNVY |
| 260. | 01D03 | VPWGDYHPRNVR |
| 261. | 01D04 | VPWGDYHPRNVQ |
| 262. | 01D05 | VPWGDYHPRNVY |
| 263. | 01D06 | VPWGDYHPRNVT |

-continued

| | | Sequence Table |
|---|---|---|
| 264. | 01D07 | VPWGDYHPRNVN |
| 265. | 01D10 | VPWGRYHPRNVY |
| 266. | 01E03 | VPWGDYHPGNVY |
| 267. | 01E04 | VPWGDYHPGNVY |
| 268. | 01E05 | VPWGKYHPRNVY |
| 269. | 01E06 | VPWGDYHPRNVY |
| 270. | 01E07 | VPWGDYHPRNVQ |
| 271. | 01E08 | VPWGDYHPGNVC |
| 272. | 01E10 | VPWGDYHPRRVY |
| 273. | 01F02 | VPWGRYHPRNVY |
| 274. | 01F03 | VPWGTYHPRNVY |
| 275. | 01F04 | VPWGDYHPGNVY |
| 276. | 01F05 | VPWGRYHPRNVY |
| 277. | 01F07 | VPWGDYHPGNVY |
| 278. | 01F08 | VPWGDYHPTNVY |
| 279. | 01F09 | VPWGRYHPRNVY |
| 280. | 01F10 | VPWGDYHPRNVT |
| 281. | 01F12 | VPWGRYHPRNVY |
| 282. | 01G01 | VPWGDYHPRRVY |
| 283. | 01G04 | VPWGDYHPRMVY |
| 284. | 01G06 | VPWGDYHPRNVL |
| 285. | 01G08 | VPWGDYHPGNVY |
| 286. | 01G09 | VPWGRYHPRNVY |
| 287. | 01G10 | VPWGAYHPRNVY |
| 288. | 01G11 | VPWGDYHPRNVA |
| 289. | 01H01 | VPWGDYHPQNVY |
| 290. | 01H04 | VPWGDYHPRNVT |
| 291. | 01H05 | VPWGRYHPRNVY |
| 292. | 01H06 | VPWGDYHPGNVY |
| 293. | 01H08 | VPWGDYHPGNVY |
| 294. | 01H09 | VPWGDYHPGNVY |
| 295. | 01H10 | VPWGDYHPRNVY |
| 296. | 01H11 | VPWGDYHPGNVY |
| 297. | 02A04 | VPWGDYHPSNVY |
| 298. | 02A05 | VPWGDYHPGNVY |
| 299. | 02A07 | VPWGDYHPREVY |
| 300. | 02A08 | VPWGRYHPGNVY |
| 301. | 02A11 | VPWGDYHPRVVY |
| 302. | 02B01 | VPWGDYHPRNVM |

-continued

| | | Sequence Table |
|---|---|---|
| 303. | 02B04 | VPWGDYHPLNVY |
| 304. | 02B05 | VPWGDYHPGNVY |
| 305. | 02B06 | VPWGDYHPGNVY |
| 306. | 02B07 | VPWGDYHPRNVT |
| 307. | 02B11 | VPWGDYHPRNVS |
| 308. | 02B12 | VPWGDYHPRNVY |
| 309. | 02C01 | VPWGDYHPGNVY |
| 310. | 02C03 | VPWGDYHPGNVY |
| 311. | 02C05 | VPWGDYHPRNVT |
| 312. | 02C06 | VPWGDYHPGNVY |
| 313. | 02D06 | VPWGRYHPRNVY |
| 314. | 02D09 | VPWGDYHPNNVY |
| 315. | 02D11 | VPWGDYHPGNVY |
| 316. | 02E03 | VPWGDYHPRNVT |
| 317. | 02E05 | VPWGDYHPGNVY |
| 318. | 02E06 | VPWGDYHPGNVY |
| 319. | 02E09 | VPWGDYHPRNVA |
| 320. | 02F02 | VPWGDYHPGNVY |
| 321. | 02F03 | VPWGDYHPKNVY |
| 322. | 02F04 | VPWGDYHPGNVY |
| 323. | 02F05 | VPWGKYHPRNVY |
| 324. | 02F06 | VPWGRYHPRNVY |
| 325. | 02F07 | VPWGDYHPGNVY |
| 326. | 02F11 | VPWGDYHPRNVQ |
| 327. | 02F12 | VPWGDYHPGNVY |
| 328. | 02G01 | VPWGDYHPRNVS |
| 329. | 02G02 | VPWGDYHPGNVY |
| 330. | 02G05 | VPWGDYHPGNVY |
| 331. | 02G06 | VPWGDYHPGNVY |
| 332. | 02G07 | VPWGDYHPRDVY |
| 333. | 02G08 | VPWGDYHPRNVT |
| 334. | 02G09 | VPWGDYHPRNVA |
| 335. | 02G11 | VPWGDYHPRNVT |
| 336. | 02H01 | VPWGDYHPRNVY |
| 337. | 02H04 | VPWGDYHPRNVY |
| 338. | 02H05 | VPWGDYHPRNVV |
| 339. | 02H06 | VPWGDYHPRNVV |
| 340. | 02H09 | VPWGDYHPGNVY |

| | Sequence Table | |
|---|---|---|
| 341. | 02H11 | VPWGDYHPRNVY |
| 342. | 01F07-M34Y | VPWGDYHPGNVY |
| 343. | 01F01-M34G | VPWGDYHPGNVY |
| 344. | 02G02-M34Y | VPWGDYHPGNVY |
| 345. | 02G02-M34G | VPWGDYHPGNVY |

| SEQ ID NO | Construct Name | VHH Sequences |
|---|---|---|
| 346 | BH2T | EVQLVESGGGLVQPGRSLTLSCAASTNIFSISPMGWYRQAPGKQRELVAAIHGFSTLYADSVKGRFTISRDNAKNSIYLQMNSLRPEDTALYYCNKVPWGDYHPRNVYWGQGTQVTVSS |
| 347 | 01A01 | EVQLVESGGGLVQPGRSLTLSCAASTDIFSISPMGWYRQAPGKQRELVAAIHGGSTLYADSVKGRFTISRDNAKNSIYLQMNSLRPEDTALYYCNKVPWGDYHPRNVAWGQGTQVTVSS |
| 348 | 02E09 | EVQLVESGGGLVQPGRSLTLSCAASTNDFSISPMGWYRQAPGKQRELVAAIHGGSTLYADSVKGRFTISRDNAKNSIYLQMNSLRPEDTALYYCNKVPWGDYHPRNVAWGQGTQVTVSS |
| 349 | 01B03 | EVQLVESGGGLVQPGRSLTLSCAASTNIFSKSPMGWYRQAPGKQRELVAAIHGKSTLYADSVKGRFTISRDNAKNSIYLQMNSLRPEDTALYYCNKVPWGDYHPRNVVWGQGTQVTVSS |
| 350 | 01B04 | EVQLVESGGGLVQPGRSLTLSCAASTNDFSISPMGWYRQAPGKQRELVAAIHGKSTLYADSVKGRFTISRDNAKNSIYLQMNSLRPEDTALYYCNKVPWGDYHPRNVKWGQGTQVTVSS |
| 351 | 02H05 | EVQLVESGGGLVQPGRSLTLSCAASTNQFSISPMGWYRQAPGKQRELVAAIHGKSTLYADSVKGRFTISRDNAKNSIYLQMNSLRPEDTALYYCNKVPWGDYHPRNVVWGQGTQVTVSS |
| 352 | 01A02 | EVQLVESGGGLVQPGRSLTLSCAASTNIFSSSPMGWYRQAPGKQRELVAAINGFSTLYADSVKGRFTISRDNAKNSIYLQMNSLRPEDTALYYCNKVPWGDYHPRNVHWGQGTQVTVSS |
| 353 | 01A05 | EVQLVESGGGLVQPGRSLTLSCAASTNIFSSSPMGWYRQAPGKQRELVAAIHGFSTLYADSVKGRFTISRDNAKNSIYLQMNSLRPEDTALYYCNKVPWGDYHPRNVYWGQGTQVTVSS |
| 354 | 01B12 | EVQLVESGGGLVQPGRSLTLSCAASTNIFSTSPMGWYRQAPGKQRELVAAIHGFQTLYADSVKGRFTISRDNAKNSIYLQMNSLRPEDTALYYCNKVPWGDYHPRNVVWGQGTQVTVSS |
| 355 | 01G06 | EVQLVESGGGLVQPGRSLTLSCAASTNIFSRSPMGWYRQAPGKQRELVAAIHGFETLYADSVKGRFTISRDNAKNSIYLQMNSLRPEDTALYYCNKVPWGDYHPRNVLWGQGTQVTVSS |
| 356 | 02C05 | EVQLVESGGGLVQPGRSLTLSCAASTNIFSESPMGWYRQAPGKQRELVAAIHGFTTLYADSVKGRFTISRDNAKNSIYLQMNSLRPEDTALYYCNKVPWGDYHPRNVTWGQGTQVTVSS |
| 357 | 02G09 | EVQLVESGGGLVQPGRSLTLSCAASTNIFSDSPMGWYRQAPGKQRELVAAIHGFSTLYADSVKGRFTISRDNAKNSIYLQMNSLRPEDTALYYCNKVPWGDYHPRNVAWGQGTQVTVSS |
| 358 | 01C08 | EVQLVESGGGLVQPGRSLTLSCAASTNIFSNSPMGWYRQAPGKQRELVAAIHGGSTLYADSVKGRFTISRDNAKNSIYLQMNSLRPEDTALYYCNKVPWGDYHPRNVHWGQGTQVTVSS |
| 359 | 02B01 | EVQLVESGGGLVQPGRSLTLSCAASTNIFSNSPMGWYRQAPGKQRELVAAIHGRSTLYADSVKGRFTISRDNAKNSIYLQMNSLRPEDTALYYCNKVPWGDYHPRNVMWGQGTQVTVSS |
| 360 | 02E03 | EVQLVESGGGLVQPGRSLTLSCAASTNIFSNSPMGWYRQAPGKQRELVAAIHGPSTLYADSVKGRFTISRDNAKNSIYLQMNSLRPEDTALYYCNKVPWGDYHPRNVTWGQGTQVTVSS |
| 361 | 01D03 | EVQLVESGGGLVQPGRSLTLSCAASTNIFSNSPMGWYRQAPGKQRELVAAIHGDSTLYADSVKGRFTISRDNAKNSIYLQMNSLRPEDTALYYCNKVPWGDYHPRNVRWGQGTQVTVSS |

-continued

| | | Sequence Table |
|---|---|---|
| 362 | 01D06 | EVQLVESGGGLVQPGRSLTLSCAASTNIFSRSPMGWYRQAPGKQRELVAAIHGDS TLYADSVKGRFTISRDNAKNSIYLQMNSLRPEDTALYYCNKVPWGDYHPRNVTWG QGTQVTVSS |
| 363 | 01H04 | EVQLVESGGGLVQPGRSLTLSCAASTNIFSKSPMGWYRQAPGKQRELVAAIHGQS TLYADSVKGRFTISRDNAKNSIYLQMNSLRPEDTALYYCNKVPWGDYHPRNVTWG QGTQVTVSS |
| 364 | 02B07 | EVQLVESGGGLVQPGRSLTLSCAASTNIFSSSPMGWYRQAPGKQRELVAAIHGHS TLYADSVKGRFTISRDNAKNSIYLQMNSLRPEDTALYYCNKVPWGDYHPRNVTWG QGTQVTVSS |
| 365 | 01A08 | EVQLVESGGGLVQPGRSLTLSCAASTNIFSSSPMGWYRQAPGKQRELVAAIHGES TLYADSVKGRFTISRDNAKNSIYLQMNSLRPEDTALYYCNKVPWGDYHPRKVYWG QGTQVTVSS |
| 366 | 01B07 | EVQLVESGGGLVQPGRSLTLSCAASTNIFSRSPMGWYRQAPGKQRELVAAIHGNS TLYADSVKGRFTISRDNAKNSIYLQMNSLRPEDTALYYCNKVPWGIYHPRNVYWG QGTQVTVSS |
| 367 | 01F03 | EVQLVESGGGLVQPGRSLTLSCAASTNIFSESPMGWYRQAPGKQRELVAAIHGNS TLYADSVKGRFTISRDNAKNSIYLQMNSLRPEDTALYYCNKVPWGTYHPRNVYWG QGTQVTVSS |
| 368 | 02F05 | EVQLVESGGGLVQPGRSLTLSCAASTNIFSVSPMGWYRQAPGKQRELVAAIHGNS TLYADSVKGRFTISRDNAKNSIYLQMNSLRPEDTALYYCNKVPWGKYHPRNVYWG QGTQVTVSS |
| 369 | 02H04 | EVQLVESGGGLVQPGRSLTLSCAASTNIFSVSPMGWYRQAPGKQRELVAAIHGNS TLYADSVKGRFTISRDNAKNSIYLQMNSLRPEDTALYYCNKVPWGDYHPRNVYWG QGTQVTVSS |
| 370 | 02A07 | EVQLVESGGGLVQPGRSLTLSCAASTNIFSKSPMGWYRQAPGKQRELVAAIHGNS TLYADSVKGRFTISRDNAKNSIYLQMNSLRPEDTALYYCNKVPWGDYHPREVYWG QGTQVTVSS |
| 371 | 01D05 | EVQLVESGGGLVQPGRSLTLSCAASTNIFSDSPMGWYRQAPGKQRELVAAIHGTS TLYADSVKGRFTISRDNAKNSIYLQMNSLRPEDTALYYCNKVPWGDYHPRNVYWG QGTQVTVSS |
| 372 | 01E05 | EVQLVESGGGLVQPGRSLTLSCAASTNIFSRSPMGWYRQAPGKQRELVAAIHGTS TLYADSVKGRFTISRDNAKNSIYLQMNSLRPEDTALYYCNKVPWGKYHPRNVYWG QGTQVTVSS |
| 373 | 01F02 | EVQLVESGGGLVQPGRSLTLSCAASTNIFSHSPMGWYRQAPGKQRELVAAIHGTS TLYADSVKGRFTISRDNAKNSIYLQMNSLRPEDTALYYCNKVPWGRYHPRNVYWG QGTQVTVSS |
| 374 | 02C06 | EVQLVESGGGLVQPGRSLTLSCAASTNIFSTSPMGWYRQAPGKQRELVAAIHGTS TLYADSVKGRFTISRDNAKNSIYLQMNSLRPEDTALYYCNKVPWGDYHPGNVYWG QGTQVTVSS |
| 375 | 02F11 | EVQLVESGGGLVQPGRSLTLSCAASTNIFSTSPMGWYRQAPGKQRELVAAIHGTS TLYADSVKGRFTISRDNAKNSIYLQMNSLRPEDTALYYCNKVPWGDYHPRNVQWG QGTQVTVSS |
| 376 | 01E06 | EVQLVESGGGLVQPGRSLTLSCAASTNIFSLSPMGWYRQAPGKQRELVAAIHGDS TLYADSVKGRFTISRDNAKNSIYLQMNSLRPEDTALYYCNKVPWGDYHPRNVYWG QGTQVTVSS |
| 377 | 01A03 | EVQLVESGGGLVQPGRSLTLSCAASTNIFSISPGGWYRQAPGKQRELVAAIHGSS TLYADSVKGRFTISRDNAKNSIYLQMNSLRPEDTALYYCNKVPWGDYHPRNVYWG QGTQVTVSS |
| 378 | 02A11 | EVQLVESGGGLVQPGRSLTLSCAASTNHFSISPMGWYRQAPGKQRELVAAIHGSS TLYADSVKGRFTISRDNAKNSIYLQMNSLRPEDTALYYCNKVPWGDYHPRWYWG QGTQVTVSS |
| 379 | 01D07 | EVQLVESGGGLVQPGRSLTLSCAASTNIFSASPMGWYRQAPGKQRELVAAIHGSS TLYADSVKGRFTISRDNAKNSIYLQMNSLRPEDTALYYCNKVPWGDYHPRNVNWG QGTQVTVSS |
| 380 | 01D10 | EVQLVESGGGLVQPGRSLTLSCAASTNIFSASPMGWYRQAPGKQRELVAAIHGSS TLYADSVKGRFTISRDNAKNSIYLQMNSLRPEDTALYYCNKVPWGRYHPRNVYWG QGTQVTVSS |

| | | Sequence Table |
|---|---|---|
| 381 | 01A07 | EVQLVESGGGLVQPGRSLTLSCAASTNISSISPMGWYRQAPGKQRELVAAIHGTS<br>TLYADSVKGRFTISRDNAKNSIYLQMNSLRPEDTALYYCNKVPWGDYHPGNVYWG<br>QGTQVTVSS |
| 382 | 02F12 | EVQLVESGGGLVQPGRSLTLSCAASTNIESISPMGWYRQAPGKQRELVAAIHGTS<br>TLYADSVKGRFTISRDNAKNSIYLQMNSLRPEDTALYYCNKVPWGDYHPGNVYWG<br>QGTQVTVSS |
| 383 | 02B05 | EVQLVESGGGLVQPGRSLTLSCAASTNIFSISPYGWYRQAPGKQRELVAAIHGTS<br>TLYADSVKGRFTISRDNAKNSIYLQMNSLRPEDTALYYCNKVPWGDYHPGNVYWG<br>QGTQVTVSS |
| 384 | 01E04 | EVQLVESGGGLVQPGRSLTLSCAASTNIASISPMGWYRQAPGKQRELVAAIHGTS<br>TLYADSVKGRFTISRDNAKNSIYLQMNSLRPEDTALYYCNKVPWGDYHPGNVYWG<br>QGTQVTVSS |
| 385 | 02A05 | EVQLVESGGGLVQPGRSLTLSCAASTNIASISPMGWYRQAPGKQRELVAAIHGKS<br>TLYADSVKGRFTISRDNAKNSIYLQMNSLRPEDTALYYCNKVPWGDYHPGNVYWG<br>QGTQVTVSS |
| 386 | 02C03 | EVQLVESGGGLVQPGRSLTLSCAASTNIASISPMGWYRQAPGKQRELVAAIHGSS<br>TLYADSVKGRFTISRDNAKNSIYLQMNSLRPEDTALYYCNKVPWGDYHPGNVYWG<br>QGTQVTVSS |
| 387 | 01E03 | EVQLVESGGGLVQPGRSLTLSCAASTNITSISPMGWYRQAPGKQRELVAAIHGDS<br>TLYADSVKGRFTISRDNAKNSIYLQMNSLRPEDTALYYCNKVPWGDYHPGNVYWG<br>QGTQVTVSS |
| 388 | 01H09 | EVQLVESGGGLVQPGRSLTLSCAASTNIMSISPMGWYRQAPGKQRELVAAIHGNS<br>TLYADSVKGRFTISRDNAKNSIYLQMNSLRPEDTALYYCNKVPWGDYHPGNVYWG<br>QGTQVTVSS |
| 389 | 02G05 | EVQLVESGGGLVQPGRSLTLSCAASTNITSISPMGWYRQAPGKQRELVAAIHGNS<br>TLYADSVKGRFTISRDNAKNSIYLQMNSLRPEDTALYYCNKVPWGDYHPGNVYWG<br>QGTQVTVSS |
| 390 | 01C01 | EVQLVESGGGLVQPGRSLTLSCAASTNIVSISPMGWYRQAPGKQRELVAAIHGHS<br>TLYADSVKGRFTISRDNAKNSIYLQMNSLRPEDTALYYCNKVPWGDYHPGNVYWG<br>QGTQVTVSS |
| 391 | 01D02 | EVQLVESGGGLVQPGRSLTLSCAASTNIVSISPMGWYRQAPGKQRELVAAIHGKS<br>TLYADSVKGRFTISRDNAKNSIYLQMNSLRPEDTALYYCNKVPWGDYHPGNVYWG<br>QGTQVTVSS |
| 392 | 02D09 | EVQLVESGGGLVQPGRSLTLSCAASTNWSISPMGWYRQAPGKQRELVAAIHGKS<br>TLYADSVKGRFTISRDNAKNSIYLQMNSLRPEDTALYYCNKVPWGDYHPNNVYWG<br>QGTQVTVSS |
| 393 | 02C01 | EVQLVESGGGLVQPGRSLTLSCAASTNIISISPMGWYRQAPGKQRELVAAIHGAS<br>TLYADSVKGRFTISRDNAKNSIYLQMNSLRPEDTALYYCNKVPWGDYHPGNVYWG<br>QGTQVTVSS |
| 394 | 02G02 | EVQLVESGGGLVQPGRSLTLSCAASTNIFSITPMGWYRQAPGKQRELVAAIHGAS<br>TLYADSVKGRFTISRDNAKNSIYLQMNSLRPEDTALYYCNKVPWGDYHPGNVYWG<br>QGTQVTVSS |
| 395 | 01B05 | EVQLVESGGGLVQPGRSLTLSCAASTNITSISPMGWYRQAPGKQRELVAAIHGFE<br>TLYADSVKGRFTISRDNAKNSIYLQMNSLRPEDTALYYCNKVPWGDYHPGNVYWG<br>QGTQVTVSS |
| 396 | 01G08 | EVQLVESGGGLVQPGRSLTLSCAASTNIQSISPMGWYRQAPGKQRELVAAIHGFE<br>TLYADSVKGRFTISRDNAKNSIYLQMNSLRPEDTALYYCNKVPWGDYHPGNVYWG<br>QGTQVTVSS |
| 397 | 01H06 | EVQLVESGGGLVQPGRSLTLSCAASTSDFSISPMGWYRQAPGKQRELVAAIHGFE<br>TLYADSVKGRFTISRDNAKNSIYLQMNSLRPEDTALYYCNKVPWGDYHPGNVYWG<br>QGTQVTVSS |
| 398 | 01F04 | EVQLVESGGGLVQPGRSLTLSCAASTNIDSISPMGWYRQAPGKQRELVAAIHGFQ<br>TLYADSVKGRFTISRDNAKNSIYLQMNSLRPEDTALYYCNKVPWGDYHPGNVYWG<br>QGTQVTVSS |
| 399 | 01H08 | EVQLVESGGGLVQPGRSLTLSCAASTNIMSISPMGWYRQAPGKQRELVAAIHGFS<br>TVYADSVKGRFTISRDNAKNSIYLQMNSLRPEDTALYYCNKVPWGDYHPGNVYWG<br>QGTQVTVSS |

| | | Sequence Table |
|---|---|---|
| 400 | 02F07 | EVQLVESGGGLVQPGRSLTLSCAASTNIESISPMGWYRQAPGKQRELVAAIHGFS<br>TLYADSVKGRFTISRDNAKNSIYLQMNSLRPEDTALYYCNKVPWGDYHPGNVYWG<br>QGTQVTVSS |
| 401 | 01C05 | EVQLVESGGGLVQPGRSLTLSCAASTNIFSSSPMGWYRQAPGKQRELVAAIHGFK<br>TLYADSVKGRFTISRDNAKNSIYLQMNSLRPEDTARYYCNKVPWGDYHPGNVYWG<br>QGTQVTVSS |
| 402 | 02F04 | EVQLVESGGGLVQPGRSLTLSCAASTNIFSSSPMGWYRQAPGKQRELVAAIHGFS<br>TLYADSVKGRFTISRDNAKNSIYLQMNSLRPEDTALYYCNKVPWGDYHPGNVYWG<br>QGTQVTVSS |
| 403 | 02B06 | EVQLVESGGGLVQPGRSLTLSCAASTNIFSNSPMGWYRQAPGKQRELVAAIHGFS<br>TLYADSVKGRFTISRDNAKNSIYLQMNSLRPEDTALYYCNKVPWGDYHPGNVYWG<br>QGTQVTVSS |
| 404 | 01F07 | EVQLVESGGGLVQPGRSLTLSCAASTNIFSTSPMGWYRQAPGKQRELVAAIHGFS<br>TIYADSVKGRFTISRDNAKNSIYLQMNSLRPEDTALYYCNKVPWGDYHPGNVYWG<br>QGTQVTVSS |
| 405 | 02B04 | EVQLVESGGGLVQPGRSLTLSCAASTNIFSTSPMGWYRQAPGKQRELVAAIHGFS<br>TIYADSVKGRFTISRDNAKNSIYLQMNSLRPEDTALYYCNKVPWGDYHPLNVYWG<br>QGTQVTVSS |
| 406 | 01H11 | EVQLVESGGGLVQPGRSLTLSCVASTNIFSTSPMGWYRQAPGKQRELVAAIHGFS<br>TLYADSVKGRFTISRDNAKNSIYLQMNSLRPEDTALYYCNKVPWGDYHPGNVYWG<br>QGTQVTVSS |
| 407 | 02E06 | EVQLVESGGGLVQPGRSLTLSCAASTNIFSDSPMGWYRQAPGKQRELVAAIHGFS<br>TFYADSVKGRFTISRDNAKNSIYLQMNSLRPEDTALYYCNKVPWGDYHPGNVYWG<br>QGTQVTVSS |
| 408 | 01E08 | EVQLVESGGGLVQPGRSLTLSCAASTNIFSQSPMGWYRQAPGKQRELVAAIHGDS<br>TLYADSVKGRFTISRDNAKNSIYLQMNSLRPEDTALYYCNKVPWGDYHPGNVCWG<br>QGTQVTVSS |
| 409 | 02A04 | EVQLVESGGGLVQPGRSLTLSCAASTNIFSQSPMGWYRQAPGKQRELVAAIHGKS<br>TLYADSVKGRFTISRDNAKNSIYLQMNSLRPEDTALYYCNKVPWGDYHPSNVYWG<br>KGTQVTVSS |
| 410 | 02A08 | EVQLVESGGGLVQPGRSLTLSCAASTNIFSRSPMGWYRQAPGKQRELVAAIHGES<br>TLYADSVKGRFTISRDNAKNSIYLQMNSLRPEDTALYYCNKVPWGRYHPGNVYWG<br>QGTQVTVSS |
| 411 | 02E05 | EVQLVESGGGLVQPGRSLTLSCAASTNIFSRSPMGWYRQAPGKQRELVAAIHGIS<br>TLYADSVKGRFTISRDNAKNSIYLQMNSLRPEDTALYYCNKVPWGDYHPGNVYWG<br>QGTQVTVSS |
| 412 | 02H09 | EVQLVESGGGLVQPGRSLTLSCAASTNIFSRSPMGWYRQAPGKQRELVAAIHGSS<br>TLYADSVKGRFTISRDNAKNSIYLQMNSLRPEDTALYYCNKVPWGDYHPGNVYWG<br>QGTQVTVSS |
| 413 | 02G06 | EVQLVESGGGLVQPGRSLTLSCAASTNIFSGSPMGWYRQAPGKQRELVAAIHGNS<br>TLYADSVKGRFTISRDNAKNSIYLQMNSLRPEDTALYYCNKVPWGDYHPGNVYWG<br>QGTQVTVSS |
| 414 | 01B09 | EVQLVESGGGLVQPGRSLTLSCAASSNIFSISPMGWYRQAPGKQRELVAAIHGSS<br>TLYADSVKGRFTISRDNAKNSIYLQMNSLRPEDTALYYCNKVPWGDYHPGNVYWG<br>QGTQVTVSS |
| 415 | 02F03 | EVQLVESGGGLVQPGRSLTLSCAASTNIFSIYPMGWYRQAPGKQRELVAAIHGSS<br>TLYADSVKGRFTISRDNAKNSIYLQMNSLRPEDTALYYCNKVPWGDYHPKNVYWG<br>QGTQVTVSS |
| 416 | 02F02 | EVQLVESGGGLVQPGRSLTLSCAASTNIFSKSPMGWYRQAPGKQRELVAAIHGSS<br>TLYADSVKGRFTISRDNAKNSIYLQMNSLRPEDTALYYCNKVPWGDYHPGNVYWG<br>QGTQVTVSS |
| 417 | 02H01 | EVQLVESGGGLVQPGRSLTLSCAASTNIFSKSPMGWYRQAPGKQRELVAAIHGSS<br>TLYADSVKGRFTISRDNAKNSIYLQMNSLRPEDTALYYCNKVPWGDYHPRNVYWG<br>QGTQVTVSS |
| 418 | 01G10 | EVQLVESGGGLVQPGRSLTLSCAASTNEFSISPMGWYRQAPGKQRELVAAIHGLS<br>TLYADSVKGRFTISRDNAKNSIYLQMNSLRPEDTALYYCNKVPWGAYHPRNVYWG<br>QGTQVTVSS |

Sequence Table (continued)

| | | |
|---|---|---|
| 419 | 02D11 | EVQLVESGGGLVQPGRSLTLSCAASTNEFSISPMGWYRQAPGKQRELVAAIHGES<br>TLYADSVKGRFTISRDNAKNSIYLQMNSLRPEDTALYYCNKVPWGDYHPGNVYWG<br>QGTQVTVSS |
| 420 | 01B01 | EVQLVESGGGLVQPGRSLTLSCAASTNIPSISPMGWYRQAPGKQRELVAAIHGES<br>TLYADSVKGRFTISRDNAKNSIYLQMNSLRPEDTALYYCNKVPWGDYHPRNVAWG<br>QGTQVTVSS |
| 421 | 01G11 | EVQLVESGGGLVQPGRSLTLSCAASTNIPSISPMGWYRQAPGKQRELVAAIHGAS<br>TLYADSVKGRFTISRDNAKNSIYLQMNSLRPEDTALYYCNKVPWGDYHPRNVAWG<br>QGTQVTVSS |
| 422 | 01H10 | EVQLVESGGGLVQPGRSLTLSCAASTNIPSISPMGWYRQAPGKQRELVAAIHGES<br>TLYADSVKGRFTISRDNAKNSIYLQMNSLRPEDTALYYCNKVPWGDYHPRNVYWG<br>QGTQVTVSS |
| 423 | 01C04 | EVQLVESGGGLVQPGRSLTLSCAASTNIPSISPMGWYRQAPGKQRELVAAIHGDS<br>TLYADSVKGRFTISRDNAKNSIYLQMNSLRPEDTALYYCNKVPWGDYHPRNVYWG<br>QGTQVTVSS |
| 424 | 01D04 | EVQLVESGGGLVQPGRSLTLSCAASTNITSISPMGWYRQAPGKQRELVAAIHGVS<br>TLYADSVKGRFTISRDNAKNSIYLQMNSLRPEDTALYYCNKVPWGDYHPRNVQWG<br>QGTQVTVSS |
| 425 | 01E07 | EVQLVESGGGLVQPGRSLTLSCAASTNIPSISPMGWYRQAPGKQRELVAAIHGQS<br>TLYADSVKGRFTISRDNAKNSIYLQMNSLRPEDTALYYCNKVPWGDYHPRNVQWG<br>QGTQVTVSS |
| 426 | 02B11 | EVQLVESGGGLVQPGRSLTLSCAASTNIVSISPMGWYRQAPGKQRELVAAIHGDS<br>TLYADSVKGRFTISRDNAKNSIYLQMNSLRPEDTALYYCNKVPWGDYHPRNVSWG<br>QGTQVTVSS |
| 427 | 01F10 | EVQLVESGGGLVQPGRSLTLSCAASSNIFSISPMGWYRQAPGKQRELVAAIHGES<br>TLYADSVKGRFTISRDNAKNSIYLQMNSLRPEDTALYYCNKVPWGDYHPRNVTWG<br>QGTQVTVSS |
| 428 | 02G08 | EVQLVESGGGLVQPGRSLTLSCAASTNIDSISPMGWYRQAPGKQRELVAAIHGES<br>TLYADSVKGRFTISRDNAKNSIYLQMNSLRPEDTALYYCNKVPWGDYHPRNVTWG<br>QGTQVTVSS |
| 429 | 02G11 | EVQLVESGGGLVQPGRSLTLSCAASTNIDSISPMGWYRQAPGKQRELVAAIHGSS<br>TLYADSVKGRFTISRDNAKNSIYLQMNSLRPEDTALYYCNKVPWGDYHPRNVTWG<br>QGTQVTVSS |
| 430 | 02H06 | EVQLVESGGGLVQPGRSLTLSCAASTNIRSISPMGWYRQAPGKQRELVAAIHGSS<br>TLYADSVKGRFTISRDNAKNSIYLQMNSLRPEDTALYYCNKVPWGDYHPRNWWG<br>QGTQVTVSS |
| 431 | 01B02 | EVQLVESGGGLVQPGRSLTLSCAASTNITSISPMGWYRQAPGKQRELVAAISGFS<br>TLYADSVKGRFTISRDNAKNSIYLQMNSLRPEDTALYYCNEVPWGDYHPRNVYWG<br>QGTQVTVSS |
| 432 | 02H11 | EVQLVESGGGLVQPGRSLTLSCAASTNITSISPMGWYRQAPGKQRELVAAIHGES<br>TLYADSVKGRFTISRDNAKNSIYLQMNSLRPEDTALYYCNKVPWGDYHPRNVYWG<br>QGTQVTVSS |
| 433 | 01F08 | EVQLVESGGGLVQPGRSLTLSCAASTNITSVSPMGWYRQAPGKQRELVAAIHGPS<br>TLYADSVKGRFTISRDNAKNSIYLQMNSLRPEDTALYYCNKVPWGDYHPTNVYWG<br>QGTQVTVSS |
| 434 | 01H01 | EVQLVESGGGLVQPGRSLTLSCAASTNIGSISPMGWYRQAPGKQRELVAAIHGQS<br>TLYADSVKGRFTISRDNAKNSIYLQMNSLRPEDTALYYCNKVPWGDYHPQNVYWG<br>QGTQVTVSS |
| 435 | 01E10 | EVQLVESGGGLVQPGRSLTLSCAASTNIESISPMGWYRQAPGKQRELVAAIHGKS<br>TLYADSVKGRFTISRDNAKNSIYLQMNSLRPEDTALYYCNKVPWGDYHPRRVYWG<br>QGTQVTVSS |
| 436 | 01G01 | EVQLVESGGGLVQPGRSLTLSCAASTNIVSISPMGWYRQAPGKQRELVAAIHGDS<br>TLYADSVKGRFTISRDNAKNSIYLQMNSLRPEDTALYYCNKVPWGDYHPRRVYWG<br>QGTQVTVSS |
| 437 | 01G04 | EVQLVESGGGLVQPGRSLTLSCAASTNIDSISPMGWYRQAPGKQRELVAAIHGNS<br>TLYADSVKGRFTISRDNAKNSIYLQMNSLRPEDTALYYCNKVPWGDYHPRMVYWG<br>QGTQVTVSS |

| | | Sequence Table |
|---|---|---|
| 438 | 01A04 | EVQLVESGGGLVQPGRSLTLSCAASTNIFMISPMGWYRQAPGKQRELVAAIHGDS<br>TLYADSVKGRFTISRDNAKNSIYLQMNSLRPEDTALYYCNKVPWGRYHPRNVYWG<br>QGTQVTVSS |
| 439 | 01F12 | EVQLVESGGGLVQPGRSLTLSCAASTNIFRISPMGWYRQAPGKQRELVAAIHGDS<br>TLYADSVKGRFTISRDNAKNSIYLQMNSLRPEDTALYYCNKVPWGRYHPRNVYWG<br>QGTQVTVSS |
| 440 | 01B06 | EVQLVESGGGLVQPGRSLTLSCAASTNIFSISPMGWYRQAPGKQRELVAAIHGDS<br>TLYADSVKGRFTISRDNAKNSIYLQMNSLRPEDTALYYCNKVPWGEYHPRNVYWG<br>QGTQVTVSS |
| 441 | 01C06 | EVQLVESGGGLVQPGRSLTLSCAASTNIFSISPMGWYRQAPGKQRELVAAIHGDS<br>TLYADSVKGRFTISRDNAKNSIYLQMNSLRPEDTALYYCNKVPWGKYHPRNVYWG<br>QGTQVTVSS |
| 442 | 01B08 | EVQLVESGGGLVQPGRSLTLSCAASTNIESISPMGWYRQAPGKQRELVAAIHGSS<br>TLYADSVKGRFTISRDNAKNSIYLQMNSLRPEDTALYYCNKVPWGRYHPRNVYWG<br>QGTQVTVSS |
| 443 | 01C02 | EVQLVESGGGLVQPGRSLTLSCAASTNIESISPMGWYRQAPGKQRELVAAIHGNS<br>TLYADSVKGRFTISRDNAKNSIYLQMNSLRPEDTALYYCNKVPWGRYHPRNVYWG<br>QGTQVTVSS |
| 444 | 01C10 | EVQLVESGGGLVQPGRSLTLSCAASTNISSISPMGWYRQAPGKQRELVAAIHGFS<br>TLYADSVKGRFTISRDNAKNSIYLQMNSLRPEDTALYYCNKVPWGYYHPRNVYWG<br>QGTQVTVSS |
| 445 | 01F09 | EVQLVESGGGLVQPGRSLTLSCAASTNISSISPMGWYRQAPGKQRELVAAIHGHS<br>TLYADSVKGRFTISRDNAKNSIYLQMNSLRPEDTALYYCNKVPWGRYHPRNVYWG<br>QGTQVTVSS |
| 446 | 02D06 | EVQLVESGGGLVQPGRSLTLSCAASTNISSISPMGWYRQAPGKQRELVAAIHGFS<br>TVYADSVKGRFTISRDNAKNSIYLQMNSLRPEDTALYYCNKVPWGRYHPRNVYWG<br>QGTQVTVSS |
| 447 | 01A06 | EVQLVESGGGLVQPGRSLTLSCAASTNIFSIRPMGWYRQAPGKQRELVAAIHGFS<br>TVYADSVKGRFTISRDNAKNSIYLQMNSLRPEDTALYYCNKVPWGDYHPRNVYWG<br>QGTQVTVSS |
| 448 | 01C07 | EVQLVESGGGLVQPGRSLTLSCAASTNIFSIYPMGWYRQAPGKQRELVAAIHGFS<br>TYYADSVKGRFTISRDNAKNSIYLQMNSLRPEDTALYYCNKVPWGSYHPRNVYWG<br>QGTQVTVSS |
| 449 | 01G09 | EVQLVESGGGLVQPGRSLTLSCAASTNIFNISPMGWYRQAPGKQRELVAAIHGFS<br>TYYADSVKGRFTISRDNAKNSIYLQMNSLRPEDTALYYCNKVPWGRYHPRNVYWG<br>QGTQVTVSS |
| 450 | 01F05 | EVQLVESGGGLVQPGRSLTLSCAASTNIFSSSPMGWYRQAPGKQRELVAAIHGFS<br>TWYADSVKGRFTISRDNAKNSIYLQMNSLRPEDTALYYCNKVPWGRYHPRNVYWG<br>QGTQVTVSS |
| 451 | 02B12 | EVQLVESGGGLVQPGRSLTLSCAASTNISSISPMGWYRQAPGKQRELVAAIHGFD<br>TLYADSVKGRFTISRDNAKNSIYLQMNSLRPEDTALYYCNKVPWGDYHPRNVYWG<br>QGTQVTVSS |
| 452 | 02G01 | EVQLVESGGGLVQPGRSLTLSCAASTNIFSINPMGWYRQAPGKQRELVAAIHGFD<br>TLYADSVKGRFTISRDNAKNSIYLQMNSLRPEDTALYYCNKVPWGDYHPRNVSWG<br>QGTQVTVSS |
| 453 | 01A09 | EVQLVESGGGLVQPGRSLTLSCAASTNIFSITPMGWYRQAPGKQRELVAAIHGRS<br>TLYADSVKGRFTISRDNAKNSIYLQMNSLRPEDTALYYCNKVPWGSYHPRNVYWG<br>QGTQVTVSS |
| 454 | 01H05 | EVQLVESGGGLVQPGRSLTLSCAASTNIFSITPMGWYRQAPGKQRELVAAIHGTS<br>TLYADSVKGRFTISRDNAKNSIYLQMNSLRPEDTALYYCNKVPWGRYHPRNVYWG<br>QGTQVTVSS |
| 455 | 02F06 | EVQLVESGGGLVQPGRSLTLSCAASTNIFSITPMGWYRQAPGKQRELVAAIHGES<br>TLYADSVKGRFTISRDNAKNSIYLQMNSLRPEDTALYYCNKVPWGRYHPRNVYWG<br>QGTQVTVSS |
| 456 | 02G07 | EVQLVESGGGLVQPGRSLTLSCAASTNIFSITPMGWYRQAPGKQRELVAAIHGES<br>TLYADSVKGRFTISRDNAKNSIYLQMNSLRPEDTALYYCNKVPWGDYHPRDVYWG<br>QGTQVTVSS |

| | | |
|---|---|---|
| 457 | 01F07-M34Y | EVQLVESGGGLVQPGRSLTLSCAASTNIFSTSPYGWYRQAPGKQRELVAAIHGFSTIYADSVKGRFTISRDNAKNSIYLQMNSLRPEDTALYYCNKVPWGDYHPGNVYWGQGTQVTVSS |
| 458 | 01F01-M34G | EVQLVESGGGLVQPGRSLTLSCAASTNIFSTSPGGWYRQAPGKQRELVAAIHGFSTIYADSVKGRFTISRDNAKNSIYLQMNSLRPEDTALYYCNKVPWGDYHPGNVYWGQGTQVTVSS |
| 459 | 02G02-M34Y | EVQLVESGGGLVQPGRSLTLSCAASTNIFSITPYGWYRQAPGKQRELVAAIHGASTLYADSVKGRFTISRDNAKNSIYLQMNSLRPEDTALYYCNKVPWGDYHPGNVYWGQGTQVTVSS |
| 460 | 02G02-M34G | EVQLVESGGGLVQPGRSLTLSCAASTNIFSITPGGWYRQAPGKQRELVAAIHGASTLYADSVKGRFTISRDNAKNSIYLQMNSLRPEDTALYYCNKVPWGDYHPGNVYWGQGTQVTVSS |
| 461 | F1 | EVQLVESGGGLVQPGRSLTLSCAAS |
| 462 | F1 | EVQLVESGGGLVQPGRSLTLSCVAS |
| 463 | F2 | WYRQAPGKQRELVA |
| 464 | F3 | GRFTISRDNAKNSIYLQMNSLRPEDTALYYCNK |
| 465 | F3 | GRFTISRDNAKNSIYLQMNSLRPEDTALYYCNE |
| 466 | F4 | WGQGTQVTVSS |
| 467 | F4 | WGKGTQVTVSS |
| 468 | Human BCMA | MLQMAGQCSQNEYFDSLLHACIPCQLRCSSNTPPLTCQRYCNASVTNSVKGTNAILWTCLGLSLIISLAVFVLMFLLRKINSEPLKDEFKNTGSGLLGMANIDLEKSRTGDEIILPRGLEYTVEECTCEDCIKSKPKVDSDHCFPLPAMEEGATILVTTKTNDYCKSLPAALSATEIEKSISAR |
| 469 | Murine BCMA | MAQQCFHSEYFDSLLHACKPCHLRCSNPPATCQPYCDPSVTSSVKGTYTVLWIFLGLTLVLSLALFTISFLLRKMNPEALKDEPQSPGQLDGSAQLDKADTELTRIRAGDDRIFPRSLEYTVEECTCEDCVKSKPKGDSDHFFPLPAMEEGATILVTTKTGDYGKSSVPTALQSVMGMEKPTHTR |
| 470 | Cynomolgus BCMA | MLQMARQCSQNEYFDSLLHDCKPCQLRCSSTPPLTCQRYCNASMTNSVKGMNAILWTCLGLSLIISLAVFVLTFLLRKMSSEPLKDEFKNTGSGLLGMANIDLEKGRTGDElVLPRGLEYTVEECTCEDCIKNKPKVDSDHCFPLPAMEEGATILVTTKTNDYCNSLSAALSVTEIEKSISAR |
| 471 | 6x His tag | His-His-His-His-His-His |
| 472 | 253BH10 (llama anti-BCMA antibody) | QVQLVESGGGLVQPGESLRLSCAASTNIFSISPMGWYRQAPGKQRELVAAIHGFSTLYADSVKGRFTISRDNAKNTIYLQMNSLKPEDTAVYYCNKVPWGDYHPRNVYWGQGTQVTVSS |
| 473 | 253BH10 CDR1 | TNIFSISPMG |
| 474 | 253BH10 CDR2 | AIHGFSTLYADSVK |
| 475 | 253BH10 CDR3 | VPWGDYHPRNVY |

What is claimed is:

1. A method for the treatment or amelioration of a B cell lineage cancer in a subject in need thereof, comprising administering to the subject a single domain B cell maturation agent (BCMA) binding protein comprising complementarity determining regions CDR1, CDR2, and CDR3,
wherein the CDR1 comprises an amino acid sequence selected from the group consisting of SEQ ID NOS: 5, 15, 18, 19, 22, 29, 34, 35, 43, 46, 76, and 95, the CDR2 comprises an amino acid sequence selected from the group consisting of SEQ ID NOS: 118, 121, 122, 125, 126, 129, 133, 137, 147, 156, 164, 173, 174, 190, and 203, and the CDR3 comprises an amino acid sequence set forth as SEQ ID NO: 304, and
wherein the BCMA binding protein is from 80% to 99% identical to the sequence set forth as SEQ ID NO: 472.

2. The method of claim 1, wherein said single domain BCMA binding protein comprises the following formula:

$$f1\text{-}r1\text{-}f2\text{-}r2\text{-}f3\text{-}r3\text{-}f4$$

wherein r1 is the CDR1, r2 is the CDR2, and r3 is the CDR3; and wherein f1, f2, f3 and f4 are framework residues.

3. The method of claim 2, wherein f1 comprises SEQ ID NO: 461 or 462.

4. The method of claim 2, wherein f2 comprises SEQ ID NO: 463.

5. The method of claim 2, wherein f3 comprises SEQ ID NO: 464 or 465.

6. The method of claim 2, wherein f4 comprises SEQ ID NO: 466 or 467.

7. The method of claim 2, wherein r1 comprises SEQ ID NO: 76.

8. The method of claim 2, wherein r2 comprises SEQ ID NO: 190.

9. The method of claim 2, wherein r3 comprises SEQ ID NO: 304.

10. The method of claim 1, wherein said single domain BCMA binding protein has an elimination half-time of at least 12 hours, at least 20 hours, at least 25 hours, at least 30 hours, at least 35 hours, at least 40 hours, at least 45 hours, at least 50 hours, or at least 100 hours, when administered to a subject.

11. The method of claim 1, wherein said single domain BCMA binding protein is humanized or affinity matured.

12. The method of claim 1, wherein said single domain BCMA binding protein further comprises an Fc domain.

13. The method of claim 1, wherein said single domain BCMA binding protein further comprises an anti-cancer agent.

14. The method of claim 13, wherein the anti-cancer agent is conjugated to the single domain BCMA binding protein.

15. The method of claim 1, wherein said single domain BCMA binding protein comprises a sequence that is at least 90% identical to a sequence selected from the group consisting of SEQ ID NOS: 374, 383, 402, 403, 406, 411, 412, and 416.

16. The method of claim 1, wherein said single domain BCMA binding protein comprises a sequence that is at least 95% identical to a sequence selected from the group consisting of SEQ ID NOS: 374, 383, 402, 403, 406, 411, 412, and 416.

17. The method of claim 1, wherein said single domain BCMA binding protein comprises an amino sequence set forth as SEQ ID NO: 374, 383, 402, 403, 406, 411, 412, or 416.

18. The method of claim 1, wherein said single domain BCMA binding protein recognizes an epitope within the human BCMA protein comprising the sequence set forth as SEQ ID NO: 468.

19. A method for the treatment or amelioration of a B cell lineage cancer in a subject in need thereof, comprising administering to the subject a single domain BCMA binding protein comprising complementarity determining regions CDR1, CDR2, and CDR3, wherein the CDR1 comprises the amino acid sequence of SEQ ID NO: 76, the CDR2 comprises the amino acid sequence of SEQ ID NO: 190, and the CDR3 comprises the amino acid sequence of SEQ ID NO: 304, and wherein the BCMA binding protein is from 80% to 99% identical to the amino acid sequence set forth as SEQ ID NO: 472.

20. A method for the treatment or amelioration of a B cell lineage cancer in a subject in need thereof, comprising administering to the subject a single domain BCMA binding protein comprising:
(i) a CDR1 comprising the sequence of SEQ ID NO: 76, a CDR2 comprising the sequence of SEQ ID NO: 190, and a CDR3 comprising the sequence of SEQ ID NO: 304;
(ii) a CDR1 comprising the sequence of SEQ ID NO: 114, a CDR2 comprising the sequence of SEQ ID NO: 163, and a CDR3 comprising the sequence of SEQ ID NO: 304;
(iii) a CDR1 comprising the sequence of SEQ ID NO: 115, a CDR2 comprising the sequence of SEQ ID NO: 163, and a CDR3 comprising the sequence of SEQ ID NO: 304;
(iv) a CDR1 comprising the sequence of SEQ ID NO: 116, a CDR2 comprising the sequence of SEQ ID NO: 174, and a CDR3 comprising the sequence of SEQ ID NO: 304; or
(v) a CDR1 comprising the sequence of SEQ ID NO: 117, a CDR2 comprising the sequence of SEQ ID NO: 174, and a CDR3 comprising the sequence of SEQ ID NO: 304.

* * * * *